(12) United States Patent
Masakari et al.

(10) Patent No.: US 11,208,466 B2
(45) Date of Patent: Dec. 28, 2021

(54) CYTOCHROME-FUSED GLUCOSE DEHYDROGENASE AND GLUCOSE MEASUREMENT METHOD

(71) Applicant: KIKKOMAN CORPORATION, Chiba (JP)

(72) Inventors: Yosuke Masakari, Chiba (JP); Seiichi Hara, Chiba (JP)

(73) Assignee: KIKKOMAN CORPORATION, Chiba (JP)

( * ) Notice: Subject to any disclaimer, the term of this patent is extended or adjusted under 35 U.S.C. 154(b) by 122 days.

(21) Appl. No.: 15/778,726

(22) PCT Filed: Nov. 30, 2016

(86) PCT No.: PCT/JP2016/085556
§ 371 (c)(1),
(2) Date: May 24, 2018

(87) PCT Pub. No.: WO2017/094776
PCT Pub. Date: Jun. 8, 2017

(65) Prior Publication Data
US 2018/0355022 A1    Dec. 13, 2018

(30) Foreign Application Priority Data

Nov. 30, 2015  (JP) .............................. JP2015-233983

(51) Int. Cl.
| | |
|---|---|
| *C07K 14/80* | (2006.01) |
| *C12Q 1/32* | (2006.01) |
| *C12N 15/09* | (2006.01) |
| *C12Q 1/00* | (2006.01) |
| *C12N 9/04* | (2006.01) |
| *C07K 19/00* | (2006.01) |
| *C12P 21/02* | (2006.01) |
| *G01N 27/327* | (2006.01) |
| *C12N 15/10* | (2006.01) |

(52) U.S. Cl.
CPC .............. *C07K 14/80* (2013.01); *C07K 19/00* (2013.01); *C12N 9/0006* (2013.01); *C12N 15/09* (2013.01); *C12N 15/102* (2013.01); *C12P 21/02* (2013.01); *C12Q 1/006* (2013.01); *C12Q 1/32* (2013.01); *G01N 27/327* (2013.01); *C07K 2319/00* (2013.01); *C07K 2319/70* (2013.01); *G01N 2333/904* (2013.01)

(58) Field of Classification Search
CPC .......... G01N 27/327; G01N 2333/904; C07K 14/80; C07K 19/00; C07K 2319/00; C07K 2319/70; C12N 9/0006; C12N 15/102; C12N 15/09; C12Q 1/32; C12Q 1/006; C12P 21/02
See application file for complete search history.

(56) References Cited

U.S. PATENT DOCUMENTS

| | | | |
|---|---|---|---|
| 8,716,442 B2 * | 5/2014 | Takenaka ........... | A61B 5/14532 530/350 |
| 9,493,814 B2 * | 11/2016 | Araki ..................... | C12Q 1/006 |
| 11,066,690 B2 | 7/2021 | Masakari et al. | |
| 2004/0023330 A1 | 2/2004 | Sode | |
| 2005/0067278 A1 | 3/2005 | Sode | |
| 2006/0258959 A1 | 11/2006 | Sode | |
| 2007/0267301 A1 | 11/2007 | Sode | |
| 2011/0045513 A1 | 2/2011 | Takenaka et al. | |
| 2014/0287445 A1 | 9/2014 | Tajima et al. | |
| 2015/0031059 A1 | 1/2015 | Sumida et al. | |
| 2016/0319246 A1 | 11/2016 | Araki | |
| 2019/0136285 A1 | 5/2019 | Masakari et al. | |
| 2019/0185907 A1 | 6/2019 | Masakari | |
| 2019/0257781 A1 | 8/2019 | Masakari | |

FOREIGN PATENT DOCUMENTS

| | | | |
|---|---|---|---|
| WO | 2002036779 A1 | 5/2002 | |
| WO | 2002073181 A1 | 9/2002 | |
| WO | 2005023111 A1 | 3/2005 | |
| WO | 2005030807 A1 | 4/2005 | |

(Continued)

OTHER PUBLICATIONS

Devos et al., Practical limits of function prediction. Proteins: Structure, Function, and Genetics. 2000, vol. 41: 98-107. (Year: 2000).*
Kisselev L., Polypeptide release factors in prokaryotes and eukaryotes: same function, different structure. Structure, 2002, vol. 10: 8-9. (Year: 2002).*
Tan et al., Structural basis for cellobiose dehydrogenase action during oxidative cellulose degradation. Nat. Commun., 2015, vol. 6: 7542, pp. 1-11. (Year: 2015).*
Whisstock et al., Prediction of protein function from protein sequence. Q. Rev. Biophysics., 2003, vol. 36 (3): 307-340. (Year: 2003).*
Wishart et al., A single mutation converts a novel phosphotyrosine binding domain into a dual-specificity phosphatase. J. Biol. Chem., 1995, vol. 270(45): 26782-26785. (Year: 1995).*

(Continued)

*Primary Examiner* — Ganapathirama Raghu
(74) *Attorney, Agent, or Firm* — Lucas & Mercanti, LLP

(57) ABSTRACT

A cytochrome b-glucose dehydrogenase fusion protein having modified electron transfer properties, and a glucose measurement method and measuring kit using the cytochrome b-glucose dehydrogenase fusion protein are provided. Provided are a cytochrome b-glucose dehydrogenase fusion protein in which glucose dehydrogenase having homology with SEQ ID NO: 1 or SEQ ID NO: 4 and cytochrome b are linked together, as well as a glucose measurement method, a measurement reagent kit and a sensor using the cytochrome b-glucose dehydrogenase fusion protein. The cytochrome b-glucose dehydrogenase fusion protein of the present invention has modified electron transfer properties, and can be used for measuring glucose in the presence of a free-form mediator in reduced concentration or in the absence of a free-form mediator, and can be used, for example, in continuous glucose monitoring.

5 Claims, 14 Drawing Sheets

Specification includes a Sequence Listing.

(56) References Cited

FOREIGN PATENT DOCUMENTS

| WO | 2010097462 A1 | 9/2010 |
|----|---------------|--------|
| WO | 2010126139 A1 | 11/2010 |
| WO | 2012169512 A1 | 12/2012 |
| WO | 2013118798 A1 | 8/2013 |
| WO | 2015099112 A1 | 7/2015 |

OTHER PUBLICATIONS

Witkowski et al., Conversion of b-ketoacyl synthase to a Malonyl Decarboxylase by replacement of the active cysteine with glutamine. Biochemistry, 1999, vol. 38: 11643-11650. (Year: 1999).*

Zamocky et al., Cloning, sequence analysis and heterologous expression in Pichia pastoris of a gene encoding a thermostable cellobiose dehydrogenase from Myriococcum thermophilum. Prot. Express. Purification., 2008, vol. 59: 258-265. (Year: 2008).*

Guo et al., Protein tolerance to random amino acid change. PNAS., 2004, vol. 101 (25): 9205-9210. (Year: 2004).*

Degani, Y. et al., "Direct Electrical Communication between Chemically Modified Enzymes and Metal Electrodes. 1. Electron Transfer from Glucose Oxidase to Metal Electrodes via Electron Relays, Bound Covalently to the Enzyme", The Journal of Physical Chemistry, vol. 91, No. 6, 1987 (pp. 1285-1289).

International Search Report for the corresponding PCT/JP2016/085556 dated Feb. 28, 2017 (total 5 pages).

* cited by examiner

```
MpGDH  359 TNSVFTVNETLAQEQREETEANKTGIWATTPNNLGYPTPEQLFNTTEFYSGKEFADKIRNS 418
MhGDH  356 TDSVFQVNETLAEEQRQQTYYNNKTGIWTTTPNNLGYPSPSQLFDGTSFESGQAFANRNS 415
MdrGDH 356 TNSVFTVNETLAEEQKDLYYNNKTGIWTTTPNNLGYPSPSQLFTNTTEFSGKEFAAMIRNS 415
MsGDH  358 TDSVFTVNETLAEEQKDLFYNNKTGIWTTTPNNLGYPSPSQLFTNTTEFRSGKQFAAIRNS 417
MgGDH  354 TDSVFUNSTLASEQREQFEYDNNKTGIWSGTPNNLGYPTPAQLFNGTEFMDGKAFAAIRNS 413
CsGDH  358 TNSIFTNDALAERTAAEEREQEYDNNKTGIWTTTPNNLGYPSPSQLFRTTSFVSGKQFAAIRNS 417
CrGDH  358 TNSLFTNDALAERTQEYDNNKTGIWTTTPNNLGYPSPSQLFRTSFVSGKQFAARIRNT 417
McGDH  360 TNSVFTNETLAQEQREQVEANKTGIWTTTPNNLGYPTPEQLFNGTIEFYSGKEFAAKIRNS 419

MpGDH  419 TDEWANYYAST-NASNVELLKKQYAIVASRYEENYLSPIEINFTPGYEISNVDLQNNKY    477
MhGDH  416 TDEWAEYYAST-NATNIELLKKQYAIVASRYEENYLSPIEINFTPGYGGTTDVDLQNNKY    474
MdrGDH 416 WAETYAQYYAAN-NATNVELLKKQYAIVARRYEENYLSPIEINFTPGYGGTGMADLQNKKY    474
MsGDH  418 TDKYAQYYASTK-NATNIQLELLKKQYSIVASIVARYEEDYLSPIEINLTPGYGGTGEVDLQNNKY   477
MgGDH  414 SQEWAQYYASK-NASTVELLKKQMEVEIVASRYEEDLSPIEINLTPGYGGTGVTADVDLKTNKY    472
CsGDH  418 TDEWAERYAAD-NATNAELLKKQYAIIASRYEEDLSPIEINLTPGYGGTADVDLTNNKY    476
CrGDH  418 TDEWAERYAAD-NATNADLLKKQYAILASRYEEDLSPIEINLTPGYGGTADVDLNNKY    476
McGDH  420 TDEWANYYAST-NASNVASRYEENYLSPIEINLTPGYGGTGSPDLQNNKY    478

MpGDH  478 QTVNHVLIAPLSRGYTHINSSDMEDHSWINPQYYSHPMDLDVHIASTKLAREITASPGL    537
MhGDH  475 QTVNHVLIAPLSRGYTHINSSNIEDPVVINPQYYSHPMDVDVHLASTKLAREIILGAFPGL    534
MdrGDH 475 QTVNHVLIAPLSRGYTHINSSDIEDPVVIDPQYYSHPMDVDVHVASTQLARSIILN-APGL    533
MsGDH  478 QTVNHVLIAPLSRGYTHINSSDIEDPVVIDPQYYSHPMDVDVHVASTKLAREIISASPGL    536
MgGDH  473 QTVNHVLIAPLSRGETHINSSDIEDPYNINPQYYSHPMDVDVHVASTKLAREIIS-AFAL    531
CsGDH  477 QTVNHVLIAPLSRGYTHIKSADINPQYYSHPMDVDVHVASTKLAREIISASPGL    536
CrGDH  477 QTVNHVLIAPLSRGYTHIKSADIEDPYYSHPMDVDVHVASTKLAREIISASPGL    536
McGDH  479 QTVNHVLIAPLSRGYAHINSSDIEEPSVINPQYYSHPLDTDVHVASTKLAREIITASPGL    538
```

Fig. 1-4

| | | |
|---|---|---|
| MpGDH | 538 | GDINSGEIEPGMNITSEDDLRSWLSNNVRSDWHPVGTCAMLPKELGGVVSPALMVYGTSN 597 |
| MhGDH | 535 | ASINSGELQPGSNLTSDEDVKQWLADNVRSDWHPVGTCAMLPRELGGVVDPNLLVYGTAN 594 |
| MdrGDH | 534 | ASINSGEVEPGEKVQSDEDVRKWLSDNVRSDWHPVGTCAMLPRKLGGVVDSKLKVYGTAN 593 |
| MsGDH | 537 | AAINSGEVEPGEKITPQDVRKWLSDNVRSDWHPVGTCAMLPKELGGVVDSNLKVYGTAN 596 |
| MgGDH | 532 | GDLNSGEVEPGMDITSDSDVRAWLADNVRSDWHPVGTCAMLPKELGGVVDSLKVYGTAN 591 |
| CsGDH | 537 | GDINSGETEPGKEITSDSDVRKWLADNVRSDWHPVGTCAMLPKELGGVVDPNLKVYGTSN 596 |
| CrGDH | 537 | GDINSGEHEPGKEITSDSDVRKWLADNVRSDWHPVGTCAMLPKELGGVVDPNLKVYGTSN 596 |
| McGDH | 539 | GDLNSGEVEPGMNVTSEDDLRSWLSNNVRSDWHPVGTCAMLPQELGGVVSPALMVYGTSN 598 |

| | | | |
|---|---|---|---|
| MpGDH | 598 | LRVVDASIMPLEVSSHLMQPTYGIAEKAADIIKNFYKTQHKNQN---- | 641 (SEQ ID NO: 1) |
| MhGDH | 595 | LRVVDASIMPLEISSHLMQPTYGVAEKAADIIKMSRKNNNN------ | 635 (SEQ ID NO: 3) |
| MdrGDH | 594 | LRVVDASIPLEISSHLMQPTYGVAEKAADIIKSSSKK---------- | 631 (SEQ ID NO: 4) |
| MsGDH | 597 | LRVVDASILPLEISSHLMQPTYGVAEKAADIIKGSRN---------- | 633 (SEQ ID NO: 5) |
| MgGDH | 592 | LRVVDASVMPLEVSSHLMQPTFGVYAVSERAEYKKKAQ--------- | 633 (SEQ ID NO: 6) |
| CsGDH | 597 | LRVVDASUMPLEVSSHLMQPTEGVAMVSERAEKAADIIKSANKKRSN- | 637 (SEQ ID NO: 7) |
| CrGDH | 597 | LRVVDASIMPLEVSSHLMQPTFGIAEKAADIIKSANKKRSN------ | 637 (SEQ ID NO: 8) |
| McGDH | 599 | LRVVDASIMPLEVSSHLMQPTYGIAEKAADIIKNYYLSQYSGAGKN-- | 644 (SEQ ID NO: 9) |

Fig. 3

```
            10          20          30          40          50          60
CtCgtb   1  MKLLSRVGATALAAT SLK CAAQMT EG TY THE ATGI T FKTWTPSDGSTFTFGLALP DA  60
HiCgtb   1  MK E LSR IG ATALAAASLYLTSGAAG ATDAYTDSETGI K F QTWSP-DL-PQFTFGLALPP DA  58
TtCgtb   1  MKLLSR IG ATTLAASLCL Q CVAQMTAG N YTDPATGIK LKTWTA TDG AFTFGLALP I S DA  60

70          80          90         100         110         120
CtCgtb  61  LT N DATEYIGLLRC Q I DPSSPGYCGISHGQ SGQMTQALLVAWAS E DVYTSFRYATGY  120
HiCgtb  59  L E KDATEYIGLLRC T R ADPS D PGYCG LSHGQ V GQMTQALLVAWAY E N QVYTSFRYATGY  118
TtCgtb  61  LTKDATEYIGLLRC E L A NATSPGM CGISHGQ SGQMTQALLVAW QI NGTVYTSFRYATGY  120

130         140         150         160         170         180
CtCgtb 121  TLP E LYTGD AKLTQ I ASSVSGDSFEV L RCENCFSWDQ G ATG SVSTSN A LVLGY AA SK   180
HiCgtb 119  TLPGLYTG NAKLTQ L SVNITDTSFELI YRCENCSWEH EG S TGSSTSQ YL VLG R AS AR    178
TtCgtb 121  TLPGLYTGNAKLTQ I STNITAT S TELLYRC N CFSWDQ D TS Q N VSTSS G SLVLGHA A AK  180

190         200         210         220
CtCgtb 181  SGLT G I ATCPDTA E FGFH NN GFGQWGAV LEGATSD S YE EWA 220 (SEQ ID NO: 14)
HiCgtb 179  R G VV G PTCPDIATFG FHDNGFGQWG L GLEN A V S EQ Y SEWA 218 (SEQ ID NO: 21)
TtCgtb 181  Q G LEN PTCPDKATFGFHDNGIY G GWGAPLD G AAQA S YSTW-  219 (SEQ ID NO: 22)
```

CYTOCHROME-FUSED GLUCOSE DEHYDROGENASE AND GLUCOSE MEASUREMENT METHOD

CROSS-REFERENCE TO RELATED APPLICATIONS

This application is a 371 of PCT/JP2016/085556, filed Nov. 30, 2016, which claims benefit of Japanese Patent Application No. 2015-233983 filed on Nov. 30, 2015.

TECHNICAL FIELD

The present invention relates to a glucose dehydrogenase and a method for measuring glucose. More specifically, the present invention relates to a cytochrome-fused glucose dehydrogenase and a method for measuring glucose using such glucose dehydrogenase. The present invention also relates to a cytochrome-fused glucose dehydrogenase that can be advantageously used as a diagnostic enzyme for diabetes, as a glucose sensor, and in a glucose measurement kit.

BACKGROUND ART

Glucose measurement is among other things used for monitoring blood glucose of diabetic patients. Quantification of glucose is usually carried out by using glucose oxidase (also referred to as GOD herein) or glucose dehydrogenase (also referred to as GDH herein). These are used in self-monitoring of blood glucose (SMBG) apparatuses that can be used at home, continuous glucose monitoring (also referred to as CGM herein) apparatuses and flash glucose monitoring (also referred to as FGM herein) apparatuses.

Glucose oxidase is an oxidoreductase, which catalyzes the reaction of oxidizing β-D-glucose into D-glucono-1,5-lactone (gluconolactone). Glucose oxidase uses oxygen as an electron acceptor and flavin adenine dinucleotide (FAD) as a cofactor.

Glucose dehydrogenase is classified as an oxidoreductase, uses glucose and an electron acceptor as substrates, and catalyzes a reaction which generates gluconolactone and a reduced-form acceptor. Examples of the glucose dehydrogenase include nicotinamide dinucleotide-dependent GDH, nicotinamide dinucleotide phosphate-dependent GDH, pyrroloquinoline quinone (PQQ)-dependent GDH and FAD-dependent-GDH (flavin binding GDH).

When using GOD for glucose measurement, a hydrogen peroxide electrode can be used. In this method, a voltage of +0.6 V (vs. Ag/AgCl) to +0.9 V (vs. Ag/AgCl) is applied to the hydrogen peroxide electrode, and the hydrogen peroxide generated when gluconolactone is produced from glucose is measured. This method is mainly used in SMBG and CGM. However, this method is problematic in that since a relatively high voltage is applied, measurement can be affected by contaminants such as ascorbic acid contained in the measurement solution.

Next, a method using an artificial electron mediator (also referred to herein simply as a mediator) instead of hydrogen peroxide was developed. In this method, when glucose is enzymatically converted into gluconolactone, an oxidized-form mediator is converted into a reduced-form mediator. The reduced-form mediator transfers an electron to an electrode and returns to the oxidized-form mediator. An advantage of the method using a mediator is that the applied voltage can be lowered compared to the method using a hydrogen peroxide electrode. An artificial electron mediator, such as a metal complex, e.g., potassium ferricyanide, may be deleterious if it enters the human body.

In the cases of GODs and GDHs, the cofactor FAD is usually buried (resides) deep inside the enzyme molecule. Because of this, when GODs and GDHs are used for glucose measurement, usually the electron cannot be transferred to the electrode if a mediator is not present. However, it is difficult to immobilize a mediator onto an electrode surface. For example, in glucose measurement of diabetic patients, if a mediator is used without immobilizing the same onto an electrode in a self-contained continuous glucose monitoring (CGM) apparatus or an FGM apparatus, the artificial electron mediator present in the measurement solution may flow into the body. However, it is undesirable for a bio-incompatible or toxic mediator to flow into the body. Because of this, glucose measurement methods using artificial electron mediators which may be toxic are not suitable for self-contained continuous glucose monitoring (CGM) and FGM apparatuses. Furthermore, when comparing GOD to GDH, there is the possibility that GOD can be influenced by dissolved oxygen present in the system and, therefore, GDHs are needed more than GODs. As such, a GDH, which can be used for compounds measurable even when a low-voltage is applied, is needed. Moreover, a GDH capable of transferring an electron directly to an electrode in the absence of a free-form mediator as a molecule different from the GDH enzyme, is needed.

Non Patent Literature 1 reports a method for modifying GOD with a mediator apart from an approach to immobilizing the mediator to an electrode. However, due to decrease in enzyme activity due to chemical modification and since the possibility that the artificial electron mediator may flow into the body cannot be denied, practical use of this method has not yet been implemented.

On the other hand, there is an approach which uses a proteinous mediator as the mediator instead of a metal complex such as potassium ferricyanide. For example, Patent Literature 1 describes an enzyme electrode using a cytochrome. However, the cytochrome must be prepared separately, and the cytochrome must be mixed at an amount much larger than that of the enzyme.

Moreover, for example, Patent Literature 2 describes a fusion enzyme obtained by fusing a cytochrome derived from the genus *Aspergillus* to a GDH. Although it is demonstrated that the fusion enzyme transfers an electron to a free-form cytochrome c, it is not described whether the electron can be transferred from the fusion enzyme directly to an electrode.

Patent Literature 3 describes a GDH derived from *Burkholderia cepacia*. The GDH described therein is a complex protein consisting of an α subunit and a β subunit. The α subunit comprises FAD and an FeS cluster. The β subunit is cytochrome c and plays a role in electron transfer from the FAD to the electrode. Patent Literature 4 describes glucose measurement and a glucose sensor using the GDH from *Burkholderia cepacia*. Patent Literature 4 also describes that if the β subunit responsible for electron transfer is not present, the activity to directly transfer the electron from the GDH to the electrode is markedly decreased.

The direct electron transfer type-GDH known in the art has the possibility of acting not only on glucose but also on sugars other than glucose and, therefore, the substrate specificity thereof is not necessarily sufficient for use in glucose sensors. Further, the direct electron transfer type-GDH known in the art requires an electron transfer domain, which plays a role analogous to a mediator and, therefore, is accompanied with problems such as a large molecular weight of the enzyme, stability and productivity of the enzyme. Furthermore, since this enzyme is a membrane bound enzyme from *Burkholderia cepacia*, complicated treatments such as solubilization are required in order to obtain a subunit of the enzyme or the enzyme itself. In addition, the enzyme obtained by solubilization treatment is unstable and if submitted to a treatment such as a drying, it is difficult to maintain the structure of the enzyme or subunit thereof.

CITATION LIST

Patent Literatures

Patent Literature 1: WO 2002/073181
Patent Literature 2: WO 2010/126139
Patent Literature 3: JP Patent No. 4107386 (WO 2002/036779)
Patent Literature 4: JP Patent No. 4359595 (WO 2005/023111)

Non Patent Literatures

Non Patent Literature 1: The Journal of Physical Chemistry, 91 (6), 1285-9, 1987

SUMMARY OF INVENTION

Technical Problem

An object of the present invention is to provide a glucose dehydrogenase having modified electron transfer properties which can overcome the problem(s) mentioned above.

Solution to Problem

As a result of conducting intensive studies in order to solve the problems mentioned above, the present inventors have produced a fusion protein in which a cytochrome b is linked to a glucose dehydrogenase, instead of immobilizing a mediator to an electrode surface, and as a result obtained a glucose dehydrogenase fusion protein having modified electron transfer properties. Based on this finding, the present invention was made.

The present invention encompasses the following embodiments.

[1] A cytochrome b-glucose dehydrogenase fusion protein having modified electron transfer properties and being capable of transferring an electron from the enzyme directly to an electrode, wherein (i) a glucose dehydrogenase moiety from a glucose dehydrogenase not having any cytochrome domain in nature and (ii) a cytochrome b moiety are fused together in said fusion protein.

[2] The cytochrome b-glucose dehydrogenase fusion protein according to [1], wherein response current $A2_{300}$ under an applied voltage of 300 mV (vs. Ag/AgCl) in the absence of a free-form mediator of cytochrome b-glucose dehydrogenase is 1.5 times or more larger than response current $A1_{300}$ under the same applied voltage in the absence of a free-form mediator when the glucose dehydrogenase moiety in the cytochrome b-glucose dehydrogenase fusion protein is present as single glucose dehydrogenase, that is, $A2_{300}/A1_{300}$ is 1.5 or larger, or response current $A2_{500}$ under an applied voltage of 500 mV (vs. Ag/AgCl) in the absence of a free-form mediator of cytochrome b-glucose dehydrogenase is 1.5 times or more larger than response current $A1_{500}$ under the same applied voltage in the absence of a free-form mediator when the glucose dehydrogenase moiety in the cytochrome b-glucose dehydrogenase fusion protein is present as single glucose dehydrogenase, that is, $A2_{500}/A1_{500}$ is 1.5 or larger, wherein each of the response currents $A1_{300}$, $A2_{300}$, $A1_{500}$, and $A2_{500}$ is the response current 40 seconds after initiation of measurement by voltage application after sample addition, wherein said response current is the response current when 80 μg of the protein of cytochrome b-glucose dehydrogenase or glucose dehydrogenase is used, and the value is obtained by subtracting the response current value when a solution of the cytochrome b-glucose dehydrogenase or glucose dehydrogenase is used in the absence of a free-form mediator and in the absence of glucose from the response current value when a solution of the cytochrome b-glucose dehydrogenase or glucose dehydrogenase is used in the absence of a free-form mediator and in the presence of glucose.

[3] A fusion protein selected from the following:
(i) the cytochrome b-glucose dehydrogenase fusion protein according to [1] or [2], wherein the full length amino acid sequence of the glucose dehydrogenase moiety in the cytochrome b-glucose dehydrogenase fusion protein has 70% or more amino acid sequence identity with the amino acid sequence of SEQ ID NO: 1 or SEQ ID NO: 4, and the amino acid sequence of the homologous region consisting of the amino acid sequences of 32 to 34th position, 58 to 62nd position, 106 to 109th position, 111 to 116th position, 119 to 126th position, 132 to 134th position, 136 to 144th position, 150 to 153rd position, 167 to 171st position, 222 to 225th position, 253 to 262nd position, 277 to 281st position, 301 to 303rd position, 305 to 312th position, 314 to 319th position, 324 to 326th position, 332 to 337th position, 339 to 346th position, 388 to 390th position, 415 to 417th position, 454 to 459th position, 486 to 491st position, 508 to 511th position, 564 to 567th position, 570 to 574th position, 584 to 586th position, 592 to 594th position, 597 to 599th position, 601 to 604th position, 607 to 609th position, 611 to 617th position, and 625 to 630th position of SEQ ID NO: 1 and the amino acid sequence of the homologous region of the corresponding positions of the glucose dehydrogenase have 90% or more amino acid sequence identity, and the cytochrome b-glucose dehydrogenase fusion protein has a glucose dehydrogenase activity capable of transferring an electron from the enzyme directly to an electrode;
(ii) the cytochrome b-glucose dehydrogenase fusion protein according to [1] or [2], wherein the full length amino acid sequence of the cytochrome b moiety in the cytochrome b-glucose dehydrogenase fusion protein has 50% or more amino acid sequence identity with the amino acid sequence of SEQ ID NO: 12 and, the amino acid sequence of the homologous region consisting of the amino acid sequences of 35 to 36th position, 52 to 53rd position, 59 to 61st position, 64 to 69th position, 73 to 76th position, 99 to 100th position, 119 to 120th position, 133 to 134th position, 143 to 144th position, 148 to 150th position, 152 to 154th position, 167 to 168th position, 174 to 176th position, 188 to 189th position, and 216 to 217th position of SEQ ID NO: 12 and the amino acid sequence of the homologous region of the corresponding positions of the cytochrome b have 90% or more amino acid sequence identity;

(iii) the cytochrome b-glucose dehydrogenase fusion protein according to [1] or [2], wherein the full length amino acid sequence of the cytochrome b moiety in the cytochrome b-glucose dehydrogenase fusion protein has 50% or more amino acid sequence identity with the amino acid sequence of SEQ ID NO: 14, and the amino acid sequence of the homologous region consisting of the amino acid sequences of 1 to 2nd position, 8 to 10th position, 12 to 14th position, 23 to 24th position, 30 to 31st position, 35 to 37th position, 41 to 42nd position, 50 to 57th position, 59 to 61st position, 64 to 74th position, 82 to 83rd position, 85 to 86th position, 88 to 91st position, 93 to 97th position, 99 to 104th position, 110 to 123rd position, 125 to 128th position, 130 to 134th position, 149 to 150th position, 152 to 156th position, 166 to 168th position, 172 to 175th position, 187 to 190th position, 194 to 197th position, 199 to 200th position, and 202 to 205th position of SEQ ID NO: 14 and the amino acid sequence of the homologous region of the corresponding positions of the cytochrome b have 90% or more amino acid sequence identity;

(iv) the cytochrome b-glucose dehydrogenase fusion protein according to [1] or [2], wherein the full length amino acid sequence of the cytochrome b moiety in the cytochrome b-glucose dehydrogenase fusion protein has 45% or more amino acid sequence identity with the amino acid sequence of SEQ ID NO: 16, and the amino acid sequence of the homologous region consisting of the amino acid sequences of 35 to 36th position, 52 to 53rd position, 59 to 61st position, 64 to 69th position, 73 to 76th position, 99 to 100th position, 119 to 120th position, 133 to 134th position, 143 to 144th position, 148 to 150th position, 152 to 154th position, 167 to 168th position, 174 to 176th position, 188 to 189th position, and 216 to 217th position of SEQ ID NO: 12 and the amino acid sequence of the homologous region of the corresponding positions of the cytochrome b have 90% or more amino acid sequence identity;

(v) the cytochrome b-glucose dehydrogenase fusion protein according to [1] or [2], wherein regarding the cytochrome b moiety described in (ii), (iii), or (iv) above, the amino acid at the position corresponding to the 95th position of the amino acid sequence of SEQ ID NO: 12 is methionine, the amino acid at the position corresponding to the 197th position is histidine, the sequence at the position corresponding to the 93 to 95th position of the amino acid sequence of SEQ ID NO: 12 is Gly-Xaa-Met, where Xaa represents any amino acid, the sequence at the position corresponding to the 120 to 123rd position of the amino acid sequence of SEQ ID NO: 12 is Tyr-Xaa-Xaa-Pro, where Xaa represents any amino acid, and the sequence at the position corresponding to the 150 to 153rd position of the amino acid sequence of SEQ ID NO: 12 is Cys-Xaa-Xaa-Cys, where Xaa represents any amino acid; or (vi) the cytochrome b-glucose dehydrogenase fusion protein according to [1] or [2], wherein the glucose dehydrogenase moiety in the cytochrome b-glucose dehydrogenase fusion protein is as described in (i) above, and the cytochrome b moiety in the cytochrome b-glucose dehydrogenase fusion protein is as described in (ii), (iii), (iv), or (v) above, or (vii) the cytochrome b-glucose dehydrogenase fusion protein according to [1] or [2], wherein, regarding the fusion protein described in (vi) above, the fusion protein comprises an amino acid sequence having a substitution, deletion or addition of one or several amino acids at position(s) other than those specified in said (v) in the glucose dehydrogenase moiety and/or cytochrome b moiety and has glucose dehydrogenase activity capable of transferring an electron from the enzyme directly to an electrode.

[4] The fusion protein according to any one of [1] to [3], wherein the glucose dehydrogenase moiety and the cytochrome b moiety in the fusion protein are linked together via a liker.

[5] The fusion protein according to any one of [1] to [4], wherein the glucose dehydrogenase moiety in the fusion protein is from the genus *Mucor*, the genus *Absidia*, the genus *Actinomucor*, the genus *Circinella*, *Mucor prainii*, *Mucor circinelloides*, *Mucor hiemalis*, *Mucor subtilissimus*, *Mucor guilliermondii*, *Mucor javanicus*, *Mucor dimorphosporus*, *Absidia cylindrospora*, *Absidia hyalospora*, *Actinomucor elegans*, *Circinella simplex*, *Circinella* sp., *Circinella angarensis*, *Circinella chinensis*, *Circinella lacrymispora*, *Circinella minor*, *Circinella mucoroides*, *Circinella rigida*, *Circinella umbellata* or *Circinella muscae*.

[6] The fusion protein according to any one of [1] to [5], wherein the cytochrome b moiety in the fusion protein is from the Cytb domain in the cellobiose dehydrogenase (CDH) from the genus *Myriococcum*, the Cytb domain in the CDH from *Myriococcum thermophilum*, the Cytb domain in the CDH from the genus *Corynascud*, the Cytb domain in the CDH from *Corynascud thermophiles*, the Cytb domain in the CDH from the genus *Aspergillus*, the Cytb domain in the CDH from *Aspergillus sojae* or the Cytb domain in the CDH from *Aspergillus oryzae*, the Cytb domain in the CDH from the genus *Hypoxylon*, the Cytb domain in the CDH from *Hypoxylon haematostroma*, the Cytb domain in the CDH from the genus *Chaetomium*, the Cytb domain in the CDH from *Chaetomium attrobruneum*, the Cytb domain in the CDH from the genus *Neurospora*, the Cytb domain in the CDH from *Neurospora crassa*, the Cytb domain in the CDH from the genus *Humicola*, the Cytb domain in the CDH from *Humicola insolens*, the Cytb domain in the CDH from the genus *Thielavia*, or the Cytb domain in the CDH from *Thielavia terrestris*.

[7] The fusion protein according to any one of [1] to [6], wherein the glucose dehydrogenase moiety in the fusion protein has the following characteristics:

Action: exhibits glucose dehydrogenase activity,
Molecular weight: has a molecular weight of about 70 kDa estimated based on the primary sequence of the polypeptide chain moiety of the protein or has a molecular weight of about 80 kDa measured by SDS-polyacrylamide electrophoresis,
Substrate specificity: has low reactivity to maltose and D-xylose compared to the reactivity to D-glucose,
Cofactor characteristics: is a flavin-binding type.

[8] A gene encoding a cytochrome b-glucose dehydrogenase fusion protein having modified electron transfer properties, said gene consisting of
(a) DNA encoding the fusion protein according to any one of [1] to [7],
(b) DNA encoding the amino acid sequence of SEQ ID NO: 33, 35, 37, 39, 41, 43, 114, 116, or 118, (c) DNA having the nucleotide sequence of SEQ ID NO: 34, 36, 38, 40, 42, 44, 115, 117, or 119, or
(d) DNA comprising a nucleotide sequence having 60% or more sequence identity with the nucleotide sequence of SEQ ID NO: 34, 36, 38, 40, 42, 44, 115, 117, or 119 and encoding a fusion protein having a glucose dehydrogenase activity capable of directly transferring an electron in the absence of a free-form mediator.
[9] A vector comprising the gene of [8].
[10] A host cell comprising the vector of [9].
[11] A method for producing a cytochrome b-glucose dehydrogenase fusion protein comprising the following steps:
culturing the host cell of [10],
expressing the cytochrome b-glucose dehydrogenase fusion protein gene contained in the host cell, and
recovering cytochrome b-glucose dehydrogenase fusion protein from the culture.
[12] A method for measuring glucose comprising using the cytochrome b-glucose dehydrogenase fusion protein according to any one of [1] to [7].
[13] A glucose measuring kit comprising the cytochrome b-glucose dehydrogenase fusion protein according to any one of [1] to [7].
[14] A glucose sensor comprising the cytochrome b-glucose dehydrogenase fusion protein according to any one of [1] to [7].

The present specification incorporates and contains the contents disclosed in JP Patent Application No. 2015-233983, which is a priority document of the present application.

Advantageous Effects of Invention

One effect (advantage) of the present invention is that glucose can be measured in the presence of an artificial electron mediator reduced in concentration or in the absence of an artificial electron mediator. While artificial electron mediators can be toxic to diabetic patients, a free-form mediator is not required in glucose measurement in the present invention and, therefore, the glucose dehydrogenase of the present invention can be used in a self-contained system for continuous measurement of glucose. Further, the glucose measurement method according to the present invention can be performed at a low cost since expensive mediator molecules are not required or the amount thereof can be reduced. In addition, a wide variety of electron acceptors (compounds) can be employed with the glucose dehydrogenase according to the present invention compared to conventional glucose dehydrogenases and the present invention can provide more alternatives. Furthermore, compared to glucose oxidases, the glucose dehydrogenase according to the present invention is relatively unaffected by dissolved oxygen and, therefore, capable of more accurate glucose measurement.

BRIEF DESCRIPTION OF DRAWINGS

FIG. 1-1 shows a multiple alignment of GDHs derived from various species. MpGDH represents a GDH from *Mucor prainii* (SEQ ID NO: 1); MhGDH represents a GDH from *Mucor hiemalis* (SEQ ID NO: 3), MrdGDH represents a GDH from *Mucor* RD056860 (SEQ ID NO: 4), MsGDH represents a GDH from *Mucor subtilissimus* (SEQ ID NO: 5), MgGDH represents a GDH from *Mucor guilliermondii* (SEQ ID NO: 6), CsGDH represents a GDH from *Circinella simplex* (SEQ ID NO: 7), CrGDH represents a GDH from *Circinella* genus (SEQ ID NO: 8) and McGDH represents a GDH from *Mucor circinelloides* (SEQ ID NO: 9).

FIG. 1-2 shows the multiple alignment continued from FIG. 1-1.

FIG. 1-3 shows the multiple alignment continued from FIG. 1-1.

FIG. 1-4 shows the multiple alignment continued from FIG. 1-1.

FIG. 2 shows a multiple alignment of Cytbs from various species. MtCytb represents the amino acid sequence of the cytb domain in a CDH from *Myriococcum thermophilum* (SEQ ID NO: 12); AsCytb represents the amino acid sequence of the cytb domain in a CDH from *Aspergillus sojae* (SEQ ID NO: 16); HhCytb represents the amino acid sequence of the cytb domain in a CDH from *Hypoxylon haematostrom* (SEQ ID NO: 18); CaCytb represents the amino acid sequence of the cytb domain in a CDH from *Chaetomium attrobruneum* (SEQ ID NO: 19); and NcCytb represents the amino acid sequence of the cytb domain in a CDH from *Neurospora crassa* (SEQ ID NO: 20).

FIG. 3 shows a multiple alignment of Cytbs from various species. CtCytb represents the amino acid sequence of the cytb domain in a CDH from *Corynascud thermophiles* (SEQ ID NO: 14); HiCytb represents the amino acid sequence of the cytb domain in a CDH from *Humicola insolens* (SEQ ID NO: 21); and TtCytb represents the amino acid sequence of the cytb domain in a CDH from *Thielavia terrestris* (SEQ ID NO: 22).

FIG. 4 shows chronoamperometry measurement results of GDH. "500 mV" represents results without glucose content (control), and "500 mV+Glu" represents results with addition of glucose and application of +500 mV (glucose may also be referred to herein as Glu).

Figure 2:
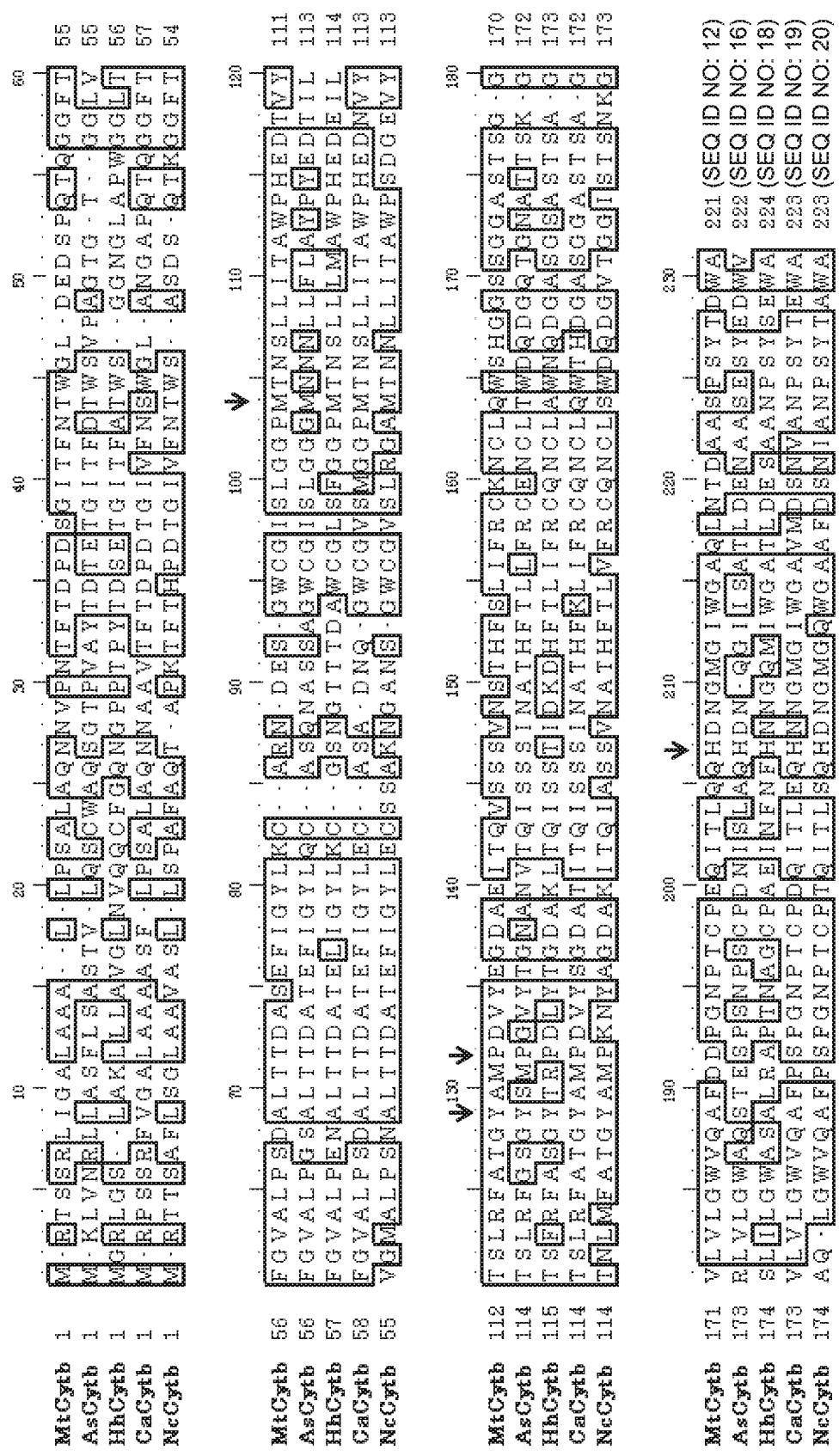

DESCRIPTION OF EMBODIMENTS (Cytochrome b-Glucose Dehydrogenase Fusion Protein According to the Present Invention)

In the first embodiment, the present invention provides a cytochrome b-glucose dehydrogenase fusion protein. This fusion protein may also be referred to herein as Cytb-GDH. In the fusion protein, the cytochrome b may be linked to the amino terminal (which may also be referred to herein as the N terminal) side of the glucose dehydrogenase, or the cytochrome b may be linked to the carboxy terminal (which may also be referred to herein as the C terminal) side of the glucose dehydrogenase. Unless stated otherwise, the description "Cytb-GDH" encompasses both of the cases. Incidentally, the description "GDH-Cytb" refers to a fusion protein in which Cytb is linked to the C terminal side of the glucose dehydrogenase, and does not encompass a fusion protein in which Cytb is linked to the N terminal side of the glucose dehydrogenase. One or multiple Cytbs may be linked to the glucose dehydrogenase. For convenience, the description "Cytb-GDH" further encompasses a fusion protein in which multiple Cytbs are linked. Incidentally, the description "Cytbx2-GDH" indicates a fusion protein in which two Cytbs are linked to glucose dehydrogenase, unless stated otherwise. The Cytb moiety and the glucose dehydrogenase moiety in the fusion protein may be linked via a linker. When multiple Cytbs are linked, neighboring Cytbs may optionally be linked to each other via a linker. The description "Cytb-GDH" further encompasses such aspects.

The Cytb-GDH according to the present invention has modified electron transfer properties. (Having) "modified electron transfer properties" means the response current of a Cytb-GDH under a given applied voltage in the presence of glucose in a given glucose concentration is higher than that under the same applied voltage with the same glucose concentration when the glucose dehydrogenase moiety within the Cytb-GDH is present as single glucose dehydrogenase. In one embodiment, in the Cytb-GDH according to the present invention, response current $A2_{300}$ under an applied voltage of 300 mV (vs. Ag/AgCl) in the absence of a free-form mediator of the Cytb-GDH, is 1.5 times, 1.6 times, 1.7 times, 1.8 times, 1.9 times, 2 times, 2.5 times, 3 times, 4 times, 5 times, 6 times, 7 times, 8 times, 9 times, or 10 times or higher than response current $A1_{300}$ under the same applied voltage in the absence of a free-form mediator when the glucose dehydrogenase moiety of the Cytb-GDH is present as single glucose dehydrogenase, ($A2_{300}/A1_{300} \geq 10$). Unless stated otherwise, a silver/silver chloride electrode is used as the reference electrode for application of voltage. In one embodiment, in the Cytb-GDH according to the present invention, response current $A2_{500}$ under an applied voltage of 500 mV in the absence of a free-form mediator of the Cytb-GDH, is 1.5 times, 1.6 times, 1.7 times, 1.8 times, 1.9 times, 2 times, 2.5 times, 3 times, 4 times, 5 times, 6 times, 7 times, 8 times, 9 times, or 10 times or higher than response current $A1_{500}$ under the same applied voltage in the absence of a free-form mediator when the glucose dehydrogenase moiety of the Cytb-GDH is present as single glucose dehydrogenase ($A2_{500}/A1_{500} \geq 10$). Here, the response current (such as $A1_{300}$, $A2_{300}$, $A1_{500}$, $A2_{500}$) is a response current as a value 40 seconds after initiation of measurement through voltage application after (glucose-containing or blank) sample addition, wherein 80 μg of the protein of cytochrome b-glucose dehydrogenase or glucose dehydrogenase is used, and the value is obtained by subtracting the value of the response current when a solution of the Cytb-GDH or glucose dehydrogenase is used in the absence of a free-form mediator and in the absence of glucose (blank) from the value of the response current when a solution of the Cytb-GDH or glucose dehydrogenase is used in the absence of a free-form mediator and in the presence of glucose (+Glu). When the same measurement is performed with 130 μg of protein, it is plausible that a higher response current can be obtained simply in association with increased oxidation rate. That is, it is highly plausible that a higher response current (such as $A1_{300}$, $A2_{300}$, $A1_{500}$, $A2_{500}$) can be obtained in the case where 130 μg of the protein is used than in the case where 80 μg of the protein is used.

In the present specification, "free-form mediator" refers to a mediator not linked to GDH, and, for example, includes free-form cytochromes (e.g., free-form Cytb), that is, cytochromes not fused to GDH, and free-form low-molecular-weight compounds, that is, low-molecular-weight compounds not fused to GDH.

In one embodiment, the Cytb-GDH according to the present invention not only has modified electron transfer properties but also can transfer an electron from the fusion protein directly to a solid phase electrode even in the absence of a free-form mediator such as potassium ferricyanide. Such Cytb-GDH may also be referred to herein as direct electron transferring Cytb-GDH. Without wishing to be bound by any particular theory, it is believed that when direct electron transferring occurs, the electron is primarily transferred from a cofactor such as FAD contained in the GDH moiety to the Cytb moiety, and further transferred from the Cytb moiety to the solid phase electrode. However, the present invention is not limited to any particular mechanism, and if a current from the fusion protein to the solid phase electrode is observed even in the absence of a free-form mediator such as potassium ferricyanide, then such fusion protein falls under the direct electron transferring (type) Cytb-GDH according to the present invention. Such electron transfer between chemical species to solid phase electrode is referred to as heterogeneous electron transfer. Electron transfer is a type of elementary reaction involving electron transfer and includes inner-sphere, outer-sphere and heterogeneous electron transfer. The direct electron transfer of the present invention is not particularly limited as long as an electron is transferred from the enzyme to the solid phase electrode. In one embodiment, electron transfer by the Cytb-GDH of the present invention is heterogeneous electron transfer.

(GDH Moiety)

In one embodiment, the glucose dehydrogenase moiety in the Cytb-GDH of the present invention is a mutant of a glucose dehydrogenase, produced based on a glucose dehydrogenase from the genus *Mucor* and having the amino acid sequence of SEQ ID NO: 1, SEQ ID NO: 4 or SEQ ID NO: 10. Examples of such mutant include a glucose dehydrogenase comprising an amino acid sequence having a high sequence identity (for example, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more) with SEQ ID NO: 1, SEQ ID NO: 4 or SEQ ID NO: 10; as well as a glucose dehydrogenase comprising an amino acid sequence having a modification or mutation, or deletion, substitution, addition and/or insertion of one to several amino acids in the amino acid sequence of SEQ ID NO: 1, SEQ ID NO: 4 or SEQ ID NO: 10.

Glucose dehydrogenases are found throughout nature and can be obtained by searching for enzymes from microorganisms, animals and plants. In microorganisms, glucose dehydrogenase can be obtained from, e.g., filamentous fungi, yeast or bacteria. The glucose dehydrogenase of the present invention may be produced based on a GDH from, for example, a microorganism classified in the subphylum *Mucor*, the class *Mucor*, the order *Mucor* or the family *Mucor*, for example, species such as those of the genus *Mucor*, the genus *Absidia*, the genus *Actinomucor* or the genus *Circinella*.

Examples of microorganisms belonging to the genus *Mucor* include *Mucor prainii, Mucor circinelloides, Mucor hiemalis, Mucor subtilissimus, Mucor guilliermondii, Mucor javanicus* and *Mucor dimorphosporus*. Examples of microorganisms belonging to the genus *Absidia* include *Absidia cylindrospora* and *Absidia hyalospora*. Examples of microorganisms belonging to the genus *Actinomucor* include *Actinomucor elegans*. Examples of microorganisms belonging to the genus *Circinella* include *Circinella simplex*, *Circinella* sp., *Circinella angarensis*, *Circinella chinensis*, *Circinella lacrymispora*, *Circinella minor*, *Circinella Mucoroides*, *Circinella rigida*, *Circinella umbellata* and *Circinella muscae*.

The glucose dehydrogenase moiety in the Cytb-GDH of the present invention is derived from a GDH not having any Cyt domain in nature. Accordingly, the GDH moiety from types of GDH having a Cyt domain in nature is excluded from the glucose dehydrogenase moiety in the Cytb-GDH of the present invention, and, for example, the GDH from *Burkholderia cepacia* described in Patent Literature 3 is excluded. Further, the glucose dehydrogenase moiety in the Cytb-GDH of the present invention is a type of GDH soluble in water in nature, and membrane-bound GDHs are excluded.

In one embodiment, the glucose dehydrogenase moiety of the Cytb-GDH of the present invention is linked to Cytb via the N terminal side of the primary amino acid sequence thereof. In another embodiment, the glucose dehydrogenase moiety of the Cytb-GDH of the present invention is linked to Cytb via the C terminal side of the primary amino acid sequence thereof. The glucose dehydrogenase moiety of the fusion protein of the present invention may further have a deletion, insertion, addition and/or substitution of one or several (for example, 1 to 15, 1 to 10, 1 to 5, for example 1 to 3) amino acids. The glucose dehydrogenase moiety of the fusion protein of the present invention may further have amino acid substitution mutation(s) for improving properties such as substrate specificity and thermal stability; has an amino acid sequence identity of for example, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more, with the amino acid sequence of SEQ ID NO: 1, SEQ ID NO: 4, or SEQ ID NO: 10; and has glucose dehydrogenase activity. Examples of the Cytb-GDH comprising such glucose dehydrogenase moiety and having modified electron transfer properties include the direct electron transfer type Cytb-GDH.

(Homologous Region)

The amino acid sequence identity or homology can be computed by using a program such as maximum matching or search homology of GENETYX Ver. 11 (manufactured by Genetics Inc.), or a program such as maximum matching or multiple alignment of DNASIS Pro (Hitachi Solutions Co., Ltd.). In order to compute amino acid sequence identity, positions having identical amino acids between two or more GDHs when said two or more GDHs are aligned can be investigated. Further, when two or more Cytbs are aligned, positions having identical amino acids between said two or more Cytbs can be investigated. Based on such information, identical regions within the amino acid sequences can be determined.

Positions having similar amino acids in two or more GDHs can also be investigated. Further, positions having similar amino acids in two or more Cytbs can be investigated. For example, multiple amino acid sequences can be aligned with CLUSTALW. In this case, using the Blosum62 algorithm, amino acids determined as being similar (analogous) when a plurality of amino acid sequences are aligned, may be referred to as similar amino acids. In the mutants of the present invention, amino acid substitution(s) may be between such similar amino acids. By such alignment, regions having identical amino acid sequences and positions occupied by similar amino acids can be investigated for a plurality of amino acid sequences. Based on such information, a homologous region (conserved region) in an amino acid sequence can be determined.

When determining a homologous region, parameters for multiple alignment by CLUSTALW can be appropriately configured. For example, Cytb is known to comprise a methionine and histidine as amino acid residues to bind to the heme iron, and in the case of the Cytb having the amino acid sequence of SEQ ID NO: 12, the methionine at 95th position and the histidine at 197th position are believed to correspond to these residues. Accordingly, when aligning the Cytb having the amino acid sequence of SEQ ID NO: 12 with a Cytb from another origin, if the amino acids corresponding to these positions are not conserved, then parameters for multiple alignment by CLUSTALW, for example, the gap penalty, can be configured such that the positions are conserved. For example, the Gap opening penalty can be set as 1. Further, the Gap extension penalty can be set as 1.

In the present specification, the "homologous region" of a GDH is specified as a region consisting of identical amino acids or similar amino acids which are present in the corresponding positions between a standard GDH and a GDH being compared when two or more GDHs are aligned, wherein said region consists of 3 or more, 4 or more, 5 or more, 6 or more, 7 or more, 8 or more, 9 or more or 10 or more continuous amino acids. For example, in FIG. 1, GDHs having 70% or more full-length amino acid sequence identity were aligned. Of these, taking the GDH from the genus *Mucor* and represented by SEQ ID NO: 1 as the standard (basis), amino acids from the 31st to 41st position consist of identical amino acids and, therefore, the region from the 31st to 41st position is a homologous region. Likewise, when using the GDH from the genus *Mucor* of SEQ ID NO: 1 as the standard, the regions consisting of 58 to 62nd position, 71 to 85th position, 106 to 116th position, 119 to 127th position, 132 to 134th position, 136 to 144th position, 150 to 157th position, 167 to 171st position, 219 to 225th position, 253 to 262nd position, 277 to 281st position, 301 to 303rd position, 305 to 312th position, 314 to 319th position, 324 to 326th position, 332 to 337th position, 339 to 346th position, 348 to 354th position, 388 to 394th position, 415 to 417th position, 454 to 459th position, 477 to 484th position, 486 to 491st position, 508 to 511th position, 564 to 579th position, 584 to 586th position, 592 to 605th position, 607 to 617th position, and 625 to 630th position may be homologous regions. In one embodiment, the homologous region of GDH consists of these regions.

In one embodiment, the homologous region of GDH is, based on the GDH from the genus *Mucor* of SEQ ID NO: 1 as the standard, the region consisting of amino acid sequences from 32 to 38th position, 58 to 62nd position, 76 to 82nd position, 106 to 109th position, 111 to 116th position, 119 to 126th position, 132 to 134th position, 136 to 144th position, 150 to 153rd position, 167 to 171st position, 222 to 225th position, 253 to 262nd position, 277 to 281st position, 301 to 303rd position, 305 to 312th position, 314 to 319th position, 324 to 326th position, 332 to 337th position, 339 to 346th position, 348 to 354th position, 388 to 390th position, 415 to 417th position, 454 to 459th position, 477 to 482nd position, 486 to 491st position, 508 to 511th position, 564 to 567th position, 570 to 579th position, 584 to 586th position, 592 to 595th position, 597 to 599th position, 601 to 604th position, 607 to 609th position, 611 to 617th position, and 625 to 630th position.

In one embodiment, the homologous region of GDH is, based on the GDH from the genus *Mucor* of SEQ ID NO: 1 as the standard, the region consisting of the amino acid sequences of 32 to 34th position, 58 to 62nd position, 106 to 109th position, 111 to 116th position, 119 to 126th position, 132 to 134th position, 136 to 144th position, 150 to 153rd position, 167 to 171st position, 222 to 225th position, 253 to 262nd position, 277 to 281st position, 301 to 303rd position, 305 to 312th position, 314 to 319th position, 324 to 326th position, 332 to 337th position, 339 to 346th position, 388 to 390th position, 415 to 417th position, 454 to 459th position, 486 to 491st position, 508 to 511th position, 564 to 567th position, 570 to 574th position, 584 to 586th position, 592 to 594th position, 597 to 599th position, 601 to 604th position, 607 to 609th position, 611 to 617th position, and 625 to 630th position.

The GDH moiety in the fusion protein according to the present invention has, for example, 50% or more, 55% or more, 60% or more, 65% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more amino acid sequence identity over the full length when aligned with the GDH having the amino acid sequence of SEQ ID NO: 1, SEQ ID NO: 4, or SEQ ID NO: 10, and has glucose dehydrogenase activity. Further, the amino acid sequence of the homologous region of the mutant GDH in the fusion protein of the present invention has a sequence identity of, for example, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more, with the amino acid sequence of the homologous region in SEQ ID NO: 1, SEQ ID NO: 4, or SEQ ID NO: 10.

(Further Substitutions)

(Amino Acid Substitutions Improving Thermal Stability of GDH)

The present inventors previously reported that the thermal stability of GDH can be improved by substituting an amino acid residue thereof (see, for example, WO 2012/169512, the entire content of which is incorporated in the present specification by reference). The GDH moiety in the fusion protein of the present invention may optionally have such further amino acid substitution(s).

As amino acid substitutions for altering substrate specificity or improving thermal stability of a GDH, amino acid substitutions to positions corresponding to the following positions in the amino acid sequence of SEQ ID NO: 1 may be mentioned.

(a) 232nd position
(b) 387th position
(c) 545th position.

Optionally, the amino acid at the position corresponding to (a) the 232nd position may be substituted with alanine, methionine, cysteine, glutamine or glutamic acid.

Optionally, the amino acid at the position corresponding to glutamine at (b) the 387th position may be substituted with alanine, valine, glycine, serine or cysteine.

Optionally, the amino acid at the position corresponding to alanine at (c) 545th position may be substituted with valine, threonine, serine, proline, alanine, tyrosine, lysine, histidine, phenylalanine or glutamic acid.

For example, similar amino acid substitution may be introduced to the corresponding position(s) in the amino acid sequence of SEQ ID NO: 4. That is, (a) the 228th position, (b) the 384th position, and/or (c) the 541st position of SEQ ID NO: 4 may have the substitution(s) above.

Further, the present inventors previously reported that the thermal stability of GDH can be improved by substituting an amino acid residue thereof (see, for example, WO 2015/099112, the entire content of which is incorporated in the present specification by reference). The GDH moiety in the fusion protein of the present invention may optionally have such further amino acid substitution(s).

As amino acid substitutions for improving thermal stability of GDH, amino acid substitutions to positions corresponding to the following positions in the amino acid sequence of SEQ ID NO: 1 may be mentioned.

(d) 66th position
(e) 68th position
(f) 88th position
(g) 158th position
(h) 233rd position
(i) 385th position
(j) 391st position
(k) 557th position
(l) 559th position Optionally, the amino acid at the position corresponding to (d) the 66th position may be substituted with tyrosine.
Optionally, the amino acid at the position corresponding to (e) the 68th position may be substituted with glycine.
Optionally, the amino acid at the position corresponding to (f) the 88th position may be substituted with alanine.
Optionally, the amino acid at the position corresponding to (g) the 158th position may be substituted with histidine.
Optionally, the amino acid at the position corresponding to (h) the 233rd position may be substituted with arginine.
Optionally, the amino acid at the position corresponding to (i) the 385th position may be substituted with threonine.
Optionally, the amino acid at the position corresponding to (j) the 391st position may be substituted with isoleucine.
Optionally, the amino acid at the position corresponding to (k) the 557th position may be substituted with valine.
Optionally, the amino acid at the position corresponding to (l) the 559th position may be substituted with lysine.

For example, similar amino acid substitution may be introduced at the corresponding position(s) in the amino acid sequence of SEQ ID NO: 4. That is, (d) the 62nd position, (e) the 64th position, (f) the 84th position, (g) the 154th position, (h) the 229th position, (i) the 382nd position, (j) the 388th position, (k) the 553rd position and/or (l) the 555th position of SEQ ID NO: 4 may have the substitution(s) above.

(Amino Acid Substitution for Improving Specific Activity of GDH)

The present inventors previously reported that the thermal stability of GDH can be improved by substituting amino acid residue(s) thereof (see, for example, JP Patent Application No. 2014-037737, the entire content of which is incorporated in the present specification by reference). The GDH moiety in the fusion protein of the present invention may optionally include such further amino acid substitution.

As amino acid substitutions for altering substrate specificity or improving thermal stability of GDH, amino acid substitutions to positions corresponding to the following positions in the amino acid sequence of SEQ ID NO: 1 may be mentioned.
(m) 88th position
(n) 554th position Optionally, the amino acid at the position corresponding to (m) the 88th position may be substituted with alanine. Optionally, the amino acid at the position corresponding to (n) the 554th position may be substituted with aspartic acid.

For example, similar amino acid substitution may be introduced to the corresponding position(s) in the amino acid sequence of SEQ ID NO: 4. That is, (m) the 84th position and/or (n) the 550th position of SEQ ID NO: 4 may have the substitution(s) above.

Enzyme Chemical Characteristics of GDH Moiety in the Fusion Protein of the Present Invention In one embodiment, the GDH moiety in the Cytb-GDH of the present invention is a flavin-binding (type) GDH. Where the GDH moiety is a flavin-binding (type) GDH, the GDH moiety in the fusion protein of the present invention may have the following properties.

Action: exhibits glucose dehydrogenase activity,
Molecular weight: has a molecular weight of about 70 kDa estimated based on the primary sequence of a polypeptide chain moiety of the protein or has a molecular weight of about 80 kDa measured by SDS-polyacrylamide electrophoresis,
Substrate specificity: has low reactivity to maltose and D-xylose compared to the reactivity to D-glucose,
Cofactor characteristics: is a flavin binding (bound) type.

In one embodiment, the GDH moiety in the fusion protein of the present invention further has low reactivity to D-galactose, compared to the reactivity to D-glucose. In the present specification, the phrase reactivity to a sugar is low compared to the reactivity to D-glucose means that the activity to the sugar is less than 5%, for example, less than 4%, less than 3%, less than 2%, for example, less than 1.5%, wherein activity to D-glucose is set as 100%.

The molecular weight can be calculated based on the information of a primary sequence by using a program such as GENETYX Ver. 11 (manufactured by Genetics Inc.) and ExPASy (http://web dot expasy dot org/compute_pi/) or can be measured by SDS-polyacrylamide electrophoresis. When calculation is made by using, for example, GENETYX Ver. 11, the molecular weight estimated from the primary sequence of the flavin-binding GDH having the amino acid sequence of SEQ ID NO: 1 is about 70 kDa. Further, when measurement is made by using, for example, SDS-polyacrylamide electrophoresis, the molecular weight of the flavin-binding GDH having the amino acid sequence of SEQ ID NO: 1 when the sugar chain is removed is about 80 kDa (see JP Patent No. 4648993). When calculation is made by using GENETYX Ver. 11, the molecular weight estimated from the primary sequence of the flavin-binding GDH having the amino acid sequence of SEQ ID NO: 4 is about 70 kDa.

(Cytb Moiety)

In one embodiment, the Cytb moiety in the Cytb-GDH of the present invention is a mutant of a Cytb, which is produced based on the Cytb having the amino acid sequence of SEQ ID NO: 12, 14, 16 or 21. Examples of such mutant include a Cytb comprising an amino acid sequence having high sequence identity (for example, 45% or more, 46% or more, 47% or more, 48% or more, 49% or more, 50% or more, 51% or more, 52% or more, 53% or more, 54% or more, 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more) with SEQ ID NO: 12, 14, 16 or 21; as well as a Cytb comprising an amino acid sequence having a modification or mutation, or deletion, substitution, addition and/or insertion of one to several amino acids in the amino acid sequence of SEQ ID NO: 12, 14, 16 or 21. In an embodiment, the Cytb moiety in the Cytb-GDH of the present invention may also be referred to as fusion type Cytb.

In one embodiment, examples of the Cytb moiety in the Cytb-GDH of the present invention include a Cytb comprising an amino acid sequence having a high sequence identity (for example, 50% or more, 51% or more, 52% or more, 53% or more, 54% or more, 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more) with a partial sequence of SEQ ID NO: 12, 14, 16 or 21, for example, an amino acid sequence consisting of the amino acid sequence of 52nd to 221st position of SEQ ID NO: 12, an amino acid sequence consisting of the amino acid sequence of 50th to 220th position of SEQ ID NO: 14, an amino acid sequence consisting of the amino acid sequence of 52nd to 222nd position of SEQ ID NO: 16, or an amino acid sequence consisting of the amino acid sequence of 48th to 218th position of SEQ ID NO: 21; as well as a Cytb comprising an amino acid sequence having a modification or mutation, or deletion, substitution, addition and/or insertion of one to several amino acids in said partial amino acid sequence of SEQ ID NO: 12, 14, 16 or 21.

Cytbs are found throughout nature and can be obtained by searching for enzymes from microorganisms, animals and plants. In microorganisms, Cytb can be obtained from, e.g., fungi, yeast or bacteria. Examples of Cytb include Cytbs of type A (microsomal), Cytb5 of type B (outer mitochondrial membrane), Cytb ascorbate-dependent 3 (CYBASC3), and Cytb encoded by mitochondria, but are not limited thereto. The Cytb of the present invention may be produced based on a Cytb from, for example, species such as those of genus *Myriococcum*, genus *Corynascud*, genus *Aspergillus*, genus *Hypoxylon*, genus *Chaetomium*, genus *Neurospora*, genus *Humicola* or genus *Thielavia*. The Cytb used in the fusion protein of the present invention need not be a Cytb present as a single polypeptide in nature, and the Cytb domain within a protein can be also used. Examples of such Cytb domain include the Cytb domain in a CDH from the genus *Myriococcum*, e.g., the Cytb domain in the CDH from *Myriococcum thermophilum*, the Cytb domain in a CDH from the genus *Corynascud*, e.g., the Cytb domain in the CDH from *Corynascud thermophiles*, the Cytb domain in a CDH from the genus *Aspergillus*, e.g., the Cytb domain in the CDH from *Aspergillus sojae* and the Cytb domain in the CDH from *Aspergillus oryzae*, the Cytb domain in a CDH from the genus *Hypoxylon*, e.g., the Cytb domain in the CDH from *Hypoxylon haematostroma*, the Cytb domain in a CDH from the genus *Chaetomium*, e.g., the Cytb domain in the CDH from *Chaetomium attrobruneum*, the Cytb domain in a CDH from the genus *Neurospora*, e.g., the Cytb domain in the CDH from *Neurospora crassa*, the Cytb domain in a CDH from the genus *Humicola*, e.g., the Cytb domain in the CDH from *Humicola insolens*, and the Cytb domain in a CDH from the genus *Thielavia*, e.g., the Cytb domain in the CDH from *Thielavia terrestris*, but are not limited thereto.

Further, the electron transfer heme-containing domain positioned at the N terminus of the CDH (cellobiose dehydrogenase) having the known sequence of Accession no. AB 193288, XM_382527, or XM_369170, which are extracellular cytochrome genes, may be used (see APPLIED AND ENVIRONMENTAL MICROBIOLOGY, 71, 4548-4555 (2005)). In addition, a cytochrome can be used wherein the polypeptide composing the cytochrome has the sequence "G-X-M" being a heme-binding ligand, where X represents any amino acid, at the positions corresponding to 93 to 95th positions, has the motif "Y-X-X-P", where X represents any amino acid, at the positions corresponding to 120 to 123rd positions, has the sequence "C-X-X-C" being an S-S-bonding motif, where X represents any amino acid, at the positions corresponding to 150 to 153rd positions, and a histidine residue being a heme-binding ligand at the position corresponding to 197th position in the amino acid sequence of SEQ ID NO: 12.

In the present specification, the "homologous region" of a Cytb is specified as a region consisting of identical amino acids or similar amino acids which are present in the corresponding positions between a standard Cytb and a comparative Cytb when two or more Cytbs are aligned, wherein said region consists of 2 or more, 3 or more, 4 or more, 5 or more, 6 or more, 7 or more, 8 or more, 9 or more or 10 or more continuous amino acids.

(Homologous Region Based on MtCytb)

For example, in FIG. 2, Cytbs having full-length amino acid sequence identity of 52% or more with the Cytb domain in the CDH of *Myriococcum thermophilum* (also referred to herein as MtCytb) comprising the amino acid sequence of SEQ ID NO: 12 were aligned. Among the sequences, when taking MtCytb represented by SEQ ID NO: 12 as the standard, positions 52 to 53rd are composed of identical amino acids and, therefore, the region from the 52 to 53rd position falls under a homologous region. Likewise, when taking MtCytb represented by SEQ ID NO: 12 as the standard, the regions consisting of 35 to 36th position, 59 to 61st position, 64 to 69th position, 73 to 76th position, 99 to 100th position, 119 to 120th position, 133 to 134th position, 143 to 144th position, 148 to 150th position, 152 to 154th position, 167 to 168th position, 174 to 176th position, 188 to 189th position, and 216 to 217th position may fall under (amount to be) a homologous region of MtCytb. In one embodiment, the homologous region of MtCytb consist of these regions.

(Homologous Region Based on CtCytb)

As another example, in FIG. 3, Cytbs having a full-length amino acid sequence of 50% or more with the Cytb domain in the CDH from *Corynascud thermophiles* (also referred to as CtCytb) comprising the amino acid sequence of SEQ ID NO: 14 were aligned. Among the sequences, when taking CtCytb represented by SEQ ID NO: 14 as the standard, positions 1 to 2 are composed of identical amino acids and the region from the 1 to 2nd position falls under a homologous region. Likewise, when taking CtCytb represented by SEQ ID NO: 14 as the standard, the regions consisting of 8 to 10th position, 12 to 14th position, 23 to 24th position, 30 to 31st position, 35 to 37th position, 41 to 42nd position, 50 to 57th position, 59 to 61st position, 64 to 74th position, 82 to 83rd position, 85 to 86th position, 88 to 91st position, 93 to 97th position, 99 to 104th position, 110 to 123rd position, 125 to 128th position, 130 to 134th position, 149 to 150th position, 152 to 156th position, 166 to 168th position, 172 to 175th position, 187 to 190th position, 194 to 197th position, 199 to 200th position, and 202 to 205th position may fall under a homologous region of CtCytb. In one embodiment, the homologous regions of CtCytb consist of these regions.

(Conserved Amino Acid Residue or Conserved Amino Acid Motif Associated with Activity)

A conserved amino acid residue or conserved amino acid motif within an amino acid sequence can be determined by using the same method as that for determining a homologous region (conserved region) in an amino acid sequence. Amino acid sequences are aligned by using a multiple alignment program or the like, and then a conserved amino acid residue or amino acid motif is identified. Then, comparison is made between an amino acid residue known to be associated with activity through introduction of site-directed mutagenesis or an amino acid residue at a particular position believed to be associated with activity within an amino acid sequence whose three dimensional structure has been elucidated by way of crystal structure analysis and a conserved amino acid residue obtained from the alignment. If these amino acid residues match, the conserved amino acid residue is believed to be associated with activity. This can be applied not only to a single amino acid residue but also to amino acid motifs having multiple amino acids.

For example, when using MtCytb represented by SEQ ID NO: 12 as the standard, methionine at 95th position and histidine at 197th position are conserved in various Cytbs. On the other hand, the crystal structure of the Cytb domain of the CDH from *Phanerochaele chrysosporium* has been reported (Structure 8, 79-88 (2000), PDB ID: 1D7B), and Met at 65th position and His at 163rd position in the sequence are known to be heme-binding residues. When MtCytb and PcCytbt are aligned, Met at the 95th position in the sequence of SEQ ID NO: 12 corresponds to Met at 65th position of PcCytbt, and His at the 197th position in the sequence of SEQ ID NO: 12 corresponds to His at 163rd position of PcCytbt. Accordingly, each of Met at the position corresponding to the 95th position and His at the position corresponding to the 197th position when taking MtCytb of SEQ ID NO: 12 as the standard is believed to be a conserved amino acid residue associated with activity. Indeed, Met at the position corresponding to the 95th position and His at the position corresponding to the 197th position have been confirmed to bind to heme from the crystal structure of MtCytb (PDB ID: 4QI6) reported in Nature Communications, 6, 7542 (2015). Likewise, the motif sequence "G-X-M", where X represents any amino acid, at positions corresponding to 93 to 95th positions in the amino acid sequence of SEQ ID NO: 12 is believed to be a heme-binding ligand. Further, the sequence "Y-X-X-P", where X represents any amino acid, at positions corresponding to 120 to 123rd positions in the amino acid sequence of SEQ ID NO: 12 is believed to be a conserved amino acid motif. Further, the sequence "C-X-X-C", where X represents any amino acid, at positions corresponding to 150 to 153rd positions in the amino acid sequence of SEQ ID NO: 12 is believed to be a disulfide-bonding motif. Preferably, the Cytb moiety to be used for the Cytb-GDH of the present invention comprises such conserved amino acid residue or conserved amino acid motif believed (expected) to be associated with activity.

(Enzyme Chemical Characteristics of Cytb Moiety in Fusion Protein of the Present Invention)

In one embodiment, the Cytb moiety in the Cytb-GDH of the present invention may have the following properties.

Action: the Cytb moiety can receive an electron from the glucose dehydrogenase moiety, and can transfer a received electron to an electrode in the absence of a free-form mediator, Molecular weight: the molecular weight estimated based on the primary sequence of the polypeptide chain moiety of the protein is about 20 to about 25 kDa, for example, about 22.9 to about 23.4 kDa, for example, about 23 kDa, Spectral characteristics: is of reduced form, and exhibits absorption spectrum characteristic to Cytb, Dissolution characteristics: is a soluble protein, Structure: comprises a signal sequence at the amino terminus.

In one embodiment, as the spectral characteristics, the Cytb moiety exists in reduced form, and has characteristic absorption spectra at 563 nm and 533 nm.

If a microorganism such as *Escherichia coli* is used as the host, the N terminal signal peptide of the cytochrome moiety in the fusion protein of the present invention may optionally be truncated.

The N terminal signal peptide of Cytb contained in the cellobiose dehydrogenase from *Myriococcum thermophilum*, and represented by SEQ ID NO: 12, is a peptide consisting of amino acids from the 1 to 21st position of the amino acid sequence of SEQ ID NO: 12. Cleavage occurs between alanine at the 21st position and glutamine at the 22nd position. In order to delete the N terminal signal peptide from this polypeptide, a codon encoding alanine at the 21st position or a codon encoding glutamine at the 22nd position may be substituted with an initiation codon. The same applies to the positions corresponding to the 21st positions or 22nd positions of SEQ ID NO: 12 in other Cytbs having sequence identity with SEQ ID NO: 12.

Likewise, the N terminal signal peptide of Cytb contained in the cellobiose dehydrogenase from *Corynascud thermophilus*, and represented by SEQ ID NO: 14, is a peptide consisting of amino acids from the 1 to 23rd position of the amino acid sequence of SEQ ID NO: 14. Cleavage occurs between alanine at the 23rd position and glutamine at the 24th position. In order to delete the N terminal signal peptide from this polypeptide, a codon encoding alanine at the 23rd position or a codon encoding glutamine at the 24th position may be substituted with an initiation codon. The same applies to the positions corresponding to the 23rd positions or 24th positions of SEQ ID NO: 14 in other Cytbs having sequence identity with SEQ ID NO: 14.

In embodiments where Cytb is fused to the C terminus of the GDH moiety, a sequence obtained by removing the signal sequence from Cytb can be ligated. In embodiments where Cytb is fused to the N terminus of the GDH moiety, the signal sequence of Cytb may be removed and a signal sequence from GDH may be added.

(Linker Moiety)

In one embodiment, regarding the Cytb-GDH of the present invention, the N terminal side of the GDH moiety is linked to the Cytb moiety. In another embodiment, regarding the Cytb-GDH of the present invention, the C terminal side of the GDH moiety is linked to the Cytb moiety. Here, the GDH moiety and the Cytb moiety may be linked together via a linker moiety. As the linker, for example, a natural linker or a partial sequence thereof or a modified sequence thereof, a genetically-engineered linker sequence, a sequence of repeated identical or different linkers, a sequence wherein a portion of a natural linker is deleted, as well as combinations thereof can be used. A natural linker refers to a moiety linking one domain and another domain in a natural polypeptide sequence. For example, a natural CDH has a flavodehydrogenase domain and a Cytb domain, and the moiety linking the flavodehydrogenase domain and the Cytb domain is a linker. A sequence of repeated identical linkers refers to a sequence obtained by appropriately repeating linker L, such as L-L and L-L-L. A sequence of repeated different linkers refers to a sequence for example where regarding linker $L_1$ and linker $L_2$, either one of or both of $L_1$ and $L_2$ are repeated in suitable permutation, such as $L_1$-$L_2$-$L_1$, $L_1$-$L_1$-$L_2$, $L_1$-$L_2$-$L_2$, $L_1$-$L_2$-$L_1$-$L_2$, $L_1$-$L_1$-$L_2$-$L_2$, and $L_1$-$L_1$-$L_1$-$L_2$. The length of the linker may, for example, be 1 to 60 amino acids, 2 to 50 amino acids, 3 to 40 amino acids, 4 to 35 amino acids, or 5 to 31 amino acids and the like.

Examples of the natural linker include liker sequences or putative linker sequences including a putative linker sequence of the cellobiose dehydrogenase (CDH) from *Myriococcum thermophilum*) (SEQ ID NO: 23), an putative linker sequence of the CDH from *Corynascud thermophiles* CDH (SEQ ID NO: 25), an putative linker sequence of the CDH from *Aspergillus sojae* (SEQ ID NO: 27 or 29), the putative linker sequence GDCSGDGGGGSGPEPVPVPDG of the CDH from *Aspergillus terreus*, the HSP70-derived linker sequence GGGGSLVPRGSGGGGS, the hen egg lysozyme-derived linker sequence GGGGSLVPRGSGGGGS, and the hemagglutinin HA peptide-derived linker sequence GGSGGGGG, but are not limited thereto. The natural linker sequence can be obtained from a known peptide sequence database. Examples of natural linker sequences are shown, for example, in Table 1 in Protein Sci. 2013; 22(2): 153-167. A linker moiety in a protein can be predicted by using known sequence analysis software or tool such as DomCut software and Pfam software. A region between moieties predicted to be a flavodehydrogenase domain and a Cytb domain by using a domain prediction tool can be predicted to be a linker moiety. Alternatively, a linker moiety can be predicted based on information of the crystal structure of the CDH from *Myriococcum thermophilum* (PDB ID: 4QI6). Although the boundary between a linker moiety and a protein domain moiety is not necessarily clear, the sequence of a predicted linker may differ from the actual sequence in about one or several amino acid residues as long as the Cytb-GDH of the present invention is capable of transferring an electron directly to an electrode. Optimization of the chain length of a linker is described, for example, in PNAS 1998; 95(11): 5929-5934.

A sequence where a portion of a natural linker is deleted (a partially deleted natural linker) may be a linker sequence having a deletion of, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid residues from the N terminal side, or may be a linker sequence having a deletion of, for example, 1, 2, 3, 4, 5, 6, 7, 8, 9, 10, 11, 12, 13, 14, 15, 16, 17, 18, 19, or 20 amino acid residues from the C terminal side, or may be a linker sequence having a deletion of any amino acid residue, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid residues at positions other than the N terminus and the C terminus, or may be a combination of these.

A partial sequence of a natural linker sequence can be a partial sequence consisting of, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 amino acid residues of a natural linker sequence from the N terminal side. The partial sequence of a natural linker sequence can be a partial sequence consisting of, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 amino acid residues of a natural linker sequence from the C terminal side. The partial sequence of a natural linker sequence can be a partial sequence consisting of any amino acid residue, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 amino acid residues of a natural linker sequence in a moiety other than the N terminus and the C terminus.

Examples of genetically-engineered linker sequences include the linker sequence linking the heavy chain (VH) and the light chain (VL) of a single-chain variable fragment (scFv) in an antibody, but are not limited thereto. The linker may include one or more glycine residues to ensure mobility, and may include one or more serine or threonine residues to ensure solubility.

Examples of the linker include a glycine linker, for example, $G_x$, where x can be any natural number, including GG, GGG, GGGG, and GGGGG.

Examples of the linker include a glycine-alanine linker, for example, $G_x$-$A_y$ (where x and y can be each independently 0 or any natural number) and $G_x$-$A_y$-$G_z$ (where x, y, and z can be independently 0 or any natural number), including a GA linker, and a linker obtained by repeating the GA linker such as GA-GA, GA-GA-GA, and GA-GA-GA-GA; a GGGA linker, and a linker obtained by repeating the GGGA linker such as GGGA-GGGA, GGGA-GGGA-GGGA, and GGGA-GGGA-GGGA-GGGA; a GGAG linker, and a linker obtained by repeating the GGAG linker such as GGAG-GGAG, GGAG-GGAG-GGAG, and GGAG-GGAG-GGAG-GGAG; a GGGGA linker, and a linker obtained by repeating the GGGGA linker such as GGGGA-GGGGA and GGGGA-GGGGA-GGGGA; a GGAGG linker, and a linker obtained by repeating the GGAGG linker such as GGAGG-GGAGG; and any combination of these, such as GGGA-A-GGG-GGGA and GGGGA-GGGA-GGGGA.

Examples of the linker include a glycine-serine linker, for example, $G_x$-$S_y$ (where x and y can be each independently 0 or any natural number) and $G_x$-$S_y$-$G_z$ (where x, y, and z can be each independently 0 or any natural number). Examples include a GS linker, and a linker obtained by repeating the GS linker such as GS-GS, GS-GS-GS, and GS-GS-GS-GS; a GSG linker, and a linker obtained by repeating the GSG linker such as GSG-GSG, GSG-GSG-GSG, and GSG-GSG-GSG-GSG; a GGGS linker, and a linker obtained by repeating the GGGS linker such as GGGS-GGGS, GGGS-GGGS-GGGS, and GGGS-GGGS-GGGS-GGGS; a GGSG linker, and a linker obtained by repeating the GGSG linker such as GGSG-GGSG, GGSG-GGSG-GGSG, and GGSG-GGSG-GGSG-GGSG; a GGGGS linker, and a linker obtained by repeating the GGGGS linker such as GGGGS-GGGGS and GGGGS-GGGGS-GGGGS; a GGSGG linker, and a linker obtained by repeating the GGSGG linker such as GGSGG-GGSGG; and any combination of these, such as GGGS-GGGGS-GGGS and GGGGS-GGGS-GGGGS (SEQ ID NOs: 71 to 111).

The glycine-alanine linker and glycine-serine linker may be combined together. In the above, "S" can be arbitrarily substituted with "T".

(Cytb-GDH According to the Present Invention)

In one embodiment, in the Cytb-GDH of the present invention, the N terminus of the GDH moiety is linked to the Cytb moiety, or the C terminus of the GDH moiety is linked to the Cytb moiety. Here, the amino acid sequence of the Cytb moiety is merely required to be an amino acid sequence constituting a polypeptide having electron mediator function, and a partial amino acid sequence obtained by deleting a portion thereof may be used. For example, the Cytb moiety may have an amino acid sequence having a deletion of a portion of the amino acid sequence, for example, 1 to 60 amino acids such as 2 to 55 amino acids, 3 to 54 amino acids, 4 to 53 amino acids, 5 to 52 amino acids, 6 to 51 amino acids, for example, 7 to 50 amino acids on the N terminal side or C terminal side in the Cytb moiety. The amino acid sequence of the GDH moiety is merely required to be an amino acid sequence constituting a polypeptide having a glucose dehydrogenase activity, and a partial amino acid sequence obtained by deleting a portion thereof may be used. For example, the GDH moiety may have an amino acid sequence having a deletion of a portion of the amino acid sequence, for example, 1 to 60 amino acids, such as 2 to 55 amino acids, 3 to 50 amino acids, 4 to 45 amino acids, 5 to 40 amino acids, 6 to 35 amino acids, 7 to 30 amino acids, 8 to 29 amino acids, for example, 11 to 28 amino acids on the N terminal side or C terminal side in the GDH moiety.

In the case that a portion of the amino acid sequence is deleted, for example, a portion or the entire sequence predicted to be a signal sequence can be deleted. Prediction of a signal sequence can be performed by using a Neural Networks algorithm or a Hidden Markov Models algorithm, for example, by using known software or tool such as PSORT II, SignalP, and Signal-BLAST. Whether a signal sequence is to be deleted can be appropriately determined depending on the origin of GDH or Cytb as well as the type of host to be used for recombinant expression.

In one embodiment, in the Cytb-GDH of the present invention having modified electron transfer properties, the N terminus of the GDH moiety is linked to the Cytb moiety, or the C terminus of the GDH moiety is linked to the Cytb moiety, and optionally the GDH moiety and the Cytb moiety may be linked together via a linker, wherein the GDH moiety has the amino acid sequence of SEQ ID NO: 1 or SEQ ID NO: 4 or SEQ ID NO: 10 or has an amino acid sequence having, for example, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, for example, 99% or more sequence identity over the full length with the amino acid sequence of SEQ ID NO: 1 or SEQ ID NO: 4 or SEQ ID NO: 10, and the amino acid sequence of the homologous region of SEQ ID NO: 1 and the amino acid sequence of the homologous region composed of corresponding positions in said glucose dehydrogenase have 90% or more amino acid sequence identity wherein the homologous region of SEQ ID NO: 1 consists of the amino acid sequences of 31 to 41st position, 58 to 62nd position, 71 to 85th position, 106 to 116th position, 119 to 127th position, 132 to 134th position, 136 to 144th position, 150 to 157th position, 167 to 171st position, 219 to 225th position, 253 to 262nd position, 277 to 281st position, 301 to 303rd position, 305 to 312th position, 314 to 319th position, 324 to 326th position, 332 to 337th position, 339 to 346th position, 348 to 354th position, 388 to 394th position, 415 to 417th position, 454 to 459th position, 477 to 484th position, 486 to 491st position, 508 to 511th position, 564 to 579th position, 584 to 586th position, 592 to 605th position, 607 to 617th position, and 625 to 630th position of SEQ ID NO: 1, or has a deletion, substitution or addition of one or several amino acids in said amino acid sequence and has glucose dehydrogenase activity;

the Cytb moiety has, for example, 45% or more, 46% or more, 47% or more, 48% or more, 49% or more, 50% or more, 51% or more, 52% or more, 53% or more, 54% or more, 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more amino acid sequence identity over the full length with the amino acid sequence of SEQ ID NO: 12 or 16, and the amino acid sequence of the homologous region of SEQ ID NO: 12 and the amino acid sequence of the homologous region composed of corresponding positions in said Cytb have 90% or more amino acid sequence identity wherein the homologous region of SEQ ID NO: 12 consists of the amino acid sequences of 35 to 36th position, 52 to 53rd position, 59 to 61st position, 64 to 69th position, 73 to 76th position, 99 to 100th position, 119 to 120th position, 133 to 134th position, 143 to 144th position, 148 to 150th position, 152 to 154th position, 167 to 168th position, 174 to 176th position, 188 to 189th position, and 216 to 217th position, or the Cytb moiety has, for example, 45% or more, 46% or more, 47% or more, 48% or more, 49% or more, 50% or more, 51% or more, 52% or more, 53% or more, 54% or more, 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, for example, 99% or more amino acid sequence identity over the full length with the amino acid sequence of SEQ ID NO: 14 or SEQ ID NO: 21, and the amino acid sequence of the homologous region of SEQ ID NO: 14 and the amino acid sequence of the homologous region composed of corresponding positions in said Cytb have 90% or more amino acid sequence identity wherein the homologous region of SEQ ID NO: 14 consists of the amino acid sequences of 1 to 2nd position, 8 to 10th position, 12 to 14th position, 23 to 24th position, 30 to 31st position, 35 to 37th position, 41 to 42nd position, 50 to 57th position, 59 to 61st position, 64 to 74th position, 82 to 83rd position, 85 to 86th position, 88 to 91st position, 93 to 97th position, 99 to 104th position, 110 to 123rd position, 125 to 128th position, 130 to 134th position, 149 to 150th position, 152 to 156th position, 166 to 168th position, 172 to 175th position, 187 to 190th position, 194 to 197th position, 199 to 200th position, and 202 to 205th position, or the Cytb moiety has a deletion, substitution or addition of one or several amino acids in the amino acid sequence, and the amino acid at the position corresponding to 95th position of the amino acid sequence of SEQ ID NO: 12 is methionine and the amino acid at the position corresponding to 197th position of SEQ ID NO: 12 is histidine, and optionally the sequence at positions corresponding to 93 to 95th positions in the amino acid sequence of SEQ ID NO: 12 is Gly-Xaa-Met, where Xaa represents any amino acid, and optionally the sequence at positions corresponding to 120 to 123rd positions in the amino acid sequence of SEQ ID NO: 12 is Tyr-Xaa-Xaa-Pro, where Xaa represents any amino acid, and optionally the sequence at positions corresponding to 150 to 153rd positions in the amino acid sequence of SEQ ID NO: 12 is Cys-Xaa-Xaa-Cys, where Xaa represents any amino acid, and;

the Cytb moiety can receive an electron from the GDH moiety, and can transfer a received electron to an electrode in the absence of a free-form mediator, that is, the Cytb-GDH is capable of transferring an electron directly to an electrode.

In one embodiment, the present invention provides a DNA encoding a Cytb-GDH fusion protein. In one embodiment, the present invention provides a DNA construct comprising a nucleotide sequence of SEQ ID NO: 34, 36, 38, 40, 42, 44, 115, 117, or 119. In one embodiment, the present invention provides DNA having a nucleotide sequence having a sequence identity of 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 90%, 90%, 91%, 92%, 93%, 94%, 95%, 96%, 97%, 98%, or 99% or more with the nucleotide sequence of SEQ ID NO: 34, 36, 38, 40, 42, 44, 115, 117, or 119, and encoding a Cytb-GDH fusion protein having glucose dehydrogenase activity capable of directly transferring an electron in the absence of a free-form mediator.

(GDH Gene)

In order to obtain a gene encoding a GDH, gene cloning methods widely carried out in the art can be used. For example, chromosomal DNA or mRNA can be extracted from microbial cells or various cells having GDH productivity by routine methods, for example, methods described in Current Protocols by Molecular Biology (WILEY Interscience, 1989). Further, cDNA can be synthesized using mRNA as a template. Using chromosomal DNA or cDNA thus obtained, a library of chromosomal DNA or cDNA can be prepared.

Next, an appropriate probe DNA can be synthesized based on the amino acid sequence of the GDH above and a GDH gene can be screened from the chromosomal DNA or cDNA library by using the probe DNA or, alternatively, appropriate primer DNA(s) can be prepared based on the amino acid sequence above and the DNA containing the gene fragment of interest encoding the GDH can be amplified with an appropriate polymerase chain reaction (PCR method) such as the 5'RACE method and the 3'RACE method, and then, these DNA fragments can be linked to obtain a DNA containing the full-length GDH gene of interest.

Examples of a gene encoding a GDH obtained as mentioned above include the GDH gene from the genus *Mucor* (described in JP Patent No. 4648993). A gene obtained by modifying this GDH gene may be used including, for example, modified genes described in WO 2012/169512 and WO 2015/099112.

(Cytb Gene)

In the present specification, the term "Cytb gene" encompasses not only a gene encoding Cytb but also a gene encoding a Cytb domain. In order to obtain a gene encoding a Cytb or a gene encoding a Cytb domain gene cloning methods widely carried out in the art can be used. For example, chromosomal DNA or mRNA can be extracted from microbial cells or various cells having Cytb productivity by routine methods, for example, methods described in Current Protocols by Molecular Biology (WILEY Interscience, 1989). Further, cDNA can be synthesized using mRNA as a template. Using chromosomal DNA or cDNA thus obtained, a library of chromosomal DNA or cDNA can be prepared.

Next, an appropriate probe DNA can be synthesized based on the above amino acid sequence of Cytb and a Cytb gene can be screened from the chromosomal DNA or cDNA library by using the probe DNA or, alternatively, appropriate primer DNA(s) can be prepared based on the above amino acid sequence and the DNA containing a gene fragment of interest encoding the Cytb can be amplified with an appropriate polymerase chain reaction (PCR method) such as the 5'RACE method and the 3'RACE method, and then, these DNA fragments can be linked to obtain a DNA containing the full-length Cytb gene of interest.

Examples of the gene encoding Cytb obtained as mentioned above include the Cytb domain in the CDH from *Myriococcum thermophilum*, the Cytb domain in the CDH from *Corynascud thermophiles*, the Cytb domain in the CDH from *Aspergillus sojae* and the Cytb domain in the CDH from *Aspergillus oryzae*, but are not limited thereto.

(Gene Encoding Cytb-GDH)

A gene encoding Cytb-GDH (which may also be referred to as "Cytb-GDH gene" herein) can be produced by ligating the GDH gene and the Cytb gene by using conventional genetic engineering methods. The GDH gene may be placed to the 5' side or 3' side of the Cytb gene. Multiple Cytb genes may be ligated. A nucleotide sequence encoding a linker peptide may be placed between the GDH gene and said one or multiple Cytb genes.

Where the Cytb gene is a Cytb domain gene, for example, where the Cytb gene is a Cytb domain gene within a CDH gene, first a nucleotide sequence encoding the Cytb domain and linker moiety within the cellobiose dehydrogenase gene can be amplified using an appropriate primer pair. Then, this can be ligated to a nucleotide sequence encoding a GDH. Alternatively, the Cytb domain in a cellobiose dehydrogenase gene can be amplified by using an appropriate primer pair and a nucleotide sequence encoding a linker from the same or different origin can be amplified using a different primer pair. Then, these can be ligated to a nucleotide sequence encoding a GDH.

The GDH gene and Cytb gene, or the Cytb-GDH gene mentioned above may be ligated or inserted into various vectors or integrated into a chromosome or a genome. In the case of a vector, cloning (of the gene) into the vector can be carried out by using a commercially available kit such as TA Cloning Kit (Invitrogen) and In-Fusion HD Cloning Kit (Clontech); a commercially available plasmid vector DNA such as pUC119 (manufactured by Takara Bio Inc.), pUC18 (manufactured by Takara Bio Inc.), pBR322 (manufactured by Takara Bio Inc.), pBluescript SK+(Stratagene) and pYES2/CT (Invitrogen); and/or a commercially available bacteriophage vector DNA such as λEMBL3 (Stratagene). A host organism, for example, *Escherichia coli*, preferably *Escherichia coli* JM109 strain (manufactured by Takara Bio Inc.) or *Escherichia coli* DH5α strain (manufactured by Takara Bio Inc.) can be transformed with such recombinant DNA. Recombinant DNA contained in the resultant transformants can be purified e.g., by QIAGEN Plasmid Mini Kit (manufactured by QIAGEN Genomics Inc.).

(Treatment for Inducing Mutation of GDH Gene, Cytb Gene or Cytb-GDH Gene)

A method for obtaining a GDH to be used for the fusion protein according to the present invention starting from a known GDH is as follows. A mutation is introduced into the starting GDH gene and GDHs expressed by various mutant genes can be subjected to selection or screening based on enzymological properties as indices.

A method for obtaining a Cytb to be used for the fusion protein according to the present invention starting from a known Cytb is as follows. A mutation is introduced into the starting Cytb gene and Cytbs expressed by various mutant genes can be subjected to selection or screening based on enzymological properties as indices.

A Cytb-GDH gene can be produced by functionally ligating a known GDH gene or modified GDH gene and a known Cytb gene or modified Cytb gene. A mutation is introduced into the starting Cytb-GDH gene and Cytb-GDH fusion proteins expressed by various mutant genes can be subjected to selection or screening based on enzymological properties as indices.

Mutation of the starting GDH gene, Cytb gene, or Cytb-GDH gene can be performed by any known method depending on the intended form of mutation. That is, methods of bringing a chemical agent serving as a mutagen into contact with and allowing to act on a GDH gene, Cytb gene, or Cytb-GDH gene, or recombinant DNA comprising said gene integrated therein; ultraviolet irradiation methods; genetic engineering techniques; protein engineering methods; or a combination of these can be used extensively.

Examples of the chemical agent serving as the mutagen used in the above mutation treatment include hydroxylamine, N-methyl-N'-nitro-N-nitrosoguanidine, nitrous acid, sulfurous acid, hydrazine, formic acid or 5-bromouracil and the like.

The conditions for allowing a chemical agent to contact and act can be determined depending on the type of chemical agent being used and the like and the conditions are not particularly limited as long as the desire mutation can actually be induced in the GDH gene or Cytb gene. A desired mutation can be induced usually by allowing a chemical agent preferably having a concentration of 0.5 to 12 M to contact and act on (the gene) at a reaction temperature of 20 to 80° C. for 10 minutes or more and preferably 10 to 180 minutes. In the case of ultraviolet irradiation, a mutation can be induced with a routine method as mentioned above (Modern Chemistry, p. 24 to 30, June, 1989).

As a method of employing protein engineering procedures, in general, a method known as a Site-Specific Mutagenesis can be used. Examples thereof include the Kramer method (Nucleic Acids Res., 12, 9441 (1984): Methods Enzymol., 154, 350 (1987): Gene, 37, 73 (1985)), the Eckstein method (Nucleic Acids Res., 13, 8749 (1985): Nucleic Acids Res., 13, 8765 (1985): Nucleic Acids Res, 14, 9679 (1986)) and the Kunkel method (Proc. Natl. Acid. Sci. U.S.A., 82, 488 (1985): Methods Enzymol., 154, 367 (1987)). Examples of a specific method for converting the nucleotide sequence in DNA include methods using a commercially available kit (e.g., Transformer Mutagenesis Kit;

Clonetech, EXOIII/Mung Bean Deletion Kit; manufactured by Stratagene, Quick Change Site Directed Mutagenesis Kit; manufactured by Stratagene).

Further, the method known as the general PCR method (Polymerase Chain Reaction) can be used (Technique, 1, 11 (1989)). Incidentally, apart from the above gene modifying methods, a modified GDH gene or Cytb gene of interest can be directly synthesized using organic synthesis methods or enzyme synthesis methods.

The nucleotide sequence of DNA of the GDH gene, Cytb gene, or Cytb-GDH gene obtained by the above method can be determined or confirmed by using, for example, multi-capillary DNA analysis system CEQ2000 (manufactured by Beckman Coulter, Inc.) and the like.

(Vector and Host Cell Having an Insertion of the Cytb-GDH Gene of the Present Invention)

The Cytb-GDH gene of the present invention obtained as described above can be integrated into a vector such as a bacteriophage, cosmid, or a plasmid used in transformation of prokaryote cells or eukaryote cells using routine methods. Then, a host cell corresponding to each vector can be transformed or transduced using routine methods.

Examples of the prokaryotic host cell that can be used herein include, microorganisms belonging to the genus *Escherichia* such as *Escherichia coli* K-12 strain, *Escherichia coli* BL21 (DE3), *Escherichia coli* JM109, *Escherichia coli* DH5α, *Escherichia coli* W3110, and *Escherichia coli* C600 (all manufactured by Takara Bio Inc.). These microbial cells can be transformed or transduced to obtain host cells having DNA introduced herein (transformants). As a method for introducing a recombinant vector to a host cell, if the host cell is a microorganism belonging to *Escherichia coli*, a method of transferring recombinant DNA in the presence of a calcium ion can be employed. Furthermore, electroporation methods may be used. Moreover, commercially available competent cells (for example, ECOS Competent *Escherichia coli* BL21 (DE3); manufactured by Nippon Gene Co., Ltd.) may be used.

Incidentally, the present inventors have previously confirmed that by truncating the N terminal signal peptide of a natural GDH, the productivity thereof in a microbial host such as *Escherichia coli* can be improved (see, for example, WO 2012/169512). If a microorganism such as *Escherichia coli* is used as the host, then the N terminal signal peptide of the GDH moiety in the fusion protein of the present invention may optionally be truncated.

The N terminal signal peptide of GDH from the genus *Mucor* of SEQ ID NO: 1 is a peptide consisting of amino acids from the 1 st to 20th position of the amino acid sequence of SEQ ID NO: 1. Cleavage occurs between alanine at the 20th position and glutamine at the 21st position. In order to delete the N terminal signal peptide from this polypeptide, a codon encoding alanine at the 20th position or a codon encoding glutamine at the 21st position may be substituted with an initiation codon. The same applies to the positions corresponding to the 20th positions or 21 st positions (SEQ ID NO: 1) of other GDHs having a sequence identity with SEQ ID NO: 1. The nucleotide sequence of the Cytb-GDH gene may be manipulated by genetic engineering so that the amino acid sequence of Cytb is linked to 20th position or 21st position of GDH of the genus *Mucor* of SEQ ID NO: 1.

Examples of the eukaryotic host cell include yeast. Examples of microorganisms classified as yeast include yeasts belonging to the genus *Zygosaccharomyces*, the genus *Saccharomyces*, the genus *Pichia* and the genus *Candida*. The gene insert may contain a marker gene which enables selecting transformed cells. Examples of the marker gene include genes which compensate auxotrophy of a host cell, such as URA3 and TRP1. The gene insert may desirably contain a promoter enabling expression of the gene of the present invention in a host cell or other regulatory sequences (for example, secretory signal sequence, enhancer sequence, terminator sequence, polyadenylation sequence and the like). Specific examples of the promoter include GAL1 promoter and ADH1 promoter. As methods for transforming yeast, known methods such as the method of using lithium acetate (Methods Mol. Cell. Biol., 5, 255-269 (1995)) as well as electroporation (J Microbiol Methods 55 (2003) 481-484) can suitably be used although the transformation method is not limited thereto. Various methods including the spheroplast method and glass bead method can be used for transformation.

Other examples of the eukaryotic host cell include filamentous fungi such as those of the genus *Aspergillus* and the genus *Tricodernma*. The method for preparing a transformant of a filamentous fungus is not particularly limited and includes, for example, a method of inserting a Cytb-GDH gene to a host filamentous fungus with routine methods such that the Cytb-GDH gene is expressed. More specifically, a DNA construct is prepared by inserting a Cytb-GDH gene between an expression inducing promoter and a terminator; and then, a host filamentous fungus is transformed with the DNA construct containing the Cytb-GDH gene to obtain transformants overexpressing the Cytb-GDH gene. In the present specification, a DNA fragment consisting of an expression inducing promoter-Cytb-GDH encoding gene-terminator, and a recombinant vector comprising said DNA fragment, produced to transform a host filamentous fungus, are collectively referred to as DNA constructs.

The method for inserting a gene encoding a Cytb-GDH into a host filamentous fungus such that the gene is expressed is not particularly limited and includes, for example, a method of directly inserting the gene into the chromosome of a host organism by using homologous recombination; and a method of ligating the gene to a plasmid vector and introducing the vector to a host filamentous fungus.

In the method using homologous recombination, a DNA construct is inserted into the genome of the host filamentous fungus by ligating the DNA construct between sequences homologous to the upstream region and downstream region of a recombination site on the chromosome. By overexpressing the gene under control of its own high expression promotor in the host filamentous fungus, a transformant by self-cloning can be obtained. Examples of the high expression promoter include, but are not particularly limited to, the promoter region of TEF1 gene (tef1) serving as a translation elongation factor, the promoter region of α-amylase gene (amy) and the promoter region of an alkaline protease gene (alp).

In the method using a vector, a DNA construct is integrated into a plasmid vector used for transformation of filamentous fungi by routine methods and then the corresponding host filamentous fungus can be transformed (with the plasmid vector) using routine methods.

Such suitable vector-host system is not particularly limited as long as the Cytb-GDH can be produced in the host filamentous fungus and includes, for example, pUC19 and filamentous fungus system, pSTA14 (Mol. Gen. Genet. 218, 99-104, 1989) and filamentous fungus system.

It is preferable to use the DNA construct by introducing the same into the chromosome of a host filamentous fungus. However, as an alternative method, the DNA construct can be integrated into an autonomous replicating vector (Ozeki et al. Biosci. Biotechnol. Biochem. 59, 1133 (1995)). In this manner, the DNA construct can be used without being introduced into the chromosome.

The DNA construct may comprise a marker gene which enables a transformed cell to be selected. Examples of the marker gene include, but are not particularly limited to, genes compensating auxotrophy of a host such as pyrG, niaD, adeA; and drug resistance genes against chemical agents such as pyrithiamine, hygromycin B and oligomycin. Further, the DNA construct preferably comprises a promoter enabling overexpression of the gene encoding the GDH in the host cell, a terminator and other regulatory sequences (for example, enhancer, polyadenylation sequence). Examples of the promoter include, but are not particularly limited to, suitable expression induction promoters and constitutive promoters, such as the tef1 promoter, alp promoter, amy promoter and the like. Examples of the terminator include, but are not particularly limited to, the alp terminator, amy terminator and tef1 terminator and the like.

In the DNA construct, if the DNA fragment containing the gene encoding the Cytb-GDH to be inserted has a sequence having expression regulating function, then an expression regulatory sequence for the gene encoding the Cytb-GDH need not be required. When transformation is carried out by a co-transformation method, the DNA construct need not have a marker gene in some cases.

One embodiment of a DNA construct is, for example, a DNA construct prepared by ligating the tef1 gene promoter, a gene encoding Cytb, a gene encoding a linker peptide which may optionally be present, a gene encoding GDH, the alp gene terminator and the pyrG marker gene to the In-Fusion Cloning Site within the multiple cloning site of pUC19.

As a method for transforming filamentous fungi, methods known to those skilled in the art can appropriately be selected, for example, a protoplast PEG method can be used, in which a protoplast of a host filamentous fungus is prepared, and then, polyethylene glycol and calcium chloride are used (see, for example, Mol. Gen. Genet. 218, 99-104, 1989, JP Patent Publication (Kokai) No. 2007-222055A). As the culture medium for regenerating a transformed filamentous fungus, an appropriate culture medium is used depending on the host filamentous fungus to be used and the transformation marker gene. For example, if *Aspergillus* soya is used as the host filamentous fungus and pyrG gene is used as the transformation marker gene, the transformed filamentous fungus can be regenerated in Czapek-Dox minimal medium (Difco) containing for example, 0.5% agar and 1.2 M sorbitol.

To obtain, for example, the transformed filamentous fungus of the present invention, the promoter of the gene encoding the Cytb-GDH that the host filamentous fungus originally has in the chromosome may be substituted with a high expression promoter such as tef1, by using homologous recombination. In this case, a transformation marker gene such as pyrG is preferably inserted in addition to the high expression promoter. For example, for this purpose, a transformation cassette consisting of an upstream region of a gene encoding Cytb-GDH-transformation marker gene-high expression promoter-whole or part of gene encoding Cytb-GDH, can be used (see, Example 1 and FIG. 1 in JP Patent Publication (Kokai) No. 2011-239681A). In this case, the upstream region of a gene encoding Cytb-GDH and the whole or part of the gene encoding Cytb-GDH are used for homologous recombination. As the whole or part of the gene encoding Cytb-GDH, a region containing the initiation codon up to a midstream region can be used. The length of the region suitable for homologous recombination is preferably 0.5 kb or more.

Whether the transformed filamentous fungus of the present invention was produced or not can be confirmed by culturing the transformed filamentous fungus of the present invention under conditions where Cytb-GDH enzyme activity can be confirmed and then confirming the Cytb-GDH activity in a culture obtained after culturing.

Further, whether the transformed filamentous fungus of the present invention was produced or not can be confirmed by extracting chromosomal DNA from a transformed filamentous fungus, subjecting the chromosomal DNA to PCR using the chromosomal DNA as the template and confirming production of a PCR product that can be amplified if transformation took place.

For example, PCR is carried out by using a forward primer to the nucleotide sequence of the applied promoter in combination with a reverse primer to the nucleotide sequence of the transformation marker gene, and then, whether or not a product having the predicted length is obtained, is confirmed.

(Screening of Host Cell Producing the Cytb-GDH of the Present Invention)

To efficiently screen a transformed filamentous fungus producing the Cytb-GDH of the present invention, the following method, for example, may be used. From a minimal medium containing 0.5% agar and having colonies of host cells (transformants) formed thereon, a colony is picked up, inoculated in a DPY liquid medium (1% (w/v) polypeptone, 2% (w/v) dextrin, 0.5% (w/v) yeast extract, 0.5% (w/v) $KH_2PO_4$, 0.05% (w/v) $MgSO_4.7H_2O$) and cultured for 3 days while shaking. The resultant culture supernatant is mixed with a reaction solution (10 mM phosphate buffer (pH 7.0) containing glucose, DCIP or cytochrome c) having a composition that can develop color or change color if Cytb-GDH acts thereon, and then the degree of color change of purple color from DCIP or reddish brown from cytochrome c is observed. In the case of a Cytb-GDH which requires a mediator such as PMS for transferring electrons, the degree of color change is low in the reaction solution without any mediator; however, in the case of the Cytb-GDH of the present invention having modified electron transfer properties, for example, in the case of Cytb-GDH which can directly transfer electrons, the degree of color change of the reaction solution is high. Utilizing this and by comparing with the degree of color change in the reaction solution containing a strain producing a Cytb-GDH composed of a wild type Cytb and a wild type GDH, transformants which can produce Cytb-GDH having modified electron transfer properties, for example, Cytb-GDH which can directly transfer electrons, can be screened.

To efficiently screen transformed *Escherichia coli* producing the Cytb-GDH of the present invention, for example, the following method may be used. Several sheets of replicas are produced from LB agar medium having colonies of the resultant host cells (transformants) by using sterilized velvet fabric and the like onto new agar media and then the same is cultured. When colonies of the replica agar mediums reach a sufficient size, a membrane impregnated with a lysing agent such as lysozyme is overlaid on the culture medium and allowed to stand at room temperature for about one hour to allow for lysis. Here, the crude enzyme solution of the lysate is adsorbed onto the membrane.

Then, said membrane with the adsorbed crude enzyme solution is allowed to stand at 35° C. for one minute to one hour and a membrane impregnated with a reaction solution (10 mM phosphate buffer (pH 7.0) containing glucose, DCIP or cytochrome c) whose composition is prepared such that if GDH functions, a color changes is overlaid thereon. Then, the degree of a change of purple color from DCIP or reddish brown from cytochrome c is observed. In the case of a Cytb-GDH requiring a mediator such as PMS for transferring electrons, the degree of color-change of colonies is low in a reaction solution without any mediator; however, in the Cytb-GDH of the present invention having modified electron transfer properties, for example, in the case of Cytb-GDH that can directly transfer an electron, the degree of color change of colonies is high. Utilizing this and by comparing the degree of color change to that of a strain producing a Cytb-GDH composed of a wild type Cytb and a wild type GDH, transformants producing a Cytb-GDH having modified electron transfer properties, for example, a Cytb-GDH capable of directly transferring an electron, can be screened.

If necessary, mutation(s) can further be repeatedly introduced to the gene encoding a Cytb-GDH having modified electron transfer properties found in this manner, and further excellently modified Cytb-GDHs and transformants having the capability to produce the same can be obtained.

If necessary, mutagenesis and screening can be performed once or multiple times only for the gene encoding the GDH moiety in the Cytb-GDH, mutagenesis and screening can be performed once or multiple times only for the gene encoding the Cytb moiety in the Cytb-GDH, and then the gene encoding the mutated Cytb and the gene encoding the mutated GDH can be used to obtain a modified Cytb-GDH gene, and a transformant producing the same can be obtained.

(High Throughput Screening)

A Cytb-GDH can further be subjected to high throughput screening in order to obtain a functional Cytb-GDH mutant. For example, a library of transformed strains or transduced strains comprising mutated Cytb-GDH genes can be prepared and then the library may be subjected to high throughput screening based on a microtiter plate or to ultrahigh-throughput screening based on droplet microfluids. As an example, a combinatorial library of mutant genes encoding variants is constructed and then a large population of modified GDHs is screened by using, e.g., phage display (for example, Chem. Rev. 105 (11): 4056-72, 2005); yeast display (for example, Comb Chem High Throughput Screen. 2008; 11 (2): 127-34); bacterial display (for example, Curr Opin Struct Biol 17: 474-80, 2007) and the like. Also see, Agresti, et al., "Ultrahigh-throughput screening in drop-based microfluidics for directed evolution" Proceedings of the National Academy of Sciences 107 (9): 4004-4009 (March, 2010). The contents of this document on the ultra-high-throughput screening method that may be used for screening Cytb-GDH variants is incorporated herein by reference. For example, a library can be constructed by an error-prone PCR method. Further, saturation mutagenesis may be used to introduce mutations into the region(s) or position(s) described herein or the corresponding region(s) or position(s) thereto as the target to construct a library. Using such library, appropriate cells such as electrocompetent EBY-100 cells, can be transformed and about 10 to the power of seven mutants can be obtained. Yeast cells transformed with said library can subsequently be subjected to cell sorting. A polydimethoxysiloxane (PDMS) microfluidic device prepared by a standard soft lithography method may be used. Monodispersed droplets can be formed using a flow focus device. Formed droplets containing individual mutants can be subjected to an appropriate sorting device. When screening cells, the presence or absence of GDH activity can be utilized. For this purpose, a reaction solution having a composition capable of developing color or undergoing a color change if the Cytb-GDH functions may, for example, be used. For example, in the case of using cytochrome c, absorbance at 550 nm may be measured using a 96 well plate, a 192 well plate, a 384 well plate or a 9600 well plate and a plate reader. Mutation and screening can be repeated multiple times.

(Production of Cytb-GDH of the Present Invention)

The Cytb-GDH of the present invention may be produced by culturing a host cell producing the Cytb-GDH of the present invention and obtained as mentioned above, expressing the Cytb-GDH gene contained in said host cell, and then isolating a Cytb-GDH protein from the culture.

Both synthetic medium and natural medium can be used, as long as it is a culture medium usually used for culturing filamentous fungi, i.e., containing a carbon source, a nitrogen source, inorganic substances and other nutrients in appropriate ratios. As the culture medium for culturing the above microbial host cell, a culture medium prepared by adding, one or more nitrogen source such as yeast extract, tryptone, peptone, meat extract, corn steep liquor or soy or wheat bran steep liquor, one or more inorganic salts such as sodium chloride, primary potassium phosphate, secondary phosphate, magnesium sulfate, magnesium chloride, ferric chloride, ferric sulfate or manganese sulfate, and if necessary, further adding a sugar source, and vitamins and the like where appropriate, is used.

For culture conditions, culture conditions for filamentous fungi widely known to those skilled in the art can be employed and, for example, the initial pH of a culture medium can be adjusted to 5 to 10; for example, the culture temperature can be 20 to 40° C., the culture time can be from several hours to several days, preferably 1 to 7 days, and more preferably 2 to 5 days. The culture means is not particularly limited and although aeration stirring deep culture, shaking culture and static culture and the like can be employed, it is preferable that culture is performed in conditions where sufficient dissolved oxygen is present. Examples of culture medium and culture conditions for culturing *Aspergillus* microorganism include a shaking culture using a DPY culture medium performed at 30° C. and 160 rpm for 3 to 5 days, described later in the Examples. When culturing a microbial host cell, culturing can be carried out at a culture temperature of 10 to 42° C., preferably about 25° C. for 4 hours to 24 hours, further preferably at a culture temperature of about 25° C. for 4 to 8 hours with aerated and agitated deep culture, shaking culture or stationary culture.

After completion of culture, the Cytb-GDH of the present invention is recovered from the culture. This can be carried out by known enzyme sampling means used routinely. For example, the supernatant of the culture is collected, or a fungus body is subjected to, a routine treatment such as ultrasonication disruption treatment or grinding treatment; or the enzyme of the invention is extracted using a lytic enzyme such as lysozyme or yatarase. Alternatively, the fungus body is shaken or allowed to stand in the presence of toluene and the like to cause cell lysis and in this manner, the enzyme of the invention can be discharged out of the fungus body. Subsequently, the lysis solution is filtered or centrifuged and solid matter is removed and, if necessary, nucleic acid is removed by streptomycin sulfate, protamine sulfate, or manganese sulfate and the like. To the resultant, ammonium sulfate, an alcohol and/or acetone is(are) added, the mixture is fractionated and a precipitate is collected to obtain a crude enzyme of the Cytb-GDH of the present invention.

The crude enzyme of the Cytb-GDH of the present invention can be further purified by any means known in the art. A purified enzyme preparation can be obtained by a method appropriately selected from, for example, a gel filtration method using Sephadex, ultrogel or bio gel; an adsorption elution method using an ion exchanger; an electrophoretic method using, e.g., polyacrylamide gel; an adsorption elution method using hydroxyapatite; a sedimentation method such as a sucrose density gradient centrifugation method; an affinity chromatography method; and a fractionation method using, e.g., a molecular sieve membrane or a hollow fiber membrane, or by using these methods in combination. In this manner, a purified Cytb-GDH enzyme preparation of the present invention can be obtained.

(Measurement of Activity of the Cytb-GDH of the Present Invention)

The GDH moiety in the Cytb-GDH of the present invention catalyzes the reaction of oxidizing a hydroxyl group of a glucose to generate glucono-5-lactone. For convenience, this may be referred to herein as GDH activity.

The GDH activity of the Cytb-GDH of the present invention can be measured based on This principle of action and by using, for example, the following measurement system, which employs phenazine methosulfate (PMS) and 2,6-dichloroindophenol (DCIP) as electron acceptors.

D-glucose+*PMS*(oxidized form)→D-glucono-δ-lactone+*PMS*(reduced form)   (Reaction 1)

*PMS*(reduced form)+*DCIP*(oxidized form)→*PMS*(oxidized form)+*DCIP*(reduced form)   (Reaction 2)

More specifically, first, in (Reaction 1), as oxidation of D-glucose proceeds, PMS (reduced form) is generated. Subsequently, as (Reaction 2) proceeds, oxidation of PMS (reduced form) proceeds and with this, DCIP is reduced. The degree of disappearance of "DCIP (oxidized form)" is detected as a change in absorbance at a wavelength of 600 nm. Base on the change in absorbance, the enzyme activity can be determined.

More specifically, the activity of GDH can be measured by the following procedure. A 100 mM phosphate buffer (pH7.0) (2.05 mL), a 1M D-glucose solution (0.6 mL) and a 2 mM DCIP solution (0.15 mL) are mixed and the solution mixture is kept warm at 37° C. for 5 minutes. To the solution mixture, a 15 mM PMS solution (0.1 mL) and an enzyme sample solution (0.1 mL) are added to initiate a reaction. Absorbance is measured at the initiation of the reaction and over time. The decrease of absorbance at 600 nm per minute as the enzymatic reaction proceeds (ΔA600) is obtained and GDH activity is computed with the following formula. Here, 1 U of GDH activity is defined as the amount of enzyme required for reducing 1 μmol of DCIP at 37° C. in the presence of D-glucose (concentration 200 mM) per minute.

$$GDH \text{ activity (U/mL)} = \frac{-(\Delta A600 - \Delta A600_{blank}) \times 3.0 \times df}{16.3 \times 0.1 \times 1.0}$$   [Formula 1]

Note that, in the formula, the numerical value 3.0 represents the amount (mL) of a liquid (reaction reagent+enzyme reagent), the numerical value 16.3 represents the millimole molecular extinction coefficient (cm²/μmol) under this activity measurement condition; the numerical value 0.1 represents the amount of enzyme solution (mL), the numerical value 1.0 represents the optical path length (cm) of a cell, ΔA600 blank represents the decrease in the absorbance at 600 nm per minute of 100 mM phosphate buffer (pH7.0), in the case where the buffer is added instead of the enzyme sample solution and the reaction is initiated; and df represents the dilution factor.

(Method for Measuring Glucose by Using the Cytb-GDH of the Present Invention)

In one embodiment, the present invention provides a glucose assay kit comprising the Cytb-GDH of the present invention. By using this kit, glucose (blood glucose level) in the blood can be measured using the Cytb-GDH of the present invention. The measurement may be carried out continuously.

The glucose assay kit of the present invention comprises the Cytb-GDH of the present invention at an amount sufficient for at least one assay. Typically, the glucose assay kit of the present invention comprises, other than the Cytb-GDH of the present invention, a buffer solution required for the assay, a glucose standard solution for preparing a calibration curve and instructions. In one embodiment, the glucose assay kit of the present invention, for example, the glucose assay kit for SMBG, CGM or FGM, comprises a free-form mediator. In one embodiment, the glucose assay kit of the present invention, for example, the glucose assay kit for SMBG, CGM or FGM need not include a free-form mediator. The Cytb-GDH of the present invention can be provided in various forms, for example, as a freeze dried reagent, a reagent immobilized onto beads or an electrode surface, or a solution stored in an appropriate preservation solution.

Measurement of glucose concentration in the case of a colorimetric glucose assay kit can, for example, be carried out as follows. In the reaction layer (vessel) of the glucose assay kit, a liquid or solid state composition comprising Cytb-GDH and at least one agent selected from the group consisting of N-(2-acetamide)imide diacetate (ADA), bis(2-hydroxyethyl)iminotris(hydroxy methyl) methane (Bis-Tris), sodium carbonate and imidazole as a reaction accelerator are placed. If necessary, a pH buffer and a coloring reagent (discoloration reagent) are added. To this, a sample containing glucose is added and allowed to react for a predetermined time. During this time period, a dye polymerized and generated by directly receiving an electron from the Cytb-GDH during the reaction or the absorbance corresponding to the maximum absorption wavelength of the dye reduced is monitored. The glucose concentration in the sample can be calculated from the rate of change of absorbance per time if a rate method is used or from the rate of change of absorbance up to the time point where glucose in the sample is completely oxidized if an endpoint method is employed, based on a calibration curve prepared in advance by using a standard-concentration glucose solution.

Examples of a coloring reagent (discoloration reagent) to be used in this method include 2,6-dichloroindophenol (DCIP) which can be added as an electron acceptor and the amount of glucose can be determined by monitoring the decrease in absorbance at 600 nm. Further, glucose concentration can be calculated by adding nitrotetrazolium blue (NTB) as a coloring reagent and measuring the absorbance at 570 nm to determine the amount of generated diformnnazan. Incidentally, needless to say, the coloring reagent (discoloration reagent) to be used is not limited to these.

(Glucose Sensor Containing the Cytb-GDH of the Present Invention)

In one embodiment, the present invention provides a glucose sensor using the Cytb-GDH of the present invention. As an electrode, e.g., a carbon electrode, a gold electrode or a platinum electrode can be used and the Cytb-GDH enzyme of the present invention can be applied or immobilized onto the electrode. Examples of the immobilization method include a method using a cross-linking agent, a method of embedding in a polymer matrix, a method of coating (covering) with a dialysis membrane, methods of using a photo-crosslinkable polymer, conductive polymer or redox polymer and the like, and the Cytb-GDH may be immobilized in a polymer or may be immobilized by adsorption on an electrode, or these methods may be used in combination. Typically, the Cytb-GDH of the present invention is immobilized onto a carbon electrode by using glutaraldehyde and then treated with a reagent having an amine group to block glutaraldehyde.

The Cytb-GDH of the present invention can be applied to various electrochemical measurement methods by using, a potentiostat, a galvanostat and the like. Examples of the electrochemical measurement method include, various methods such as amperometry, voltammetry, potentiometry and coulometry and the like. For example, by using the amperometric method and measuring the current when glucose is reduced, it is possible to calculate the glucose concentration of a sample. The voltage to be applied varies depending on the conditions and setting of the apparatus and can be set to be, for example, −1000 mV to +1000 mV (vs. Ag/AgCl).

Glucose concentration can be measured as follows. To a constant-temperature cell, a buffer solution is added and the temperature is held constant. An electrode to which the Cytb-GDH of the present invention is immobilized is used as the working electrode, and a counter electrode (for example, platinum electrode) and a reference electrode (for example, Ag/AgCl electrode) are used. A constant voltage is applied to the carbon electrode and when the current becomes stationary, a sample containing glucose is added and the increase of current is measured. Based on a calibration curve prepared by using a standard-concentration glucose solution, the glucose concentration of the sample can be calculated.

As a specific example, 0.2 U to 1000 U, more preferably, 0.5 U to 700 U of the Cytb-GDH of the present invention is immobilized to a glassy carbon (GC) electrode and the response current value against the glucose concentration is measured. Further, 0.5 µg to 5000 µg, more preferably, 1 µg to 2000 µg of the Cytb-GDH of the present invention is immobilized to a GC electrode, and the response current value against the glucose concentration is measured. By measuring specific activity of GDH or Cytb-GDH, the activity value can be calculated from the amount of protein. To an electrolytic cell is added 10.0 ml of 100 mM potassium phosphate buffer (pH 7.0). A GC electrode is connected to a potentiostat, BAS100B/W (manufactured by BAS), and the solution is stirred at 37° C. and then, a voltage of +500 mV is applied to a silver/silver chloride reference electrode. To this system, a 1 M D-glucose solution is added so as to obtain a final concentration of 0.1, 0.2, 0.5, 1, 3, 5, 10, 20, 30, 40, 50 mM and for each addition, the current value at a constant state is measured. These current values are plotted relative to the corresponding glucose concentrations already known (0.1, 0.2, 0.5, 1, 3, 5, 10, 20, 30, 40, 50 mM) to obtain a calibration curve. At this time, current densities ($nA/cm^2$) normalized by the working electrode area may be plotted. In this manner, the amount of glucose can be determined by an enzyme-immobilized electrode using the glucose dehydrogenase of the present invention.

Further, a printed electrode can also be used for electrochemical measurement. This enables reducing the amount of solution required for measurement. In this case, it is preferable that the electrode is formed on an insulating substrate. More specifically, it is desirable to form the electrode on a substrate by a printing technique such as photolithographic technology, screen printing, gravure printing and flexographic printing. Exemplary materials for the insulating substrate include, silicon, glass, ceramic, polyvinyl chloride, polyethylene, polypropylene and polyester and it is more preferable to use a material having high resistance to various solvents and chemical agents.

In one embodiment, a Cytb-GDH solution comprising 0.2 U to 1000 U, preferably, 0.5 U to 700 U of the Cytb-GDH of the present invention is applied onto a printed electrode. The applied Cytb-GDH may optionally be dried in air. Then, a glucose solution is added, a voltage is applied, and the response current value to the glucose concentration is measured. In another embodiment, a solution containing the Cytb-GDH of the present invention and glucose can be added to a printed electrode and a voltage can be applied, and the response current can be measured. In these embodiments, the activity value can be calculated in a similar manner from the amount of protein by measuring the specific activity of GDH or Cytb-GDH. The Cytb-GDH and the glucose solution are contacted on the printed electrode, and a voltage is applied (for example, +500 mV or +300 mV to a silver/silver chloride reference electrode). Glucose can be added by adding a 1 M D-glucose solution so as to obtain a final concentration of 0.1, 0.2, 0.5, 1, 3, 5, 10, 20, 30, 40, or 50 mM. For each of the added concentrations, the current value, for example, 40 seconds after initiation of measurement by applying voltage is measured. These current values are plotted relative to the corresponding glucose concentrations already known (0.1, 0.2, 0.5, 1, 3, 5, 10, 20, 30, 40, 50 mM) to produce a calibration curve. At this time, current densities ($nA/cm^2$) normalized by the working electrode area may be plotted. In this manner, the amount of glucose can be determined by an enzyme-immobilized electrode using the glucose dehydrogenase of the present invention.

Free-Form Mediator

In one embodiment, regarding the measuring method, kit, apparatus and sensor of the present invention, a free-form mediator (also referred to as an artificial electron mediator, an artificial electron acceptor, an electron mediator) can be used. The free-form mediator is not particularly limited as long as it can receive an electron from the Cytb-GDH of the present invention. Examples of the free-form mediator include free-forms of quinones, phenazines, viologens, cytochromes (for example, Cytb, Cytc), phenoxazines, phenothiazines, a ferricyanide, for example potassium ferricyanide, ferredoxins, ferrocene, an osmium complex, and derivatives thereof. Examples of the phenazine compound include, but are not limited to, for example PMS, and methoxy PMS. Incidentally, the phrase "free-form mediator" as used in the present specification is merely a phrase for convenience to contrast with the fused Cytb comprised within the Cytb-GDH. So long as a mediator is neither fused nor linked to the GDH, then even if the mediator is embedded in a membrane or immobilized to an electrode, such mediator is encompassed by the phrase "free-form mediator" as used in the present specification. Further, a free-form mediator may also be referred to as a non-fused type mediator herein.

The Cytb-GDH of the present invention comprises a Cytb domain, and has modified electron transfer properties. In one embodiment, since the Cytb-GDH of the present invention comprises a Cytb domain, electron transfer from the Cytb-GDH fusion protein to another electron acceptor substance is facilitated. In one embodiment, electron transfer from the Cytb-GDH fusion protein of the present invention to another electron acceptor substance can occur in the presence of a free-form mediator reduced in concentration, compared to the case of single GDH enzyme. In one embodiment, electron transfer from the Cytb-GDH enzyme of the present invention to another electron acceptor substance can occur even in the absence of a free-form mediator. In one embodiment, the Cytb-GDH fusion protein of the present invention is capable of directly transferring an electron from the fusion protein to an electrode.

In one embodiment, electron transfer from the Cytb-GDH fusion protein of the present invention to another electron acceptor substance is possible even for certain types of mediators for which electron transfer was difficult when using a single GDH enzyme not linked to a Cytb. For example, a ruthenium compound does not produce a glucose concentration-dependent response current in a glucose measurement using a conventional glucose dehydrogenase unless the ruthenium compound co-exists with a second mediator such as mPMS in the measurement (see, JP Patent Publication (KOKAI) No. 2013-083634A). The Cytb-GDH of the present invention having modified electron transfer properties can be used for glucose measurement in combination with a ruthenium compound without a second mediator such as mPMS. As another example, the Cytb-GDH of the present invention having modified electron transfer properties can be used in glucose measurement without using a second mediator such as mPMS.

The Cytb-GDH of the present invention having modified electron transfer properties can be used in the same applications as those of conventional GDHs. The Cytb-GDH of the present invention can be used for measuring glucose concentration in a sample and this is useful for diagnosing diabetes and self-monitoring a blood glucose level. The Cytb-GDH of the present invention can be used as an enzyme electrode and this can be applied in various electrochemical measurements. Further, the Cytb-GDH of the present invention can be used as an enzyme sensor. Further, the Cytb-GDH of the present invention can be used in a glucose measurement kit as well as a glucose sensor. These are merely examples and use of the modified Cytb-GDH of the present invention is not limited thereto.

The present invention will be further illustrated by way of the following Examples. However, the technical scope of the present invention is not limited by these examples in any way.

EXAMPLES

Example 1

1. Introduction of the GDH Gene from the Genus *Mucor* Gene to a Host and Confirmation of GDH Activity To the gene encoding a GDH from the genus *Mucor* (MpGDH, SEQ ID NO: 1), individual mutations of N66Y/N68G/C88A/Q233R/T387C/E554D/L557V/S559K were introduced to obtain a gene encoding a modified GDH (also referred to as MpGDH-M1 herein). The amino acid sequence of MpGDH-M1 is shown in SEQ ID NO: 10. The nucleotide sequence of the gene is shown in SEQ ID NO: 11. The target MpGDH-M1 gene was inserted into the multiple cloning site of plasmid pUC19 with routine methods to obtain a DNA construct. More specifically, as pUC19, the pUC19 linearized Vector provided with the In-Fusion HD Cloning Kit (Clontech) was used. To the In-Fusion Cloning Site present in the multiple cloning site of pUC19, the MpGDH-M1 gene was ligated by using the In-Fusion HD Cloning Kit mentioned above according to the protocol attached to the kit to obtain a plasmid construct (pUC19-MpGDH-M1).

SEQ ID NO: 12 is the amino acid sequence of the Cytb contained the cellobiose dehydrogenase from *Myriococcum thermophilum* (also referred to as MtCytb herein) (WO 2010/097462). A gene encoding the amino acid sequence of SEQ ID NO: 12 (SEQ ID NO: 13) and a gene encoding a linker sequence of SEQ ID NO: 23 (SEQ ID NO: 24) were obtained by conventional methods of total synthesis of cDNAs by totally synthesizing the gene fragments with PCR. The full length amino acid sequences predicted from the cloned gene sequences were confirmed to match the linker sequence and the sequence of MtCytb in FIG. 1. Subsequently, by using In-Fusion HD Cloning Kit with synthetic oligonucleotides of SEQ ID NOs: 45 to 48, the sequence of MtCytb and the linker sequence of SEQ ID NO: 23 were inserted using pUC19-MpGDH-M1 as the template and *Escherichia coli* JM109 was transformed and this was inoculated on a LB-amp agar medium. The colonies that grew were inoculated on 2.5 ml of LB-amp medium [1% (W/V) bactotrypton, 0.5% (W/V) peptone, 0.5% (W/V) NaCl, 50 µg/ml Ampicillin] and subjected to shaking culture at 37° C. for 20 hours to obtain a culture. The culture was centrifuged at 7,000 rpm for 5 minutes and a bacterial body was collected. Then, from the bacterial body, the recombinant plasmid was extracted and purified with QIAGEN tip-100 (manufactured by QIAGEN) to obtain 2.5 µg of DNA. The nucleotide sequence (SEQ ID NO: 34) of DNA encoding MtCytb-MpGDH-M1 (SEQ ID NO: 33) in the plasmid was sequenced using the multicapillary DNA analysis system of Applied Biosystems 3130×1 genetic analyzer (manufactured by Life Technologies) and as a result, the plasmid for the construct MtCytb-MpGDH-M1, which is a cytochrome fusion product, was obtained (pUC19-MtCytb-MpGDH-M1). In doing so, the signal peptide of 1 to 20th positions in the MpGDH-M1 was deleted.

Next, SEQ ID NO: 14 is the amino acid sequence of the Cytb contained in the cellobiose dehydrogenase from *Corynascud thermophilus* (also referred to as CtCytb herein) (WO 2010/097462). A gene encoding the amino acid sequence of SEQ ID NO: 14 (SEQ ID NO: 15) and a gene encoding a linker sequence of SEQ ID NO: 25 (SEQ ID NO: 26) were obtained by conventional methods of total synthesis of cDNAs by totally synthesizing the gene fragments with PCR. Based on the method above by using In-Fusion HD Cloning Kit with synthetic oligonucleotides of SEQ ID NOs: 49 to 52, the sequence of CtCytb and the linker sequence as shown in SEQ ID NO: 25 were inserted using pUC19-MpGDH-M1 as the template. As a result, the plasmid for the construct CtCytb-MpGDH-M1 (SEQ ID NO: 35), which is a cytochrome fusion product, was obtained (pUCI 9-CtCytb-MpGDH-M1).

Next, SEQ ID NO: 16 is the amino acid sequence of the Cytb contained in the cellobiose dehydrogenase from *Aspergillus sojae* (also referred to as AsCytb herein). The gene encoding the amino acid sequence of SEQ ID NO: 16 (SEQ ID NO: 17) and the gene encoding the linker sequence of SEQ ID NO: 27 (SEQ ID NO: 28) were obtained by conventional methods of total synthesis of cDNAs by totally synthesizing the gene fragments with PCR. Based on the method above by using In-Fusion HD Cloning Kit with synthetic oligonucleotides of SEQ ID NOs: 53 to 56, the sequence of AsCytb and the linker sequence as shown in SEQ ID NO: 27 were inserted using pUC19-MpGDH-M1 as the template. As a result, the plasmid for the construct AsCytb-L1-MpGDH-M1 (SEQ ID NO: 37), which is a cytochrome fusion product, was obtained (pUC19-AsCytb-L1-MpGDH-M1).

Further, by using In-Fusion HD Cloning Kit with synthetic oligonucleotides of SEQ ID NOs: 57 to 60, the sequence of AsCytb and the linker sequence as shown in SEQ ID NO: 27 were inserted into pUC19-AsCytb-MpGDH-M and as a result, the plasmid for the construct AsCytbx2-MpGDH-M1 (SEQ ID NO: 39), in which two sets of the AsCytb and linker sequence are linked, was obtained (pUC19-AsCytbx2-MpGDH-M1).

Further, using the resultant recombinant plasmid pUC19-AsCytb-L1-MpGDH-M1 DNA as the template and the synthetic oligonucleotides of SEQ ID NOs: 61 and 62 and KOD-Plus-(manufactured by Toyobo Co., Ltd.), PCR was performed under the following conditions.

That is, 5 μl of 10×KOD-Plus-buffer solution, 5 μl of a dNTP mixture solution prepared such that each of the dNTPs is contained in a concentration of 2 mM, 2 μl of 25 mM $MgSO_4$ solution, 50 ng of pUC19-AsCytb-L1-MpGDH-M1 DNA as the template, 15 pmol each of the synthetic oligonucleotides mentioned above and 1 unit of KOD-Plus— were mixed and then sterile water was added up to a total amount of 50 μl. The prepared reaction solution was subjected to a thermal cycler (manufactured by Eppendorf) in which incubation was performed at 94° C. for 2 minutes, and then, a cycle consisting of a reaction at "94° C. for 15 seconds", a reaction at "50° C. for 30 seconds" and a reaction at "68° C. for 8 minutes" was repeated 30 times.

An aliquot was taken from the reaction solution and electrophoresed on a 1.0% agarose gel to confirm that a DNA fragment of about 8,000 bp in size was specifically amplified. The DNA fragment thus obtained was treated with restriction enzyme DpnI (manufactured by NEW ENGLAND BIOLABS) to cleave the residual template DNA. Mixed together were 2 μl of the DpnI-treated PCR product, 7 μl of sterile water, 5 μl of Ligation high (manufactured by Toyobo Co., Ltd.), and 1 μl of T4 Polynucleotide Kinase (5 U/μl, manufactured by Toyobo Co., Ltd.), and reacted at 16° C. for 1 hour. *Escherichia coli* JM109 was transformed with an aliquot of the reaction solution (approximately 10 μl) and inoculated on a LB-amp agar medium. The colonies that grew were inoculated on a LB-amp medium and subjected to shaking culture, and plasmid DNA was isolated by using the method above. The nucleotide sequence of DNA encoding Cytb-GDH in the plasmid was sequenced using the multicapillary DNA analysis system of Applied Biosystems 3130×1 genetic analyzer (manufactured by Life Technologies). As a result, the plasmid for the construct Ascytb-L2-MPGDH-M1 (SEQ ID NO: 41), with a linker length shorter than that of pUC19-Ascytb-L1-MpGDH-M1 shortened by 9 amino acids, was obtained (pUC19-Ascytb-L2-MpGDH-M1).

Next, based on methods similar to the above and by using In-Fusion HD Cloning Kit with the synthetic oligonucleotides of SEQ ID NOs: 63 to 66, the sequence of CtCytb and the linker sequence as shown in SEQ ID NO: 31 were inserted using pUC19-MpGDH-M1 as the template and as a result the plasmid for the construct MpGDH-M1-CtCytb, in which cytochrome was fused to the C terminus of MpGDH, was obtained (pUC19-MpGDH-M1-CtCytb). In doing so, the signal peptide at 1 to 23rd positions in the CtCytb was deleted.

Next, based on methods similar to the above and by using In-Fusion HD Cloning Kit with the synthetic oligonucleotides of SEQ ID NOs: 126 to 129, the sequence of HiCytb and the linker sequence as shown in SEQ ID NO: 31 were inserted using pUC19-CtCytb-MpGDH-M1 as the template and as a result the plasmid for the construct HiCytb-MpGDH-M1, in which cytochrome was fused to the N terminus of MpGDH, was obtained (pUC19-HiCytb-MpGDH-M 1).

These genes were expressed in *Aspergillus sojae* and their GDH activities were evaluated.

Double-joint PCR (Fungal Genetics and Biology, Vol. 41, p973-981, 2004) was carried out to construct a cassette consisting of 5' arm region—PyrG gene (uracil auxotrophic marker)—TEF1 promoter gene—flavin-binding type GDH gene (SEQ ID NO: 2)-3' arm region. The cassette was used for transformation of *Aspergillus soya* NBRC4239-derived pyrG disrupted strain (strain deficient in 48 bp upstream, 896 bp of code region, 240 bp downstream of the pyrG gene). To 100 ml of polypeptone dextrin liquid medium containing 20 mM uridine and placed in a 500 ml Erlenmeyer flask, conidia of the pyrG disrupted strain from *Aspergillus soya* NBRC4239 were inoculated and subjected to shaking culture at 30° C. for about 20 hours, and then, fungus bodies were collected. A protoplast was prepared from the fungus bodies collected. Using the resultant protoplast and 20 μg of DNA construct comprising the insert target gene, transformation was carried out using the protoplast PEG method. Then, incubation was carried out using Czapek-Dox minimal medium (Difco; pH6) containing 0.5% (w/v) agar and 1.2 M sorbitol at 30° C. for 5 days or more to obtain transformed *Aspergillus* soya having colony forming ability. In the same manner, a cassette consisting of 5' arm region—PyrG gene (uracil auxotrophic marker)—TEF1 promoter gene—cytochrome-fused flavin-binding type GDH gene-3' arm region was constructed using each of pUC19-MtCytb-MpGDH-M1, pUC19-CtCytb-MpGDH-M1, pUC19-AsCytb-L1-MpGDH-M1, pUC19-AsCytbx2-MpGDH-M1, pUC19-AsCytb-L2-MpGDH-M1, pUC19-MpGDH-M1-CtCytb, and HiCytb-MpGDH-M1, to obtain transformed *Aspergillus soya*.

The resultant transformed *Aspergillus soya* is capable of growing on uridine-free medium due to introduction of the pyrG gene which complements uridine auxotrophy, thereby enabling selection of strains having the target gene introduced therein. Of the resultant strains, a transformant of interest was confirmed with PCR and selected.

Each GDH was produced using transformants of *Aspergillus soya*, transformed with a gene of MpGDH-M1 or MtCytb-MpGDH-M1, CtCytb-MpGDH-M1, AsCytb-L1-MpGDH-M1, AsCytbx2-MpGDH-M1, AsCytb-L2-MpGDH-M1, MpGDH-M1-CtCytb, or HiCytb-MpGDH-M 1.

To 40 ml of DPY liquid medium (1% (w/v) polypeptone, 2% (w/v) dextrin, 0.5% (w/v) yeast extract, 0.5% (w/v) $KH_2PO_4$, 0.05% (w/v) $MgSO_4.7H_2O$; pH not adjusted) placed in a 200 ml-Erlenmeyer flask, conidia of each strain were inoculated and subjected to shaking culture at 160 rpm at 30° C. for 4 days. Then, after culturing, the fungus body was filtered from the culture. The resultant supernatant fraction was concentrated using Amicon Ultra-15, 30K NMWL (manufactured by Millipore) up to 10 mL and applied to HiLoad 26/60 Superdex 200 pg (manufactured by GE healthcare) equilibrated with a 20 mM potassium phosphate buffer (pH6.5) containing 150 mM NaCl and eluted with the same buffer. The fraction exhibiting GDH activity and confirmed by SDS-PAGE analysis to have the target molecular weight was collected to obtain purified products of MpGDH-M1, or MtCytb-MpGDH-M1, CtCytb-MpGDH-M1, AsCytb-L1-MpGDH-M1, AsCytbx2-MpGDH-M1, AsCytb-L2-MpGDH-M1, MpGDH-M1-CtCytb, and HiCytb-MpGDH-M1.

Chronoamperometry

Using the purified enzyme of MpGDH-M1, or MtCytb-MpGDH-M1, CtCytb-MpGDH-M1, AsCytb-L1-MpGDH-M1, AsCytbx2-MpGDH-M1, AsCytb-L2-MpGDH-M1, or MpGDH-M1-CtCytb, chronoamperometry with printed electrode measurement was carried. More specifically, on a DEP Chip electrode (attached with a circular carbon dam ring; manufactured by BioDevice Technology) having a glassy carbon working electrode and a silver-silver chloride reference electrode printed thereon, a solution in which a phosphate buffer (pH7.0) having a final concentration of about 100 mM and 130 µg purified enzyme MpGDH-M1 solution, or 80 µg purified enzyme MtCytb-MpGDH-M1 solution, 80 µg purified enzyme CtCytb-MpGDH-M1 solution, 80 µg purified enzyme AsCytb-L1-MpGDH-M1 solution, 80 µg purified enzyme AsCytbx2-MpGDH-M1 solution, 80 µg purified enzyme AsCytb-L2-MpGDH-M1 solution, or 80 µg purified enzyme MpGDH-M1-CtCytb solution were dissolved in 10 µL was placed. Then, the DEP Chip electrode was connected to Automatic Polarization System HSV-100 (manufactured by HOKUTO DENKO CORPORATION) by using a DEP Chip specific connector. Then, a voltage of +300 mV or +500 mV (vs. Ag/AgCl) was applied and a 5 µL solution of 100 mM glucose was placed on the electrode to carry out the reaction and a current value was measured for 40 seconds.

Figure 4:
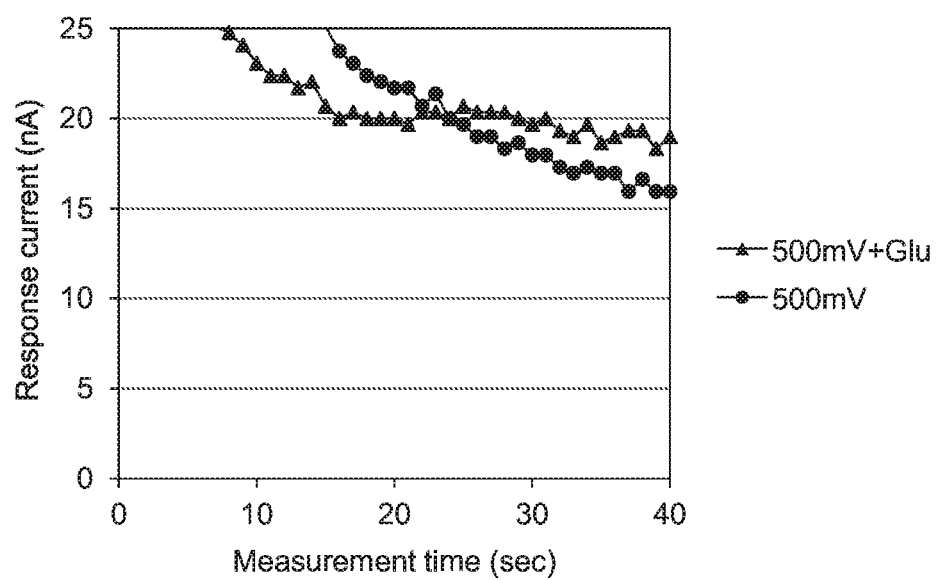

The results are shown in FIGS. 4 to 10. FIG. 4 shows the chronoamperometric measurement results of MpGDH-M1 enzyme having no Cytb domain when a voltage of +500 mV (vs. Ag/AgCl) was applied. The response current 40 seconds after initiation of measurement in the presence of glucose was 19 nA, and 16 nA in the absence of glucose. The difference between the former and the latter was 3 nA, and thus no significant difference was observed for the response current between the presence and absence of glucose. Similarly, as a result of chronoamperometric measurement of the MpGDH-M1 enzyme having no Cytb domain by applying a voltage of +300 mV (vs. Ag/AgCl) thereto, and from the response current 40 seconds after the initiation of measurement in the presence of glucose, the difference from the response current in absence of glucose was 4 nA, and thus no significant difference was observed for the response current between the presence and absence of glucose.

Figure 5:
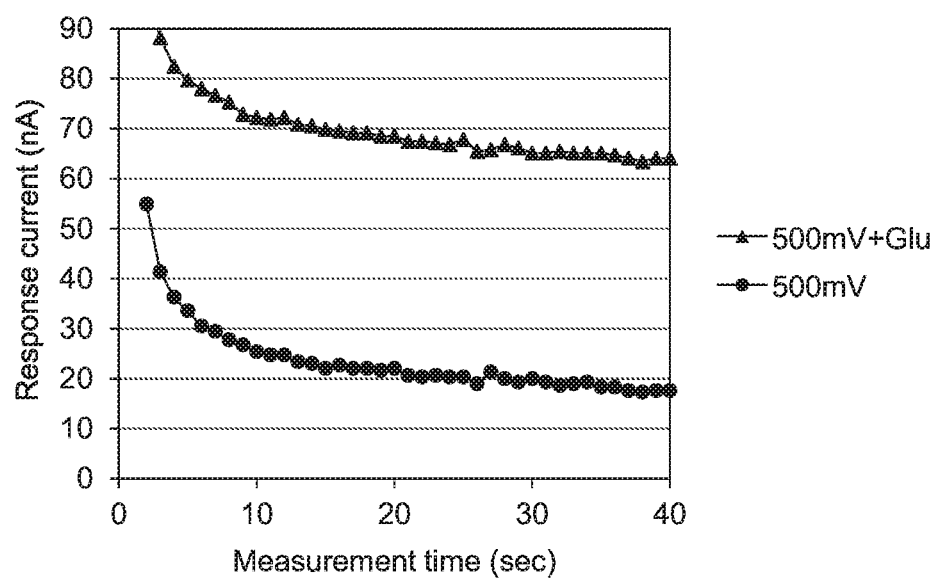
FIG. 5 shows chronoamperometry measurement results of MtCytb-MpGDH-M1.

FIG. 5 shows the chronoamperometric measurement results of MtCytb-MpGDH-M1 when a voltage of +500 mV (vs. Ag/AgCl) was applied. The response current 40 seconds after initiation of measurement in the presence of glucose was 64 nA, and 18 nA in the absence of glucose. The difference between the former and the latter was 46 nA, and thus a significantly high response current was observed when glucose was added. Even at an applied voltage of +300 mV (vs. Ag/AgCl), a response current as high as 30 nA was shown 40 seconds after initiation of measurement when glucose was added. The response current was 18 nA in the absence of glucose. The difference between the former and the latter was 12 nA, and thus a significantly high response current was observed when glucose was added.

Figure 6:
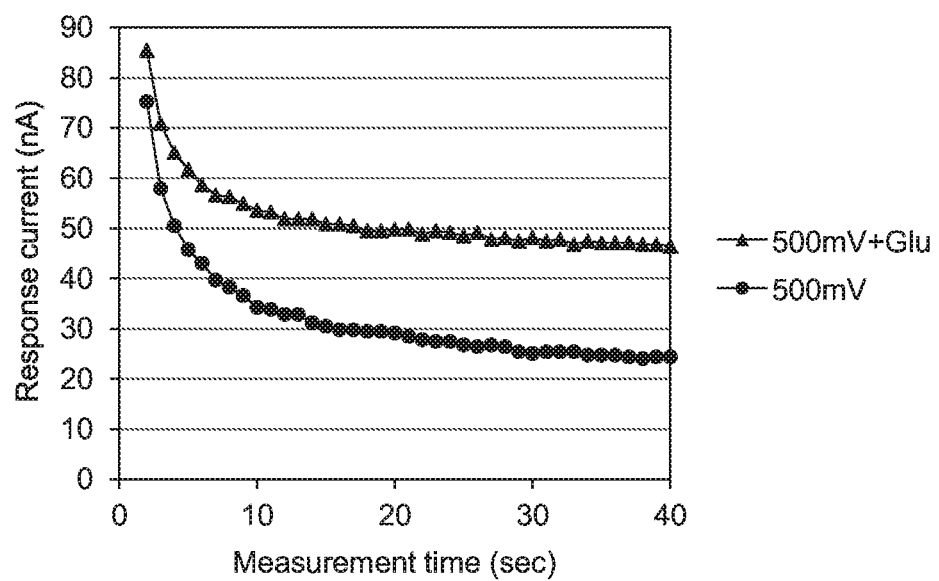
FIG. 6 shows chronoamperometry measurement results of CtCytb-MpGDH-M1.

FIG. 6 shows the chronoamperometric measurement results of CtCytb-MpGDH-M1 when a voltage of +500 mV (vs. Ag/AgCl) was applied. In both cases of +300 mV and +500 mV (vs. Ag/AgCl), a significantly high response current was observed when glucose was added. Even at an applied voltage of +300 mV (vs. Ag/AgCl), a detectable value of 19 nA was shown as the response current 40 seconds after initiation of measurement. The response current was 10 nA in the absence of glucose. The difference between the former and the latter was 9 nA, and thus a significantly high response current was observed when glucose was added. By using similar methods, comparison can be made between the Cytb-GDH fusion protein and MpGDH-M1 enzyme having no Cytb domain in the examples below.

Figure 7:
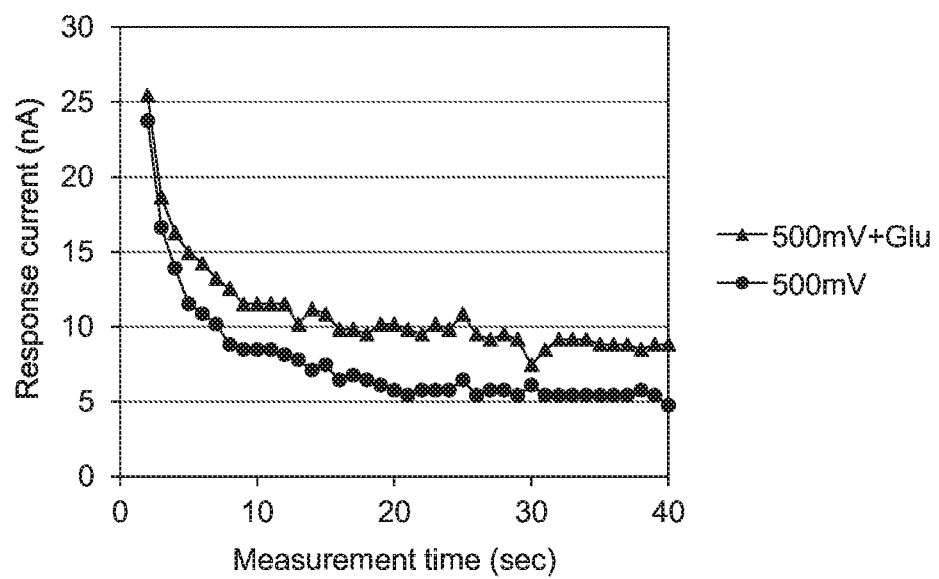
FIG. 7 shows chronoamperometry measurement results of AsCytb-L1-MpGDH-M1.

FIG. 7 shows the chronoamperometric measurement results of AsCytb-L1-MpGDH-M when a voltage of +500 mV (vs. Ag/AgCl) was applied. In the case of +500 mV (vs. Ag/AgCl), a significantly high response current was observed when glucose was added. At an applied voltage of +500 mV (vs. Ag/AgCl), a detectable value of 9 nA was shown as the response current 40 seconds after initiation of measurement.

Figure 8:
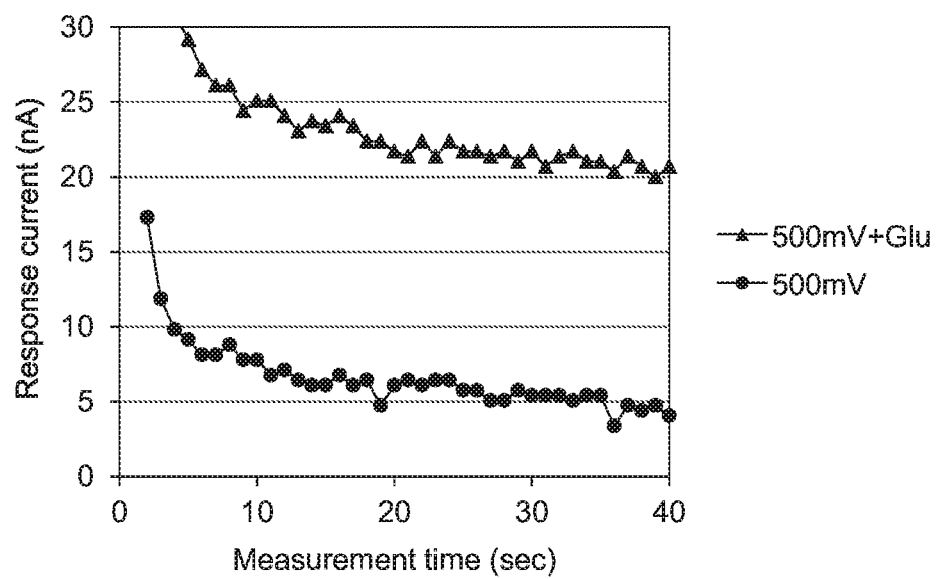
FIG. 8 shows chronoamperometry measurement results of AsCytbx2-MpGDH-M1.

FIG. 8 shows the chronoamperometric measurement results of AsCytbx2-MpGDH-M1 when a voltage of +500 mV (vs. AgAgCl) was applied. In both cases of +300 mV and +500 mV (vs. Ag/AgCl), a significantly high response current was observed when glucose was added. At an applied voltage of +300 mV (vs. Ag/AgCl), a detectable value of 15 nA was shown as the response current 40 seconds after initiation of measurement.

Figure 9:
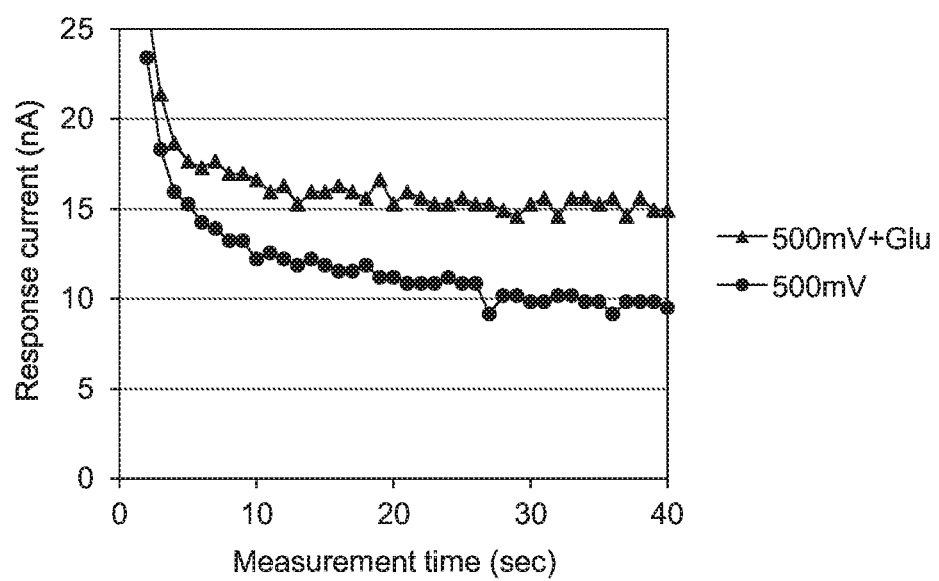
FIG. 9 shows chronoamperometry measurement results of AsCytb-L2-MpGDH-M1.

FIG. 9 shows the chronoamperometric measurement results of AsCytb-L2-MpGDH-M1 when a voltage of +500 mV (vs. Ag/AgCl) was applied. In the case of +500 mV (vs. Ag/AgCl), a significantly high response current was observed when glucose was added. At an applied voltage of +500 mV (vs. Ag/AgCl), a detectable value of 15 nA was shown as the response current 40 seconds after initiation of measurement.

Figure 10:
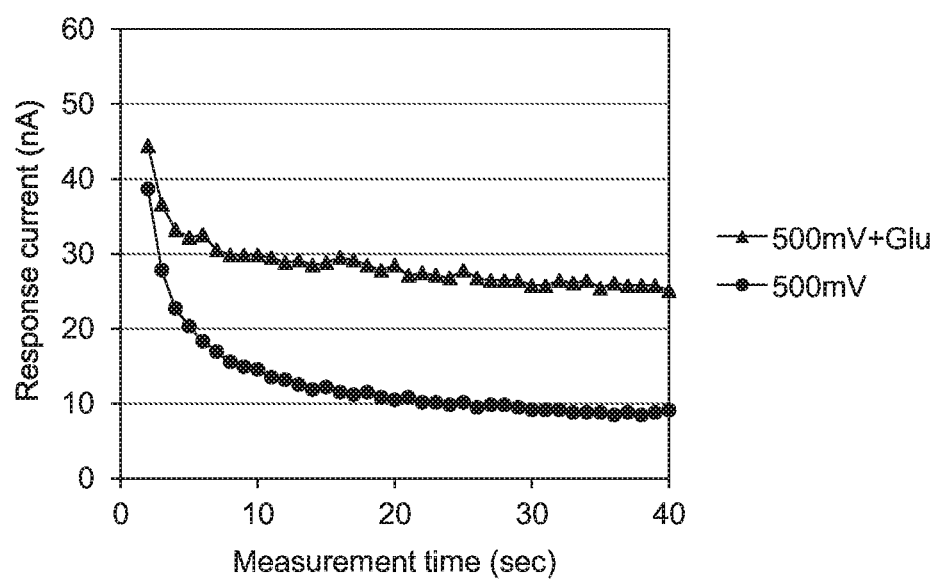
FIG. 10 shows chronoamperometry measurement results of MpGDH-M1-CtCytb.
Figure 11:
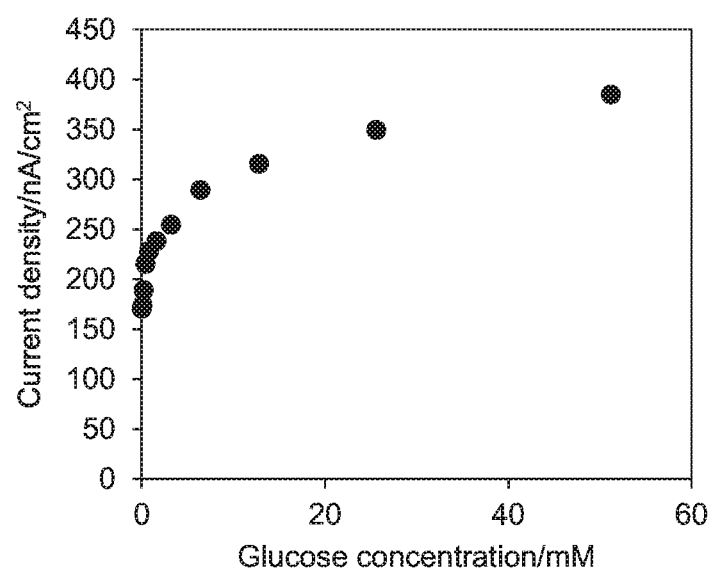
FIG. 11 shows the relation between current density and glucose concentration when using MtCytb-MpGDH-M1.

FIG. 10 shows the chronoamperometric measurement results of MpGDH-M1-CtCytb when a voltage of +500 mV (vs. Ag/AgCl) was applied. In both cases of +300 mV and +500 mV (vs. Ag/AgCl), a significantly high response current was observed when glucose was added. At an applied voltage of +300 mV (vs. Ag/AgCl), a detectable value of 11 nA was shown as the response current 40 seconds after initiation of measurement.

Subsequently, chronoamperometry measurement was carried out using MpGDH-M1 or HiCytb-MpGDH-M1. More specifically, onto the working electrode of a DEP Chip electrode (attached with a circular carbon dam ring; manufactured by BioDevice Technology) comprising a glassy carbon working electrode and a silver/silver chloride reference electrode printed thereon, a solution comprising 80 µg of purified enzyme MpGDH-M1 or a solution comprising 80 µg of purified enzyme HiCytb-MpGDH-M1 was added, and then dried in air at room temperature. Then, the DEP Chip electrode was connected to ALS electrochemical analyzer 814D (manufactured by BAS) by using a DEP Chip specific connector. Subsequently, a 20 mM (final concentration) phosphate buffer (pH7.5)/1.5 M potassium chloride/20 mM glucose solution (10 µL) was placed on the electrode to carry out the reaction and then, a voltage of +300 mV (vs. Ag/AgCl) was applied and the current value was measured for 40 seconds. As a control, a solution containing no glucose was subjected to the same measurement as well.

As a result, the response current 40 seconds after initiation of measurement was 3 nA in the presence of glucose, and 1 nA in the absence of glucose. The difference between the former and the latter was 2 nA, and thus no significant difference was observed for the response current between the presence and absence of glucose in chronoamperometry measurement of the MpGDH-M1 enzyme having no Cytb domain even under these conditions.

When HiCytb-MpGDH-M1 was used, a detectable value of 16 nA was shown as the response count 40 seconds after initiation of measurement at an applied voltage of +300 mV (vs. Ag/AgCl).

Example 2

A gene encoding a GDH from *Mucor* RD056860 (MrdGDH) was obtained (see, WO 2013/118798). The amino acid sequence of MrdGDH is shown in SEQ ID NO: 4, and the nucleotide sequence of the gene of MrdGDH is shown in SEQ ID NO: 112.

In a manner similar to the Example above and by using In-Fusion HD Cloning Kit with the synthetic oligonucleotides of SEQ ID NOs: 130 to 133, the sequence of MtCytb and the linker sequence as shown in SEQ ID NO: 122 were inserted using pUC19-MrdGDH as the template to obtain the plasmid for the construct MtCytb-MrdGDH in which the cytochrome was fused to the N terminus of MrdGDH (pUC19-MtCytb-MrdGDH). Further, in a similar manner and by using the synthetic oligonucleotides of SEQ ID NOs: 134 to 137, the sequence of CtCytb and the linker sequence as shown in SEQ ID NO: 124 were inserted using pUC19-MrdGDH as the template to obtain the plasmid for the construct CtCytb-MrdGDH in which cytochrome was fused to the N terminus of MrdGDH (pUC19-CtCytb-MrdGDH). Subsequently, in a manner similar to the example above, each of the genes encoding MrdGDH, MtCytb-MrdGDH, and CtCytb-MrdGDH was expressed in *A. sojae* to obtain a purified product and the response current measurement was carried out.

In the same manner as in Example 1 and onto the working electrode of a DEP Chip electrode, a solution containing 80 µg of purified enzyme MrdGDH, a solution containing 80 µg of purified enzyme MtCytb-MrdGDH, or a solution containing 80 µg of purified enzyme CtCytb-MrdGDH was added, and then dried in air at room temperature. Subsequently, a phosphate buffer with final concentration of 20 mM (pH7.5)/1.5 M potassium chloride/20 mM glucose solution (10 µL) was placed on the electrode and allowed to react. A voltage of +300 mV (vs. Ag/AgCl) was applied and the current value was measured for 40 seconds.

Chronoamperometry results showed that, when using MrdGDH and when applying a voltage of +300 mV (vs. Ag/AgCl), the response current was 7 nA at 40 seconds after initiation of measurement. The response current was 4 nA in the absence of glucose. The difference between the former and the latter was 3 nA, and thus no significant difference was observed for the response current between the presence and absence of glucose. On the other hand, when MtCytb-MrdGDH was used, the response current was 13 nA 40 seconds after initiation of measurement at an applied voltage of +300 mV (vs. Ag/AgCl), and 6 nA in the absence of glucose. The difference between the former and the latter was 7 nA, and thus a significantly high response current was observed as compared to the case without comprising any cytochrome. Further, when CtCytb-MrdGDH was used, the response current was 27 nA 40 seconds after initiation of measurement at an applied voltage of +300 mV (vs. Ag/AgCl), and 7 nA in the absence of glucose. The difference between the former and the latter was 20 nA, and thus a significantly high response current was exhibited as compared to the case without comprising any cytochrome.

Example 3

Onto a working electrode of SCREEN-PRINTED ELECTRODES (manufactured by DropSens, DRP-110) having a carbon working electrode of carbon and a silver reference electrode printed thereon, 875 µg of MtCytb-MpGDH-M1 was applied and dried at 37° C. Then, 25 µL of 3 wt % Agarose L (manufactured by Nippon Gene Co., Ltd.) dissolved at 37° C. was applied, and cooled at room temperature to embed and immobilize. Subsequently, the enzyme-immobilized printed electrode was connected as a working electrode to ALS electrochemical analyzer 814D (manufactured by BAS) by using a specific connector (manufactured by DropSens, DRP-CAC). Further, a saturated KCl silver/silver chloride reference electrode (manufactured by BAS) as a reference electrode, and a platinum electrode (manufactured by BAS) as a counter electrode were each connected to the ALS electrochemical analyzer 814D. The three electrodes were placed in 30 mL of 100 mM potassium phosphate solution (pH7.0). To this, 1M glucose was appropriately added under stirring with a stirrer, and the response current at an applied voltage of +500 mV (vs. Ag/AgCl) was measured. A cycle comprising adding glucose, and then measuring the value after the response current reached a constant value and then adding glucose again, was repeated. As a result, over a range of from 0.1 mM to 50 mM glucose, increase of the response current was observed even without addition of any free-form mediator into the solution.

To sum the above up, since a response current was observed even in the absence of a free-form mediator, it is believed that when the Cytb-GDH of the present invention oxidizes glucose to gluconolactone, an electron is directly transferred from the enzyme to the electrode. Further, since a response current was observed even for MtCytb, CtCytb, and AsCytb, it is considered that, regarding the Cytb to be linked to the GDH, Cytbs of other origins can be used. Further, since a response current was observed even when CtCytb was linked to the N terminus of the GDH or when CtCytb was linked to the C terminus of the GDH, it is considered that when a Cytb of another origin is linked to the GDH, the Cytb may likewise be ligated to the N terminus or the C terminus of the GDH.

INDUSTRIAL APPLICABILITY

By using the Cytb-GDH of the present invention, glucose measurement can be carried out in the presence of a free-form mediator in reduced concentration compared to conventional conditions or in the absence of a free-form mediator. Further, the Cytb-GDH of the present invention can be used in a glucose sensor and can be used in continuous glucose monitoring.

All publications, patents and patent applications referred to in the present specification are incorporated herein in their entirety by reference.

BRIEF DESCRIPTION OF THE SEQUENCES

SEQ ID NO: 1 Amino acid sequence of a GDH from *Mucor prainii* (MpGDH)
SEQ ID NO: 2 Nucleotide sequence of the MpGDH gene
SEQ ID NO: 3 Amino acid sequence of a GDH from *Mucor hiemalis* (MhGDH)

SEQ ID NO: 4 Amino acid sequence of a GDH from *Mucor* RD056860 (MrdGDH)
SEQ ID NO: 5 Amino acid sequence of a GDH from *Mucor subtilissimus* (MsGDH)
SEQ ID NO: 6 Amino acid sequence of a GDH from *Mucor guilliermondii* (MgGDH)
SEQ ID NO: 7 Amino acid sequence of a GDH from *Circinella simplex* (CsGDH)
SEQ ID NO: 8 Amino acid sequence of a GDH from the genus *Circinella* (CrGDH)
SEQ ID NO: 9 Amino acid sequence of a GDH from *Mucor circinelloides* (McGDH)
SEQ ID NO: 10 Amino acid sequence of MpGDH-M1 glucose dehydrogenase
SEQ ID NO: 11 Nucleotide sequence of the MpGDH-M1 gene
SEQ ID NO: 12 Amino acid sequence of Mt Cytb
SEQ ID NO: 13 Nucleotide sequence of gene encoding the polypeptide of SEQ ID NO: 12
SEQ ID NO: 14 Amino acid sequence of Ct Cytb
SEQ ID NO: 15 Nucleotide sequence of gene encoding the polypeptide of SEQ ID NO: 14
SEQ ID NO: 16 Putative amino acid sequence of As Cytb
SEQ ID NO: 17 Nucleotide sequence of gene encoding the polypeptide of SEQ ID NO: 16
SEQ ID NO: 18 Amino acid sequence of Cytb from *Hypoxylon haematostroma*
SEQ ID NO: 19 Amino acid sequence of Cytb from *Chaetomium attrobruneum*
SEQ ID NO: 20 Amino acid sequence of Cytb from *Neurospora crassa*
SEQ ID NO: 21 Amino acid sequence of Cytb from *Humicola insolens*
SEQ ID NO: 22 Amino acid sequence of Cytb from *Thielavia terrestris*
SEQ ID NO: 23 Linker sequence Mt
SEQ ID NO: 24 Nucleotide sequence of Linker sequence Mt
SEQ ID NO: 25 Linker sequence Ct
SEQ ID NO: 26 Nucleotide sequence of Linker sequence Ct
SEQ ID NO: 27 Linker sequence AsL1
SEQ ID NO: 28 Nucleotide sequence of linker sequence AsL1
SEQ ID NO: 29 Linker sequence AsL2
SEQ ID NO: 30 Nucleotide sequence of linker sequence AsL2
SEQ ID NO: 31 Linker sequence C terminal Ct
SEQ ID NO: 32 Nucleotide sequence of linker sequence C terminal Ct
SEQ ID NO: 33 Amino acid sequence of MtCytb-MpGDH-M1
SEQ ID NO: 34 Nucleotide sequence of MtCytb-MpGDH-M1 gene
SEQ ID NO: 35 Amino acid sequence of CtCytb-MpGDH-M11
SEQ ID NO: 36 Nucleotide sequence of CtCytb-MpGDH-M1 gene
SEQ ID NO: 37 Amino acid sequence of AsCytb-L1-MpGDH-M11
SEQ ID NO: 38 Nucleotide sequence of AsCytb-L1-MpGDH-M1 gene
SEQ ID NO: 39 Amino acid sequence of AsCytbx2-MpGDH-M11
SEQ ID NO: 40 Nucleotide sequence of AsCytbx2-MpGDH-M1 gene
SEQ ID NO: 41 Amino acid sequence of AsCytb-L2-MpGDH-M11
SEQ ID NO: 42 Nucleotide sequence of AsCytb-L2-MpGDH-M1 gene
SEQ ID NO: 43 Amino acid sequence of MpGDH-M1-CtCytb
SEQ ID NO: 44 Nucleotide sequence of MpGDH-M1-CtCytb gene
SEQ ID NO: 45 to 48 Primers for producing MtCytb-MpGDH-M1
SEQ ID NO: 49 to 52 Primers for producing CtCytb-MpGDH-M1
SEQ ID NO: 53 to 56 Primers for producing AsCytb-L1-MpGDH-M1
SEQ ID NO: 57 to 60 Primers for producing AsCytbx2-MpGDH-M1
SEQ ID NO: 61 to 62 Primers for producing AsCytb-L2-MpGDH-M1
SEQ ID NO: 63 to 66 Primers for producing MpGDH-M1-CtCytb
SEQ ID NO: 67 Linker sequence GDCSGDGGGGSG-PEPVPVPDG of CDH from *Aspergillus terreus*
SEQ ID NO: 68 Linker sequence GGGGSLVPRGSGGGGS derived from HSP70
SEQ ID NO: 69 Hen egg lysozyme-derived linker sequence GGGGSLVPRGSGGGGS
SEQ ID NO: 70 Hemagglutinin HA peptide-derived linker sequence GGSGGGGG
SEQ ID NO: 71-111 Linkers
SEQ ID NO: 112 Nucleotide sequence of gene encoding the polypeptide of SEQ ID NO: 4
SEQ ID NO: 113 Nucleotide sequence of gene encoding the polypeptide of SEQ ID NO: 21
SEQ ID NO: 114 Amino acid sequence of HiCytb-MpGDH-M11
SEQ ID NO: 115 Nucleotide sequence of gene encoding the polypeptide of SEQ ID NO: 114
SEQ ID NO: 116 Amino acid sequence of MtCytb-MrdGDH
SEQ ID NO: 117 Nucleotide sequence of gene encoding the polypeptide of SEQ ID NO: 116
SEQ ID NO: 118 Amino acid sequence of CtCytb-MrdGDH
SEQ ID NO: 119 Nucleotide sequence of gene encoding the polypeptide of SEQ ID NO: 118
SEQ ID NO: 120 Linker sequence Hi
SEQ ID NO: 121 Nucleotide sequence of linker sequence Hi
SEQ ID NO: 122 Linker sequence Mt-Mrd
SEQ ID NO: 123 Nucleotide sequence of linker sequence Mt-Mrd
SEQ ID NO: 124 Linker sequence Ct-Mrd
SEQ ID NO: 125 Nucleotide sequence of linker sequence Ct-Mrd
SEQ ID NO: 126 to 129 Primers for producing HiCytb-MpGDH-M1
SEQ ID NO: 130 to 133 Primers for producing MtCytb-MrdGDH
SEQ ID NO: 134 to 137 Primers for producing CtCytb-MrdGDH All publications, patents and patent applications referred to in the specification are incorporated herein in their entirety by reference.

The invention claimed is:

1. A method for measuring glucose in a sample, the method comprising contacting the sample to be measured with a sensor, wherein the sensor comprises an electrode and a cytochrome b-glucose dehydrogenase fusion protein capable of transferring an electron from the enzyme directly to the electrode, wherein said cytochrome b-glucose dehydrogenase fusion protein is a fusion protein comprising (i) a flavin-binding glucose dehydrogenase moiety, and (ii) a cytochrome b moiety, wherein the cytochrome b-glucose dehydrogenase fusion protein is included in the sensor in an amount ranging from 0.5 µg to 5000 µg, wherein, with regard to the (i) flavin-binding glucose dehydrogenase moiety, (A) the flavin-binding glucose dehydrogenase moiety has 90% or more amino acid sequence identity over the full length with the amino acid sequence of SEQ ID NO: 1, or (B) the flavin-binding glucose dehydrogenase moiety has 95% or more amino acid sequence identity over the full length with the amino acid sequence of SEQ ID NO: 1, and wherein, with regard to the (ii) cytochrome b moiety, (C) the cytochrome b moiety has 90% or more amino acid sequence identity over the full length with the amino acid sequence of SEQ ID NO: 12, or (D) the cytochrome b moiety has 95% or more amino acid sequence identity over the full length with the amino acid sequence of SEQ ID NO: 12, or wherein, with regard to the cytochrome b-glucose dehydrogenase fusion protein, (E) the cytochrome b-glucose dehydrogenase fusion protein has 90% or higher sequence identity with SEQ ID NO: 33, wherein the cytochrome b moiety of (C), (D), or (E), further comprises methionine at the position corresponding to position 95 of SEQ ID NO: 12, histidine at the position corresponding to position 197 of SEQ ID NO: 12, Gly-Xaa-Met at the positions corresponding to positions 93 to 95 of SEQ ID NO: 12 wherein Xaa represents any amino acid, Tyr-Xaa-Xaa-Pro at the positions corresponding to positions 120 to 123rd of SEQ ID NO: 12 where Xaa represents any amino acid, and Cys-Xaa-Xaa-Cys at the positions corresponding to positions 150 to 153 of SEQ ID NO: 12 where Xaa represents any amino acid.

2. The method of claim 1, wherein the glucose dehydrogenase moiety in the fusion protein has glucose dehydrogenase activity, a molecular weight of about 70 kDa estimated based on the primary sequence of the polypeptide chain moiety of the protein, or has a molecular weight of about 80 kDa measured by SDS-polyacrylamide electrophoresis, and has low reactivity to maltose and D-xylose compared to the reactivity to D-glucose, wherein the glucose dehydrogenase moiety characteristic is of a flavin-binding type.

3. The method of claim 1, wherein, apart from the cytochrome b-glucose dehydrogenase fusion protein, no free-form cytochrome molecule is added to the sample in said method for measuring glucose.

4. The method of claim 1, wherein,
(E) the cytochrome b-glucose dehydrogenase fusion protein has 95% or higher sequence identity with SEQ ID NO: 33.

5. The method of claim 1, wherein,
(E) the cytochrome b-glucose dehydrogenase fusion protein is encoded by a nucleotide sequence having a sequence identity of 90% or more with SEQ ID NO: 34.

* * * * *

SEQUENCE LISTING

<160> NUMBER OF SEQ ID NOS: 137

<210> SEQ ID NO 1
<211> LENGTH: 641
<212> TYPE: PRT
<213> ORGANISM: Mucor prainii

<400> SEQUENCE: 1

```
Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Thr Asp Thr Tyr
            20                  25                  30

Asp Tyr Val Ile Val Gly Gly Gly Val Ala Gly Leu Ala Leu Ala Ser
                35                  40                  45

Arg Ile Ser Glu Asn Lys Asp Val Thr Val Ala Val Leu Glu Ser Gly
    50                  55                  60

Pro Asn Ala Asn Asp Arg Phe Val Val Tyr Ala Pro Gly Met Tyr Gly
65                  70                  75                  80

Gln Ala Val Gly Thr Asp Leu Cys Pro Leu Ile Pro Thr Thr Pro Gln
                85                  90                  95

Glu Asn Met Gly Asn Arg Ser Leu Thr Ile Ala Thr Gly Arg Leu Leu
            100                 105                 110

Gly Gly Gly Ser Ala Ile Asn Gly Leu Val Trp Thr Arg Gly Gly Leu
        115                 120                 125

Lys Asp Tyr Asp Ala Trp Glu Glu Leu Gly Asn Pro Gly Trp Asn Gly
130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Ala His
                165                 170                 175

Gly Lys Lys Gly Pro Ile Asp Val Ser Phe Thr Asn Tyr Glu Phe Ser
            180                 185                 190

Gln Ser Ala Ser Trp Asn Ala Ser Leu Glu Thr Leu Asp Phe Thr Ala
        195                 200                 205

Leu Pro Asp Ile Leu Asn Gly Thr Leu Ala Gly Tyr Ser Thr Thr Pro
    210                 215                 220

Asn Ile Leu Asp Pro Glu Thr Val Gln Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255

His Thr Val Ser Arg Ile Gln Phe Ala Pro Lys Asn Gly Ser Glu Pro
            260                 265                 270

Leu Lys Ala Thr Gly Val Glu Trp Tyr Pro Thr Gly Asn Lys Asn Gln
        275                 280                 285

Lys Gln Ile Ile Lys Ala Arg Tyr Glu Val Ile Ile Ser Ser Gly Ala
    290                 295                 300

Ile Gly Ser Pro Lys Leu Leu Glu Ile Ser Gly Ile Gly Asn Lys Asp
305                 310                 315                 320

Ile Val Ser Ala Ala Gly Val Glu Ser Leu Ile Asp Leu Pro Gly Val
                325                 330                 335

Gly Ser Asn Met Gln Asp His Val His Ala Ile Thr Val Ser Thr Thr
            340                 345                 350

Asn Ile Thr Gly Tyr Thr Thr Asn Ser Val Phe Val Asn Glu Thr Leu
        355                 360                 365
```

```
Ala Gln Glu Gln Arg Glu Glu Tyr Glu Ala Asn Lys Thr Gly Ile Trp
    370                 375                 380

Ala Thr Thr Pro Asn Asn Leu Gly Tyr Pro Thr Pro Glu Gln Leu Phe
385                 390                 395                 400

Asn Gly Thr Glu Phe Val Ser Gly Lys Glu Phe Ala Asp Lys Ile Arg
                405                 410                 415

Asn Ser Thr Asp Glu Trp Ala Asn Tyr Tyr Ala Ser Thr Asn Ala Ser
            420                 425                 430

Asn Val Glu Leu Leu Lys Lys Gln Tyr Ala Ile Val Ala Ser Arg Tyr
        435                 440                 445

Glu Glu Asn Tyr Leu Ser Pro Ile Glu Ile Asn Phe Thr Pro Gly Tyr
    450                 455                 460

Glu Gly Ser Gly Asn Val Asp Leu Gln Asn Asn Lys Tyr Gln Thr Val
465                 470                 475                 480

Asn His Val Leu Ile Ala Pro Leu Ser Arg Gly Tyr Thr His Ile Asn
                485                 490                 495

Ser Ser Asp Val Glu Asp His Ser Val Ile Asn Pro Gln Tyr Tyr Ser
            500                 505                 510

His Pro Met Asp Ile Asp Val His Ile Ala Ser Thr Lys Leu Ala Arg
        515                 520                 525

Glu Ile Ile Thr Ala Ser Pro Gly Leu Gly Asp Ile Asn Ser Gly Glu
    530                 535                 540

Ile Glu Pro Gly Met Asn Ile Thr Ser Glu Asp Asp Leu Arg Ser Trp
545                 550                 555                 560

Leu Ser Asn Asn Val Arg Ser Asp Trp His Pro Val Gly Thr Cys Ala
                565                 570                 575

Met Leu Pro Lys Glu Leu Gly Gly Val Val Ser Pro Ala Leu Met Val
            580                 585                 590

Tyr Gly Thr Ser Asn Leu Arg Val Val Asp Ala Ser Ile Met Pro Leu
        595                 600                 605

Glu Val Ser Ser His Leu Met Gln Pro Thr Tyr Gly Ile Ala Glu Lys
    610                 615                 620

Ala Ala Asp Ile Ile Lys Asn Phe Tyr Lys Thr Gln His Lys Asn Gln
625                 630                 635                 640

Asn
```

<210> SEQ ID NO 2
<211> LENGTH: 1926
<212> TYPE: DNA
<213> ORGANISM: Mucor prainii

<400> SEQUENCE: 2

```
atgaagatca cagctgccat tatcactgtt gccacagcat ttgcttcttt tgcttctgct      60
caacaagaca caaattcttc ctcaactgat acttatgatt atgttatcgt tggcggcggt     120
gtagctggtt tggctttggc tagtcgtatc tctgaaaaca aggatgtcac tgttgctgtt     180
ctcgagtccg gtcctaatgc caatgataga tttgttgttt atgctcctgg catgtatggc     240
caagctgttg gcactgatct ctgtcctctc attcctacta ctcctcaaga aaatatgggc     300
aacagaagtc tcacaatcgc tactggtaga ttgctcggtg gtggcagtgc tattaatggt     360
ctcgtttgga cccgtggtgg cttgaaggat tacgatgctt gggaggagct cggtaaccct     420
ggatggaacg tgccaacctt gttcaagtac tttaagaagg tcgaaaactt cactcctcct     480
actcctgccc aaattgaata cggcgctact tatcagaaaa gtgctcatgg caagaaggga     540
```

| | |
|---|---|
| cctattgatg tctctttcac gaactacgag ttctctcaat ctgctagctg gaacgcctca | 600 |
| ctcgaaaccc ttgatttcac tgcacttcct gatatcttga acggtacttt ggccggttac | 660 |
| tctaccactc ccaacatttt ggaccctgag actgttcaac gtgttgattc ctatactggt | 720 |
| tacattgctc cttacactag ccgtaacaac ctcaatgttt tggccaacca taccgtctcc | 780 |
| cgcattcaat ttgctcccaa gaatggtagc gaacctctca aggctaccgg tgttgaatgg | 840 |
| tatcccactg gcaacaagaa tcaaaagcaa attatcaagg cccgttatga agttatcatc | 900 |
| tcatctggtg ccattggtag tcctaagctt ttggaaatct ctggtatcgg taataaggat | 960 |
| atcgtctctg ctgctggtgt cgagtccttg attgacttgc ctggcgttgg ttccaacatg | 1020 |
| caagatcacg ttcatgctat cactgtctct actaccaata ttactggcta tactaccaac | 1080 |
| agcgtctttg tcaatgaaac ccttgcccaa gaacaaagag aagaatatga agccaacaag | 1140 |
| actggtatct gggctactac tcccaacaac ctcggttatc ctacgcccga caactcttc | 1200 |
| aatggcaccg aattcgtttc tggaaaggag tttgctgaca agattcgtaa ctctactgat | 1260 |
| gaatgggcca actattatgc ttccaccaac gcctccaatg tcgagttatt aaagaagcaa | 1320 |
| tatgctattg tcgcctctcg ttacgaagag aactacttgt ctcctattga aatcaacttc | 1380 |
| actcctggtt atgagggtag cggtaatgtc gatttgcaaa acaacaagta ccaaactgtc | 1440 |
| aaccatgtct tgattgctcc tttaagtcgt ggttatactc acattaactc ttctgatgtg | 1500 |
| gaggatcatt ctgtcattaa tccccaatac tactctcatc ctatggatat tgatgtccat | 1560 |
| atcgcttcca ctaaacttgc tcgcgaaatc atcactgcct ctcccggtct tggtgacatt | 1620 |
| aacagtggcg aaatcgaacc cggtatgaat attacttctg aagacgacct tagatcttgg | 1680 |
| ttgagtaata atgtccgttc tgactggcat cctgttggta cttgtgctat gcttcccaag | 1740 |
| gaattaggtg tgttgtcag ccccgctctc atggtttacg gcacttccaa cttgcgtgtt | 1800 |
| gttgatgctt cgattatgcc cctcgaagtc tcttctcatt tgatgcaacc cacctacggt | 1860 |
| attgctgaga aggctgctga cattattaag aatttctaca agactcaaca caagaaccaa | 1920 |
| aattag | 1926 |

<210> SEQ ID NO 3
<211> LENGTH: 635
<212> TYPE: PRT
<213> ORGANISM: Mucor hiemalis

<400> SEQUENCE: 3

Met Lys Ile Ser Val Ala Ile Val Thr Ile Ala Ala Ala Phe Ala Ser
1               5                   10                  15

Phe Ala Asn Ala Gln Lys Thr Ala Thr Ser Asn Thr Tyr Asp Tyr Val
                20                  25                  30

Ile Val Gly Gly Gly Val Gly Gly Leu Ala Leu Ala Ser Arg Leu Ser
            35                  40                  45

Glu Asp Lys Ser Val Thr Val Ala Val Leu Glu Ala Gly Pro Asn Ala
        50                  55                  60

Asp Glu Gln Phe Val Val Tyr Ala Pro Gly Met Tyr Gly Gln Ala Val
65                  70                  75                  80

Gly Thr Asp Leu Cys Pro Leu Arg Pro Thr Val Pro Gln Glu Ala Met
                85                  90                  95

Asn Asn Arg Thr Leu Thr Ile Ala Thr Gly Lys Leu Leu Gly Gly Gly
            100                 105                 110

Ser Ala Ile Asn Gly Leu Val Trp Thr Arg Gly Ala Leu Lys Asp Phe
        115                 120                 125

```
Asp Ala Trp Glu Glu Leu Gly Asn Pro Gly Trp Asn Gly Arg Thr Met
        130                 135                 140

Phe Lys Tyr Phe Lys Lys Val Glu Arg Phe His Pro Pro Thr Lys Ala
145                 150                 155                 160

Gln Val Gln Tyr Gly Ala Thr Tyr Gln Lys Gly Val His Gly Lys Asn
                165                 170                 175

Gly Arg Ile Asp Ile Ser Phe Pro Glu Phe Gln Phe Pro Gln Ser Ala
            180                 185                 190

Asn Trp Asn Ala Ser Leu Ala Thr Leu Asp Phe Thr His Gln Gln Asp
                195                 200                 205

Leu Leu Asn Gly Ser Leu His Gly Tyr Ser Thr Thr Pro Asn Thr Leu
        210                 215                 220

Asp Pro Lys Thr Ala Arg Arg Val Asp Ser Tyr Thr Gly Tyr Ile Ala
225                 230                 235                 240

Pro Phe Val Ser Arg Lys Asn Leu Phe Val Leu Ala Asn His Thr Val
                245                 250                 255

Ser Arg Ile Gln Phe Lys Pro Lys Asn Gly Thr Glu Leu Leu Lys Ala
            260                 265                 270

Val Gly Val Glu Trp Tyr Thr Thr Gly Asp Asn Ser Asn Lys Gln Thr
        275                 280                 285

Ile Lys Ala Arg Arg Glu Val Ile Val Ser Ser Gly Ser Ile Gly Ser
290                 295                 300

Pro Lys Leu Leu Glu Ile Ser Gly Ile Gly Asn Lys Asp Ile Val Thr
305                 310                 315                 320

Ala Ala Gly Val Gln Ser Leu Ile Asp Leu Pro Gly Val Gly Ser Asn
                325                 330                 335

Met Gln Asp His Val His Ala Val Thr Val Ser Thr Thr Asn Ile Thr
            340                 345                 350

Gly Phe Thr Thr Asp Ser Val Phe Gln Asn Glu Thr Leu Ala Glu Glu
        355                 360                 365

Gln Arg Gln Gln Tyr Tyr Asn Asn Lys Thr Gly Ile Trp Thr Thr Thr
        370                 375                 380

Pro Asn Asn Leu Gly Tyr Pro Ser Pro Ser Gln Leu Phe Asp Gly Thr
385                 390                 395                 400

Ser Phe Glu Ser Gly Gln Ala Phe Ala Asn Arg Ile Arg Asn Ser Thr
                405                 410                 415

Asp Gln Trp Ala Glu Tyr Tyr Ala Ser Thr Asn Ala Thr Asn Ile Glu
            420                 425                 430

Leu Leu Lys Lys Gln Tyr Ala Ile Val Ala Ser Arg Tyr Glu Glu Asn
        435                 440                 445

Tyr Leu Ser Pro Ile Glu Ile Asn Phe Thr Pro Gly Tyr Gly Gly Thr
450                 455                 460

Thr Asp Val Asp Leu Lys Asn Asn Lys Tyr Gln Thr Val Asn His Val
465                 470                 475                 480

Leu Ile Ala Pro Leu Ser Arg Gly Tyr Thr His Ile Asn Ser Ser Asn
                485                 490                 495

Ile Glu Asp Pro Val Val Ile Asn Pro Gln Tyr Tyr Thr His Pro Met
            500                 505                 510

Asp Val Asp Val His Ile Ala Ser Thr Lys Leu Ala Arg Arg Ile Leu
        515                 520                 525

Gly Ala Glu Pro Gly Leu Ala Ser Ile Asn Ser Gly Glu Ile Gln Pro
530                 535                 540
```

```
Gly Ser Asn Ile Thr Ser Asp Glu Asp Val Lys Gln Trp Leu Ala Asp
545                 550                 555                 560

Asn Val Arg Ser Asp Trp His Pro Val Gly Thr Cys Ala Met Leu Pro
                565                 570                 575

Arg Glu Leu Gly Gly Val Val Asp Pro Asn Leu Leu Val Tyr Gly Thr
            580                 585                 590

Ala Asn Leu Arg Val Val Asp Ala Ser Ile Met Pro Leu Glu Ile Ser
        595                 600                 605

Ser His Leu Met Gln Pro Thr Tyr Gly Val Ala Glu Lys Ala Ala Asp
    610                 615                 620

Ile Ile Lys Met Ser Arg Lys Asn Asn Asn
625                 630                 635

<210> SEQ ID NO 4
<211> LENGTH: 631
<212> TYPE: PRT
<213> ORGANISM: Mucor DR056860

<400> SEQUENCE: 4

Met Arg Leu Ser Val Ala Ile Leu Thr Leu Thr Ser Ala Leu Ala Ser
1               5                   10                  15

Val Thr Ser Ala Gln Gln Asn Asn Thr Asp Thr Tyr Asp Tyr Val Ile
            20                  25                  30

Val Gly Gly Gly Val Gly Leu Ala Leu Ala Ser Arg Leu Ser Glu
        35                  40                  45

Asp Lys Asn Val Thr Val Ala Val Leu Glu Ser Gly Pro Tyr Ala Asp
    50                  55                  60

Asp Lys Phe Val Val Tyr Ala Pro Gly Met Tyr Gly Gln Ala Val Gly
65                  70                  75                  80

Thr Asp Leu Cys Pro Leu Leu Pro Thr Val Pro Gln Pro Ser Met Asn
                85                  90                  95

Asn Arg Thr Ile Thr Ile Ala Thr Gly Arg Leu Leu Gly Gly Gly Ser
            100                 105                 110

Ala Val Asn Gly Leu Val Trp Thr Arg Gly Ala Met Lys Asp Phe Asp
        115                 120                 125

Ala Trp Gln Glu Leu Gly Asn Pro Gly Trp Asn Gly Thr Thr Met Phe
130                 135                 140

Lys Tyr Phe Lys Lys Ile Glu Asn Phe His Pro Pro Thr Glu Glu Gln
145                 150                 155                 160

Ile Gln Tyr Gly Ala Thr Tyr Asn Lys Ser Val His Gly Phe Asn Gly
                165                 170                 175

Pro Ile Asp Ile Ala Phe Pro Val Phe Glu Phe Pro Gln Ser Ala Asn
            180                 185                 190

Trp Asn Ala Ser Leu Ala His Leu Asn Phe Thr Arg Arg Gln Asp Leu
        195                 200                 205

Leu Asp Gly Ser Leu His Gly Tyr Ser Thr Thr Pro Asn Thr Leu Asn
    210                 215                 220

Pro Gln Thr Ala Arg Arg Ala Asp Ala Tyr Ala Gly Tyr Ile Gln Pro
225                 230                 235                 240

Asn Val Asn Arg Thr Asn Leu Ala Val Leu Ala Asn His Thr Val Ser
                245                 250                 255

Arg Ile Gln Phe Glu Ala Arg Asn Gly Ser Gln Pro Leu Lys Ala Ile
            260                 265                 270

Gly Val Glu Trp Tyr Thr Thr Gly Gly Asp Lys Thr Ser Lys Gln Thr
        275                 280                 285
```

```
Ile Lys Ala Arg Arg Glu Ile Leu Ser Ser Gly Ala Ile Gly Ser
    290                 295                 300

Pro Lys Leu Leu Glu Val Ser Gly Ile Gly Asn Lys Ala Ile Val Thr
305                 310                 315                 320

Ala Ala Gly Val Gln Ser Leu Ile Asp Leu Pro Gly Val Gly Ser Asn
                325                 330                 335

Met Gln Asp His Val His Ala Val Thr Val Ser Thr Thr Asn Ile Asp
                340                 345                 350

Gly Tyr Thr Thr Asn Ser Val Phe Thr Asn Glu Thr Leu Ala Gln Glu
                355                 360                 365

Gln Lys Asp Leu Tyr Tyr Asn Asn Lys Thr Gly Ile Trp Thr Thr Thr
    370                 375                 380

Pro Asn Asn Leu Gly Tyr Pro Ser Pro Ser Gln Leu Phe Thr Asn Thr
385                 390                 395                 400

Thr Phe Lys Ser Gly Lys Glu Phe Ala Ala Met Ile Arg Asn Ser Thr
                405                 410                 415

Asp Lys Tyr Ala Gln Tyr Tyr Ala Ala Asn Asn Ala Thr Asn Val Glu
                420                 425                 430

Leu Leu Lys Lys Gln Tyr Ser Ile Val Ala Arg Arg Tyr Glu Glu Asn
            435                 440                 445

Tyr Ile Ser Pro Ile Glu Ile Asn Phe Thr Pro Gly Tyr Gly Gly Thr
450                 455                 460

Gly Met Ala Asp Leu Gln Asn Lys Lys Tyr Gln Thr Val Asn His Val
465                 470                 475                 480

Leu Val Ala Pro Leu Ser Arg Gly Tyr Thr His Ile Asn Ser Ser Asp
                485                 490                 495

Ile Glu Asp Pro Val Val Ile Asp Pro Gln Tyr Tyr Ser His Pro Leu
                500                 505                 510

Asp Val Asp Val His Val Ala Ser Thr Gln Leu Ala Arg Ser Ile Leu
            515                 520                 525

Asn Ala Pro Gly Leu Ala Ser Ile Asn Ser Gly Glu Val Glu Pro Gly
            530                 535                 540

Glu Lys Val Gln Ser Asp Glu Asp Val Arg Lys Trp Leu Ser Asp Asn
545                 550                 555                 560

Val Arg Ser Asp Trp His Pro Val Gly Thr Cys Ala Met Leu Pro Arg
                565                 570                 575

Lys Leu Gly Gly Val Val Asp Ser Lys Leu Lys Val Tyr Gly Thr Ala
                580                 585                 590

Asn Leu Arg Ile Val Asp Ala Ser Ile Ile Pro Leu Glu Ile Ser Ser
            595                 600                 605

His Leu Met Gln Pro Val Tyr Ala Val Ser Glu Arg Ala Ala Asp Ile
    610                 615                 620

Ile Lys Ser Ser Ser Lys Lys
625                 630

<210> SEQ ID NO 5
<211> LENGTH: 633
<212> TYPE: PRT
<213> ORGANISM: Mucor subtilissimus

<400> SEQUENCE: 5

Met Arg Leu Ser Leu Ala Ile Leu Ser Leu Thr Ser Ala Leu Val Thr
1               5                   10                  15

Val Thr Ser Ala Gln Gln Asn Gly Thr Ser Asn Asp Thr Tyr Asp Tyr
```

```
                  20                  25                  30
Val Ile Val Gly Gly Gly Val Gly Gly Leu Ser Leu Ala Ser Arg Leu
            35                  40                  45
Ser Glu Asp Lys Gly Val Thr Val Ala Val Leu Glu Ser Gly Pro Tyr
        50                  55                  60
Ala Asp Asp Arg Phe Val Val Tyr Ala Pro Gly Met Tyr Gly Gln Ala
65                  70                  75                  80
Val Gly Thr Glu Leu Cys Pro Leu Leu Pro Thr Val Pro Gln Val Gly
                85                  90                  95
Met Asn Asn Arg Thr Ile Thr Ile Ala Thr Gly Arg Leu Leu Gly Gly
            100                 105                 110
Gly Ser Ala Val Asn Gly Leu Val Trp Thr Arg Gly Ala Met Lys Asp
        115                 120                 125
Phe Asp Ala Trp Glu Glu Leu Gly Asn Pro Gly Trp Asn Gly Lys Thr
    130                 135                 140
Met Phe Lys Tyr Phe Lys Lys Ile Glu Asn Phe His Pro Pro Thr Glu
145                 150                 155                 160
Glu Gln Val Gln Tyr Gly Ala Thr Tyr Gln Lys Asn Val His Gly Ser
                165                 170                 175
Gly Gly Pro Ile Asp Ile Ser Phe Pro Val Phe Glu Phe Pro Gln Ser
            180                 185                 190
Ala Asn Trp Asn Ala Ser Leu Ala Tyr Leu Asn Phe Thr His Gln Gln
        195                 200                 205
Asp Leu Leu Asn Gly Ser Leu His Gly Tyr Ser Thr Thr Pro Asn Thr
    210                 215                 220
Leu Asn Pro Glu Thr Ala Arg Arg Ala Asp Ala Tyr Ala Gly Tyr Ile
225                 230                 235                 240
Gln Pro Asn Val Asn Arg Thr Asn Leu Ala Val Leu Ala Asn His Thr
                245                 250                 255
Val Ser Arg Ile Gln Phe Glu Lys Ser Asn Gly Ser Gln Pro Leu Lys
            260                 265                 270
Ala Ile Gly Val Glu Trp Tyr Thr Thr Gly Gly Asp Lys Ser Thr Lys
        275                 280                 285
Gln Thr Ile Lys Ala Arg Arg Glu Val Ile Ile Ser Ser Gly Ala Ile
    290                 295                 300
Gly Ser Pro Lys Leu Leu Glu Val Ser Gly Ile Gly Asn Lys Gln Ile
305                 310                 315                 320
Val Thr Ala Ala Gly Val Glu Ser Leu Ile Asp Leu Pro Gly Val Gly
                325                 330                 335
Ser Asn Met Gln Asp His Val His Ala Val Thr Val Ser Thr Thr Asn
            340                 345                 350
Ile Glu Gly Tyr Thr Thr Asn Ser Val Phe Thr Asn Glu Thr Leu Ala
        355                 360                 365
Gln Glu Gln Lys Asp Leu Tyr Tyr Asn Lys Thr Gly Ile Trp Thr
    370                 375                 380
Thr Thr Pro Asn Asn Leu Gly Tyr Pro Ser Pro Ser Gln Leu Phe Thr
385                 390                 395                 400
Asn Thr Thr Phe Arg Ser Gly Lys Gln Phe Ala Ala Met Ile Arg Asn
                405                 410                 415
Ser Thr Asp Lys Tyr Ala Gln Tyr Tyr Ala Ser Thr Lys Asn Ala Thr
            420                 425                 430
Asn Ile Gln Leu Leu Lys Lys Gln Tyr Ala Ile Val Ala Arg Arg Tyr
        435                 440                 445
```

Glu Asp Tyr Ile Ser Pro Ile Glu Ile Asn Phe Thr Pro Gly Tyr
450                 455                 460

Gly Gly Thr Gly Glu Val Asp Leu Gln Asn Asn Lys Tyr Gln Thr Val
465                 470                 475                 480

Asn His Val Leu Val Ala Pro Leu Ser Arg Gly Tyr Thr His Ile Asn
            485                 490                 495

Ser Ser Asp Ile Glu Asp Pro Val Val Ile Asp Pro Gln Tyr Tyr Ser
            500                 505                 510

His Pro Leu Asp Val Asp Val His Val Ala Ser Thr Gln Leu Ala Arg
            515                 520                 525

Ser Ile Leu Asn Ala Pro Ala Leu Ala Ile Asn Ser Gly Glu Val
530                 535                 540

Glu Pro Gly Glu Lys Ile Gln Thr Asp Gln Asp Val Arg Lys Trp Leu
545                 550                 555                 560

Ser Asp Asn Val Arg Ser Asp Trp His Pro Val Gly Thr Cys Ala Met
            565                 570                 575

Leu Pro Lys Gly Leu Gly Val Val Asp Ser Asn Leu Lys Val Tyr
            580                 585                 590

Gly Thr Ala Asn Leu Arg Val Val Asp Ala Ser Ile Ile Pro Leu Glu
            595                 600                 605

Ile Ser Ser His Leu Met Gln Pro Val Tyr Ala Val Ser Glu Arg Ala
610                 615                 620

Ala Asp Ile Ile Lys Gly Ser Arg Asn
625                 630

<210> SEQ ID NO 6
<211> LENGTH: 633
<212> TYPE: PRT
<213> ORGANISM: Mucor guilliermondii

<400> SEQUENCE: 6

Met Lys Ile Ser Ala Ala Ile Val Thr Ile Ala Thr Ala Phe Ala Ser
1               5                   10                  15

Leu Val Ser Ala Gln Ser Asn Thr Asp Thr Tyr Asp Tyr Val Ile Val
                20                  25                  30

Gly Gly Gly Val Gly Gly Leu Ala Leu Ala Asn Arg Leu Ser Glu Asn
            35                  40                  45

Lys Gln Val Thr Val Ala Val Leu Glu Ala Gly Pro Asn Ala Asn Asp
        50                  55                  60

Glu Phe Ile Val Tyr Ala Pro Gly Met Tyr Gly Gln Ala Val Gly Thr
65                  70                  75                  80

Tyr Leu Ala Pro Leu Arg Pro Thr Val Pro Gln Glu Asn Met Asn Asn
                85                  90                  95

Arg Ser Leu Ser Ile Ala Thr Gly Lys Leu Leu Gly Gly Gly Ser Ala
            100                 105                 110

Val Asn Gly Leu Val Trp Thr Arg Gly Ala Thr Lys Asp Phe Asp Ala
        115                 120                 125

Trp Glu Glu Leu Gly Asn Pro Gly Trp Asn Gly Ala Ser Met Phe Lys
130                 135                 140

Tyr Phe Lys Lys Val Glu Asn Phe Thr Ala Pro Thr Pro Tyr Gln Val
145                 150                 155                 160

Asn Tyr Gly Ala Thr Tyr Gln Lys Asn Thr His Gly Tyr Lys Gly Pro
                165                 170                 175

Val Gln Val Ser Phe Thr Asn Tyr Glu Phe Pro Gln Ser Ala His Trp

```
            180                 185                 190
Asn Gln Ser Leu Ala Ser Leu Gly Phe Asp His Leu Pro Asp Leu Leu
            195                 200                 205
Asn Gly Thr Leu Ser Gly Tyr Ser Thr Thr Pro Asn Ile Leu Asp Pro
            210                 215                 220
Asn Thr Asp Gln Arg Cys Asp Ala Tyr Ala Tyr Ile Ala Pro Tyr
225                 230                 235                 240
Thr Ala Arg Thr Asn Leu His Val Leu Ala Asn His Thr Val Ser Arg
                245                 250                 255
Ile Glu Phe Asn Gln Thr Asn Ala Asn Gln Pro Leu Val Ala Ser Gly
                260                 265                 270
Val Glu Trp Tyr Pro Thr Gly Asp Asn Thr Lys Lys Gln Thr Ile Lys
            275                 280                 285
Ala Arg Leu Glu Val Ile Val Ser Ser Gly Ser Ile Gly Ser Pro Lys
            290                 295                 300
Leu Leu Glu Ile Ser Gly Ile Gly Asn Lys Asp Ile Val Thr Ala Ala
305                 310                 315                 320
Gly Val Lys Ser Leu Leu Asp Leu Pro Gly Val Gly Ser Asn Met Gln
                325                 330                 335
Asp His Val His Ala Val Thr Val Ser Thr Thr Asn Ile Thr Gly Tyr
                340                 345                 350
Thr Thr Asp Ser Val Phe Val Asn Ser Thr Leu Ala Ser Glu Gln Arg
                355                 360                 365
Glu Gln Tyr Glu Lys Asp Lys Ser Gly Ile Trp Thr Thr Thr Pro Asn
                370                 375                 380
Asn Leu Gly Tyr Pro Thr Pro Ala Gln Leu Phe Asn Gly Thr Glu Phe
385                 390                 395                 400
Met Asp Gly Lys Ala Phe Ala Ala Arg Ile Arg Asn Ser Ser Gln Glu
                405                 410                 415
Trp Ala Gln Tyr Tyr Ala Ser Lys Asn Ala Ser Thr Val Glu Leu Leu
                420                 425                 430
Met Lys Gln Tyr Glu Ile Val Ala Ser Arg Tyr Glu Glu Asn Tyr Leu
                435                 440                 445
Ser Pro Ile Glu Ile Asn Leu Thr Pro Gly Tyr Gly Gly Val Gly Thr
                450                 455                 460
Val Asp Lys Thr Lys Asn Lys Tyr Gln Thr Val Asn His Val Leu Ile
465                 470                 475                 480
Ala Pro Leu Ser Arg Gly Phe Thr His Ile Asn Ser Ser Asp Ile Glu
                485                 490                 495
Asp Pro Val Asn Ile Asn Pro Gln Tyr Tyr Ser His Pro Met Asp Ile
                500                 505                 510
Asp Val His Val Ala Ser Thr Lys Leu Ala Arg Arg Ile Ile Asn Ala
                515                 520                 525
Pro Gly Leu Gly Asp Leu Asn Ser Gly Glu Val Glu Pro Gly Met Asp
            530                 535                 540
Ile Thr Ser Asp Ser Asp Val Arg Ala Trp Leu Ala Asn Asn Val Arg
545                 550                 555                 560
Ser Asp Trp His Pro Val Gly Thr Cys Ala Met Leu Pro Lys Glu Leu
                565                 570                 575
Gly Gly Val Val Asp Ser Ser Leu Lys Val Tyr Gly Thr Ala Asn Leu
                580                 585                 590
Arg Val Val Asp Ala Ser Ile Met Pro Leu Glu Val Ser Ser His Leu
                595                 600                 605
```

-continued

```
Met Gln Pro Thr Phe Gly Val Ala Glu Lys Ala Ala Asp Ile Ile Lys
        610                 615                 620
Ala Glu Tyr Lys Lys Gln Lys Ala Gln
625                 630
```

<210> SEQ ID NO 7
<211> LENGTH: 637
<212> TYPE: PRT
<213> ORGANISM: Circinella simplex

<400> SEQUENCE: 7

```
Met Lys Ile Ser Ala Ala Val Val Thr Ile Val Thr Ala Phe Ala Ser
1               5                   10                  15
Val Ala Thr Ala Gln Gln Gln Asn Thr Ser Glu Thr Asn Thr Tyr Asp
                20                  25                  30
Tyr Val Ile Gly Gly Gly Val Gly Gly Leu Ala Leu Ala Ser Arg
            35                  40                  45
Leu Ser Glu Asn Lys Gly Val Ser Val Ala Val Leu Glu Ala Gly Pro
        50                  55                  60
Tyr Ala Gly Asp Gln Phe Val Val Tyr Ala Pro Gly Met Tyr Gly Gln
65                  70                  75                  80
Ala Val Gly Thr Asp Leu Cys Pro Leu Leu Pro Thr Thr Pro Gln Glu
                85                  90                  95
Asn Met Gly Asn Arg Ser Leu Ser Ile Ala Thr Gly Lys Leu Leu Gly
            100                 105                 110
Gly Gly Ser Ser Val Asn Gly Leu Val Trp Thr Arg Gly Gly Leu Lys
        115                 120                 125
Asp Phe Asp Ala Trp Glu Glu Leu Gly Asn Pro Gly Trp Asn Gly Ala
130                 135                 140
Ser Met Phe Asn Tyr Phe Lys Lys Val Glu Asn Phe Thr Pro Pro Thr
145                 150                 155                 160
Pro Ala Gln Ala Ala Tyr Gly Ala Thr Tyr Gln Lys Asn Ala His Gly
                165                 170                 175
Thr Lys Gly Pro Met Asp Val Ser Phe Thr Asn Phe Glu Phe Pro Gln
            180                 185                 190
Ser Gly Asn Trp Asn Ala Ser Leu Asn Ala Val Gly Phe Thr Ala Val
        195                 200                 205
Pro Asp Leu Leu Asn Gly Thr Leu His Gly Tyr Ser Thr Thr Pro Asn
210                 215                 220
Ile Leu Asp Pro Val Asn Ala Arg Arg Ala Asp Ala Tyr Ala Gly Tyr
225                 230                 235                 240
Ile Lys Pro Tyr Ile Ser Arg Asn Asn Leu Ala Val Leu Ala Asn His
                245                 250                 255
Thr Val Ser Arg Ile Gln Phe Ala Pro Gln Ser Gly Ser Gln Pro Leu
            260                 265                 270
Arg Ala Thr Gly Val Glu Trp Tyr Pro Thr Gly Asp Lys Ser Gln Lys
        275                 280                 285
Gln Val Leu Asn Ala Arg Tyr Glu Val Ile Leu Ser Ser Gly Ala Ile
    290                 295                 300
Gly Ser Pro Lys Leu Leu Glu Leu Ser Gly Ile Gly Asn Lys Asp Ile
305                 310                 315                 320
Val Ala Ala Ala Gly Ile Gln Ser Leu Leu Asp Leu Pro Gly Val Gly
                325                 330                 335
Ser Asn Met Gln Asp His Val His Ala Val Thr Val Ser Thr Thr Asn
```

```
            340                 345                 350
Ile Thr Gly Tyr Thr Thr Asn Ser Ile Phe Thr Asn Asp Ala Leu Ala
            355                 360                 365

Ala Glu Glu Arg Gln Glu Tyr Asp Asn Asn Lys Thr Gly Ile Tyr Thr
        370                 375                 380

Thr Thr Pro Asn Asn Leu Gly Tyr Pro Ser Pro Ser Gln Leu Phe Arg
385                 390                 395                 400

Gly Thr Ser Phe Val Ser Gly Lys Gln Phe Ala Ala Arg Ile Arg Asn
                405                 410                 415

Thr Thr Asp Glu Trp Ala Glu Arg Tyr Ala Ala Asp Asn Ala Thr Asn
            420                 425                 430

Ala Glu Leu Leu Lys Lys Gln Tyr Ala Ile Ile Ala Ser Arg Tyr Glu
        435                 440                 445

Glu Asp Tyr Leu Ser Pro Ile Glu Ile Asn Leu Thr Pro Gly Tyr Gly
    450                 455                 460

Gly Thr Ala Asp Val Asp Leu Thr Asn Asn Lys Tyr Gln Thr Val Asn
465                 470                 475                 480

His Val Leu Ile Ala Pro Leu Ser Arg Gly Tyr Thr His Ile Lys Ser
                485                 490                 495

Ala Asp Ile Glu Asp Ala Val Asp Ile Asn Pro Gln Tyr Tyr Ser His
            500                 505                 510

Pro Met Asp Val Asp Val His Val Ala Ser Thr Lys Leu Ala Arg Glu
        515                 520                 525

Ile Ile Ser Ala Ser Pro Gly Leu Gly Asp Ile Asn Ser Gly Glu Thr
    530                 535                 540

Glu Pro Gly Lys Glu Ile Thr Ser Asp Ser Asp Val Arg Lys Trp Leu
545                 550                 555                 560

Ala Asp Asn Val Arg Ser Asp Trp His Pro Val Gly Thr Cys Ala Met
                565                 570                 575

Leu Pro Lys Glu Leu Gly Gly Val Val Asp Pro Asn Leu Lys Val Tyr
            580                 585                 590

Gly Thr Ser Asn Leu Arg Val Val Asp Ala Ser Val Met Pro Leu Glu
        595                 600                 605

Val Ser Ser His Leu Met Gln Pro Thr Phe Gly Ile Ala Glu Lys Ala
    610                 615                 620

Ala Asp Ile Ile Lys Ser Ala Asn Lys Lys Arg Ser Asn
625                 630                 635

<210> SEQ ID NO 8
<211> LENGTH: 637
<212> TYPE: PRT
<213> ORGANISM: Circinella

<400> SEQUENCE: 8

Met Lys Ile Ser Ala Ala Val Val Thr Ile Val Thr Ala Phe Ala Ser
1               5                   10                  15

Val Ala Thr Ala Gln Gln Gln Asn Thr Ser Glu Thr Asn Thr Tyr Asp
            20                  25                  30

Tyr Val Ile Val Gly Gly Gly Val Gly Gly Leu Ala Leu Ala Ser Arg
        35                  40                  45

Leu Ser Glu Asn Lys Gly Val Ser Val Ala Val Leu Glu Ala Gly Pro
    50                  55                  60

Tyr Ala Gly Asp Gln Phe Val Val Tyr Ala Pro Gly Met Tyr Gly Gln
65                  70                  75                  80
```

```
Ala Val Gly Thr Asp Leu Cys Pro Leu Leu Pro Thr Thr Pro Gln Glu
                85                  90                  95

Asn Met Gly Asn Arg Ser Leu Ser Ile Ala Thr Gly Lys Leu Leu Gly
            100                 105                 110

Gly Gly Ser Ser Val Asn Gly Leu Val Trp Thr Arg Gly Gly Leu Lys
        115                 120                 125

Asp Phe Asp Ala Trp Glu Glu Leu Gly Asn Pro Gly Trp Asn Gly Ala
    130                 135                 140

Ser Met Phe Asn Tyr Phe Lys Lys Val Glu Asn Phe Thr Pro Pro Thr
145                 150                 155                 160

Pro Ala Gln Ala Ala Tyr Gly Ala Thr Tyr Gln Lys Asn Ala His Gly
                165                 170                 175

Thr Lys Gly Pro Met Asp Val Ser Phe Thr Asn Phe Glu Phe Pro Gln
            180                 185                 190

Ser Gly Asn Trp Asn Ala Ser Leu Asn Ala Val Gly Phe Thr Ala Val
        195                 200                 205

Pro Asp Leu Leu Asn Gly Thr Leu His Gly Tyr Ser Thr Thr Pro Asn
    210                 215                 220

Ile Leu Asp Pro Val Asn Ala Arg Arg Ala Asp Ala Tyr Ala Gly Tyr
225                 230                 235                 240

Ile Lys Pro Tyr Ile Ser Arg Asn Asn Leu Ala Val Leu Ala Asn His
                245                 250                 255

Thr Val Ser Arg Ile Gln Phe Ala Pro Gln Ser Gly Ser Gln Pro Leu
            260                 265                 270

Arg Ala Thr Gly Val Glu Trp Tyr Pro Thr Gly Asp Lys Ser Gln Lys
        275                 280                 285

Gln Val Leu Asn Ala Arg Tyr Glu Val Ile Leu Ser Ser Gly Ala Ile
    290                 295                 300

Gly Ser Pro Lys Leu Leu Glu Leu Ser Gly Ile Gly Asn Lys Asp Ile
305                 310                 315                 320

Val Ala Ala Ala Gly Ile Gln Ser Leu Leu Asp Leu Pro Gly Val Gly
                325                 330                 335

Ser Asn Met Gln Asp His Val His Ala Val Thr Val Ser Thr Thr Asn
            340                 345                 350

Ile Thr Gly Tyr Thr Thr Asn Ser Ile Phe Thr Asn Asp Ala Leu Ala
        355                 360                 365

Ala Glu Glu Arg Gln Glu Tyr Asp Asn Asn Lys Thr Gly Ile Tyr Thr
    370                 375                 380

Thr Thr Pro Asn Leu Gly Tyr Pro Ser Pro Ser Gln Leu Phe Arg
385                 390                 395                 400

Gly Thr Ser Phe Val Ser Gly Lys Gln Phe Ala Ala Arg Ile Arg Asn
                405                 410                 415

Thr Thr Asp Glu Trp Ala Glu Arg Tyr Ala Ala Asp Asn Ala Thr Asn
            420                 425                 430

Ala Glu Leu Leu Lys Lys Gln Tyr Ala Ile Ile Ala Ser Arg Tyr Glu
        435                 440                 445

Glu Asp Tyr Leu Ser Pro Ile Glu Ile Asn Leu Thr Pro Gly Tyr Gly
    450                 455                 460

Gly Thr Ala Asp Val Asp Leu Thr Asn Asn Lys Tyr Gln Thr Val Asn
465                 470                 475                 480

His Val Leu Ile Ala Pro Leu Ser Arg Gly Tyr Thr His Ile Lys Ser
                485                 490                 495

Ala Asp Ile Glu Asp Ala Val Asp Ile Asn Pro Gln Tyr Tyr Ser His
```

```
                500                 505                 510
Pro Met Asp Val Asp Val His Val Ala Ser Thr Lys Leu Ala Arg Glu
    515                 520                 525

Ile Ile Ser Ala Ser Pro Gly Leu Gly Asp Ile Asn Ser Gly Glu Thr
    530                 535                 540

Glu Pro Gly Lys Glu Ile Thr Ser Asp Ser Asp Val Arg Lys Trp Leu
545                 550                 555                 560

Ala Asp Asn Val Arg Ser Asp Trp His Pro Val Gly Thr Cys Ala Met
                565                 570                 575

Leu Pro Lys Glu Leu Asp Gly Val Val Asp Pro Asn Leu Lys Val Tyr
            580                 585                 590

Gly Thr Ser Asn Leu Arg Val Val Asp Ala Ser Val Met Pro Leu Glu
        595                 600                 605

Val Ser Ser His Leu Met Gln Pro Thr Phe Gly Ile Ala Glu Lys Ala
    610                 615                 620

Ala Asp Ile Ile Lys Ser Ala Asn Lys Lys Arg Ser Asn
625                 630                 635

<210> SEQ ID NO 9
<211> LENGTH: 644
<212> TYPE: PRT
<213> ORGANISM: Mucor circinelloides

<400> SEQUENCE: 9

Met Lys Ile Ser Ala Ala Ile Ile Thr Val Val Thr Ala Phe Ala Ser
1               5                   10                  15

Phe Ala Ser Ala Gln Gln Asp Thr Asn Asn Thr Ser Ser Thr Asp Thr
            20                  25                  30

Tyr Asp Tyr Val Ile Val Gly Gly Gly Val Ala Gly Leu Ala Leu Ala
        35                  40                  45

Ser Arg Ile Ser Glu Asn Lys Asp Val Thr Val Ala Val Leu Glu Ser
    50                  55                  60

Gly Pro Asn Ala Glu Asp Gln Phe Val Val Tyr Ala Pro Gly Met Tyr
65              70                  75                  80

Gly Gln Ala Val Gly Thr Glu Leu Ala Pro Leu Val Pro Thr Thr Pro
            85                  90                  95

Gln Glu Asn Met Gly Asn Arg Ser Leu Ser Ile Ala Thr Gly Arg Leu
        100                 105                 110

Leu Gly Gly Gly Ser Ala Val Asn Gly Leu Val Trp Thr Arg Gly Gly
    115                 120                 125

Leu Lys Asp Tyr Asp Ala Trp Glu Glu Leu Gly Asn Pro Gly Trp Asn
130                 135                 140

Gly Ser Asn Leu Phe Lys Tyr Phe Lys Lys Val Glu Asn Phe His Pro
145                 150                 155                 160

Pro Thr Pro Ala Gln Ile Glu Tyr Gly Ala Thr Tyr Gln Lys Ser Ala
                165                 170                 175

His Gly Lys Asn Gly Pro Ile Asp Val Ser Phe Thr Asn Phe Glu Phe
            180                 185                 190

Pro Gln Ser Ala Lys Trp Asn Ala Ser Leu Glu Ser Leu Asp Phe Thr
        195                 200                 205

Ala Leu Pro Asp Leu Leu Asn Gly Thr Leu Ala Gly Tyr Ser Thr Thr
    210                 215                 220

Pro Asn Ile Leu Asp Pro Glu Thr Ala Arg Arg Val Asp Ala Tyr Ala
225                 230                 235                 240
```

```
Gly Tyr Ile Val Pro Tyr Met Gly Arg Asn Asn Leu Asn Val Leu Ala
            245                 250                 255

Asn His Thr Val Ser Arg Ile Gln Phe Ala Pro Gln Asn Gly Ser Glu
            260                 265                 270

Pro Leu Lys Ala Thr Gly Val Glu Trp Tyr Pro Thr Gly Asn Lys Asp
            275                 280                 285

Gln Lys Gln Thr Ile Lys Ala Arg Tyr Glu Val Ile Ile Ser Ser Gly
            290                 295                 300

Ala Ile Gly Ser Pro Lys Leu Leu Glu Ile Ser Gly Ile Gly Asn Lys
305                 310                 315                 320

Asp Ile Val Thr Ala Ala Gly Val Glu Ser Leu Ile Asp Leu Pro Gly
                325                 330                 335

Val Gly Ala Asn Met Gln Asp His Val His Ala Val Thr Val Ser Thr
            340                 345                 350

Thr Asn Ile Asp Gly Tyr Thr Thr Asn Ser Val Phe Thr Asn Glu Thr
            355                 360                 365

Leu Ala Gln Glu Gln Arg Glu Gln Tyr Glu Ala Asn Lys Thr Gly Ile
            370                 375                 380

Trp Thr Thr Thr Pro Asn Asn Leu Gly Tyr Pro Thr Pro Glu Gln Leu
385                 390                 395                 400

Phe Asn Gly Thr Glu Phe Val Ser Gly Lys Glu Phe Ala Ala Lys Ile
                405                 410                 415

Arg Asn Ser Thr Asp Glu Trp Ala Asn Tyr Tyr Ala Ser Thr Asn Ala
            420                 425                 430

Thr Asn Ala Asp Leu Leu Lys Lys Gln Tyr Ala Ile Val Ala Ser Arg
            435                 440                 445

Tyr Glu Glu Asn Tyr Leu Ser Pro Ile Glu Ile Asn Leu Thr Pro Gly
            450                 455                 460

Tyr Gly Gly Thr Gly Ser Pro Asp Leu Gln Asn Asn Lys Tyr Gln Thr
465                 470                 475                 480

Val Asn His Val Leu Ile Ala Pro Leu Ser Arg Gly Tyr Ala His Ile
                485                 490                 495

Asn Ser Ser Asp Ile Glu Glu Pro Ser Val Ile Asn Pro Gln Tyr Tyr
            500                 505                 510

Ser His Pro Leu Asp Ile Asp Val His Val Ala Ser Thr Lys Leu Ala
            515                 520                 525

Arg Glu Ile Ile Thr Ala Ser Pro Gly Leu Gly Asp Leu Asn Ser Gly
            530                 535                 540

Glu Val Glu Pro Gly Met Asn Val Thr Ser Glu Asp Asp Leu Arg Ser
545                 550                 555                 560

Trp Leu Ser Asn Asn Val Arg Ser Asp Trp His Pro Val Gly Thr Cys
                565                 570                 575

Ala Met Leu Pro Gln Glu Leu Gly Gly Val Val Ser Pro Ala Leu Met
            580                 585                 590

Val Tyr Gly Thr Ser Asn Leu Arg Val Val Asp Ala Ser Ile Met Pro
            595                 600                 605

Leu Glu Val Ser Ser His Leu Met Gln Pro Thr Tyr Gly Ile Ala Glu
            610                 615                 620

Lys Ala Ala Asp Ile Ile Lys Asn Tyr Tyr Lys Ser Gln Tyr Ser Gly
625                 630                 635                 640

Ala Gly Lys Asn

<210> SEQ ID NO 10
```

```
<211> LENGTH: 641
<212> TYPE: PRT
<213> ORGANISM: Mucor prainii

<400> SEQUENCE: 10

Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Thr Asp Thr Tyr
            20                  25                  30

Asp Tyr Val Ile Val Gly Gly Val Ala Gly Leu Ala Leu Ala Ser
            35                  40                  45

Arg Ile Ser Glu Asn Lys Asp Val Thr Val Ala Val Leu Glu Ser Gly
50                  55                  60

Pro Tyr Ala Gly Asp Arg Phe Val Val Tyr Ala Pro Gly Met Tyr Gly
65                  70                  75                  80

Gln Ala Val Gly Thr Asp Leu Ala Pro Leu Ile Pro Thr Thr Pro Gln
                85                  90                  95

Glu Asn Met Gly Asn Arg Ser Leu Thr Ile Ala Thr Gly Arg Leu Leu
            100                 105                 110

Gly Gly Gly Ser Ala Ile Asn Gly Leu Val Trp Thr Arg Gly Gly Leu
        115                 120                 125

Lys Asp Tyr Asp Ala Trp Glu Glu Leu Gly Asn Pro Gly Trp Asn Gly
130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Ala His
                165                 170                 175

Gly Lys Lys Gly Pro Ile Asp Val Ser Phe Thr Asn Tyr Glu Phe Ser
            180                 185                 190

Gln Ser Ala Ser Trp Asn Ala Ser Leu Glu Thr Leu Asp Phe Thr Ala
        195                 200                 205

Leu Pro Asp Ile Leu Asn Gly Thr Leu Ala Gly Tyr Ser Thr Thr Pro
210                 215                 220

Asn Ile Leu Asp Pro Glu Thr Val Arg Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255

His Thr Val Ser Arg Ile Gln Phe Ala Pro Lys Asn Gly Ser Glu Pro
            260                 265                 270

Leu Lys Ala Thr Gly Val Glu Trp Tyr Pro Thr Gly Asn Lys Asn Gln
        275                 280                 285

Lys Gln Ile Ile Lys Ala Arg Tyr Glu Val Ile Ile Ser Ser Gly Ala
290                 295                 300

Ile Gly Ser Pro Lys Leu Leu Glu Ile Ser Gly Ile Gly Asn Lys Asp
305                 310                 315                 320

Ile Val Ser Ala Ala Gly Val Glu Ser Leu Ile Asp Leu Pro Gly Val
                325                 330                 335

Gly Ser Asn Met Gln Asp His Val His Ala Ile Thr Val Ser Thr Thr
            340                 345                 350

Asn Ile Thr Gly Tyr Thr Thr Asn Ser Val Phe Val Asn Glu Thr Leu
        355                 360                 365

Ala Gln Glu Gln Arg Glu Glu Tyr Glu Ala Asn Lys Thr Gly Ile Trp
370                 375                 380

Ala Thr Cys Pro Asn Asn Leu Gly Tyr Pro Thr Pro Glu Gln Leu Phe
```

```
                385                 390                 395                 400
Asn Gly Thr Glu Phe Val Ser Gly Lys Glu Phe Ala Asp Lys Ile Arg
                    405                 410                 415
Asn Ser Thr Asp Glu Trp Ala Asn Tyr Tyr Ala Ser Thr Asn Ala Ser
                420                 425                 430
Asn Val Glu Leu Leu Lys Lys Gln Tyr Ala Ile Val Ala Ser Arg Tyr
            435                 440                 445
Glu Glu Asn Tyr Leu Ser Pro Ile Glu Ile Asn Phe Thr Pro Gly Tyr
450                 455                 460
Glu Gly Ser Gly Asn Val Asp Leu Gln Asn Asn Lys Tyr Gln Thr Val
465                 470                 475                 480
Asn His Val Leu Ile Ala Pro Leu Ser Arg Gly Tyr Thr His Ile Asn
                    485                 490                 495
Ser Ser Asp Val Glu Asp His Ser Val Ile Asn Pro Gln Tyr Tyr Ser
                500                 505                 510
His Pro Met Asp Ile Asp Val His Ile Ala Ser Thr Lys Leu Ala Arg
            515                 520                 525
Glu Ile Ile Thr Ala Ser Pro Gly Leu Gly Asp Ile Asn Ser Gly Glu
    530                 535                 540
Ile Glu Pro Gly Met Asn Ile Thr Ser Asp Asp Val Arg Lys Trp
545                 550                 555                 560
Leu Ser Asn Asn Val Arg Ser Asp Trp His Pro Val Gly Thr Cys Ala
                    565                 570                 575
Met Leu Pro Lys Glu Leu Gly Gly Val Val Ser Pro Ala Leu Met Val
                580                 585                 590
Tyr Gly Thr Ser Asn Leu Arg Val Val Asp Ala Ser Ile Met Pro Leu
            595                 600                 605
Glu Val Ser Ser His Leu Met Gln Pro Thr Tyr Gly Ile Ala Glu Lys
    610                 615                 620
Ala Ala Asp Ile Ile Lys Asn Phe Tyr Lys Thr Gln His Lys Asn Gln
625                 630                 635                 640
Asn

<210> SEQ ID NO 11
<211> LENGTH: 1926
<212> TYPE: DNA
<213> ORGANISM: Mucor prainii

<400> SEQUENCE: 11
atgaagatca cagctgccat tatcactgtt gccacagcat ttgcttcttt tgcttctgct      60
caacaagaca caaattcttc ctcaactgat acttatgatt atgttatcgt tggcggcggt     120
gtagctggtt tggctttggc tagtcgtatc tctgaaaaca aggatgtcac tgttgctgtt     180
ctcgagtccg gtccttatgc cggtgataga tttgttgttt atgctcctgg catgtatggc     240
caagctgttg gcactgatct cgctcctctc attcctacta ctcctcaaga aaatatgggc     300
aacagaagtc tcacaatcgc tactggtaga ttgctcggtg gtggcagtgc tattaatggt     360
ctcgtttgga cccgtggtgg cttgaaggat tacgatgctt gggaggagct cggtaaccct     420
ggatggaacg tgccaacttt gttcaagtac tttaagaagg tcgaaaactt cactcctcct     480
actcctgccc aaattgaata cggcgctact tatcagaaaa gtgctcatgg caagaaggga     540
cctattgatg tctctttcac gaactacgag ttctctcaat ctgctagctg aacgcctca     600 ctcgaaaccc ttgatttcac tgcacttcct gatatcttga acggtacttt ggccggttac     660
```

```
tctaccactc ccaacatttt ggaccctgag actgttcgac gtgttgattc ctatactggt      720
tacattgctc cttacactag ccgtaacaac ctcaatgttt tggccaacca taccgtctcc      780
cgcattcaat ttgctcccaa gaatggtagc gaacctctca aggctaccgg tgttgaatgg      840
tatcccactg caacaagaa tcaaaagcaa attatcaagg cccgttatga agttatcatc       900
tcatctggtg ccattggtag tcctaagctt ttggaaatct ctggtatcgg taataaggat      960
atcgtctctg ctgctggtgt cgagtccttg attgacttgc ctggcgttgg ttccaacatg     1020
caagatcacg ttcatgctat cactgtctct actaccaata ttactggcta tactaccaac     1080
agcgtctttg tcaatgaaac ccttgcccaa gaacaaagag aagaatatga agccaacaag     1140
actggtatct gggctacttg tcccaacaac ctcggttatc ctacgcccga caactcttc      1200 aatggcaccg aattcgtttc tggaaaggag tttgctgaca agattcgtaa ctctactgat     1260
gaatgggcca actattatgc ttccaccaac gcctccaatg tcgagttatt aaagaagcaa     1320
tatgctattg tcgcctctcg ttacgaagag aactacttgt ctcctattga aatcaacttc     1380
actcctggtt atgagggtag cggtaatgtc gatttgcaaa acaacaagta ccaaactgtc     1440
aaccatgtct tgattgctcc tttaagtcgt ggttatactc acattaactc ttctgatgtg     1500
gaggatcatt ctgtcattaa tccccaatac tactctcatc tatggatat tgatgtccat      1560 atcgcttcca ctaaacttgc tcgcgaaatc atcactgcct ctcccggtct tggtgacatt     1620
aacagtggcg aaatcgaacc cggtatgaat attacttctg acgacgacgt tagaaaatgg     1680
ttgagtaata atgtccgttc tgactggcat cctgttggta cttgtgctat gcttcccaag     1740
gaattaggtg tgttgtcag ccccgctctc atggtttacg gcacttccaa cttgcgtgtt      1800
gttgatgctt cgattatgcc cctcgaagtc tcttctcatt tgatgcaacc cacctacggt     1860
attgctgaga aggctgctga cattattaag aatttctaca agactcaaca caagaaccaa     1920
aattag                                                                1926
```

<210> SEQ ID NO 12
<211> LENGTH: 221
<212> TYPE: PRT
<213> ORGANISM: Myriococcum thermophilum

<400> SEQUENCE: 12

```
Met Arg Thr Ser Ser Arg Leu Ile Gly Ala Leu Ala Ala Ala Leu Leu
1               5                   10                  15

Pro Ser Ala Leu Ala Gln Asn Asn Val Pro Asn Thr Phe Thr Asp Pro
            20                  25                  30

Asp Ser Gly Ile Thr Phe Asn Thr Trp Gly Leu Asp Glu Asp Ser Pro
        35                  40                  45

Gln Thr Gln Gly Gly Phe Thr Phe Gly Val Ala Leu Pro Ser Asp Ala
    50                  55                  60

Leu Thr Thr Asp Ala Ser Glu Phe Ile Gly Tyr Leu Lys Cys Ala Arg
65                  70                  75                  80

Asn Asp Glu Ser Gly Trp Cys Gly Ile Ser Leu Gly Gly Pro Met Thr
                85                  90                  95

Asn Ser Leu Leu Ile Thr Ala Trp Pro His Glu Asp Thr Val Tyr Thr
            100                 105                 110

Ser Leu Arg Phe Ala Thr Gly Tyr Ala Met Pro Asp Val Tyr Glu Gly
        115                 120                 125

Asp Ala Glu Ile Thr Gln Val Ser Ser Ser Val Asn Ser Thr His Phe
    130                 135                 140
```

Ser Leu Ile Phe Arg Cys Lys Asn Cys Leu Gln Trp Ser His Gly Gly
145                 150                 155                 160

Ser Ser Gly Gly Ala Ser Thr Ser Gly Gly Val Leu Val Leu Gly Trp
            165                 170                 175

Val Gln Ala Phe Asp Asp Pro Gly Asn Pro Thr Cys Pro Glu Gln Ile
            180                 185                 190

Thr Leu Gln Gln His Asp Asn Gly Met Gly Ile Trp Gly Ala Gln Leu
            195                 200                 205

Asn Thr Asp Ala Ala Ser Pro Ser Tyr Thr Asp Trp Ala
            210                 215                 220

<210> SEQ ID NO 13
<211> LENGTH: 663
<212> TYPE: DNA
<213> ORGANISM: Myriococcum thermophilum

<400> SEQUENCE: 13

```
atgcgcacct cttctcgtct tattggtgca ttggctgctg cactcctgcc ttctgctctt    60
gcacagaaca atgttccgaa cacattcacg gatcctgaca gtggaatcac ttttaataca   120
tggggcctcg atgaggactc cccgcagaca caaggcggtt tcacgtttgg agtcgcgctt   180
cctagcgatg ccttgaccac tgacgcttcg gagttcatcg gctatttgaa gtgcgcacga   240
aacgatgaat ccggatggtg tgggatctct ctcggagggc aatgacaaa ttcgcttttg    300
attacggctt ggccgcatga agacacggtt tacacctcac tcagattcgc gaccggttac   360
gccatgccag atgtctatga gggagacgct gaaatcaccc aagttagctc gtcagtcaac   420
agtactcatt tctccttgat ttttcgatgc aagaattgtc tccaatggtc ccacggcggt   480
agttccggag gggcaagtac ttccggcggt gttttggtcc tgggatgggt ccaggcgttc   540
gatgaccctg gaaaccccac tgcccagag caaatcactc tgcagcaaca cgataacggc    600
atgggtattt ggggcgctca gcttaataca gatgcggcct ctccgagcta tacggactgg   660
gct                                                                663
```

<210> SEQ ID NO 14
<211> LENGTH: 220
<212> TYPE: PRT
<213> ORGANISM: Corynascud thermophiles

<400> SEQUENCE: 14

Met Lys Leu Leu Ser Arg Val Gly Ala Thr Ala Leu Ala Ala Thr Leu
1               5                   10                  15

Ser Leu Lys Gln Cys Ala Ala Gln Met Thr Glu Gly Thr Tyr Thr His
            20                  25                  30

Glu Ala Thr Gly Ile Thr Phe Lys Thr Trp Thr Pro Ser Asp Gly Ser
        35                  40                  45

Thr Phe Thr Phe Gly Leu Ala Leu Pro Gly Asp Ala Leu Thr Asn Asp
    50                  55                  60

Ala Thr Glu Tyr Ile Gly Leu Leu Arg Cys Gln Ile Thr Asp Pro Ser
65                  70                  75                  80

Ser Pro Gly Tyr Cys Gly Ile Ser His Gly Gln Ser Gly Gln Met Thr
                85                  90                  95

Gln Ala Leu Leu Leu Val Ala Trp Ala Ser Glu Asp Val Val Tyr Thr
            100                 105                 110

Ser Phe Arg Tyr Ala Thr Gly Tyr Thr Leu Pro Glu Leu Tyr Thr Gly
        115                 120                 125

Asp Ala Lys Leu Thr Gln Ile Ala Ser Ser Val Ser Gly Asp Ser Phe
    130                 135                 140

Glu Val Leu Phe Arg Cys Glu Asn Cys Phe Ser Trp Asp Gln Asn Gly
145                 150                 155                 160

Ala Thr Gly Ser Val Ser Thr Ser Asn Gly Ala Leu Val Leu Gly Tyr
                165                 170                 175

Ala Ala Ser Lys Ser Gly Leu Thr Gly Ala Thr Cys Pro Asp Thr Ala
                180                 185                 190

Glu Phe Gly Phe His Asn Asn Gly Phe Gly Gln Trp Gly Ala Val Leu
                195                 200                 205

Glu Gly Ala Thr Ser Asp Ser Tyr Glu Glu Trp Ala
    210                 215                 220

<210> SEQ ID NO 15
<211> LENGTH: 660
<212> TYPE: DNA
<213> ORGANISM: Corynascud thermophiles

<400> SEQUENCE: 15
atgaagctcc tgtcgagagt cggcgcaact gcgttggccg ctacactctc actgaaacaa      60
tgcgcagcgc agatgaccga gggcacgtac acccatgaag ctactggaat cacattcaag     120
acttggacac cgtcggatgg atcaacgttc acctttggtc ttgccttgcc tggagatgct     180
ctcacgaacg acgcaaccga gtacatcggc cttttgcgat gccagattac cgatccgtcc     240
tctcctgggt attgtggcat ctcgcacggc cagtcaggac aaatgacaca ggctctcctg     300
cttgtcgcct gggcttctga ggacgtcgtg tacacgagct ccgctacgc aacgggttat      360 accctccccg aactgtatac tggagatgct aagttgacac aaattgcaag ctcggtttct     420
ggtgactcct tcgaggtcct ctttcgttgc gaaaactgtt tttcttggga tcagaatggg     480
gctacgggct cagtcagtac ctctaatgga gcattggtgc tgggatatgc tgcttctaag     540
agcggtctga ctggagcgac atgcccggat acagccgagt tcggctttca taacaatggc     600
ttcggtcaat ggggtgcggt cctggaagga gcaacctcgg actcatatga ggaatgggca     660

<210> SEQ ID NO 16
<211> LENGTH: 222
<212> TYPE: PRT
<213> ORGANISM: Apergillus sojae

<400> SEQUENCE: 16

Met Lys Leu Val Asn Arg Leu Leu Ala Ser Phe Leu Ser Ala Ser Thr
1               5                   10                  15

Val Leu Gln Ser Cys Trp Ala Gln Ser Gly Thr Pro Val Ala Tyr Thr
                20                  25                  30

Asp Thr Glu Thr Gly Ile Thr Phe Asp Thr Trp Ser Val Pro Ala Gly
            35                  40                  45

Thr Gly Thr Gly Gly Leu Val Phe Gly Val Ala Leu Pro Gly Ser Ala
        50                  55                  60

Leu Thr Thr Asp Ala Thr Glu Phe Ile Gly Tyr Leu Gln Cys Ala Ser
65                  70                  75                  80

Gln Asn Ala Ser Ser Ala Gly Trp Cys Gly Ile Ser Leu Gly Gly Gly
                85                  90                  95

Met Asn Asn Asn Leu Leu Phe Leu Ala Tyr Pro Tyr Glu Asp Thr Ile
                100                 105                 110

Leu Thr Ser Leu Arg Phe Gly Ser Gly Tyr Ser Met Pro Gly Val Tyr
            115                 120                 125

Thr Gly Asn Ala Asn Val Thr Gln Ile Ser Ser Ile Asn Ala Thr
    130                 135                 140

His Phe Thr Leu Leu Phe Arg Cys Glu Asn Cys Leu Thr Trp Asp Gln
145                 150                 155                 160

Asp Gly Gln Thr Gly Asn Ala Thr Thr Ser Lys Gly Arg Leu Val Leu
                165                 170                 175

Gly Trp Ala Gln Ser Thr Glu Ser Pro Ser Asn Pro Ser Cys Pro Asp
            180                 185                 190

Asn Ile Ser Leu Ala Gln His Asp Asn Gln Gly Ile Ile Ser Ala Thr
        195                 200                 205

Leu Asp Glu Asn Ala Ala Ser Glu Ser Tyr Glu Asp Trp Val
    210                 215                 220

<210> SEQ ID NO 17
<211> LENGTH: 785
<212> TYPE: DNA
<213> ORGANISM: Apergillus sojae

<400> SEQUENCE: 17
atgaagctcg ttaaccgttt gctcgcttca ttcctgtcag cgagcaccgg tgagtggtgg      60
cctatcgagc taatgttgct ctctcttcgtc tgacttttct tggcagtgtt gcagtcatgc    120
tgggctcagt ccggcacacc ggttgcctac acggatactg agacgggcat acgtttgac     180 acgtggtcgg tacctgctgg tacgggtacg ggtggtctcg tcttcggtgt agccctgccg    240
ggttcggcat tgaccaccga tgcgacgag tttatcggtt acctggtgag gatctcgagc     300
taatcatgac cgctctgaag tggcgctaaa cgttctaatg tttcaagcaa tgtgcgtccc    360
aaaatgcctc gtccgctggc tggtgtggca tttccttggg tggtggcatg aacaacaatc    420
tcttgttctt ggcctatccg tacgaggata ccatcttgac ctccctgcga ttcggctcgg    480
gctatagcat gcccggggtc tataccggca atgccaacgt cacccagatt tcttcaagca    540
tcaatgccac tcactttacg ttgctttttcc gttgcgagaa ttgtctgacc tgggaccaag    600
atggtcaaac cggaaacgcg accacaagca agggtaggtt agtcctggga tgggcacagt    660
ctacggagag cccgtcgaac ccgtcctgtc cggacaatat cagcctggcg cagcacgaca    720
accagggtat tatctcagcc actctggatg agaatgcagc cagtgagtcc tacgaggact    780
gggtc                                                                785

<210> SEQ ID NO 18
<211> LENGTH: 224
<212> TYPE: PRT
<213> ORGANISM: Hypoxylon haematostroma

<400> SEQUENCE: 18

Met Gly Arg Leu Gly Ser Leu Ala Lys Leu Leu Leu Ala Val Gly Leu
1               5                   10                  15

Asn Val Gln Gln Cys Phe Gly Gln Asn Gly Pro Pro Thr Pro Tyr Thr
            20                  25                  30

Asp Ser Glu Thr Gly Ile Thr Phe Ala Thr Trp Ser Gly Gly Asn Gly
        35                  40                  45

Leu Ala Pro Trp Gly Gly Leu Thr Phe Gly Val Ala Leu Pro Glu Asn
    50                  55                  60

Ala Leu Thr Thr Asp Ala Thr Glu Leu Ile Gly Tyr Leu Lys Cys Gly
65                  70                  75                  80

Ser Asn Gly Thr Thr Thr Asp Ala Trp Cys Gly Leu Ser Phe Gly Gly

```
            85                  90                  95
Pro Met Thr Asn Ser Leu Leu Met Ala Trp Pro His Glu Asp Glu
                100                 105                 110

Ile Leu Thr Ser Phe Arg Phe Ala Ser Gly Tyr Thr Arg Pro Asp Leu
            115                 120                 125

Tyr Thr Gly Asp Ala Lys Leu Thr Gln Ile Ser Ser Thr Ile Asp Lys
    130                 135                 140

Asp His Phe Thr Leu Ile Phe Arg Cys Gln Asn Cys Leu Ala Trp Asn
145                 150                 155                 160

Gln Asp Gly Ala Ser Gly Ser Ala Ser Thr Ser Ala Gly Ser Leu Ile
                165                 170                 175

Leu Gly Trp Ala Ser Ala Leu Arg Ala Pro Thr Asn Ala Gly Cys Pro
            180                 185                 190

Ala Glu Ile Asn Phe Asn Phe His Asn Asn Gly Gln Met Ile Trp Gly
            195                 200                 205

Ala Thr Leu Asp Glu Ser Ala Ala Asn Pro Ser Tyr Ser Glu Trp Ala
    210                 215                 220
```

<210> SEQ ID NO 19
<211> LENGTH: 223
<212> TYPE: PRT
<213> ORGANISM: Chaetomium attrobruneum

<400> SEQUENCE: 19

```
Met Arg Pro Ser Ser Arg Phe Val Gly Ala Leu Ala Ala Ala Ser
1               5                   10                  15

Phe Leu Pro Ser Ala Leu Ala Gln Asn Ala Ala Val Thr Phe Thr
            20                  25                  30

Asp Pro Asp Thr Gly Ile Val Phe Asn Ser Trp Gly Leu Ala Asn Gly
        35                  40                  45

Ala Pro Gln Thr Gln Gly Gly Phe Thr Phe Gly Val Ala Leu Pro Ser
    50                  55                  60

Asp Ala Leu Thr Thr Asp Ala Thr Glu Phe Ile Gly Tyr Leu Glu Cys
65                  70                  75                  80

Ala Ser Ala Asp Asn Gln Gly Trp Cys Gly Val Ser Met Gly Gly Pro
                85                  90                  95

Met Thr Asn Ser Leu Leu Ile Thr Ala Trp Pro His Glu Asp Asn Val
                100                 105                 110

Tyr Thr Ser Leu Arg Phe Ala Thr Gly Tyr Ala Met Pro Asp Val Tyr
            115                 120                 125

Ser Gly Asp Ala Thr Ile Thr Gln Ile Ser Ser Ile Asn Ala Thr
    130                 135                 140

His Phe Lys Leu Ile Phe Arg Cys Gln Asn Cys Leu Gln Trp Thr His
145                 150                 155                 160

Asp Gly Ala Ser Gly Gly Ala Ser Thr Ser Ala Gly Val Leu Val Leu
                165                 170                 175

Gly Trp Val Gln Ala Phe Pro Ser Pro Gly Asn Pro Thr Cys Pro Asp
            180                 185                 190

Gln Ile Thr Leu Glu Gln His Asn Asn Gly Met Gly Ile Trp Gly Ala
            195                 200                 205

Val Met Asp Ser Asn Val Ala Asn Pro Ser Tyr Thr Glu Trp Ala
    210                 215                 220
```

<210> SEQ ID NO 20
<211> LENGTH: 223

<212> TYPE: PRT
<213> ORGANISM: Neurospora crassa

<400> SEQUENCE: 20

```
Met Arg Thr Thr Ser Ala Phe Leu Ser Gly Leu Ala Ala Val Ala Ser
1               5                   10                  15

Leu Leu Ser Pro Ala Phe Ala Gln Thr Ala Pro Lys Thr Phe Thr His
            20                  25                  30

Pro Asp Thr Gly Ile Val Phe Asn Thr Trp Ser Ala Ser Asp Ser Gln
        35                  40                  45

Thr Lys Gly Gly Phe Thr Val Gly Met Ala Leu Pro Ser Asn Ala Leu
    50                  55                  60

Thr Thr Asp Ala Thr Glu Phe Ile Gly Tyr Leu Glu Cys Ser Ser Ala
65                  70                  75                  80

Lys Asn Gly Ala Asn Ser Gly Trp Cys Gly Val Ser Leu Arg Gly Ala
                85                  90                  95

Met Thr Asn Asn Leu Leu Ile Thr Ala Trp Pro Ser Asp Gly Glu Val
            100                 105                 110

Tyr Thr Asn Leu Met Phe Ala Thr Gly Tyr Ala Met Pro Lys Asn Tyr
        115                 120                 125

Ala Gly Asp Ala Lys Ile Thr Gln Ile Ala Ser Ser Val Asn Ala Thr
    130                 135                 140

His Phe Thr Leu Val Phe Arg Cys Gln Asn Cys Leu Ser Trp Asp Gln
145                 150                 155                 160

Asp Gly Val Thr Gly Gly Ile Ser Thr Ser Asn Lys Gly Ala Gln Leu
                165                 170                 175

Gly Trp Val Gln Ala Phe Pro Ser Pro Gly Asn Pro Thr Cys Pro Thr
            180                 185                 190

Gln Ile Thr Leu Ser Gln His Asp Asn Gly Met Gly Gln Trp Gly Ala
        195                 200                 205

Ala Phe Asp Ser Asn Ile Ala Asn Pro Ser Tyr Thr Ala Trp Ala
    210                 215                 220
```

<210> SEQ ID NO 21
<211> LENGTH: 218
<212> TYPE: PRT
<213> ORGANISM: Humicola insolens

<400> SEQUENCE: 21

```
Met Lys Phe Leu Gly Arg Ile Gly Ala Thr Ala Leu Ala Ala Ser Leu
1               5                   10                  15

Tyr Leu Thr Ser Gly Ala Ala Gln Ala Thr Gly Asp Ala Tyr Thr Asp
            20                  25                  30

Ser Glu Thr Gly Ile Lys Phe Gln Thr Trp Ser Pro Asp Pro Gln Phe
        35                  40                  45

Thr Phe Gly Leu Ala Leu Pro Pro Asp Ala Leu Glu Lys Asp Ala Thr
    50                  55                  60

Glu Tyr Ile Gly Leu Leu Arg Cys Thr Arg Ala Asp Pro Ser Asp Pro
65                  70                  75                  80

Gly Tyr Cys Gly Leu Ser His Gly Gln Val Gly Gln Met Thr Gln Ser
                85                  90                  95

Leu Leu Leu Val Ala Trp Ala Tyr Glu Asn Gln Val Tyr Thr Ser Phe
            100                 105                 110

Arg Tyr Ala Thr Gly Tyr Thr Leu Pro Gly Leu Tyr Gly Asn Ala
        115                 120                 125
```

```
Lys Leu Thr Gln Leu Ser Val Asn Ile Thr Asp Thr Ser Phe Glu Leu
    130                 135                 140
Ile Tyr Arg Cys Glu Asn Cys Phe Ser Trp Glu His Glu Gly Ser Thr
145                 150                 155                 160
Gly Ser Ser Ser Thr Ser Gln Gly Tyr Leu Val Leu Gly Arg Ala Ser
                165                 170                 175
Ala Arg Arg Gly Val Val Gly Pro Thr Cys Pro Asp Thr Ala Thr Phe
            180                 185                 190
Gly Phe His Asp Asn Gly Phe Gly Gln Trp Gly Val Gly Leu Glu Asn
                195                 200                 205
Ala Val Ser Glu Gln Tyr Ser Glu Trp Ala
    210                 215
```

<210> SEQ ID NO 22
<211> LENGTH: 219
<212> TYPE: PRT
<213> ORGANISM: Thielavia terrestris

<400> SEQUENCE: 22

```
Met Lys Leu Leu Ser Arg Ile Gly Ala Thr Thr Leu Ala Ala Ser Leu
1               5                   10                  15
Cys Leu Gln Gln Cys Val Ala Gln Met Thr Ala Gly Asn Tyr Thr Asp
            20                  25                  30
Pro Ala Thr Gly Ile Lys Leu Lys Thr Trp Thr Ala Thr Asp Gly Gly
        35                  40                  45
Ala Phe Thr Phe Gly Leu Ala Leu Pro Ser Asp Ala Leu Thr Lys Asp
    50                  55                  60
Ala Thr Glu Tyr Ile Gly Leu Leu Arg Cys Glu Ile Ala Asn Ala Thr
65                  70                  75                  80
Ser Pro Gly Trp Cys Gly Ile Ser His Gly Gln Ser Gly Gln Met Thr
                85                  90                  95
Gln Ala Leu Leu Leu Val Ala Trp Gln Tyr Asn Gly Thr Val Tyr Thr
            100                 105                 110
Ser Phe Arg Tyr Ala Thr Gly Tyr Thr Leu Pro Gly Leu Tyr Thr Gly
        115                 120                 125
Asn Ala Lys Leu Thr Gln Ile Ser Thr Asn Ile Thr Ala Thr Ser Tyr
    130                 135                 140
Glu Leu Leu Tyr Arg Cys Gln Asn Cys Phe Ser Trp Asp Gln Asp Gly
145                 150                 155                 160
Thr Ser Gly Asn Val Ser Thr Ser Ser Gly Ser Leu Val Leu Gly His
                165                 170                 175
Ala Ala Ala Lys Gln Gly Leu Glu Asn Pro Thr Cys Pro Asp Lys Ala
            180                 185                 190
Thr Phe Gly Phe His Asp Asn Gly Tyr Gly Gln Trp Gly Ala Pro Leu
        195                 200                 205
Asp Gly Ala Ala Gln Ala Ser Tyr Ser Thr Trp
    210                 215
```

<210> SEQ ID NO 23
<211> LENGTH: 27
<212> TYPE: PRT
<213> ORGANISM: Myriococcum thermophilum

<400> SEQUENCE: 23

```
Ala Gln Ala Thr Lys Thr Val Thr Gly Asp Cys Glu Gly Pro Thr Glu
1               5                   10                  15
```

```
Thr Ser Val Val Gly Val Pro Val Pro Thr Gly
            20                  25

<210> SEQ ID NO 24
<211> LENGTH: 81
<212> TYPE: DNA
<213> ORGANISM: Myriococcum thermophilum

<400> SEQUENCE: 24
gcacaagcaa ccaagactgt cacaggcgac tgtgagggtc ctacggaaac ctctgtcgtg     60
ggagtgcctg ttcccacagg g                                              81

<210> SEQ ID NO 25
<211> LENGTH: 27
<212> TYPE: PRT
<213> ORGANISM: Corynascud thermophiles

<400> SEQUENCE: 25

Gln Leu Ala Thr Ile Thr Pro Pro Thr Thr Cys Asp Gly Asn Gly Pro
1               5                   10                  15

Gly Asp Lys Val Cys Val Pro Ala Pro Glu Asp
            20                  25

<210> SEQ ID NO 26
<211> LENGTH: 81
<212> TYPE: DNA
<213> ORGANISM: Corynascud thermophiles

<400> SEQUENCE: 26
cagcttgcga ctatcacccc tcctaccact tgcgatggaa atgggcctgg cgacaaggtt     60
tgtgtcccgg ctcctgagga t                                              81

<210> SEQ ID NO 27
<211> LENGTH: 31
<212> TYPE: PRT
<213> ORGANISM: Apergillus sojae

<400> SEQUENCE: 27

Lys Leu Ala Asn Lys Thr Val Pro Gly Asp Cys Ser Gly Asp Gly Gly
1               5                   10                  15

Gly Gly Asn Glu Pro Thr Pro Val Pro Val Pro Asp Gly Ala Thr
            20                  25                  30

<210> SEQ ID NO 28
<211> LENGTH: 93
<212> TYPE: DNA
<213> ORGANISM: Apergillus sojae

<400> SEQUENCE: 28
aagttggcta ataagactgt tcccggggac tgctccggtg acggtggtgg cggcaacgag     60
ccgactcctg tccctgtccc tgacggtgct aca                                 93

<210> SEQ ID NO 29
<211> LENGTH: 22
<212> TYPE: PRT
<213> ORGANISM: Apergillus sojae

<400> SEQUENCE: 29

Asp Cys Ser Gly Asp Gly Gly Gly Gly Asn Glu Pro Thr Pro Val Pro
1               5                   10                  15

Val Pro Asp Gly Ala Thr
            20
```

20

<210> SEQ ID NO 30
<211> LENGTH: 66
<212> TYPE: DNA
<213> ORGANISM: Apergillus sojae

<400> SEQUENCE: 30
gactgctccg gtgacggtgg tggcggcaac gagccgactc ctgtccctgt ccctgacggt    60
gctaca    66

<210> SEQ ID NO 31
<211> LENGTH: 5
<212> TYPE: PRT
<213> ORGANISM: Corynascud thermophiles

<400> SEQUENCE: 31

Lys Leu Ala Asn Lys
1               5

<210> SEQ ID NO 32
<211> LENGTH: 15
<212> TYPE: DNA
<213> ORGANISM: Corynascud thermophiles

<400> SEQUENCE: 32
aaactggcga acaaa    15

<210> SEQ ID NO 33
<211> LENGTH: 869
<212> TYPE: PRT
<213> ORGANISM: Artificial
<220> FEATURE:
<223> OTHER INFORMATION: fusion protein

<400> SEQUENCE: 33

Met Arg Thr Ser Ser Arg Leu Ile Gly Ala Leu Ala Ala Ala Leu Leu
1               5                   10                  15

Pro Ser Ala Leu Ala Gln Asn Asn Val Pro Asn Thr Phe Thr Asp Pro
                20                  25                  30

Asp Ser Gly Ile Thr Phe Asn Thr Trp Gly Leu Asp Glu Asp Ser Pro
            35                  40                  45

Gln Thr Gln Gly Gly Phe Thr Phe Gly Val Ala Leu Pro Ser Asp Ala
        50                  55                  60

Leu Thr Thr Asp Ala Ser Glu Phe Ile Gly Tyr Leu Lys Cys Ala Arg
65                  70                  75                  80

Asn Asp Glu Ser Gly Trp Cys Gly Ile Ser Leu Gly Gly Pro Met Thr
                85                  90                  95

Asn Ser Leu Leu Ile Thr Ala Trp Pro His Glu Asp Thr Val Tyr Thr
            100                 105                 110

Ser Leu Arg Phe Ala Thr Gly Tyr Ala Met Pro Asp Val Tyr Glu Gly
        115                 120                 125

Asp Ala Glu Ile Thr Gln Val Ser Ser Val Asn Ser Thr His Phe
        130                 135                 140

Ser Leu Ile Phe Arg Cys Lys Asn Cys Leu Gln Trp Ser His Gly Gly
145                 150                 155                 160

Ser Ser Gly Gly Ala Ser Thr Ser Gly Gly Val Leu Val Leu Gly Trp
                165                 170                 175

Val Gln Ala Phe Asp Asp Pro Gly Asn Pro Thr Cys Pro Glu Gln Ile

```
                180             185             190
Thr Leu Gln Gln His Asp Asn Gly Met Gly Ile Trp Gly Ala Gln Leu
            195                 200                 205

Asn Thr Asp Ala Ala Ser Pro Ser Tyr Thr Asp Trp Ala Ala Gln Ala
210                 215                 220

Thr Lys Thr Val Thr Gly Asp Cys Glu Gly Pro Thr Glu Thr Ser Val
225                 230                 235                 240

Val Gly Val Pro Val Pro Thr Gly Gln Gln Asp Thr Asn Ser Ser Ser
            245                 250                 255

Thr Asp Thr Tyr Asp Tyr Val Ile Val Gly Gly Val Ala Gly Leu
            260                 265                 270

Ala Leu Ala Ser Arg Ile Ser Glu Asn Lys Asp Val Thr Val Ala Val
            275                 280                 285

Leu Glu Ser Gly Pro Tyr Ala Gly Asp Arg Phe Val Val Tyr Ala Pro
            290                 295                 300

Gly Met Tyr Gly Gln Ala Val Gly Thr Asp Leu Ala Pro Leu Ile Pro
305                 310                 315                 320

Thr Thr Pro Gln Glu Asn Met Gly Asn Arg Ser Leu Thr Ile Ala Thr
                325                 330                 335

Gly Arg Leu Leu Gly Gly Gly Ser Ala Ile Asn Gly Leu Val Trp Thr
                340                 345                 350

Arg Gly Gly Leu Lys Asp Tyr Asp Ala Trp Glu Glu Leu Gly Asn Pro
                355                 360                 365

Gly Trp Asn Gly Ala Asn Leu Phe Lys Tyr Phe Lys Lys Val Glu Asn
            370                 375                 380

Phe Thr Pro Pro Thr Pro Ala Gln Ile Glu Tyr Gly Ala Thr Tyr Gln
385                 390                 395                 400

Lys Ser Ala His Gly Lys Lys Gly Pro Ile Asp Val Ser Phe Thr Asn
                405                 410                 415

Tyr Glu Phe Ser Gln Ser Ala Ser Trp Asn Ala Ser Leu Glu Thr Leu
                420                 425                 430

Asp Phe Thr Ala Leu Pro Asp Ile Leu Asn Gly Thr Leu Ala Gly Tyr
            435                 440                 445

Ser Thr Thr Pro Asn Ile Leu Asp Pro Glu Thr Val Arg Arg Val Asp
            450                 455                 460

Ser Tyr Thr Gly Tyr Ile Ala Pro Tyr Thr Ser Arg Asn Asn Leu Asn
465                 470                 475                 480

Val Leu Ala Asn His Thr Val Ser Arg Ile Gln Phe Ala Pro Lys Asn
                485                 490                 495

Gly Ser Glu Pro Leu Lys Ala Thr Gly Val Glu Trp Tyr Pro Thr Gly
            500                 505                 510

Asn Lys Asn Gln Lys Gln Ile Ile Lys Ala Arg Tyr Glu Val Ile Ile
            515                 520                 525

Ser Ser Gly Ala Ile Gly Ser Pro Lys Leu Leu Glu Ile Ser Gly Ile
            530                 535                 540

Gly Asn Lys Asp Ile Val Ser Ala Ala Gly Val Glu Ser Leu Ile Asp
545                 550                 555                 560

Leu Pro Gly Val Gly Ser Asn Met Gln Asp His Val His Ala Ile Thr
                565                 570                 575

Val Ser Thr Thr Asn Ile Thr Gly Tyr Thr Thr Asn Ser Val Phe Val
                580                 585                 590

Asn Glu Thr Leu Ala Gln Glu Gln Arg Glu Glu Tyr Glu Ala Asn Lys
            595                 600                 605
```

Thr Gly Ile Trp Ala Thr Cys Pro Asn Asn Leu Gly Tyr Pro Thr Pro
        610                 615                 620

Glu Gln Leu Phe Asn Gly Thr Glu Phe Val Ser Gly Lys Glu Phe Ala
625                 630                 635                 640

Asp Lys Ile Arg Asn Ser Thr Asp Glu Trp Ala Asn Tyr Tyr Ala Ser
            645                 650                 655

Thr Asn Ala Ser Asn Val Glu Leu Leu Lys Lys Gln Tyr Ala Ile Val
        660                 665                 670

Ala Ser Arg Tyr Glu Glu Asn Tyr Leu Ser Pro Ile Glu Ile Asn Phe
    675                 680                 685

Thr Pro Gly Tyr Glu Gly Ser Gly Asn Val Asp Leu Gln Asn Asn Lys
690                 695                 700

Tyr Gln Thr Val Asn His Val Leu Ile Ala Pro Leu Ser Arg Gly Tyr
705                 710                 715                 720

Thr His Ile Asn Ser Ser Asp Val Glu Asp His Ser Val Ile Asn Pro
            725                 730                 735

Gln Tyr Tyr Ser His Pro Met Asp Ile Asp Val His Ile Ala Ser Thr
        740                 745                 750

Lys Leu Ala Arg Glu Ile Ile Thr Ala Ser Pro Gly Leu Gly Asp Ile
    755                 760                 765

Asn Ser Gly Glu Ile Glu Pro Gly Met Asn Ile Thr Ser Asp Asp Asp
770                 775                 780

Val Arg Lys Trp Leu Ser Asn Asn Val Arg Ser Asp Trp His Pro Val
785                 790                 795                 800

Gly Thr Cys Ala Met Leu Pro Lys Glu Leu Gly Val Val Ser Pro
            805                 810                 815

Ala Leu Met Val Tyr Gly Thr Ser Asn Leu Arg Val Val Asp Ala Ser
        820                 825                 830

Ile Met Pro Leu Glu Val Ser Ser His Leu Met Gln Pro Thr Tyr Gly
    835                 840                 845

Ile Ala Glu Lys Ala Ala Asp Ile Ile Lys Asn Phe Tyr Lys Thr Gln
850                 855                 860

His Lys Asn Gln Asn
865

<210> SEQ ID NO 34
<211> LENGTH: 2610
<212> TYPE: DNA
<213> ORGANISM: Artificial
<220> FEATURE:
<223> OTHER INFORMATION: construct

<400> SEQUENCE: 34
atgcgcacct cttctcgtct tattggtgca ttggctgctg cactcctgcc ttctgctctt      60
gcacagaaca atgttccgaa cacattcacg gatcctgaca gtggaatcac ttttaataca     120
tggggcctcg atgaggactc cccgcagaca caaggcggtt tcacgtttgg agtcgcgctt     180
cctagcgatg ccttgaccac tgacgcttcg gagttcatcg gctatttgaa gtgcgcacga     240
aacgatgaat ccggatggtg tgggatctct ctcggagggc aatgacaaa ttcgcttttg      300 attacggctt ggccgcatga agacacggtt tacacctcac tcagattcgc gaccggttac     360
gccatgccag atgtctatga gggagacgct gaaatcaccc aagttagctc gtcagtcaac     420
agtactcatt tctccttgat ttttcgatgc aagaattgtc tccaatggtc ccacggcggt     480
agttccggag gggcaagtac ttccggcggt gttttggtcc tgggatgggt ccaggcgttc     540

-continued

```
gatgaccctg gaaaccccac ctgcccagag caaatcactc tgcagcaaca cgataacggc    600
atgggtattt ggggcgctca gcttaataca gatgcggcct ctccgagcta tacggactgg    660
gctgcacaag caaccaagac tgtcacaggc gactgtgagg gtcctacgga aacctctgtc    720
gtgggagtgc ctgttccac agggcaacaa gacacaaatt cttcctcaac tgatacttat    780
gattatgtta tcgttggcgg cggtgtagct ggtttggctt tggctagtcg tatctctgaa    840
aacaaggatg tcactgttgc tgttctcgag tccggtcctt atgccggtga tagatttgtt    900
gtttatgctc ctggcatgta tggccaagct gttggcactg atctcgctcc tctcattcct    960
actactcctc aagaaaatat gggcaacaga agtctcacaa tcgctactgg tagattgctc   1020
ggtggtggca gtgctattaa tggtctcgtt tggacccgtg gtggcttgaa ggattacgat   1080
gcttgggagg agctcggtaa ccctggatgg aacggtgcca acttgttcaa gtactttaag   1140
aaggtcgaaa acttcactcc tcctactcct gcccaaattg aatacggcgc tacttatcag   1200
aaaagtgctc atggcaagaa gggacctatt gatgtctctt tcacgaacta cgagttctct   1260
caatctgcta gctggaacgc ctcactcgaa accttgatt tcactgcact tcctgatatc   1320
ttgaacggta ctttggccgg ttactctacc actcccaaca ttttggaccc tgagactgtt   1380
cgacgtgttg attcctatac tggttacatt gctccttaca ctagccgtaa caacctcaat   1440
gttttggcca accataccgt ctcccgcatt caatttgctc ccaagaatgg tagcgaacct   1500
ctcaaggcta ccggtgttga atggtatccc actggcaaca agaatcaaaa gcaaattatc   1560
aaggcccgtt atgaagttat catctcatct ggtgccattg gtagtcctaa gcttttggaa   1620
atctctggta tcggtaataa ggatatcgtc tctgctgctg gtgtcgagtc cttgattgac   1680
ttgcctggcg ttggttccaa catgcaagat cacgttcatg ctatcactgt ctctactacc   1740
aatattactg gctatactac caacagcgtc tttgtcaatg aaacccttgc caagaacaa    1800 agagaagaat atgaagccaa caagactggt atctgggcta cttgtcccaa caacctcggt   1860
tatcctacgc ccgaacaact cttcaatggc accgaattcg tttctggaaa ggagtttgct   1920
gacaagattc gtaactctac tgatgaatgg gccaactatt atgcttccac caacgcctcc   1980
aatgtcgagt tattaaagaa gcaatatgct attgtcgcct ctcgttacga agagaactac   2040
ttgtctccta ttgaaatcaa cttcactcct ggttatgagg gtagcggtaa tgtcgatttg   2100
caaaacaaca agtaccaaac tgtcaaccat gtcttgattg ctcctttaag tcgtggttat   2160
actcacatta actcttctga tgtggaggat cattctgtca ttaatcccca atactactct   2220
catcctatgg atattgatgt ccatatcgct tccactaaac ttgctcgcga aatcatcact   2280
gcctctcccg tcttggtga cattaacagt ggcgaaatcg aacccggtat gaatattact   2340
tctgacgacg acgttagaaa atggttgagt aataatgtcc gttctgactg catcctgtt    2400 ggtacttgtg ctatgcttcc caaggaatta ggtggtgttg tcagccccgc tctcatggtt   2460
tacggcactt ccaacttgcg tgttgttgat gcttcgatta tgcccctcga gtctcttct    2520 catttgatgc aacccaccta cggtattgct gagaaggctg ctgacattat taagaatttc   2580
tacaagactc aacacaagaa ccaaaattag                                     2610
```

<210> SEQ ID NO 35
<211> LENGTH: 868
<212> TYPE: PRT
<213> ORGANISM: Artificial
<220> FEATURE:
<223> OTHER INFORMATION: fusion protein

```
<400> SEQUENCE: 35

Met Lys Leu Leu Ser Arg Val Gly Ala Thr Ala Leu Ala Ala Thr Leu
1               5                   10                  15

Ser Leu Lys Gln Cys Ala Ala Gln Met Thr Glu Gly Thr Tyr Thr His
            20                  25                  30

Glu Ala Thr Gly Ile Thr Phe Lys Thr Trp Thr Pro Ser Asp Gly Ser
            35                  40                  45

Thr Phe Thr Phe Gly Leu Ala Leu Pro Gly Asp Ala Leu Thr Asn Asp
    50                  55                  60

Ala Thr Glu Tyr Ile Gly Leu Leu Arg Cys Gln Ile Thr Asp Pro Ser
65                  70                  75                  80

Ser Pro Gly Tyr Cys Gly Ile Ser His Gly Gln Ser Gly Gln Met Thr
                85                  90                  95

Gln Ala Leu Leu Leu Val Ala Trp Ala Ser Glu Asp Val Val Tyr Thr
            100                 105                 110

Ser Phe Arg Tyr Ala Thr Gly Tyr Thr Leu Pro Glu Leu Tyr Thr Gly
        115                 120                 125

Asp Ala Lys Leu Thr Gln Ile Ala Ser Ser Val Ser Gly Asp Ser Phe
    130                 135                 140

Glu Val Leu Phe Arg Cys Glu Asn Cys Phe Ser Trp Asp Gln Asn Gly
145                 150                 155                 160

Ala Thr Gly Ser Val Ser Thr Ser Asn Gly Ala Leu Val Leu Gly Tyr
                165                 170                 175

Ala Ala Ser Lys Ser Gly Leu Thr Gly Ala Thr Cys Pro Asp Thr Ala
            180                 185                 190

Glu Phe Gly Phe His Asn Asn Gly Phe Gly Gln Trp Gly Ala Val Leu
        195                 200                 205

Glu Gly Ala Thr Ser Asp Ser Tyr Glu Glu Trp Ala Gln Leu Ala Thr
    210                 215                 220

Ile Thr Pro Pro Thr Thr Cys Asp Gly Asn Gly Pro Gly Asp Lys Val
225                 230                 235                 240

Cys Val Pro Ala Pro Glu Asp Gln Gln Asp Thr Asn Ser Ser Ser Thr
                245                 250                 255

Asp Thr Tyr Asp Tyr Val Ile Val Gly Gly Gly Val Ala Gly Leu Ala
            260                 265                 270

Leu Ala Ser Arg Ile Ser Glu Asn Lys Asp Val Thr Val Ala Val Leu
        275                 280                 285

Glu Ser Gly Pro Tyr Ala Gly Asp Arg Phe Val Val Tyr Ala Pro Gly
    290                 295                 300

Met Tyr Gly Gln Ala Val Gly Thr Asp Leu Ala Pro Leu Ile Pro Thr
305                 310                 315                 320

Thr Pro Gln Glu Asn Met Gly Asn Arg Ser Leu Thr Ile Ala Thr Gly
                325                 330                 335

Arg Leu Leu Gly Gly Gly Ser Ala Ile Asn Gly Leu Val Trp Thr Arg
            340                 345                 350

Gly Gly Leu Lys Asp Tyr Asp Ala Trp Glu Glu Leu Gly Asn Pro Gly
        355                 360                 365

Trp Asn Gly Ala Asn Leu Phe Lys Tyr Phe Lys Lys Val Glu Asn Phe
    370                 375                 380

Thr Pro Pro Thr Pro Ala Gln Ile Glu Tyr Gly Ala Thr Tyr Gln Lys
385                 390                 395                 400

Ser Ala His Gly Lys Lys Gly Pro Ile Asp Val Ser Phe Thr Asn Tyr
                405                 410                 415
```

```
Glu Phe Ser Gln Ser Ala Ser Trp Asn Ala Ser Leu Glu Thr Leu Asp
            420                 425                 430

Phe Thr Ala Leu Pro Asp Ile Leu Asn Gly Thr Leu Ala Gly Tyr Ser
        435                 440                 445

Thr Thr Pro Asn Ile Leu Asp Pro Glu Thr Val Arg Arg Val Asp Ser
450                 455                 460

Tyr Thr Gly Tyr Ile Ala Pro Tyr Thr Ser Arg Asn Asn Leu Asn Val
465                 470                 475                 480

Leu Ala Asn His Thr Val Ser Arg Ile Gln Phe Ala Pro Lys Asn Gly
                485                 490                 495

Ser Glu Pro Leu Lys Ala Thr Gly Val Glu Trp Tyr Pro Thr Gly Asn
            500                 505                 510

Lys Asn Gln Lys Gln Ile Ile Lys Ala Arg Tyr Glu Val Ile Ile Ser
        515                 520                 525

Ser Gly Ala Ile Gly Ser Pro Lys Leu Leu Glu Ile Ser Gly Ile Gly
530                 535                 540

Asn Lys Asp Ile Val Ser Ala Ala Gly Val Glu Ser Leu Ile Asp Leu
545                 550                 555                 560

Pro Gly Val Gly Ser Asn Met Gln Asp His Val His Ala Ile Thr Val
                565                 570                 575

Ser Thr Thr Asn Ile Thr Gly Tyr Thr Thr Asn Ser Val Phe Val Asn
            580                 585                 590

Glu Thr Leu Ala Gln Glu Gln Arg Glu Glu Tyr Glu Ala Asn Lys Thr
        595                 600                 605

Gly Ile Trp Ala Thr Cys Pro Asn Asn Leu Gly Tyr Pro Thr Pro Glu
610                 615                 620

Gln Leu Phe Asn Gly Thr Glu Phe Val Ser Gly Lys Glu Phe Ala Asp
625                 630                 635                 640

Lys Ile Arg Asn Ser Thr Asp Glu Trp Ala Asn Tyr Tyr Ala Ser Thr
                645                 650                 655

Asn Ala Ser Asn Val Glu Leu Leu Lys Lys Gln Tyr Ala Ile Val Ala
            660                 665                 670

Ser Arg Tyr Glu Glu Asn Tyr Leu Ser Pro Ile Glu Ile Asn Phe Thr
        675                 680                 685

Pro Gly Tyr Glu Gly Ser Gly Asn Val Asp Leu Gln Asn Asn Lys Tyr
690                 695                 700

Gln Thr Val Asn His Val Leu Ile Ala Pro Leu Ser Arg Gly Tyr Thr
705                 710                 715                 720

His Ile Asn Ser Ser Asp Val Glu Asp His Ser Val Ile Asn Pro Gln
                725                 730                 735

Tyr Tyr Ser His Pro Met Asp Ile Asp Val His Ile Ala Ser Thr Lys
            740                 745                 750

Leu Ala Arg Glu Ile Ile Thr Ala Ser Pro Gly Leu Gly Asp Ile Asn
        755                 760                 765

Ser Gly Glu Ile Glu Pro Gly Met Asn Ile Thr Ser Asp Asp Val
770                 775                 780

Arg Lys Trp Leu Ser Asn Asn Val Arg Ser Asp Trp His Pro Val Gly
785                 790                 795                 800

Thr Cys Ala Met Leu Pro Lys Glu Leu Gly Gly Val Val Ser Pro Ala
                805                 810                 815

Leu Met Val Tyr Gly Thr Ser Asn Leu Arg Val Val Asp Ala Ser Ile
            820                 825                 830
```

```
Met Pro Leu Glu Val Ser Ser His Leu Met Gln Pro Thr Tyr Gly Ile
        835                 840                 845

Ala Glu Lys Ala Ala Asp Ile Ile Lys Asn Phe Tyr Lys Thr Gln His
        850                 855                 860

Lys Asn Gln Asn
865

<210> SEQ ID NO 36
<211> LENGTH: 2607
<212> TYPE: DNA
<213> ORGANISM: Artificial
<220> FEATURE:
<223> OTHER INFORMATION: construct

<400> SEQUENCE: 36
atgaagctcc tgtcgagagt cggcgcaact gcgttggccg ctacactctc actgaaacaa      60
tgcgcagcgc agatgaccga gggcacgtac acccatgaag ctactggaat cacattcaag     120
acttggacac cgtcgatgg atcaacgttc acctttggtc ttgccttgcc tggagatgct     180
ctcacgaacg acgcaaccga gtacatcggc cttttgcgat gccagattac cgatccgtcc     240
tctcctgggt attgtggcat ctcgcacggc cagtcaggaa aaatgacaca ggctctcctg     300
cttgtcgcct gggcttctga ggacgtcgtg tacacgagct ccgctacgc aacgggttat     360 accctccccg aactgtatac tggagatgct aagttgacac aaattgcaag ctcggtttct     420
ggtgactcct tcgaggtcct ctttcgttgc gaaaactgtt tttcttggga tcagaatggg     480
gctacgggct cagtcagtac ctctaatgga gcattggtgc tgggatatgc tgcttctaag     540
agcggtctga ctggagcgac atgcccggat acagccgagt tcggctttca taacaatggc     600
ttcggtcaat ggggtgcggt cctggaagga gcaacctcgg actcatatga ggaatgggca     660
cagcttgcga ctatcacccc tcctaccact tgcgatggaa tgggcctgg cgacaaggtt     720 tgtgtcccgg ctcctgagga tcaacaagac acaaattctt cctcaactga tacttatgat     780
tatgttatcg ttggcggcgg tgtagctggt ttggctttgg ctagtcgtat tctgaaaac     840 aaggatgtca ctgttgctgt ctcgagtcc ggtccttatg ccggtgatag atttgttgtt     900
tatgctcctg gcatgtatgg ccaagctgtt ggcactgatc tcgctcctct cattcctact     960
actcctcaag aaaatatggg caacagaagt ctcacaatcg ctactggtag attgctcggt    1020
ggtggcagtg ctattaatgg tctcgttttgg acccgtggtg gcttgaagga ttacgatgct    1080
tgggaggagc tcggtaaccc tggatggaac ggtgccaact tgttcaagta ctttaagaag    1140
gtcgaaaact tcactcctcc tactcctgcc caaattgaat acggcgctac ttatcagaaa    1200
agtgctcatg gcaagaaggg acctattgat gtctctttca cgaactacga gttctctcaa    1260
tctgctagct ggaacgcctc actcgaaacc cttgatttca ctgcacttcc tgatatcttg    1320
aacggtactt tggccggtta ctctaccact cccaacattt tggaccctga gactgttcga    1380
cgtgttgatt cctatactgg ttacattgct ccttacacta gcgtaacaa cctcaatgtt    1440 ttggccaacc ataccgtctc ccgcattcaa tttgctccca gaatggtag cgaacctctc    1500 aaggctaccg tgttgaatg gtatcccact ggcaacaaga tcaaaagca aattatcaag    1560 gcccgttatg aagttatcat ctcatctggt gccattggta gtcctaagct tttggaaatc    1620
tctggtatcg gtaataagga tatcgtctct gctgctggtg tcgagtcctt gattgacttg    1680
cctggcgttg gttccaacat gcaagatcac gttcatgcta tcactgtctc tactaccaat    1740
attactggct atactaccaa cagcgtcttt gtcaatgaaa cccttgccca agaacaaaga    1800
```

```
gaagaatatg aagccaacaa gactggtatc tgggctactt gtcccaacaa cctcggttat   1860
cctacgcccg aacaactctt caatggcacc gaattcgttt ctggaaagga gtttgctgac   1920
aagattcgta actctactga tgaatgggcc aactattatg cttccaccaa cgcctccaat   1980
gtcgagttat aaagaagca atatgctatt gtcgcctctc gttacgaaga gaactacttg    2040
tctcctattg aaatcaactt cactcctggt tatgagggta gcggtaatgt cgatttgcaa   2100
aacaacaagt accaaactgt caaccatgtc ttgattgctc ctttaagtcg tggttatact   2160
cacattaact cttctgatgt ggaggatcat tctgtcatta atccccaata ctactctcat   2220
cctatggata ttgatgtcca tatcgcttcc actaaacttg ctcgcgaaat catcactgcc   2280
tctcccggtc ttggtgacat taacagtggc gaaatcgaac ccggtatgaa tattacttct   2340
gacgacgacg ttagaaaatg gttgagtaat aatgtccgtt ctgactggca tcctgttggt   2400
acttgtgcta tgcttcccaa ggaattaggt ggtgttgtca gccccgctct catggtttac   2460
ggcacttcca acttgcgtgt tgttgatgct tcgattatgc ccctcgaagt ctcttctcat   2520
ttgatgcaac ccacctacgg tattgctgag aaggctgctg acattattaa gaatttctac   2580
aagactcaac acaagaacca aaattag                                       2607
```

<210> SEQ ID NO 37
<211> LENGTH: 901
<212> TYPE: PRT
<213> ORGANISM: Artificial
<220> FEATURE:
<223> OTHER INFORMATION: fusion protein

<400> SEQUENCE: 37

```
Met Lys Leu Val Asn Arg Leu Leu Ala Ser Phe Leu Ser Ala Ser Thr
1               5                   10                  15

Val Leu Gln Ser Cys Trp Ala Gln Ser Gly Thr Pro Val Ala Tyr Thr
            20                  25                  30

Asp Thr Glu Thr Gly Ile Thr Phe Asp Thr Trp Ser Val Pro Ala Gly
        35                  40                  45

Thr Gly Thr Gly Gly Leu Val Phe Gly Val Ala Leu Pro Gly Ser Ala
    50                  55                  60

Leu Thr Thr Asp Ala Thr Glu Phe Ile Gly Tyr Leu Gln Cys Ala Ser
65                  70                  75                  80

Gln Asn Ala Ser Ser Ala Gly Trp Cys Gly Ile Ser Leu Gly Gly Gly
                85                  90                  95

Met Asn Asn Asn Leu Leu Phe Leu Ala Tyr Pro Tyr Glu Asp Thr Ile
            100                 105                 110

Leu Thr Ser Leu Arg Phe Gly Ser Gly Tyr Ser Met Pro Gly Val Tyr
        115                 120                 125

Thr Gly Asn Ala Asn Val Thr Gln Ile Ser Ser Ile Asn Ala Thr
    130                 135                 140

His Phe Thr Leu Leu Phe Arg Cys Glu Asn Cys Leu Thr Trp Asp Gln
145                 150                 155                 160

Asp Gly Gln Thr Gly Asn Ala Thr Thr Ser Lys Gly Arg Leu Val Leu
                165                 170                 175

Gly Trp Ala Gln Ser Thr Glu Ser Pro Ser Asn Pro Ser Cys Pro Asp
            180                 185                 190

Asn Ile Ser Leu Ala Gln His Asp Asn Gln Gly Ile Ile Ser Ala Thr
        195                 200                 205

Leu Asp Glu Asn Ala Ala Ser Glu Ser Tyr Glu Asp Trp Val Lys Leu
    210                 215                 220
```

```
Ala Asn Lys Thr Val Pro Gly Asp Cys Ser Gly Asp Gly Gly Gly
225                 230                 235                 240

Asn Glu Pro Thr Pro Val Pro Val Pro Asp Gly Ala Thr Gln Leu Ala
            245                 250                 255

Thr Ile Thr Pro Pro Thr Thr Cys Asp Gly Asn Gly Pro Gly Asp Lys
                260                 265                 270

Val Cys Val Pro Ala Pro Glu Asp Gln Gln Asp Thr Asn Ser Ser Ser
            275                 280                 285

Thr Asp Thr Tyr Asp Tyr Val Ile Val Gly Gly Val Ala Gly Leu
    290                 295                 300

Ala Leu Ala Ser Arg Ile Ser Glu Asn Lys Asp Val Thr Val Ala Val
305                 310                 315                 320

Leu Glu Ser Gly Pro Tyr Ala Gly Asp Arg Phe Val Val Tyr Ala Pro
                325                 330                 335

Gly Met Tyr Gly Gln Ala Val Gly Thr Asp Leu Ala Pro Leu Ile Pro
            340                 345                 350

Thr Thr Pro Gln Glu Asn Met Gly Asn Arg Ser Leu Thr Ile Ala Thr
        355                 360                 365

Gly Arg Leu Leu Gly Gly Ser Ala Ile Asn Gly Leu Val Trp Thr
370                 375                 380

Arg Gly Gly Leu Lys Asp Tyr Asp Ala Trp Glu Glu Leu Gly Asn Pro
385                 390                 395                 400

Gly Trp Asn Gly Ala Asn Leu Phe Lys Tyr Phe Lys Lys Val Glu Asn
                405                 410                 415

Phe Thr Pro Thr Pro Ala Gln Ile Glu Tyr Gly Ala Thr Tyr Gln
            420                 425                 430

Lys Ser Ala His Gly Lys Lys Gly Pro Ile Asp Val Ser Phe Thr Asn
            435                 440                 445

Tyr Glu Phe Ser Gln Ser Ala Ser Trp Asn Ala Ser Leu Glu Thr Leu
    450                 455                 460

Asp Phe Thr Ala Leu Pro Asp Ile Leu Asn Gly Thr Leu Ala Gly Tyr
465                 470                 475                 480

Ser Thr Thr Pro Asn Ile Leu Asp Pro Glu Thr Val Arg Arg Val Asp
                485                 490                 495

Ser Tyr Thr Gly Tyr Ile Ala Pro Tyr Thr Ser Arg Asn Asn Leu Asn
            500                 505                 510

Val Leu Ala Asn His Thr Val Ser Arg Ile Gln Phe Ala Pro Lys Asn
            515                 520                 525

Gly Ser Glu Pro Leu Lys Ala Thr Gly Val Glu Trp Tyr Pro Thr Gly
    530                 535                 540

Asn Lys Asn Gln Lys Gln Ile Ile Lys Ala Arg Tyr Glu Val Ile Ile
545                 550                 555                 560

Ser Ser Gly Ala Ile Gly Ser Pro Lys Leu Leu Glu Ile Ser Gly Ile
                565                 570                 575

Gly Asn Lys Asp Ile Val Ser Ala Ala Gly Val Glu Ser Leu Ile Asp
            580                 585                 590

Leu Pro Gly Val Gly Ser Asn Met Gln Asp His Val His Ala Ile Thr
    595                 600                 605

Val Ser Thr Thr Asn Ile Thr Gly Tyr Thr Thr Asn Ser Val Phe Val
    610                 615                 620

Asn Glu Thr Leu Ala Gln Glu Gln Arg Glu Glu Tyr Glu Ala Asn Lys
625                 630                 635                 640
```

```
Thr Gly Ile Trp Ala Thr Cys Pro Asn Asn Leu Gly Tyr Pro Thr Pro
                645                 650                 655

Glu Gln Leu Phe Asn Gly Thr Glu Phe Val Ser Gly Lys Glu Phe Ala
            660                 665                 670

Asp Lys Ile Arg Asn Ser Thr Asp Glu Trp Ala Asn Tyr Tyr Ala Ser
        675                 680                 685

Thr Asn Ala Ser Asn Val Glu Leu Leu Lys Lys Gln Tyr Ala Ile Val
    690                 695                 700

Ala Ser Arg Tyr Glu Glu Asn Tyr Leu Ser Pro Ile Glu Ile Asn Phe
705                 710                 715                 720

Thr Pro Gly Tyr Glu Gly Ser Gly Asn Val Asp Leu Gln Asn Asn Lys
                725                 730                 735

Tyr Gln Thr Val Asn His Val Leu Ile Ala Pro Leu Ser Arg Gly Tyr
            740                 745                 750

Thr His Ile Asn Ser Ser Asp Val Glu Asp His Ser Val Ile Asn Pro
        755                 760                 765

Gln Tyr Tyr Ser His Pro Met Asp Ile Asp Val His Ile Ala Ser Thr
    770                 775                 780

Lys Leu Ala Arg Glu Ile Ile Thr Ala Ser Pro Gly Leu Gly Asp Ile
785                 790                 795                 800

Asn Ser Gly Glu Ile Glu Pro Gly Met Asn Ile Thr Ser Asp Asp Asp
                805                 810                 815

Val Arg Lys Trp Leu Ser Asn Asn Val Arg Ser Asp Trp His Pro Val
            820                 825                 830

Gly Thr Cys Ala Met Leu Pro Lys Glu Leu Gly Gly Val Val Ser Pro
        835                 840                 845

Ala Leu Met Val Tyr Gly Thr Ser Asn Leu Arg Val Val Asp Ala Ser
    850                 855                 860

Ile Met Pro Leu Glu Val Ser Ser His Leu Met Gln Pro Thr Tyr Gly
865                 870                 875                 880

Ile Ala Glu Lys Ala Ala Asp Ile Ile Lys Asn Phe Tyr Lys Thr Gln
                885                 890                 895

His Lys Asn Gln Asn
            900

<210> SEQ ID NO 38
<211> LENGTH: 2744
<212> TYPE: DNA
<213> ORGANISM: Artificial
<220> FEATURE:
<223> OTHER INFORMATION: construct

<400> SEQUENCE: 38
atgaagctcg ttaaccgttt gctcgcttca ttcctgtcag cgagcaccgg tgagtggtgg      60
cctatcgagc taatgttgct tctcttcgtc tgacttttct tggcagtgtt gcagtcatgc     120
tgggctcagt ccggcacacc ggttgcctac acggatactg agacgggcat acgtttgac     180 acgtggtcgg tacctgctgg tacgggtacg ggtggtctcg tcttcggtgt agccctgccg     240
ggttcggcat tgaccaccga tgcgacggag tttatcggtt acctggtgag gatctcgagc     300
taatcatgac cgctctgaag tggcgctaaa cgttctaatg tttcaagcaa tgtgcgtccc     360
aaaatgcctc gtccgctggc tggtgtggca tttccttggg tggtggcatg aacaacaatc     420
tcttgttctt ggcctatccg tacgaggata ccatcttgac ctcccgtgcga ttcggctcgg     480 gctatagcat gcccggggtc tataccggca atgccaacgt cacccagatt tcttcaagca     540
```

```
tcaatgccac tcactttacg ttgcttttcc gttgcgagaa ttgtctgacc tgggaccaag    600
atggtcaaac cggaaacgcg accacaagca agggtaggtt agtcctggga tgggcacagt    660
ctacggagag cccgtcgaac ccgtcctgtc cggacaatat cagcctggcg cagcacgaca    720
accagggtat tatctcagcc actctggatg agaatgcagc cagtgagtcc tacgaggact    780
gggtcaagtt ggctaataag actgttcccg gggactgctc cggtgacggt ggtggcggca    840
acgagccgac tcctgtccct gtccctgacg gtgctacaca acaagacaca aattcttcct    900
caactgatac ttatgattat gttatcgttg gcggcggtgt agctggtttg gctttggcta    960
gtcgtatctc tgaaaacaag gatgtcactg ttgctgttct cgagtccggt ccttatgccg   1020
gtgatagatt tgttgtttat gctcctggca tgtatggcca agctgttggc actgatctcg   1080
ctcctctcat tcctactact cctcaagaaa atatgggcaa cagaagtctc acaatcgcta   1140
ctggtagatt gctcggtggt ggcagtgcta ttaatggtct cgtttggacc cgtggtggct   1200
tgaaggatta cgatgcttgg gaggagctcg gtaaccctgg atggaacggt gccaacttgt   1260
tcaagtactt taagaaggtc gaaaacttca ctcctcctac tcctgcccaa attgaatacg   1320
gcgctactta tcagaaaagt gctcatggca agaagggacc tattgatgtc tctttcacga   1380
actacgagtt ctctcaatct gctagctgga acgcctcact cgaaaccctt gatttcactg   1440
cacttcctga tatcttgaac ggtactttgg ccggttactc taccactccc aacattttgg   1500
accctgagac tgttcgacgt gttgattcct atactggtta cattgctcct tacactagcc   1560
gtaacaacct caatgttttg gccaaccata ccgtctcccg cattcaattt gctcccaaga   1620
atggtagcga acctctcaag gctaccggtg ttgaatggta tcccactggc aacaagaatc   1680
aaaagcaaat tatcaaggcc cgttatgaag ttatcatctc atctggtgcc attggtagtc   1740
ctaagctttt ggaaatctct ggtatcggta ataaggatat cgtctctgct gctggtgtcg   1800
agtccttgat tgacttgcct ggcgttggtt ccaacatgca agatcacgtt catgctatca   1860
ctgtctctac taccaatatt actggctata ctaccaacag cgtctttgtc aatgaaaccc   1920
ttgcccaaga acaaagagaa gaatatgaag ccaacaagac tggtatctgg ctacttgtc    1980 ccaacaacct cggttatcct acgcccgaac aactcttcaa tggcaccgaa ttcgtttctg   2040
gaaaggagtt tgctgacaag attcgtaact ctactgatga atgggccaac tattatgctt   2100
ccaccaacgc ctccaatgtc gagttattaa agaagcaata tgctattgtc gcctctcgtt   2160
acgaagagaa ctacttgtct cctattgaaa tcaacttcac tcctggttat gagggtagcg   2220
gtaatgtcga tttgcaaaac aacaagtacc aaactgtcaa ccatgtcttg attgctcctt   2280
taagtcgtgg ttatactcac attaactctt ctgatgtgga ggatcattct gtcattaatc   2340
cccaatacta ctctcatcct atggatattg atgtccatat cgcttccact aaacttgctc   2400
gcgaaatcat cactgcctct cccggtcttg gtgacattaa cagtggcgaa atcgaacccg   2460
gtatgaatat tacttctgac gacgacgtta gaaaatggtt gagtaataat gtccgttctg   2520
actggcatcc tgttggtact tgtgctatgc ttcccaagga attaggtggt gttgtcagcc   2580
ccgctctcat ggtttacggc acttccaact tgcgtgttgt tgatgcttcg attatgcccc   2640
tcgaagtctc ttctcatttg atgcaaccca cctacggtat tgctgagaag gctgctgaca   2700
ttattaagaa tttctacaag actcaacaca agaaccaaaa ttag                    2744
```

<210> SEQ ID NO 39
<211> LENGTH: 1130
<212> TYPE: PRT
<213> ORGANISM: Artificial
<220> FEATURE:
<223> OTHER INFORMATION: fusion protein

<400> SEQUENCE: 39

```
Met Lys Leu Val Asn Arg Leu Leu Ala Ser Phe Leu Ala Ser Thr
1               5                   10                  15

Val Leu Gln Ser Cys Trp Ala Gln Ser Gly Thr Pro Val Ala Tyr Thr
            20                  25                  30

Asp Thr Glu Thr Gly Ile Thr Phe Asp Thr Trp Ser Val Pro Ala Gly
            35                  40                  45

Thr Gly Thr Gly Gly Leu Val Phe Gly Val Ala Leu Pro Gly Ser Ala
        50                  55                  60

Leu Thr Thr Asp Ala Thr Glu Phe Ile Gly Tyr Leu Gln Cys Ala Ser
65                  70                  75                  80

Gln Asn Ala Ser Ser Ala Gly Trp Cys Gly Ile Ser Leu Gly Gly Gly
                85                  90                  95

Met Asn Asn Leu Leu Phe Leu Ala Tyr Pro Tyr Glu Asp Thr Ile
            100                 105                 110

Leu Thr Ser Leu Arg Phe Gly Ser Gly Tyr Ser Met Pro Gly Val Tyr
            115                 120                 125

Thr Gly Asn Ala Asn Val Thr Gln Ile Ser Ser Ser Ile Asn Ala Thr
        130                 135                 140

His Phe Thr Leu Leu Phe Arg Cys Glu Asn Cys Leu Thr Trp Asp Gln
145                 150                 155                 160

Asp Gly Gln Thr Gly Asn Ala Thr Thr Ser Lys Gly Arg Leu Val Leu
                165                 170                 175

Gly Trp Ala Gln Ser Thr Glu Ser Pro Ser Asn Pro Ser Cys Pro Asp
            180                 185                 190

Asn Ile Ser Leu Ala Gln His Asp Asn Gln Gly Ile Ile Ser Ala Thr
            195                 200                 205

Leu Asp Glu Asn Ala Ala Ser Glu Ser Tyr Glu Asp Trp Val Lys Leu
        210                 215                 220

Ala Asn Lys Thr Val Pro Gly Asp Cys Ser Gly Asp Gly Gly Gly Gly
225                 230                 235                 240

Asn Glu Pro Thr Pro Val Pro Val Pro Asp Gly Ala Thr Ser Gly Thr
                245                 250                 255

Pro Val Ala Tyr Thr Asp Thr Glu Thr Gly Ile Thr Phe Asp Thr Trp
            260                 265                 270

Ser Val Pro Ala Gly Thr Gly Thr Gly Gly Leu Val Phe Gly Val Ala
        275                 280                 285

Leu Pro Gly Ser Ala Leu Thr Thr Asp Ala Thr Glu Phe Ile Gly Tyr
        290                 295                 300

Leu Gln Cys Ala Ser Gln Asn Ala Ser Ser Ala Gly Trp Cys Gly Ile
305                 310                 315                 320

Ser Leu Gly Gly Gly Met Asn Asn Leu Leu Phe Leu Ala Tyr Pro
                325                 330                 335

Tyr Glu Asp Thr Ile Leu Thr Ser Leu Arg Phe Gly Ser Gly Tyr Ser
            340                 345                 350

Met Pro Gly Val Tyr Thr Gly Asn Ala Asn Val Thr Gln Ile Ser Ser
            355                 360                 365

Ser Ile Asn Ala Thr His Phe Thr Leu Leu Phe Arg Cys Glu Asn Cys
        370                 375                 380

Leu Thr Trp Asp Gln Asp Gly Gln Thr Gly Asn Ala Thr Thr Ser Lys
385                 390                 395                 400
```

```
Gly Arg Leu Val Leu Gly Trp Ala Gln Ser Thr Glu Ser Pro Ser Asn
            405                 410                 415

Pro Ser Cys Pro Asp Asn Ile Ser Leu Ala Gln His Asp Asn Gln Gly
        420                 425                 430

Ile Ile Ser Ala Thr Leu Asp Glu Asn Ala Ala Ser Glu Ser Tyr Glu
            435                 440                 445

Asp Trp Val Lys Leu Ala Asn Lys Thr Val Pro Gly Asp Cys Ser Gly
        450                 455                 460

Asp Gly Gly Gly Asn Glu Pro Thr Pro Val Pro Val Pro Asp Gly
465                 470                 475                 480

Ala Thr Gln Leu Ala Thr Ile Thr Pro Thr Thr Cys Asp Gly Asn
            485                 490                 495

Gly Pro Gly Asp Lys Val Cys Val Pro Ala Pro Glu Asp Gln Gln Asp
        500                 505                 510

Thr Asn Ser Ser Ser Thr Asp Thr Tyr Asp Tyr Val Ile Val Gly Gly
            515                 520                 525

Gly Val Ala Gly Leu Ala Leu Ala Ser Arg Ile Ser Glu Asn Lys Asp
        530                 535                 540

Val Thr Val Ala Val Leu Glu Ser Gly Pro Tyr Ala Gly Asp Arg Phe
545                 550                 555                 560

Val Val Tyr Ala Pro Gly Met Tyr Gly Gln Ala Val Gly Thr Asp Leu
            565                 570                 575

Ala Pro Leu Ile Pro Thr Thr Pro Gln Glu Asn Met Gly Asn Arg Ser
        580                 585                 590

Leu Thr Ile Ala Thr Gly Arg Leu Gly Gly Ser Ala Ile Asn
            595                 600                 605

Gly Leu Val Trp Thr Arg Gly Gly Leu Lys Asp Tyr Asp Ala Trp Glu
610                 615                 620

Glu Leu Gly Asn Pro Gly Trp Asn Gly Ala Asn Leu Phe Lys Tyr Phe
625                 630                 635                 640

Lys Lys Val Glu Asn Phe Thr Pro Pro Thr Pro Ala Gln Ile Glu Tyr
            645                 650                 655

Gly Ala Thr Tyr Gln Lys Ser Ala His Gly Lys Gly Pro Ile Asp
        660                 665                 670

Val Ser Phe Thr Asn Tyr Glu Phe Ser Gln Ser Ala Ser Trp Asn Ala
            675                 680                 685

Ser Leu Glu Thr Leu Asp Phe Thr Ala Leu Pro Asp Ile Leu Asn Gly
        690                 695                 700

Thr Leu Ala Gly Tyr Ser Thr Thr Pro Asn Ile Leu Asp Pro Glu Thr
705                 710                 715                 720

Val Arg Arg Val Asp Ser Tyr Thr Gly Tyr Ile Ala Pro Tyr Thr Ser
            725                 730                 735

Arg Asn Asn Leu Asn Val Leu Ala Asn His Thr Val Ser Arg Ile Gln
        740                 745                 750

Phe Ala Pro Lys Asn Gly Ser Glu Pro Leu Lys Ala Thr Gly Val Glu
            755                 760                 765

Trp Tyr Pro Thr Gly Asn Lys Asn Gln Lys Gln Ile Ile Lys Ala Arg
770                 775                 780

Tyr Glu Val Ile Ile Ser Ser Gly Ala Ile Gly Ser Pro Lys Leu Leu
785                 790                 795                 800

Glu Ile Ser Gly Ile Gly Asn Lys Asp Ile Val Ser Ala Ala Gly Val
            805                 810                 815
```

Glu Ser Leu Ile Asp Leu Pro Gly Val Gly Ser Asn Met Gln Asp His
            820                 825                 830

Val His Ala Ile Thr Val Ser Thr Thr Asn Ile Thr Gly Tyr Thr Thr
            835                 840                 845

Asn Ser Val Phe Val Asn Glu Thr Leu Ala Gln Glu Gln Arg Glu Glu
            850                 855                 860

Tyr Glu Ala Asn Lys Thr Gly Ile Trp Ala Thr Cys Pro Asn Asn Leu
865                 870                 875                 880

Gly Tyr Pro Thr Pro Glu Gln Leu Phe Asn Gly Thr Glu Phe Val Ser
                885                 890                 895

Gly Lys Glu Phe Ala Asp Lys Ile Arg Asn Ser Thr Asp Glu Trp Ala
                900                 905                 910

Asn Tyr Tyr Ala Ser Thr Asn Ala Ser Asn Val Glu Leu Leu Lys Lys
                915                 920                 925

Gln Tyr Ala Ile Val Ala Ser Arg Tyr Glu Glu Asn Tyr Leu Ser Pro
            930                 935                 940

Ile Glu Ile Asn Phe Thr Pro Gly Tyr Glu Gly Ser Gly Asn Val Asp
945                 950                 955                 960

Leu Gln Asn Asn Lys Tyr Gln Thr Val Asn His Val Leu Ile Ala Pro
                965                 970                 975

Leu Ser Arg Gly Tyr Thr His Ile Asn Ser Ser Asp Val Glu Asp His
            980                 985                 990

Ser Val Ile Asn Pro Gln Tyr Tyr Ser His Pro Met Asp Ile Asp Val
            995                 1000                1005

His Ile Ala Ser Thr Lys Leu Ala Arg Glu Ile Ile Thr Ala Ser
        1010                1015                1020

Pro Gly Leu Gly Asp Ile Asn Ser Gly Glu Ile Glu Pro Gly Met
        1025                1030                1035

Asn Ile Thr Ser Asp Asp Asp Val Arg Lys Trp Leu Ser Asn Asn
        1040                1045                1050

Val Arg Ser Asp Trp His Pro Val Gly Thr Cys Ala Met Leu Pro
        1055                1060                1065

Lys Glu Leu Gly Gly Val Val Ser Pro Ala Leu Met Val Tyr Gly
        1070                1075                1080

Thr Ser Asn Leu Arg Val Val Asp Ala Ser Ile Met Pro Leu Glu
        1085                1090                1095

Val Ser Ser His Leu Met Gln Pro Thr Tyr Gly Ile Ala Glu Lys
        1100                1105                1110

Ala Ala Asp Ile Ile Lys Asn Phe Tyr Lys Thr Gln His Lys Asn
        1115                1120                1125

Gln Asn
    1130

<210> SEQ ID NO 40
<211> LENGTH: 3493
<212> TYPE: DNA
<213> ORGANISM: Artificial
<220> FEATURE:
<223> OTHER INFORMATION: construct

<400> SEQUENCE: 40
atgaagctcg ttaaccgttt gctcgcttca ttcctgtcag cgagcaccgg tgagtggtgg    60
cctatcgagc taatgttgct tctcttcgtc tgacttttct tggcagtgtt gcagtcatgc   120
tgggctcagt ccggcacacc ggttgcctac acggatactg agacgggcat cacgtttgac   180

```
acgtggtcgg tacctgctgg tacgggtacg ggtggtctcg tcttcggtgt agccctgccg    240
ggttcggcat tgaccaccga tgcgacggag tttatcggtt acctggtgag gatctcgagc    300
taatcatgac cgctctgaag tggcgctaaa cgttctaatg tttcaagcaa tgtgcgtccc    360
aaaatgcctc gtccgctggc tggtgtggca tttccttggg tggtggcatg aacaacaatc    420
tcttgttctt ggcctatccg tacgaggata ccatcttgac ctccctgcga ttcggctcgg    480
gctatagcat gcccggggtc tataccggca atgccaacgt cacccagatt tcttcaagca    540
tcaatgccac tcactttacg ttgcttttcc gttgcgagaa ttgtctgacc tgggaccaag    600
atggtcaaac cggaaacgcg accacaagca agggtaggtt agtcctggga tgggcacagt    660
ctacggagag cccgtcgaac ccgtcctgtc cggacaatat cagcctggcg cagcacgaca    720
accagggtat tatctcagcc actctggatg agaatgcagc cagtgagtcc tacgaggact    780
gggtcaagtt ggctaataag actgttcccg gggactgctc cggtgacggt ggtggcggca    840
acgagccgac tcctgtccct gtccctgacg gtgctacatc cggcacaccg gttgcctaca    900
cggatactga cgggcatc acgtttgaca cgtggtcggg acctgctggt acgggtacgg    960
gtggtctcgt cttcggtgta gccctgccgg gttcggcatt gaccaccgat gcgacggagt    1020
ttatcggtta cctggtgagg atctcgagct aatcatgacc gctctgaagt ggcgctaaac    1080
gttctaatgt ttcaagcaat gtgcgtccca aaatgcctcg tccgctggct ggtgtggcat    1140
ttccttgggt ggtggcatga acaacaatct cttgttcttg gcctatccgt acgaggatac    1200
catcttgacc tccctgcgat tcggctcggg ctatagcatg cccggggtct ataccggcaa    1260
tgccaacgtc acccagattt cttcaagcat caatgccact cactttacgt tgcttttccg    1320
ttgcgagaat tgtctgacct gggaccaaga tggtcaaacc ggaaacgcga ccacaagcaa    1380
gggtaggtta gtcctgggat gggcacagtc tacggagagc ccgtcgaacc cgtcctgtcc    1440
ggacaatatc agcctggcgc agcacgacaa ccagggtatt atctcagcca ctctggatga    1500
gaatgcagcc agtgagtcct acgaggactg ggtcaagttg gctaataaga ctgttcccgg    1560
ggactgctcc ggtgacggtg gtggcggcaa cgagccgact cctgtccctg tccctgacgg    1620
tgctacacaa caagacacaa attcttcctc aactgatact tatgattatg ttatcgttgg    1680
cggcggtgta gctggtttgg ctttggctag tcgtatctct gaaaacaagg atgtcactgt    1740
tgctgttctc gagtccggtc cttatgccgg tgatagattt gttgtttatg ctcctggcat    1800
gtatggccaa gctgttggca ctgatctcgc tcctctcatt cctactactc ctcaagaaaa    1860
tatgggcaac agaagtctca caatcgctac tggtagattg ctcggtggtg gcagtgctat    1920
taatggtctc gtttggaccc gtggtggctt gaaggattac gatgcttggg aggagctcgg    1980
taaccctgga tggaacggtg ccaacttgtt caagtacttt aagaaggtcg aaaacttcac    2040
tcctcctact cctgcccaaa ttgaatacgg cgctacttat cagaaaagtg ctcatggcaa    2100
gaagggacct attgatgtct ctttcacgaa ctacgagttc tctcaatctg ctagctggaa    2160
cgcctcactc gaaacccttg atttcactgc acttcctgat atcttgaacg gtactttggc    2220
cggttactct accactccca acattttgga ccctgagact gttcgacgtg ttgattccta    2280
tactggttac attgctcctt acactagccg taacaacctc aatgttttgg ccaaccatac    2340
cgtctcccgc attcaatttg ctcccaagaa tggtagcgaa cctctcaagg ctaccggtgt    2400
tgaatggtat cccactggca acaagaatca aaagcaaatt atcaaggccc gttatgaagt    2460
tatcatctca tctggtgcca ttggtagtcc taagcttttg gaaatctctg gtatcggtaa    2520
taaggatatc gtctctgctg ctggtgtcga gtccttgatt gacttgcctg gcgttggttc    2580
```

```
caacatgcaa gatcacgttc atgctatcac tgtctctact accaatatta ctggctatac    2640
taccaacagc gtctttgtca atgaaaccct gcccaagaa  caaagagaag aatatgaagc    2700
caacaagact ggtatctggg ctacttgtcc caacaacctc ggttatccta cgcccgaaca    2760
actcttcaat ggcaccgaat tcgtttctgg aaaggagttt gctgacaaga ttcgtaactc    2820
tactgatgaa tgggccaact attatgcttc caccaacgcc tccaatgtcg agttattaaa    2880
gaagcaatat gctattgtcg cctctcgtta cgaagagaac tacttgtctc ctattgaaat    2940
caacttcact cctggttatg agggtagcgg taatgtcgat ttgcaaaaca acaagtacca    3000
aactgtcaac catgtcttga ttgctccttt aagtcgtggt tatactcaca ttaactcttc    3060
tgatgtggag gatcattctg tcattaatcc ccaatactac tctcatccta tggatattga    3120
tgtccatatc gcttccacta aacttgctcg cgaaatcatc actgcctctc ccggtcttgg    3180
tgacattaac agtggcgaaa tcgaacccgg tatgaatatt acttctgacg acgacgttag    3240
aaaatggttg agtaataatg tccgttctga ctggcatcct gttggtactt gtgctatgct    3300
tcccaaggaa ttaggtggtg ttgtcagccc cgctctcatg gtttacggca cttccaactt    3360
gcgtgttgtt gatgcttcga ttatgcccct cgaagtctct tctcatttga tgcaacccac    3420
ctacggtatt gctgagaagg ctgctgacat tattaagaat ttctacaaga ctcaacacaa    3480
gaaccaaaat tag                                                        3493

<210> SEQ ID NO 41
<211> LENGTH: 892
<212> TYPE: PRT
<213> ORGANISM: Artificial
<220> FEATURE:
<223> OTHER INFORMATION: fusion protein

<400> SEQUENCE: 41

Met Lys Leu Val Asn Arg Leu Leu Ala Ser Phe Leu Ser Ala Ser Thr
1               5                   10                  15

Val Leu Gln Ser Cys Trp Ala Gln Ser Gly Thr Pro Val Ala Tyr Thr
            20                  25                  30

Asp Thr Glu Thr Gly Ile Thr Phe Asp Thr Trp Ser Val Pro Ala Gly
        35                  40                  45

Thr Gly Thr Gly Gly Leu Val Phe Gly Val Ala Leu Pro Gly Ser Ala
    50                  55                  60

Leu Thr Thr Asp Ala Thr Glu Phe Ile Gly Tyr Leu Gln Cys Ala Ser
65                  70                  75                  80

Gln Asn Ala Ser Ser Ala Gly Trp Cys Gly Ile Ser Leu Gly Gly Gly
                85                  90                  95

Met Asn Asn Asn Leu Leu Phe Leu Ala Tyr Pro Tyr Glu Asp Thr Ile
            100                 105                 110

Leu Thr Ser Leu Arg Phe Gly Ser Gly Tyr Ser Met Pro Gly Val Tyr
        115                 120                 125

Thr Gly Asn Ala Asn Val Thr Gln Ile Ser Ser Ile Asn Ala Thr
    130                 135                 140

His Phe Thr Leu Leu Phe Arg Cys Glu Asn Cys Leu Thr Trp Asp Gln
145                 150                 155                 160

Asp Gly Gln Thr Gly Asn Ala Thr Thr Ser Lys Gly Arg Leu Val Leu
                165                 170                 175

Gly Trp Ala Gln Ser Thr Glu Ser Pro Ser Asn Pro Ser Cys Pro Asp
            180                 185                 190
```

-continued

```
Asn Ile Ser Leu Ala Gln His Asp Asn Gln Gly Ile Ser Ala Thr
            195                 200                 205
Leu Asp Glu Asn Ala Ala Ser Glu Ser Tyr Asp Trp Val Asp Cys
210                 215                 220
Ser Gly Asp Gly Gly Gly Asn Glu Pro Thr Pro Val Pro Val Pro
225                 230                 235                 240
Asp Gly Ala Thr Gln Leu Ala Thr Ile Thr Pro Pro Thr Cys Asp
            245                 250                 255
Gly Asn Gly Pro Gly Asp Lys Val Cys Val Pro Ala Pro Glu Asp Gln
                260                 265                 270
Gln Asp Thr Asn Ser Ser Thr Asp Thr Tyr Asp Tyr Val Ile Val
            275                 280                 285
Gly Gly Gly Val Ala Gly Leu Ala Leu Ala Ser Arg Ile Ser Glu Asn
290                 295                 300
Lys Asp Val Thr Val Ala Val Leu Glu Ser Gly Pro Tyr Ala Gly Asp
305                 310                 315                 320
Arg Phe Val Val Tyr Ala Pro Gly Met Tyr Gln Ala Val Gly Thr
                325                 330                 335
Asp Leu Ala Pro Leu Ile Pro Thr Thr Pro Gln Glu Asn Met Gly Asn
            340                 345                 350
Arg Ser Leu Thr Ile Ala Thr Gly Arg Leu Leu Gly Gly Gly Ser Ala
            355                 360                 365
Ile Asn Gly Leu Val Trp Thr Arg Gly Gly Leu Lys Asp Tyr Asp Ala
370                 375                 380
Trp Glu Glu Leu Gly Asn Pro Gly Trp Asn Gly Ala Asn Leu Phe Lys
385                 390                 395                 400
Tyr Phe Lys Lys Val Glu Asn Phe Thr Pro Thr Pro Ala Gln Ile
                405                 410                 415
Glu Tyr Gly Ala Thr Tyr Gln Lys Ser Ala His Gly Lys Lys Gly Pro
                420                 425                 430
Ile Asp Val Ser Phe Thr Asn Tyr Glu Phe Ser Gln Ser Ala Ser Trp
            435                 440                 445
Asn Ala Ser Leu Glu Thr Leu Asp Phe Thr Ala Leu Pro Asp Ile Leu
450                 455                 460
Asn Gly Thr Leu Ala Gly Tyr Ser Thr Thr Pro Asn Ile Leu Asp Pro
465                 470                 475                 480
Glu Thr Val Arg Arg Val Asp Ser Tyr Thr Gly Tyr Ile Ala Pro Tyr
                485                 490                 495
Thr Ser Arg Asn Asn Leu Asn Val Leu Ala Asn His Thr Val Ser Arg
            500                 505                 510
Ile Gln Phe Ala Pro Lys Asn Gly Ser Glu Pro Leu Lys Ala Thr Gly
            515                 520                 525
Val Glu Trp Tyr Pro Thr Gly Asn Lys Asn Gln Lys Gln Ile Ile Lys
530                 535                 540
Ala Arg Tyr Glu Val Ile Ile Ser Ser Gly Ala Ile Gly Ser Pro Lys
545                 550                 555                 560
Leu Leu Glu Ile Ser Gly Ile Gly Asn Lys Asp Ile Val Ser Ala Ala
                565                 570                 575
Gly Val Glu Ser Leu Ile Asp Leu Pro Gly Val Gly Ser Asn Met Gln
            580                 585                 590
Asp His Val His Ala Ile Thr Val Ser Thr Asn Ile Thr Gly Tyr
            595                 600                 605
Thr Thr Asn Ser Val Phe Val Asn Glu Thr Leu Ala Gln Glu Gln Arg
```

```
                610           615           620
Glu Glu Tyr Glu Ala Asn Lys Thr Gly Ile Trp Ala Thr Cys Pro Asn
625                 630                 635                 640

Asn Leu Gly Tyr Pro Thr Pro Glu Gln Leu Phe Asn Gly Thr Glu Phe
                645                 650                 655

Val Ser Gly Lys Glu Phe Ala Asp Lys Ile Arg Asn Ser Thr Asp Glu
            660                 665                 670

Trp Ala Asn Tyr Tyr Ala Ser Thr Asn Ala Ser Asn Val Glu Leu Leu
        675                 680                 685

Lys Lys Gln Tyr Ala Ile Val Ala Ser Arg Tyr Glu Glu Asn Tyr Leu
    690                 695                 700

Ser Pro Ile Glu Ile Asn Phe Thr Pro Gly Tyr Glu Gly Ser Gly Asn
705                 710                 715                 720

Val Asp Leu Gln Asn Asn Lys Tyr Gln Thr Val Asn His Val Leu Ile
                725                 730                 735

Ala Pro Leu Ser Arg Gly Tyr Thr His Ile Asn Ser Ser Asp Val Glu
            740                 745                 750

Asp His Ser Val Ile Asn Pro Gln Tyr Tyr Ser His Pro Met Asp Ile
        755                 760                 765

Asp Val His Ile Ala Ser Thr Lys Leu Ala Arg Glu Ile Ile Thr Ala
    770                 775                 780

Ser Pro Gly Leu Gly Asp Ile Asn Ser Gly Glu Ile Glu Pro Gly Met
785                 790                 795                 800

Asn Ile Thr Ser Asp Asp Val Arg Lys Trp Leu Ser Asn Asn Val
                805                 810                 815

Arg Ser Asp Trp His Pro Val Gly Thr Cys Ala Met Leu Pro Lys Glu
            820                 825                 830

Leu Gly Gly Val Val Ser Pro Ala Leu Met Val Tyr Gly Thr Ser Asn
        835                 840                 845

Leu Arg Val Val Asp Ala Ser Ile Met Pro Leu Glu Val Ser Ser His
    850                 855                 860

Leu Met Gln Pro Thr Tyr Gly Ile Ala Glu Lys Ala Ala Asp Ile Ile
865                 870                 875                 880

Lys Asn Phe Tyr Lys Thr Gln His Lys Asn Gln Asn
                885                 890
```

<210> SEQ ID NO 42
<211> LENGTH: 2717
<212> TYPE: DNA
<213> ORGANISM: Artificial
<220> FEATURE:
<223> OTHER INFORMATION: construct

<400> SEQUENCE: 42

| | | |
|---|---|---|
| atgaagctcg ttaaccgttt gctcgcttca ttcctgtcag cgagcaccgg tgagtggtgg | 60 |
| cctatcgagc taatgttgct tctcttcgtc tgactttct tggcagtgtt gcagtcatgc | 120 |
| tgggctcagt ccggcacacc ggttgcctac acggatactg agacgggcat acgtttgac | 180 |
| acgtggtcgg tacctgctgg tacgggtacg ggtggtctcg tcttcggtgt agccctgccg | 240 |
| ggttcggcat tgaccaccga tgcgacggag tttatcggtt acctggtgag gatctcgagc | 300 |
| taatcatgac cgctctgaag tggcgctaaa cgttctaatg tttcaagcaa tgtgcgtccc | 360 |
| aaaatgcctc gtccgctggc tggtgtggca tttccttggg tggtggcatg aacaacaatc | 420 |
| tcttgttctt ggcctatccg tacgaggata ccatcttgac ctccctgcga ttcggctcgg | 480 |

-continued

```
gctatagcat gcccggggtc tataccggca atgccaacgt cacccagatt tcttcaagca      540
tcaatgccac tcactttacg ttgcttttcc gttgcgagaa ttgtctgacc tgggaccaag      600
atggtcaaac cggaaacgcg accacaagca agggtaggtt agtcctggga tgggcacagt      660
ctacggagag cccgtcgaac ccgtcctgtc cggacaatat cagcctggcg cagcacgaca      720
accagggtat tatctcagcc actctggatg agaatgcagc cagtgagtcc tacgaggact      780
gggtcgactg ctccggtgac ggtggtggcg gcaacgagcc gactcctgtc cctgtccctg      840
acggtgctac acaacaagac acaaattctt cctcaactga tacttatgat tatgttatcg      900
ttggcggcgg tgtagctggt ttggctttgg ctagtcgtat ctctgaaaac aaggatgtca      960
ctgttgctgt tctcgagtcc ggtccttatg ccggtgatag atttgttgtt tatgctcctg     1020
gcatgtatgg ccaagctgtt ggcactgatc tcgctcctct cattcctact actcctcaag     1080
aaaatatggg caacagaagt ctcacaatcg ctactggtag attgctcggt ggtggcagtg     1140
ctattaatgg tctcgtttgg acccgtggtg gcttgaagga ttacgatgct tgggaggagc     1200
tcggtaaccc tggatggaac ggtgccaact tgttcaagta ctttaagaag gtcgaaaact     1260
tcactcctcc tactcctgcc caaattgaat acggcgctac ttatcagaaa agtgctcatg     1320
gcaagaaggg acctattgat gtctctttca cgaactacga gttctctcaa tctgctagct     1380
ggaacgcctc actcgaaacc cttgatttca ctgcacttcc tgatatcttg aacggtactt     1440
tggccggtta ctctaccact cccaacattt ggaccctga ctgttcga cgtgttgatt      1500 cctatactgg ttacattgct ccttacacta gccgtaacaa cctcaatgtt ttggccaacc     1560
ataccgtctc ccgcattcaa tttgctccca agaatggtag cgaacctctc aaggctaccg     1620
gtgttgaatg gtatcccact ggcaacaaga atcaaaagca aattatcaag gcccgttatg     1680
aagttatcat ctcatctggt gccattggta gtcctaagct tttggaaatc tctggtatcg     1740
gtaataagga tatcgtctct gctgctggtg tcgagtcctt gattgacttg cctggcgttg     1800
gttccaacat gcaagatcac gttcatgcta tcactgtctc tactaccaat attactggct     1860
atactaccaa cagcgtcttt gtcaatgaaa cccttgccca agaacaaaga gaagaatatg     1920
aagccaacaa gactggtatc tgggctactt gtcccaacaa cctcggttat cctacgcccg     1980
aacaactctt caatggcacc gaattcgttt ctggaaagga gtttgctgac aagattcgta     2040
actctactga tgaatgggcc aactattatg cttccaccaa cgcctccaat gtcgagttat     2100
taaagaagca atatgctatt gtcgcctctc gttacgaaga gaactacttg tctcctattg     2160
aaatcaactt cactcctggt tatgagggta gcggtaatgt cgatttgcaa acaacaagt      2220 accaaactgt caaccatgtc ttgattgctc ctttaagtcg tggttatact cacattaact     2280
cttctgatgt ggaggatcat tctgtcatta atccccaata ctactctcat cctatggata     2340
ttgatgtcca tatcgcttcc actaaacttg ctcgcgaaat catcactgcc tctcccggtc     2400
ttggtgacat taacagtggc gaaatcgaac ccggtatgaa tattacttct gacgacgacg     2460
ttagaaaatg gttgagtaat aatgtccgtt ctgactggca tcctgttggt acttgtgcta     2520
tgcttcccaa ggaattaggt ggtgttgtca gccccgctct catggtttac ggcacttcca     2580
acttgcgtgt tgttgatgct tcgattatgc ccctcgaagt ctcttctcat ttgatgcaac     2640
ccacctacgg tattgctgag aaggctgctg acattattaa gaatttctac aagactcaac     2700
acaagaacca aaattag                                                    2717
```

<210> SEQ ID NO 43
<211> LENGTH: 843

```
<212> TYPE: PRT
<213> ORGANISM: Artificial
<220> FEATURE:
<223> OTHER INFORMATION: fusion protein

<400> SEQUENCE: 43
```

| | | | | | | | | | | | | | | |
|---|---|---|---|---|---|---|---|---|---|---|---|---|---|---|
| Met | Lys | Ile | Thr | Ala | Ala | Ile | Ile | Thr | Val | Ala | Thr | Ala | Phe | Ala | Ser |
| 1 | | | | 5 | | | | | 10 | | | | | 15 |
| Phe | Ala | Ser | Ala | Gln | Gln | Asp | Thr | Asn | Ser | Ser | Ser | Thr | Asp | Thr | Tyr |
| | | | 20 | | | | | 25 | | | | | 30 | | |
| Asp | Tyr | Val | Ile | Val | Gly | Gly | Val | Ala | Gly | Leu | Ala | Leu | Ala | Ser |
| | | | 35 | | | | 40 | | | | | 45 | | |
| Arg | Ile | Ser | Glu | Asn | Lys | Asp | Val | Thr | Val | Ala | Val | Leu | Glu | Ser | Gly |
| | 50 | | | | | 55 | | | | | 60 | | | | |
| Pro | Tyr | Ala | Gly | Asp | Arg | Phe | Val | Val | Tyr | Ala | Pro | Gly | Met | Tyr | Gly |
| 65 | | | | | 70 | | | | | 75 | | | | | 80 |
| Gln | Ala | Val | Gly | Thr | Asp | Leu | Ala | Pro | Leu | Ile | Pro | Thr | Thr | Pro | Gln |
| | | | | 85 | | | | | 90 | | | | | 95 | |
| Glu | Asn | Met | Gly | Asn | Arg | Ser | Leu | Thr | Ile | Ala | Thr | Gly | Arg | Leu | Leu |
| | | | 100 | | | | | 105 | | | | | 110 | | |
| Gly | Gly | Gly | Ser | Ala | Ile | Asn | Gly | Leu | Val | Trp | Thr | Arg | Gly | Gly | Leu |
| | | | 115 | | | | | 120 | | | | | 125 | | |
| Lys | Asp | Tyr | Asp | Ala | Trp | Glu | Glu | Leu | Gly | Asn | Pro | Gly | Trp | Asn | Gly |
| | 130 | | | | | 135 | | | | | 140 | | | | |
| Ala | Asn | Leu | Phe | Lys | Tyr | Phe | Lys | Lys | Val | Glu | Asn | Phe | Thr | Pro | Pro |
| 145 | | | | | 150 | | | | | 155 | | | | | 160 |
| Thr | Pro | Ala | Gln | Ile | Glu | Tyr | Gly | Ala | Thr | Tyr | Gln | Lys | Ser | Ala | His |
| | | | | 165 | | | | | 170 | | | | | 175 | |
| Gly | Lys | Lys | Gly | Pro | Ile | Asp | Val | Ser | Phe | Thr | Asn | Tyr | Glu | Phe | Ser |
| | | | 180 | | | | | 185 | | | | | 190 | | |
| Gln | Ser | Ala | Ser | Trp | Asn | Ala | Ser | Leu | Glu | Thr | Leu | Asp | Phe | Thr | Ala |
| | | | 195 | | | | | 200 | | | | | 205 | | |
| Leu | Pro | Asp | Ile | Leu | Asn | Gly | Thr | Leu | Ala | Gly | Tyr | Ser | Thr | Thr | Pro |
| | 210 | | | | | 215 | | | | | 220 | | | | |
| Asn | Ile | Leu | Asp | Pro | Glu | Thr | Val | Arg | Arg | Val | Asp | Ser | Tyr | Thr | Gly |
| 225 | | | | | 230 | | | | | 235 | | | | | 240 |
| Tyr | Ile | Ala | Pro | Tyr | Thr | Ser | Arg | Asn | Asn | Leu | Asn | Val | Leu | Ala | Asn |
| | | | | 245 | | | | | 250 | | | | | 255 | |
| His | Thr | Val | Ser | Arg | Ile | Gln | Phe | Ala | Pro | Lys | Asn | Gly | Ser | Glu | Pro |
| | | | 260 | | | | | 265 | | | | | 270 | | |
| Leu | Lys | Ala | Thr | Gly | Val | Glu | Trp | Tyr | Pro | Thr | Gly | Asn | Lys | Asn | Gln |
| | | | 275 | | | | | 280 | | | | | 285 | | |
| Lys | Gln | Ile | Ile | Lys | Ala | Arg | Tyr | Glu | Val | Ile | Ile | Ser | Ser | Gly | Ala |
| | 290 | | | | | 295 | | | | | 300 | | | | |
| Ile | Gly | Ser | Pro | Lys | Leu | Leu | Glu | Ile | Ser | Gly | Ile | Gly | Asn | Lys | Asp |
| 305 | | | | | 310 | | | | | 315 | | | | | 320 |
| Ile | Val | Ser | Ala | Ala | Gly | Val | Glu | Ser | Leu | Ile | Asp | Leu | Pro | Gly | Val |
| | | | | 325 | | | | | 330 | | | | | 335 | |
| Gly | Ser | Asn | Met | Gln | Asp | His | Val | His | Ala | Ile | Thr | Val | Ser | Thr | Thr |
| | | | 340 | | | | | 345 | | | | | 350 | | |
| Asn | Ile | Thr | Gly | Tyr | Thr | Thr | Asn | Ser | Val | Phe | Val | Asn | Glu | Thr | Leu |
| | | | 355 | | | | | 360 | | | | | 365 | | |
| Ala | Gln | Glu | Gln | Arg | Glu | Glu | Tyr | Glu | Ala | Asn | Lys | Thr | Gly | Ile | Trp |
| | 370 | | | | | 375 | | | | | 380 | | | | |

```
Ala Thr Cys Pro Asn Asn Leu Gly Tyr Pro Thr Pro Glu Gln Leu Phe
385                 390                 395                 400

Asn Gly Thr Glu Phe Val Ser Gly Lys Glu Phe Ala Asp Lys Ile Arg
            405                 410                 415

Asn Ser Thr Asp Glu Trp Ala Asn Tyr Tyr Ala Ser Thr Asn Ala Ser
        420                 425                 430

Asn Val Glu Leu Leu Lys Lys Gln Tyr Ala Ile Val Ala Ser Arg Tyr
    435                 440                 445

Glu Glu Asn Tyr Leu Ser Pro Ile Glu Ile Asn Phe Thr Pro Gly Tyr
450                 455                 460

Glu Gly Ser Gly Asn Val Asp Leu Gln Asn Asn Lys Tyr Gln Thr Val
465                 470                 475                 480

Asn His Val Leu Ile Ala Pro Leu Ser Arg Gly Tyr Thr His Ile Asn
            485                 490                 495

Ser Ser Asp Val Glu Asp His Ser Val Ile Asn Pro Gln Tyr Tyr Ser
        500                 505                 510

His Pro Met Asp Ile Asp Val His Ile Ala Ser Thr Lys Leu Ala Arg
    515                 520                 525

Glu Ile Ile Thr Ala Ser Pro Gly Leu Gly Asp Ile Asn Ser Gly Glu
530                 535                 540

Ile Glu Pro Gly Met Asn Ile Thr Ser Asp Asp Val Arg Lys Trp
545                 550                 555                 560

Leu Ser Asn Asn Val Arg Ser Asp Trp His Pro Val Gly Thr Cys Ala
            565                 570                 575

Met Leu Pro Lys Glu Leu Gly Gly Val Val Ser Pro Ala Leu Met Val
        580                 585                 590

Tyr Gly Thr Ser Asn Leu Arg Val Val Asp Ala Ser Ile Met Pro Leu
    595                 600                 605

Glu Val Ser Ser His Leu Met Gln Pro Thr Tyr Gly Ile Ala Glu Lys
610                 615                 620

Ala Ala Asp Ile Ile Lys Asn Phe Tyr Lys Thr Gln His Lys Asn Gln
625                 630                 635                 640

Asn Lys Leu Ala Asn Lys Gln Met Thr Glu Gly Thr Tyr Thr His Glu
            645                 650                 655

Ala Thr Gly Ile Thr Phe Lys Thr Trp Thr Pro Ser Asp Gly Ser Thr
        660                 665                 670

Phe Thr Phe Gly Leu Ala Leu Pro Gly Asp Ala Leu Thr Asn Asp Ala
    675                 680                 685

Thr Glu Tyr Ile Gly Leu Leu Arg Cys Gln Ile Thr Asp Pro Ser Ser
690                 695                 700

Pro Gly Tyr Cys Gly Ile Ser His Gly Gln Ser Gly Gln Met Thr Gln
705                 710                 715                 720

Ala Leu Leu Leu Val Ala Trp Ala Ser Glu Asp Val Val Tyr Thr Ser
            725                 730                 735

Phe Arg Tyr Ala Thr Gly Tyr Thr Leu Pro Glu Leu Tyr Thr Gly Asp
        740                 745                 750

Ala Lys Leu Thr Gln Ile Ala Ser Ser Val Ser Gly Asp Ser Phe Glu
    755                 760                 765

Val Leu Phe Arg Cys Glu Asn Cys Phe Ser Trp Asp Gln Asn Gly Ala
770                 775                 780

Thr Gly Ser Val Ser Thr Ser Asn Gly Ala Leu Val Leu Gly Tyr Ala
785                 790                 795                 800

Ala Ser Lys Ser Gly Leu Thr Gly Ala Thr Cys Pro Asp Thr Ala Glu
```

805                 810                 815
Phe Gly Phe His Asn Asn Gly Phe Gly Gln Trp Gly Ala Val Leu Glu
        820                 825                 830

Gly Ala Thr Ser Asp Ser Tyr Glu Glu Trp Ala
        835                 840

<210> SEQ ID NO 44
<211> LENGTH: 2532
<212> TYPE: DNA
<213> ORGANISM: Artificial
<220> FEATURE:
<223> OTHER INFORMATION: construct

<400> SEQUENCE: 44

| | | | | |
|---|---|---|---|---|
| atgaagatca | cagctgccat | tatcactgtt | gccacagcat | tgcttctttt tgcttctgct | 60 |
| caacaagaca | caaattcttc | ctcaactgat | acttatgatt | atgttatcgt tggcggcggt | 120 |
| gtagctggtt | tggctttggc | tagtcgtatc | tctgaaaaca | aggatgtcac tgttgctgtt | 180 |
| ctcgagtccg | gtccttatgc | cggtgataga | tttgttgttt | atgctcctgg catgtatggc | 240 |
| caagctgttg | gcactgatct | cgctcctctc | attcctacta | ctcctcaaga aaatatgggc | 300 |
| aacagaagtc | tcacaatcgc | tactggtaga | ttgctcggtg | gtggcagtgc tattaatggt | 360 |
| ctcgtttgga | cccgtggtgg | cttgaaggat | tacgatgctt | gggaggagct cggtaaccct | 420 |
| ggatggaacg | tgccaacttg | ttcaagtac | tttaagaagg | tcgaaaactt cactcctcct | 480 |
| actcctgccc | aaattgaata | cggcgctact | tatcagaaaa | gtgctcatgg caagaaggga | 540 |
| cctattgatg | tctctttcac | gaactacgag | ttctctcaat | ctgctagctg aacgcctca | 600 |
| ctcgaaaccc | ttgatttcac | tgcacttcct | gatatcttga | acggtacttt ggccggttac | 660 |
| tctaccactc | ccaacatttt | ggaccctgag | actgttcgac | gtgttgattc ctatactggt | 720 |
| tacattgctc | cttacactag | ccgtaacaac | ctcaatgttt | tggccaacca taccgtctcc | 780 |
| cgcattcaat | tgctcccaa | gaatggtagc | gaacctctca | aggctaccgg tgttgaatgg | 840 |
| tatcccactg | gcaacaagaa | tcaaaagcaa | attatcaagg | cccgttatga agttatcatc | 900 |
| tcatctggtg | ccattggtag | tcctaagctt | ttggaaatct | ctggtatcgg taataaggat | 960 |
| atcgtctctg | ctgctggtgt | cgagtccttg | attgacttgc | ctggcgttgg ttccaacatg | 1020 |
| caagatcacg | ttcatgctat | cactgtctct | actaccaata | ttactggcta tactaccaac | 1080 |
| agcgtctttg | tcaatgaaac | ccttgcccaa | gaacaaagag | aagaatatga agccaacaag | 1140 |
| actggtatct | gggctacttg | tcccaacaac | ctcggttatc | ctacgcccga caactcttc | 1200 |
| aatggcaccg | aattcgtttc | tggaaaggag | tttgctgaca | agattcgtaa ctctactgat | 1260 |
| gaatgggcca | actattatgc | ttccaccaac | gcctccaatg | tcgagttatt aaagaagcaa | 1320 |
| tatgctattg | tcgcctctcg | ttacgaagag | aactacttgt | ctcctattga aatcaacttc | 1380 |
| actcctggtt | atgagggtag | cggtaatgtc | gatttgcaaa | caacaagta ccaaactgtc | 1440 |
| aaccatgtct | tgattgctcc | tttaagtcgt | ggttatactc | acattaactc ttctgatgtg | 1500 |
| gaggatcatt | ctgtcattaa | tccccaatac | tactctcatc | ctatggatat tgatgtccat | 1560 |
| atcgcttcca | ctaaacttgc | tcgcgaaatc | atcactgcct | ctcccggtct tggtgacatt | 1620 |
| aacagtggcg | aaatcgaacc | cggtatgaat | attacttctg | acgacgacgt tagaaaatgg | 1680 |
| ttgagtaata | atgtccgttc | tgactggcat | cctgttggta | cttgtgctat gcttcccaag | 1740 |
| gaattaggtg | gtgttgtcag | cccgctctc | atggtttacg | gcacttccaa cttgcgtgtt | 1800 |
| gttgatgctt | cgattatgcc | cctcgaagtc | tcttctcatt | tgatgcaacc cacctacggt | 1860 |

-continued

```
attgctgaga aggctgctga cattattaag aatttctaca agactcaaca caagaaccaa      1920
aataaactgg cgaacaaaca gatgaccgag ggcacgtaca cccatgaagc tactggaatc      1980
acattcaaga cttggacacc gtcggatgga tcaacgttca cctttggtct tgccttgcct      2040
ggagatgctc tcacgaacga cgcaaccgag tacatcggcc ttttgcgatg ccagattacc      2100
gatccgtcct ctcctgggta ttgtggcatc tcgcacggcc agtcaggaca aatgacacag      2160
gctctcctgc ttgtcgcctg ggcttctgag gacgtcgtgt acacgagctt ccgctacgca      2220
acgggttata ccctcccccga actgtatact ggagatgcta agttgacaca aattgcaagc      2280
tcggtttctg gtgactcctt cgaggtcctc tttcgttgcg aaaactgttt ttcttgggat      2340
cagaatgggg ctacgggctc agtcagtacc tctaatggag cattggtgct gggatatgct      2400
gcttctaaga gcggtctgac tggagcgaca tgcccggata cagccgagtt cggctttcat      2460
aacaatggct tcggtcaatg gggtgcggtc ctggaaggag caacctcgga ctcatatgag      2520
gaatgggcat ag                                                           2532
```

<210> SEQ ID NO 45
<211> LENGTH: 30
<212> TYPE: DNA
<213> ORGANISM: Artificial
<220> FEATURE:
<223> OTHER INFORMATION: primer

<400> SEQUENCE: 45
cttgttgccc tgtgggaaca ggcactccca      30

<210> SEQ ID NO 46
<211> LENGTH: 30
<212> TYPE: DNA
<213> ORGANISM: Artificial
<220> FEATURE:
<223> OTHER INFORMATION: primer

<400> SEQUENCE: 46
cgcaccacct tcaaaatgcg cacctcttct      30

<210> SEQ ID NO 47
<211> LENGTH: 30
<212> TYPE: DNA
<213> ORGANISM: Artificial
<220> FEATURE:
<223> OTHER INFORMATION: primer

<400> SEQUENCE: 47
ccacagggca acaagacaca aattcttcct      30

<210> SEQ ID NO 48
<211> LENGTH: 25
<212> TYPE: DNA
<213> ORGANISM: Artificial
<220> FEATURE:
<223> OTHER INFORMATION: primer

<400> SEQUENCE: 48
tttgaaggtg gtgcgaactt tgtag      25

<210> SEQ ID NO 49
<211> LENGTH: 30
<212> TYPE: DNA
<213> ORGANISM: Artificial
<220> FEATURE:

<223> OTHER INFORMATION: primer

<400> SEQUENCE: 49
cttgttgatc ctcaggagcc gggacacaaa                                    30

<210> SEQ ID NO 50
<211> LENGTH: 30
<212> TYPE: DNA
<213> ORGANISM: Artificial
<220> FEATURE:
<223> OTHER INFORMATION: primer

<400> SEQUENCE: 50
cgcaccacct tcaaaatgaa gctcctgtcg                                    30

<210> SEQ ID NO 51
<211> LENGTH: 30
<212> TYPE: DNA
<213> ORGANISM: Artificial
<220> FEATURE:
<223> OTHER INFORMATION: primer

<400> SEQUENCE: 51
ctgaggatca acaagacaca aattcttcct                                    30

<210> SEQ ID NO 52
<211> LENGTH: 25
<212> TYPE: DNA
<213> ORGANISM: Artificial
<220> FEATURE:
<223> OTHER INFORMATION: primer

<400> SEQUENCE: 52
tttgaaggtg gtgcgaactt tgtag                                         25

<210> SEQ ID NO 53
<211> LENGTH: 30
<212> TYPE: DNA
<213> ORGANISM: Artificial
<220> FEATURE:
<223> OTHER INFORMATION: primer

<400> SEQUENCE: 53
cgcaccacct tcaaaatgaa gctcgttaac                                    30

<210> SEQ ID NO 54
<211> LENGTH: 30
<212> TYPE: DNA
<213> ORGANISM: Artificial
<220> FEATURE:
<223> OTHER INFORMATION: primer

<400> SEQUENCE: 54
cttgttgacc gtcagggaca gggacaggag                                    30

<210> SEQ ID NO 55
<211> LENGTH: 30
<212> TYPE: DNA
<213> ORGANISM: Artificial
<220> FEATURE:
<223> OTHER INFORMATION: primer

<400> SEQUENCE: 55
ctgacggtca acaagacaca aattcttcct                                    30

<210> SEQ ID NO 56
<211> LENGTH: 25
<212> TYPE: DNA
<213> ORGANISM: Artificial
<220> FEATURE:
<223> OTHER INFORMATION: primer

<400> SEQUENCE: 56
tttgaaggtg gtgcgaactt tgtag                                    25

<210> SEQ ID NO 57
<211> LENGTH: 30
<212> TYPE: DNA
<213> ORGANISM: Artificial
<220> FEATURE:
<223> OTHER INFORMATION: primer

<400> SEQUENCE: 57
gacccagtcc tcgtaggact cactggctgc                               30

<210> SEQ ID NO 58
<211> LENGTH: 30
<212> TYPE: DNA
<213> ORGANISM: Artificial
<220> FEATURE:
<223> OTHER INFORMATION: primer

<400> SEQUENCE: 58
gactgctccg gtgacggtgg tggcggcaac                               30

<210> SEQ ID NO 59
<211> LENGTH: 30
<212> TYPE: DNA
<213> ORGANISM: Artificial
<220> FEATURE:
<223> OTHER INFORMATION: primer

<400> SEQUENCE: 59
cttgttgacc gtcagggaca gggacaggag                               30

<210> SEQ ID NO 60
<211> LENGTH: 30
<212> TYPE: DNA
<213> ORGANISM: Artificial
<220> FEATURE:
<223> OTHER INFORMATION: primer

<400> SEQUENCE: 60
ctgacggttc cggcacaccg gttgcctaca                               30

<210> SEQ ID NO 61
<211> LENGTH: 30
<212> TYPE: DNA
<213> ORGANISM: Artificial
<220> FEATURE:
<223> OTHER INFORMATION: primer

<400> SEQUENCE: 61
ctgacggtca acaagacaca aattcttcct                               30

<210> SEQ ID NO 62
<211> LENGTH: 30
<212> TYPE: DNA
<213> ORGANISM: Artificial
<220> FEATURE:
<223> OTHER INFORMATION: primer

```
<400> SEQUENCE: 62
tgccggaacc gtcagggaca gggacaggag                                30

<210> SEQ ID NO 63
<211> LENGTH: 30
<212> TYPE: DNA
<213> ORGANISM: Artificial
<220> FEATURE:
<223> OTHER INFORMATION: primer

<400> SEQUENCE: 63
tttgttcgcc agtttatttt ggttcttgtg                                30

<210> SEQ ID NO 64
<211> LENGTH: 28
<212> TYPE: DNA
<213> ORGANISM: Artificial
<220> FEATURE:
<223> OTHER INFORMATION: primer

<400> SEQUENCE: 64
gtaccaggag tacattggag agttctac                                  28

<210> SEQ ID NO 65
<211> LENGTH: 30
<212> TYPE: DNA
<213> ORGANISM: Artificial
<220> FEATURE:
<223> OTHER INFORMATION: primer

<400> SEQUENCE: 65
aaactggcga acaaacagat gaccgagggc                                30

<210> SEQ ID NO 66
<211> LENGTH: 33
<212> TYPE: DNA
<213> ORGANISM: Artificial
<220> FEATURE:
<223> OTHER INFORMATION: primer

<400> SEQUENCE: 66
atgtactcct ggtacctatg cccattcctc ata                            33

<210> SEQ ID NO 67
<211> LENGTH: 21
<212> TYPE: PRT
<213> ORGANISM: Aspergillus terreus

<400> SEQUENCE: 67

Gly Asp Cys Ser Gly Asp Gly Gly Gly Ser Gly Pro Glu Pro Val
1               5                   10                  15

Pro Val Pro Asp Gly
            20

<210> SEQ ID NO 68
<211> LENGTH: 16
<212> TYPE: PRT
<213> ORGANISM: HSP70

<400> SEQUENCE: 68

Gly Gly Gly Gly Ser Leu Val Pro Arg Gly Ser Gly Gly Gly Ser
1               5                   10                  15

<210> SEQ ID NO 69
```

```
<211> LENGTH: 16
<212> TYPE: PRT
<213> ORGANISM: Hen egg lysozyme

<400> SEQUENCE: 69

Gly Gly Gly Gly Ser Leu Val Pro Arg Gly Ser Gly Gly Gly Gly Ser
1               5                   10                  15

<210> SEQ ID NO 70
<211> LENGTH: 8
<212> TYPE: PRT
<213> ORGANISM: Influenza virus

<400> SEQUENCE: 70

Gly Gly Ser Gly Gly Gly Gly Gly
1               5

<210> SEQ ID NO 71
<211> LENGTH: 4
<212> TYPE: PRT
<213> ORGANISM: Artificial
<220> FEATURE:
<223> OTHER INFORMATION: linker

<400> SEQUENCE: 71

Gly Gly Gly Gly
1

<210> SEQ ID NO 72
<211> LENGTH: 5
<212> TYPE: PRT
<213> ORGANISM: Artificial
<220> FEATURE:
<223> OTHER INFORMATION: linker

<400> SEQUENCE: 72

Gly Gly Gly Gly Gly
1               5

<210> SEQ ID NO 73
<211> LENGTH: 4
<212> TYPE: PRT
<213> ORGANISM: Artificial
<220> FEATURE:
<223> OTHER INFORMATION: linker

<400> SEQUENCE: 73

Gly Ala Gly Ala
1

<210> SEQ ID NO 74
<211> LENGTH: 6
<212> TYPE: PRT
<213> ORGANISM: Artificial
<220> FEATURE:
<223> OTHER INFORMATION: linker

<400> SEQUENCE: 74

Gly Ala Gly Ala Gly Ala
1               5

<210> SEQ ID NO 75
<211> LENGTH: 8
<212> TYPE: PRT
<213> ORGANISM: Artificial
<220> FEATURE:
<223> OTHER INFORMATION: linker
```

<400> SEQUENCE: 75

Gly Ala Gly Ala Gly Ala Gly Ala
1               5

<210> SEQ ID NO 76
<211> LENGTH: 4
<212> TYPE: PRT
<213> ORGANISM: Artificial
<220> FEATURE:
<223> OTHER INFORMATION: linker

<400> SEQUENCE: 76

Gly Gly Gly Ala
1

<210> SEQ ID NO 77
<211> LENGTH: 8
<212> TYPE: PRT
<213> ORGANISM: Artificial
<220> FEATURE:
<223> OTHER INFORMATION: linker

<400> SEQUENCE: 77

Gly Gly Gly Ala Gly Gly Gly Ala
1               5

<210> SEQ ID NO 78
<211> LENGTH: 12
<212> TYPE: PRT
<213> ORGANISM: Artificial
<220> FEATURE:
<223> OTHER INFORMATION: linker

<400> SEQUENCE: 78

Gly Gly Gly Ala Gly Gly Gly Ala Gly Gly Gly Ala
1               5                   10

<210> SEQ ID NO 79
<211> LENGTH: 16
<212> TYPE: PRT
<213> ORGANISM: Artificial
<220> FEATURE:
<223> OTHER INFORMATION: linker

<400> SEQUENCE: 79

Gly Gly Gly Ala Gly Gly Gly Ala Gly Gly Gly Ala Gly Gly Gly Ala
1               5                   10                  15

<210> SEQ ID NO 80
<211> LENGTH: 4
<212> TYPE: PRT
<213> ORGANISM: Artificial
<220> FEATURE:
<223> OTHER INFORMATION: linker

<400> SEQUENCE: 80

Gly Gly Ala Gly
1

<210> SEQ ID NO 81
<211> LENGTH: 8
<212> TYPE: PRT
<213> ORGANISM: Artificial
<220> FEATURE:
<223> OTHER INFORMATION: linker

```
<400> SEQUENCE: 81

Gly Gly Ala Gly Gly Gly Ala Gly
1               5

<210> SEQ ID NO 82
<211> LENGTH: 12
<212> TYPE: PRT
<213> ORGANISM: Artificial
<220> FEATURE:
<223> OTHER INFORMATION: linker

<400> SEQUENCE: 82

Gly Gly Ala Gly Gly Gly Ala Gly Gly Gly Ala Gly
1               5                   10

<210> SEQ ID NO 83
<211> LENGTH: 16
<212> TYPE: PRT
<213> ORGANISM: Artificial
<220> FEATURE:
<223> OTHER INFORMATION: linker

<400> SEQUENCE: 83

Gly Gly Ala Gly Gly Gly Ala Gly Gly Gly Ala Gly Gly Gly Ala Gly
1               5                   10                  15

<210> SEQ ID NO 84
<211> LENGTH: 5
<212> TYPE: PRT
<213> ORGANISM: Artificial
<220> FEATURE:
<223> OTHER INFORMATION: linker

<400> SEQUENCE: 84

Gly Gly Gly Gly Ala
1               5

<210> SEQ ID NO 85
<211> LENGTH: 10
<212> TYPE: PRT
<213> ORGANISM: Artificial
<220> FEATURE:
<223> OTHER INFORMATION: linker

<400> SEQUENCE: 85

Gly Gly Gly Gly Ala Gly Gly Gly Gly Ala
1               5                   10

<210> SEQ ID NO 86
<211> LENGTH: 15
<212> TYPE: PRT
<213> ORGANISM: Artificial
<220> FEATURE:
<223> OTHER INFORMATION: linker

<400> SEQUENCE: 86

Gly Gly Gly Gly Ala Gly Gly Gly Gly Ala Gly Gly Gly Gly Ala
1               5                   10                  15

<210> SEQ ID NO 87
<211> LENGTH: 5
<212> TYPE: PRT
<213> ORGANISM: Artificial
<220> FEATURE:
<223> OTHER INFORMATION: linker

<400> SEQUENCE: 87
```

```
Gly Gly Ala Gly Gly
1               5

<210> SEQ ID NO 88
<211> LENGTH: 10
<212> TYPE: PRT
<213> ORGANISM: Artificial
<220> FEATURE:
<223> OTHER INFORMATION: linker

<400> SEQUENCE: 88

Gly Gly Ala Gly Gly Gly Gly Ala Gly Gly
1               5                   10

<210> SEQ ID NO 89
<211> LENGTH: 13
<212> TYPE: PRT
<213> ORGANISM: Artificial
<220> FEATURE:
<223> OTHER INFORMATION: linker

<400> SEQUENCE: 89

Gly Gly Gly Ala Gly Gly Gly Ala Gly Gly Gly Ala
1               5                   10

<210> SEQ ID NO 90
<211> LENGTH: 14
<212> TYPE: PRT
<213> ORGANISM: Artificial
<220> FEATURE:
<223> OTHER INFORMATION: linker

<400> SEQUENCE: 90

Gly Gly Gly Gly Ala Gly Gly Gly Ala Gly Gly Gly Gly Ala
1               5                   10

<210> SEQ ID NO 91
<211> LENGTH: 4
<212> TYPE: PRT
<213> ORGANISM: Artificial
<220> FEATURE:
<223> OTHER INFORMATION: linker

<400> SEQUENCE: 91

Gly Ser Gly Ser
1

<210> SEQ ID NO 92
<211> LENGTH: 6
<212> TYPE: PRT
<213> ORGANISM: Artificial
<220> FEATURE:
<223> OTHER INFORMATION: linker

<400> SEQUENCE: 92

Gly Ser Gly Ser Gly Ser
1               5

<210> SEQ ID NO 93
<211> LENGTH: 8
<212> TYPE: PRT
<213> ORGANISM: Artificial
<220> FEATURE:
<223> OTHER INFORMATION: linker

<400> SEQUENCE: 93
```

Gly Ser Gly Ser Gly Ser Gly Ser
1               5

<210> SEQ ID NO 94
<211> LENGTH: 6
<212> TYPE: PRT
<213> ORGANISM: Artificial
<220> FEATURE:
<223> OTHER INFORMATION: linker

<400> SEQUENCE: 94

Gly Ser Gly Gly Ser Gly
1               5

<210> SEQ ID NO 95
<211> LENGTH: 9
<212> TYPE: PRT
<213> ORGANISM: Artificial
<220> FEATURE:
<223> OTHER INFORMATION: linker

<400> SEQUENCE: 95

Gly Ser Gly Gly Ser Gly Gly Ser Gly
1               5

<210> SEQ ID NO 96
<211> LENGTH: 12
<212> TYPE: PRT
<213> ORGANISM: Artificial
<220> FEATURE:
<223> OTHER INFORMATION: linker

<400> SEQUENCE: 96

Gly Ser Gly Gly Ser Gly Gly Ser Gly Gly Ser Gly
1               5                   10

<210> SEQ ID NO 97
<211> LENGTH: 4
<212> TYPE: PRT
<213> ORGANISM: Artificial
<220> FEATURE:
<223> OTHER INFORMATION: linker

<400> SEQUENCE: 97

Gly Gly Gly Ser
1

<210> SEQ ID NO 98
<211> LENGTH: 8
<212> TYPE: PRT
<213> ORGANISM: Artificial
<220> FEATURE:
<223> OTHER INFORMATION: linker

<400> SEQUENCE: 98

Gly Gly Gly Ser Gly Gly Gly Ser
1               5

<210> SEQ ID NO 99
<211> LENGTH: 12
<212> TYPE: PRT
<213> ORGANISM: Artificial
<220> FEATURE:
<223> OTHER INFORMATION: linker

<400> SEQUENCE: 99

Gly Gly Gly Ser Gly Gly Gly Ser Gly Gly Gly Ser

```
1               5               10

<210> SEQ ID NO 100
<211> LENGTH: 16
<212> TYPE: PRT
<213> ORGANISM: Artificial
<220> FEATURE:
<223> OTHER INFORMATION: linker

<400> SEQUENCE: 100

Gly Gly Gly Ser Gly Gly Gly Ser Gly Gly Ser Gly Gly Gly Ser
1               5                   10                  15

<210> SEQ ID NO 101
<211> LENGTH: 4
<212> TYPE: PRT
<213> ORGANISM: Artificial
<220> FEATURE:
<223> OTHER INFORMATION: linker

<400> SEQUENCE: 101

Gly Gly Ser Gly
1

<210> SEQ ID NO 102
<211> LENGTH: 8
<212> TYPE: PRT
<213> ORGANISM: Artificial
<220> FEATURE:
<223> OTHER INFORMATION: linker

<400> SEQUENCE: 102

Gly Gly Ser Gly Gly Gly Ser Gly
1               5

<210> SEQ ID NO 103
<211> LENGTH: 12
<212> TYPE: PRT
<213> ORGANISM: Artificial
<220> FEATURE:
<223> OTHER INFORMATION: linker

<400> SEQUENCE: 103

Gly Gly Ser Gly Gly Gly Ser Gly Gly Gly Ser Gly
1               5                   10

<210> SEQ ID NO 104
<211> LENGTH: 16
<212> TYPE: PRT
<213> ORGANISM: Artificial
<220> FEATURE:
<223> OTHER INFORMATION: linker

<400> SEQUENCE: 104

Gly Gly Ser Gly Gly Gly Ser Gly Gly Gly Ser Gly Gly Gly Ser Gly
1               5                   10                  15

<210> SEQ ID NO 105
<211> LENGTH: 5
<212> TYPE: PRT
<213> ORGANISM: Artificial
<220> FEATURE:
<223> OTHER INFORMATION: linker

<400> SEQUENCE: 105

Gly Gly Gly Gly Ser
1               5
```

<210> SEQ ID NO 106
<211> LENGTH: 10
<212> TYPE: PRT
<213> ORGANISM: Artificial
<220> FEATURE:
<223> OTHER INFORMATION: linker

<400> SEQUENCE: 106

Gly Gly Gly Gly Ser Gly Gly Gly Gly Ser
1               5                   10

<210> SEQ ID NO 107
<211> LENGTH: 15
<212> TYPE: PRT
<213> ORGANISM: Artificial
<220> FEATURE:
<223> OTHER INFORMATION: linker

<400> SEQUENCE: 107

Gly Gly Gly Gly Ser Gly Gly Gly Gly Ser Gly Gly Gly Gly Ser
1               5                   10                  15

<210> SEQ ID NO 108
<211> LENGTH: 5
<212> TYPE: PRT
<213> ORGANISM: Artificial
<220> FEATURE:
<223> OTHER INFORMATION: linker

<400> SEQUENCE: 108

Gly Gly Ser Gly Gly
1               5

<210> SEQ ID NO 109
<211> LENGTH: 10
<212> TYPE: PRT
<213> ORGANISM: Artificial
<220> FEATURE:
<223> OTHER INFORMATION: linker

<400> SEQUENCE: 109

Gly Gly Ser Gly Gly Gly Gly Ser Gly Gly
1               5                   10

<210> SEQ ID NO 110
<211> LENGTH: 13
<212> TYPE: PRT
<213> ORGANISM: Artificial
<220> FEATURE:
<223> OTHER INFORMATION: linker

<400> SEQUENCE: 110

Gly Gly Gly Ser Gly Gly Gly Ser Gly Gly Gly Ser
1               5                   10

<210> SEQ ID NO 111
<211> LENGTH: 14
<212> TYPE: PRT
<213> ORGANISM: Artificial
<220> FEATURE:
<223> OTHER INFORMATION: linker

<400> SEQUENCE: 111

Gly Gly Gly Gly Ser Gly Gly Ser Gly Gly Gly Gly Ser
1               5                   10

<210> SEQ ID NO 112
<211> LENGTH: 1896
<212> TYPE: DNA
<213> ORGANISM: Mucor DR056860

<400> SEQUENCE: 112

```
atgcgtctct ctgtggcgat cctcactctc acttcggctc tggcttcggt tacctcggcc      60
caacaaaaca atactgatac ttatgactac gtgatcgtcg gaggaggagt gggtggactg     120
gctctcgctt cgcgcctctc cgaggataag aacgttaccg tggctgtcct ggaatcgggc     180
ccttatgcgg atgacaaatt cgtggtctac gccccaggga tgtatggtca ggctgtcgga     240
actgacctgt gtcctctgct cccaacggtt cctcaaccat ctatgaacaa tcgaaccatc     300
actattgcta cgggacgtct gctcggagga ggttcagctg tgaacggact ggtctggacc     360
cgtggagcta tgaaggattt cgacgcttgg caggagctgg aaacccagg atggaatggg      420
accactatgt tcaagtactt caagaaaatc gaaaacttcc atccccgac cgaggaacag      480
attcaatacg gcgctactta taacaagtct gtccacggtt tcaatggccc gatcgatatt     540
gcctttcccg tgttcgagtt ccgcagtct gctaactgga atgcgtcact ggcccatctc      600
aacttcaccc gccggcaaga tctgctcgac ggtagtctcc acggctacag cacgaccct      660
aacaccctga atccacagac tgcccgacgt gcggatgcct acgctggata tatccaacct     720
aacgtcaatc gaacgaacct ggctgtcctc gcgaatcata ccgttagtcg catccagttt     780
gaggcgcgga acgtagcca accactgaag gccattggcg tggaatggta tactacgggc      840
ggagacaaga ctagtaaaca gacgatcaag gcgcgccggg agatcattct gagtagcgga     900
gccattgggt cgcctaagct gctcgaagtg tccgggatcg gtaacaaagc cattgttacc     960
gccgctggag tgcagtctct gatcgatctc ccaggcgttg gatcaaacat gcaagaccat    1020
gtgcacgctg ttaccgtgtc gaccactaat atcgatgggt acacgaccaa ctccgtgttc    1080
acgaatgaga ccctcgccca ggaacaaaag gacctgtact acaacaacaa gactggaatc    1140
tggactacga cccctaacaa tctcgggtat cccagtccga gccagctgtt caccaacact    1200
acgtttaagt ctggcaaaga gtttgcggcc atgatccgca acagtactga taagtacgcc    1260
cagtactatg ctgcgaacaa tgctacgaac gtcgagctgc tcaagaaaca atatagtatc    1320
gtggcccgac gttacgagga aaactacatc agccctatcg aaatcaactt cacgccagga    1380
tacggggta ccgggatggc tgatctgcag aacaagaaat atcaaaccgt gaatcatgtc     1440
ctggttgccc ccctcagtcg gggctacact cacatcaact cgtccgatat tgaggacccc    1500
gttgtgatcg acccgcagta ctatagccat ccgctggatg tggacgtcca cgttgcgagt    1560
acccaactgg cccgaagcat cctcaacgcc cccggactgg cttctattaa ttcaggcgag    1620
gtggaaccgg gcgagaaggt ccagagcgat gaagacgttc gcaaatggct gtcggataac    1680
gtgccgttccg actggcatcc agtcggaacc tgcgctatgc tgccacgaaa gctcggagga    1740
gtcgttgatt cgaagctcaa agtctacggc accgcgaatc tgcgtatcgt tgacgcctcc    1800
atcattccgc tcgagatttc ttcacacctg atgcaaccag tctatgcggt ctccgaacgg    1860
gctgccgaca tcatcaaatc ctcctctaaa aaataa                              1896
```

<210> SEQ ID NO 113
<211> LENGTH: 654
<212> TYPE: DNA
<213> ORGANISM: Humicola insolens

<400> SEQUENCE: 113

```
atgaagtttt tgggagaat cggagccaca gcccttgccg catccttgta tttgacctct    60
ggagccgcac aggccacggg ggacgcatac accgattctg agactggaat caagttccag   120
acctggagcc cagacccgca gttcactttc ggcctggccc ttcctcccga tgctctggag   180
aaggacgcca ccgaatacat tggcctcctg cgttgcactc gtgctgatcc ttcggacccc   240
ggctattgtg gtctttccca tggacaggtc ggccagatga cccagtctct tttgctcgtt   300
gcctgggctt acgaaaacca ggtctatact agcttccgct acgctaccgg ctatactctg   360
ccaggacttt acaccggcaa cgccaagttg actcagctct ctgtgaatat caccgatact   420
agcttcgagc tcatctatcg ttgcgaaaat tgtttctcgt gggagcatga aggttccacc   480
ggatcctcta gcacttcgca gggttatttg gttttgggac gtgcttctgc tcgccgtggc   540
gtcgtgggtc caacctgccc ggataccgcc actttcggct tccacgacaa cggtttcggg   600
cagtggggcg tggggctgga aaatgcggtg tcggaacagt attcagagtg ggct          654
```

<210> SEQ ID NO 114
<211> LENGTH: 866
<212> TYPE: PRT
<213> ORGANISM: Artificial
<220> FEATURE:
<223> OTHER INFORMATION: fusion protein

<400> SEQUENCE: 114

```
Met Lys Phe Leu Gly Arg Ile Gly Ala Thr Ala Leu Ala Ala Ser Leu
1               5                   10                  15

Tyr Leu Thr Ser Gly Ala Ala Gln Ala Thr Gly Asp Ala Tyr Thr Asp
            20                  25                  30

Ser Glu Thr Gly Ile Lys Phe Gln Thr Trp Ser Pro Asp Pro Gln Phe
        35                  40                  45

Thr Phe Gly Leu Ala Leu Pro Pro Asp Ala Leu Glu Lys Asp Ala Thr
    50                  55                  60

Glu Tyr Ile Gly Leu Leu Arg Cys Thr Arg Ala Asp Pro Ser Asp Pro
65                  70                  75                  80

Gly Tyr Cys Gly Leu Ser His Gly Gln Val Gly Gln Met Thr Gln Ser
                85                  90                  95

Leu Leu Leu Val Ala Trp Ala Tyr Glu Asn Gln Val Tyr Thr Ser Phe
            100                 105                 110

Arg Tyr Ala Thr Gly Tyr Thr Leu Pro Gly Leu Tyr Thr Gly Asn Ala
        115                 120                 125

Lys Leu Thr Gln Leu Ser Val Asn Ile Thr Asp Thr Ser Phe Glu Leu
    130                 135                 140

Ile Tyr Arg Cys Glu Asn Cys Phe Ser Trp Glu His Glu Gly Ser Thr
145                 150                 155                 160

Gly Ser Ser Ser Thr Ser Gln Gly Tyr Leu Val Leu Gly Arg Ala Ser
                165                 170                 175

Ala Arg Arg Gly Val Val Gly Pro Thr Cys Pro Asp Thr Ala Thr Phe
            180                 185                 190

Gly Phe His Asp Asn Gly Phe Gly Gln Trp Gly Val Gly Leu Glu Asn
        195                 200                 205

Ala Val Ser Glu Gln Tyr Ser Glu Trp Ala Gln Leu Ala Thr Ile Thr
    210                 215                 220

Pro Pro Thr Thr Cys Asp Gly Asn Gly Pro Gly Asp Lys Val Cys Val
225                 230                 235                 240

Pro Ala Pro Glu Asp Gln Gln Asp Thr Asn Ser Ser Ser Thr Asp Thr
```

-continued

```
                245                 250                 255
Tyr Asp Tyr Val Ile Val Gly Gly Val Ala Gly Leu Ala Leu Ala
            260                 265                 270
Ser Arg Ile Ser Glu Asn Lys Asp Val Thr Val Ala Val Leu Glu Ser
            275                 280                 285
Gly Pro Tyr Ala Gly Asp Arg Phe Val Val Tyr Ala Pro Gly Met Tyr
            290                 295                 300
Gly Gln Ala Val Gly Thr Asp Leu Ala Pro Leu Ile Pro Thr Thr Pro
305                 310                 315                 320
Gln Glu Asn Met Gly Asn Arg Ser Leu Thr Ile Ala Thr Gly Arg Leu
                325                 330                 335
Leu Gly Gly Gly Ser Ala Ile Asn Gly Leu Val Trp Thr Arg Gly Gly
                340                 345                 350
Leu Lys Asp Tyr Asp Ala Trp Glu Glu Leu Gly Asn Pro Gly Trp Asn
                355                 360                 365
Gly Ala Asn Leu Phe Lys Tyr Phe Lys Lys Val Glu Asn Phe Thr Pro
                370                 375                 380
Pro Thr Pro Ala Gln Ile Glu Tyr Gly Ala Thr Tyr Gln Lys Ser Ala
385                 390                 395                 400
His Gly Lys Lys Gly Pro Ile Asp Val Ser Phe Thr Asn Tyr Glu Phe
                405                 410                 415
Ser Gln Ser Ala Ser Trp Asn Ala Ser Leu Glu Thr Leu Asp Phe Thr
                420                 425                 430
Ala Leu Pro Asp Ile Leu Asn Gly Thr Leu Ala Gly Tyr Ser Thr Thr
                435                 440                 445
Pro Asn Ile Leu Asp Pro Glu Thr Val Arg Arg Val Asp Ser Tyr Thr
                450                 455                 460
Gly Tyr Ile Ala Pro Tyr Thr Ser Arg Asn Asn Leu Asn Val Leu Ala
465                 470                 475                 480
Asn His Thr Val Ser Arg Ile Gln Phe Ala Pro Lys Asn Gly Ser Glu
                485                 490                 495
Pro Leu Lys Ala Thr Gly Val Glu Trp Tyr Pro Thr Gly Asn Lys Asn
                500                 505                 510
Gln Lys Gln Ile Ile Lys Ala Arg Tyr Glu Val Ile Ile Ser Ser Gly
                515                 520                 525
Ala Ile Gly Ser Pro Lys Leu Leu Glu Ile Ser Gly Ile Gly Asn Lys
                530                 535                 540
Asp Ile Val Ser Ala Ala Gly Val Glu Ser Leu Ile Asp Leu Pro Gly
545                 550                 555                 560
Val Gly Ser Asn Met Gln Asp His Val His Ala Ile Thr Val Ser Thr
                565                 570                 575
Thr Asn Ile Thr Gly Tyr Thr Thr Asn Ser Val Phe Val Asn Glu Thr
                580                 585                 590
Leu Ala Gln Glu Gln Arg Glu Glu Tyr Glu Ala Asn Lys Thr Gly Ile
                595                 600                 605
Trp Ala Thr Cys Pro Asn Asn Leu Gly Tyr Pro Thr Pro Glu Gln Leu
                610                 615                 620
Phe Asn Gly Thr Glu Phe Val Ser Gly Lys Glu Phe Ala Asp Lys Ile
625                 630                 635                 640
Arg Asn Ser Thr Asp Glu Trp Ala Asn Tyr Tyr Ala Ser Thr Asn Ala
                645                 650                 655
Ser Asn Val Glu Leu Leu Lys Lys Gln Tyr Ala Ile Val Ala Ser Arg
                660                 665                 670
```

Tyr Glu Glu Asn Tyr Leu Ser Pro Ile Glu Ile Asn Phe Thr Pro Gly
            675                 680                 685

Tyr Glu Gly Ser Gly Asn Val Asp Leu Gln Asn Asn Lys Tyr Gln Thr
        690                 695                 700

Val Asn His Val Leu Ile Ala Pro Leu Ser Arg Gly Tyr Thr His Ile
705                 710                 715                 720

Asn Ser Ser Asp Val Glu Asp His Ser Val Ile Asn Pro Gln Tyr Tyr
                725                 730                 735

Ser His Pro Met Asp Ile Asp Val His Ile Ala Ser Thr Lys Leu Ala
            740                 745                 750

Arg Glu Ile Ile Thr Ala Ser Pro Gly Leu Gly Asp Ile Asn Ser Gly
            755                 760                 765

Glu Ile Glu Pro Gly Met Asn Ile Thr Ser Asp Asp Val Arg Lys
        770                 775                 780

Trp Leu Ser Asn Asn Val Arg Ser Asp Trp His Pro Val Gly Thr Cys
785                 790                 795                 800

Ala Met Leu Pro Lys Glu Leu Gly Gly Val Val Ser Pro Ala Leu Met
                805                 810                 815

Val Tyr Gly Thr Ser Asn Leu Arg Val Val Asp Ala Ser Ile Met Pro
            820                 825                 830

Leu Glu Val Ser Ser His Leu Met Gln Pro Thr Tyr Gly Ile Ala Glu
            835                 840                 845

Lys Ala Ala Asp Ile Ile Lys Asn Phe Tyr Lys Thr Gln His Lys Asn
        850                 855                 860

Gln Asn
865

```
<210> SEQ ID NO 115
<211> LENGTH: 2601
<212> TYPE: DNA
<213> ORGANISM: Artificial
<220> FEATURE:
<223> OTHER INFORMATION: construct

<400> SEQUENCE: 115
atgaagtttt tggggagaat cggagccaca gcccttgccg catccttgta tttgacctct      60
ggagccgcac aggccacggg ggacgcatac accgattctg agactggaat caagttccag     120
acctggagcc agacccgca gttcactttc ggcctggccc ttcctcccga tgctctggag      180
aaggacgcca ccgaatacat tggcctcctg cgttgcactc gtgctgatcc ttcggacccc     240
ggctattgtg gtctttccca tggacaggtc ggccagatga cccagtctct tttgctcgtt     300
gcctgggctt acgaaaacca ggtctatact agcttccgct acgctaccgg ctatactctg     360
ccaggacttt acaccggcaa cgccaagttg actcagctct ctgtgaatat caccgatact     420
agcttcgagc tcatctatcg ttgcgaaaat tgtttctcgt gggagcatga aggttccacc     480
ggatcctcta gcacttcgca gggttatttg gttttgggac gtgcttctgc tcgccgtggc     540
gtcgtgggtc caacctgccc ggataccgcc actttcggct ccacgacaa cggtttcggg      600 cagtggggcg tggggctgga aaatgcggtg tcggaacagt attcagagtg ggctcagctt     660
gcgactatca cccctcctac cacttgcgat ggaaatgggc ctggcgacaa ggtttgtgtc     720
ccggctcctg aggatcaaca agacacaaat tcttcctcaa ctgatactta tgattatgtt     780
atcgttggcg gcggtgtagc tggtttggct ttggctagtc gtatctctga aaacaaggat     840
gtcactgttg ctgttctcga gtccggtcct tatgccggtg atagatttgt tgtttatgct     900
```

```
cctggcatgt atggccaagc tgttggcact gatctcgctc ctctcattcc tactactcct    960
caagaaaata tgggcaacag aagtctcaca atcgctactg gtagattgct cggtggtggc   1020
agtgctatta atggtctcgt ttggacccgt ggtggcttga aggattacga tgcttgggag   1080
gagctcggta accctggatg gaacggtgcc aacttgttca agtactttaa gaaggtcgaa   1140
aacttcactc ctcctactcc tgcccaaatt gaatacggcg ctacttatca gaaaagtgct   1200
catggcaaga agggacctat tgatgtctct ttcacgaact acgagttctc tcaatctgct   1260
agctggaacg cctcactcga aacccttgat tcactgcac ttcctgatat cttgaacggt   1320
actttggccg gttactctac cactcccaac attttggacc ctgagactgt tcgacgtgtt   1380
gattcctata ctggttacat tgctccttac actagccgta acaacctcaa tgttttggcc   1440
aaccataccg tctcccgcat tcaatttgct cccaagaatg gtagcgaacc tctcaaggct   1500
accggtgttg aatggtatcc cactggcaac aagaatcaaa agcaaattat caaggcccgt   1560
tatgaagtta tcatctcatc tggtgccatt ggtagtccta agcttttgga aatctctggt   1620
atcggtaata aggatatcgt ctctgctgct ggtgtcgagt ccttgattga cttgcctggc   1680
gttggttcca acatgcaaga tcacgttcat gctatcactg tctctactac caatattact   1740
ggctatacta ccaacagcgt cttttgtcaat gaaacccttg cccaagaaca aagagaagaa   1800
tatgaagcca acaagactgg tatctgggct acttgtccca acaacctcgg ttatcctacg   1860
cccgaacaac tcttcaatgg caccgaattc gtttctggaa aggagtttgc tgacaagatt   1920
cgtaactcta ctgatgaatg ggccaactat tatgcttcca ccaacgcctc caatgtcgag   1980
ttattaaaga agcaatatgc tattgtcgcc tctcgttacg aagagaacta cttgtctcct   2040
attgaaatca acttcactcc tggttatgag ggtagcggta atgtcgattt gcaaaacaac   2100
aagtaccaaa ctgtcaacca tgtcttgatt gctcctttaa gtcgtggtta tactcacatt   2160
aactcttctg atgtggagga tcattctgtc attaatcccc aatactactc tcatcctatg   2220
gatattgatg tccatatcgc ttccactaaa cttgctcgcg aaatcatcac tgcctctccc   2280
ggtcttggtg acattaacag tggcgaaatc gaacccggta tgaatattac ttctgacgac   2340
gacgttagaa aatggttgag taataatgtc cgttctgact ggcatcctgt tggtacttgt   2400
gctatgcttc ccaaggaatt aggtggtgtt gtcagccccg ctctcatggt ttacggcact   2460
tccaacttgc gtgttgttga tgcttcgatt atgcccctcg aagtctcttc tcatttgatg   2520
caacccacct acggtattgc tgagaaggct gctgacatta ttaagaattt ctacaagact   2580
caacacaaga accaaaatta g                                             2601
```

<210> SEQ ID NO 116
<211> LENGTH: 861
<212> TYPE: PRT
<213> ORGANISM: Artificial
<220> FEATURE:
<223> OTHER INFORMATION: fusion protein

<400> SEQUENCE: 116

Met Arg Thr Ser Ser Arg Leu Ile Gly Ala Leu Ala Ala Ala Leu Leu
1               5                   10                  15

Pro Ser Ala Leu Ala Gln Asn Asn Val Pro Asn Thr Phe Thr Asp Pro
            20                  25                  30

Asp Ser Gly Ile Thr Phe Asn Thr Trp Gly Leu Asp Glu Asp Ser Pro
        35                  40                  45

Gln Thr Gln Gly Gly Phe Thr Phe Gly Val Ala Leu Pro Ser Asp Ala

-continued

```
                50                  55                  60
Leu Thr Thr Asp Ala Ser Glu Phe Ile Gly Tyr Leu Lys Cys Ala Arg
 65                  70                  75                  80

Asn Asp Glu Ser Gly Trp Cys Gly Ile Ser Leu Gly Gly Pro Met Thr
                 85                  90                  95

Asn Ser Leu Leu Ile Thr Ala Trp Pro His Glu Asp Thr Val Tyr Thr
            100                 105                 110

Ser Leu Arg Phe Ala Thr Gly Tyr Ala Met Pro Asp Val Tyr Glu Gly
        115                 120                 125

Asp Ala Glu Ile Thr Gln Val Ser Ser Val Asn Ser Thr His Phe
130                 135                 140

Ser Leu Ile Phe Arg Cys Lys Asn Cys Leu Gln Trp Ser His Gly Gly
145                 150                 155                 160

Ser Ser Gly Gly Ala Ser Thr Ser Gly Gly Val Leu Val Leu Gly Trp
                165                 170                 175

Val Gln Ala Phe Asp Asp Pro Gly Asn Pro Thr Cys Pro Glu Gln Ile
            180                 185                 190

Thr Leu Gln Gln His Asp Asn Gly Met Gly Ile Trp Gly Ala Gln Leu
        195                 200                 205

Asn Thr Asp Ala Ala Ser Pro Ser Tyr Thr Asp Trp Ala Ala Gln Ala
210                 215                 220

Thr Lys Thr Val Thr Gly Asp Cys Glu Gly Pro Thr Glu Thr Ser Val
225                 230                 235                 240

Val Gly Val Pro Val Pro Thr Gly Val Ser Gln Gln Asn Asn Thr Asp
                245                 250                 255

Thr Tyr Asp Tyr Val Ile Val Gly Gly Val Gly Gly Leu Ala Leu
            260                 265                 270

Ala Ser Arg Leu Ser Glu Asp Lys Asn Val Thr Val Ala Val Leu Glu
        275                 280                 285

Ser Gly Pro Tyr Ala Asp Asp Lys Phe Val Val Tyr Ala Pro Gly Met
290                 295                 300

Tyr Gly Gln Ala Val Gly Thr Asp Leu Cys Pro Leu Leu Pro Thr Val
305                 310                 315                 320

Pro Gln Pro Ser Met Asn Asn Arg Thr Ile Thr Ile Ala Thr Gly Arg
                325                 330                 335

Leu Leu Gly Gly Gly Ser Ala Val Asn Gly Leu Val Trp Thr Arg Gly
            340                 345                 350

Ala Met Lys Asp Phe Asp Ala Trp Gln Glu Leu Gly Asn Pro Gly Trp
        355                 360                 365

Asn Gly Thr Thr Met Phe Lys Tyr Phe Lys Lys Ile Glu Asn Phe His
370                 375                 380

Pro Pro Thr Glu Glu Gln Ile Gln Tyr Gly Ala Thr Tyr Asn Lys Ser
385                 390                 395                 400

Val His Gly Phe Asn Gly Pro Ile Asp Ile Ala Phe Pro Val Phe Glu
                405                 410                 415

Phe Pro Gln Ser Ala Asn Trp Asn Ala Ser Leu Ala His Leu Asn Phe
            420                 425                 430

Thr Arg Arg Gln Asp Leu Leu Asp Gly Ser Leu His Gly Tyr Ser Thr
        435                 440                 445

Thr Pro Asn Thr Leu Asn Pro Gln Thr Ala Arg Arg Ala Asp Ala Tyr
450                 455                 460

Ala Gly Tyr Ile Gln Pro Asn Val Asn Arg Thr Asn Leu Ala Val Leu
465                 470                 475                 480
```

Ala Asn His Thr Val Ser Arg Ile Gln Phe Glu Ala Arg Asn Gly Ser
            485                 490                 495

Gln Pro Leu Lys Ala Ile Gly Val Glu Trp Tyr Thr Thr Gly Gly Asp
            500                 505                 510

Lys Thr Ser Lys Gln Thr Ile Lys Ala Arg Arg Glu Ile Ile Leu Ser
            515                 520                 525

Ser Gly Ala Ile Gly Ser Pro Lys Leu Leu Glu Val Ser Gly Ile Gly
            530                 535                 540

Asn Lys Ala Ile Val Thr Ala Ala Gly Val Gln Ser Leu Ile Asp Leu
545                 550                 555                 560

Pro Gly Val Gly Ser Asn Met Gln Asp His Val His Ala Val Thr Val
            565                 570                 575

Ser Thr Thr Asn Ile Asp Gly Tyr Thr Thr Asn Ser Val Phe Thr Asn
            580                 585                 590

Glu Thr Leu Ala Gln Glu Gln Lys Asp Leu Tyr Tyr Asn Asn Lys Thr
            595                 600                 605

Gly Ile Trp Thr Thr Thr Pro Asn Asn Leu Gly Tyr Pro Ser Pro Ser
            610                 615                 620

Gln Leu Phe Thr Asn Thr Thr Phe Lys Ser Gly Lys Glu Phe Ala Ala
625                 630                 635                 640

Met Ile Arg Asn Ser Thr Asp Lys Tyr Ala Gln Tyr Ala Ala Asn
            645                 650                 655

Asn Ala Thr Asn Val Glu Leu Leu Lys Lys Gln Tyr Ser Ile Val Ala
            660                 665                 670

Arg Arg Tyr Glu Glu Asn Tyr Ile Ser Pro Ile Glu Ile Asn Phe Thr
            675                 680                 685

Pro Gly Tyr Gly Gly Thr Gly Met Ala Asp Leu Gln Asn Lys Lys Tyr
            690                 695                 700

Gln Thr Val Asn His Val Leu Val Ala Pro Leu Ser Arg Gly Tyr Thr
705                 710                 715                 720

His Ile Asn Ser Ser Asp Ile Glu Asp Pro Val Val Ile Asp Pro Gln
            725                 730                 735

Tyr Tyr Ser His Pro Leu Asp Val Asp Val His Val Ala Ser Thr Gln
            740                 745                 750

Leu Ala Arg Ser Ile Leu Asn Ala Pro Gly Leu Ala Ser Ile Asn Ser
            755                 760                 765

Gly Glu Val Glu Pro Gly Glu Lys Val Gln Ser Asp Glu Asp Val Arg
            770                 775                 780

Lys Trp Leu Ser Asp Asn Val Arg Ser Asp Trp His Pro Val Gly Thr
785                 790                 795                 800

Cys Ala Met Leu Pro Arg Lys Leu Gly Gly Val Val Asp Ser Lys Leu
            805                 810                 815

Lys Val Tyr Gly Thr Ala Asn Leu Arg Ile Val Asp Ala Ser Ile Ile
            820                 825                 830

Pro Leu Glu Ile Ser Ser His Leu Met Gln Pro Val Tyr Ala Val Ser
            835                 840                 845

Glu Arg Ala Ala Asp Ile Ile Lys Ser Ser Ser Lys Lys
850                 855                 860

<210> SEQ ID NO 117
<211> LENGTH: 2586
<212> TYPE: DNA
<213> ORGANISM: Artificial
<220> FEATURE:

<223> OTHER INFORMATION: construct

<400> SEQUENCE: 117

```
atgcgcacct cttctcgtct tattggtgca ttggctgctg cactcctgcc ttctgctctt    60
gcacagaaca atgttccgaa cacattcacg gatcctgaca gtggaatcac ttttaataca   120
tggggcctcg atgaggactc cccgcagaca caaggcggtt tcacgtttgg agtcgcgctt   180
cctagcgatg ccttgaccac tgacgcttcg gagttcatcg gctatttgaa gtgcgcacga   240
aacgatgaat ccggatggtg tgggatctct ctcggagggc caatgacaaa ttcgcttttg   300
attacggctt ggccgcatga agacacggtt tacacctcac tcagattcgc gaccggttac   360
gccatgccag atgtctatga gggagacgct gaaatcaccc aagttagctc gtcagtcaac   420
agtactcatt tctccttgat ttttcgatgc aagaattgtc tccaatggtc ccacggcgt    480
agttccggag gggcaagtac ttccggcggt gttttggtcc tgggatgggt ccaggcgttc   540
gatgaccctg aaaccccac ctgcccagag caaatcactc tgcagcaaca cgataacggc    600
atgggtattt gggcgctca gcttaataca gatgcggcct ctccgagcta tacgactgg    660
gctgcacaag caaccaagac tgtcacaggc gactgtgagg gtcctacgga aacctctgtc   720
gtgggagtgc ctgttcccac aggggtctcc caacaaaaca atactgatac ttatgactac   780
gtgatcgtcg gaggaggagt gggtggactg gctctcgctt cgcgcctctc cgaggataag   840
aacgttaccg tggctgtcct ggaatcgggc ccttatgcgg atgacaaatt cgtggtctac   900
gccccaggga tgtatggtca ggctgtcgga actgacctgt gtcctctgct cccaacggtt   960
cctcaaccat ctatgaacaa tcgaaccatc actattgcta cggacgtct gctcggagga   1020
ggttcagctg tgaacggact ggtctggacc cgtggagcta tgaaggattt cgacgcttgg  1080
caggagctgg aaacccagg atggaatggg accactatgt tcaagtactt caagaaaatc   1140
gaaaacttcc atccccgac cgaggaacag attcaatacg gcgctactta taacaagtct   1200
gtccacggtt tcaatggccc gatcgatatt gcctttccg tgttcgagtt ccgcagtct    1260
gctaactgga atgcgtcact ggcccatctc aacttcaccc gccggcaaga tctgctcgac  1320
ggtagtctcc acggctacag cacgacccct aacaccctga tccacagac tgcccgacgt   1380
gcggatgcct acgctggata tatccaacct aacgtcaatc gaacgaacct ggctgtcctc   1440
gcgaatcata ccgttagtcg catccagttt gaggcgcgga acggtagcca accactgaag  1500
gccattggcg tggaatggta tactacgggc ggagacaaga ctagtaaaca gacgatcaag   1560
gcgcgccggg agatcattct gagtagcgga gccattgggt cgcctaagct gctcgaagtg   1620
tccgggatcg gtaacaaagc cattgttacc gccgctggag tgcagtctct gatcgatctc   1680
ccaggcgttg gatcaaacat gcaagaccat gtgcacgctg ttaccgtgtc gaccactaat   1740
atcgatgggt acacgaccaa ctccgtgttc acgaatgaga ccctcgccca ggaacaaaag  1800
gacctgtact acaacaacaa gactggaatc tggactacga ccctaacaa tctcgggtat   1860
cccagtccga gccagctgtt caccaacact acgtttaagt ctggcaaaga gtttgcggcc  1920
atgatccgca acagtactga taagtacgcc cagtactatg ctgcgaacaa tgctacgaac  1980
gtcgagctgc tcaagaaaca atatagtatc gtggcccgac gttacgagga aaactacatc   2040
agccctatcg aaatcaactt cacgccagga tacgggggta ccgggatggc tgatctgcag  2100
aacaagaaat atcaaaccgt gaatcatgtc ctggttgccc ccctcagtcg gggctacact  2160
cacatcaact cgtccgatat tgaggacccc gttgtgatcg accgcagta ctatagccat   2220
ccgctggatg tggacgtcca cgttgcgagt acccaactgg cccgaagcat cctcaacgcc  2280
```

```
cccggactgg cttctattaa ttcaggcgag gtggaaccgg gcgagaaggt ccagagcgat   2340
gaagacgttc gcaaatggct gtcgataacg gtgcgttccg actggcatcc agtcggaacc   2400
tgcgctatgc tgccacgaaa gctcggagga gtcgttgatt cgaagctcaa agtctacggc   2460
accgcgaatc tgcgtatcgt tgacgcctcc atcattccgc tcgagatttc ttcacacctg   2520
atgcaaccag tctatgcggt ctccgaacgg gctgccgaca tcatcaaatc ctcctctaaa   2580
aaataa                                                              2586
```

<210> SEQ ID NO 118
<211> LENGTH: 859
<212> TYPE: PRT
<213> ORGANISM: Artificial
<220> FEATURE:
<223> OTHER INFORMATION: fusion protein

<400> SEQUENCE: 118

```
Met Lys Leu Leu Ser Arg Val Gly Ala Thr Ala Leu Ala Ala Thr Leu
1               5                   10                  15

Ser Leu Lys Gln Cys Ala Ala Gln Met Thr Glu Gly Thr Tyr Thr His
            20                  25                  30

Glu Ala Thr Gly Ile Thr Phe Lys Thr Trp Thr Pro Ser Asp Gly Ser
        35                  40                  45

Thr Phe Thr Phe Gly Leu Ala Leu Pro Gly Asp Ala Leu Thr Asn Asp
    50                  55                  60

Ala Thr Glu Tyr Ile Gly Leu Leu Arg Cys Gln Ile Thr Asp Pro Ser
65                  70                  75                  80

Ser Pro Gly Tyr Cys Gly Ile Ser His Gly Gln Ser Gly Gln Met Thr
                85                  90                  95

Gln Ala Leu Leu Leu Val Ala Trp Ala Ser Glu Asp Val Val Tyr Thr
            100                 105                 110

Ser Phe Arg Tyr Ala Thr Gly Tyr Thr Leu Pro Glu Leu Tyr Thr Gly
        115                 120                 125

Asp Ala Lys Leu Thr Gln Ile Ala Ser Ser Val Ser Gly Asp Ser Phe
    130                 135                 140

Glu Val Leu Phe Arg Cys Glu Asn Cys Phe Ser Trp Asp Gln Asn Gly
145                 150                 155                 160

Ala Thr Gly Ser Val Ser Thr Ser Asn Gly Ala Leu Val Leu Gly Tyr
                165                 170                 175

Ala Ala Ser Lys Ser Gly Leu Thr Gly Ala Thr Cys Pro Asp Thr Ala
            180                 185                 190

Glu Phe Gly Phe His Asn Asn Gly Phe Gly Gln Trp Gly Ala Val Leu
        195                 200                 205

Glu Gly Ala Thr Ser Asp Ser Tyr Glu Glu Trp Ala Gln Leu Ala Thr
    210                 215                 220

Ile Thr Pro Pro Thr Thr Cys Asp Gly Asn Gly Pro Gly Asp Lys Val
225                 230                 235                 240

Cys Val Pro Ala Pro Glu Asp Thr Gln Gln Asn Asn Thr Asp Thr Tyr
                245                 250                 255

Asp Tyr Val Ile Val Gly Gly Gly Val Gly Gly Leu Ala Leu Ala Ser
            260                 265                 270

Arg Leu Ser Glu Asp Lys Asn Val Thr Val Ala Val Leu Glu Ser Gly
        275                 280                 285

Pro Tyr Ala Asp Asp Lys Phe Val Val Tyr Ala Pro Gly Met Tyr Gly
    290                 295                 300
```

```
Gln Ala Val Gly Thr Asp Leu Cys Pro Leu Leu Pro Thr Val Pro Gln
305                 310                 315                 320

Pro Ser Met Asn Asn Arg Thr Ile Thr Ile Ala Thr Gly Arg Leu Leu
            325                 330                 335

Gly Gly Gly Ser Ala Val Asn Gly Leu Val Trp Thr Arg Gly Ala Met
            340                 345                 350

Lys Asp Phe Asp Ala Trp Gln Glu Leu Gly Asn Pro Gly Trp Asn Gly
            355                 360                 365

Thr Thr Met Phe Lys Tyr Phe Lys Lys Ile Glu Asn Phe His Pro Pro
    370                 375                 380

Thr Glu Glu Gln Ile Gln Tyr Gly Ala Thr Tyr Asn Lys Ser Val His
385                 390                 395                 400

Gly Phe Asn Gly Pro Ile Asp Ile Ala Phe Pro Val Phe Glu Phe Pro
                405                 410                 415

Gln Ser Ala Asn Trp Asn Ala Ser Leu Ala His Leu Asn Phe Thr Arg
            420                 425                 430

Arg Gln Asp Leu Leu Asp Gly Ser Leu His Gly Tyr Ser Thr Thr Pro
            435                 440                 445

Asn Thr Leu Asn Pro Gln Thr Ala Arg Arg Ala Asp Ala Tyr Ala Gly
450                 455                 460

Tyr Ile Gln Pro Asn Val Asn Arg Thr Asn Leu Ala Val Leu Ala Asn
465                 470                 475                 480

His Thr Val Ser Arg Ile Gln Phe Glu Ala Arg Asn Gly Ser Gln Pro
            485                 490                 495

Leu Lys Ala Ile Gly Val Glu Trp Tyr Thr Thr Gly Gly Asp Lys Thr
            500                 505                 510

Ser Lys Gln Thr Ile Lys Ala Arg Arg Glu Ile Ile Leu Ser Ser Gly
            515                 520                 525

Ala Ile Gly Ser Pro Lys Leu Leu Glu Val Ser Gly Ile Gly Asn Lys
            530                 535                 540

Ala Ile Val Thr Ala Ala Gly Val Gln Ser Leu Ile Asp Leu Pro Gly
545                 550                 555                 560

Val Gly Ser Asn Met Gln Asp His Val His Ala Val Thr Val Ser Thr
            565                 570                 575

Thr Asn Ile Asp Gly Tyr Thr Thr Asn Ser Val Phe Thr Asn Glu Thr
            580                 585                 590

Leu Ala Gln Glu Gln Lys Asp Leu Tyr Tyr Asn Asn Lys Thr Gly Ile
            595                 600                 605

Trp Thr Thr Thr Pro Asn Asn Leu Gly Tyr Pro Ser Pro Ser Gln Leu
            610                 615                 620

Phe Thr Asn Thr Thr Phe Lys Ser Gly Lys Glu Phe Ala Ala Met Ile
625                 630                 635                 640

Arg Asn Ser Thr Asp Lys Tyr Ala Gln Tyr Tyr Ala Ala Asn Asn Ala
            645                 650                 655

Thr Asn Val Glu Leu Leu Lys Lys Gln Tyr Ser Ile Val Ala Arg Arg
            660                 665                 670

Tyr Glu Glu Asn Tyr Ile Ser Pro Ile Glu Ile Asn Phe Thr Pro Gly
            675                 680                 685

Tyr Gly Gly Thr Gly Met Ala Asp Leu Gln Asn Lys Lys Tyr Gln Thr
            690                 695                 700

Val Asn His Val Leu Val Ala Pro Leu Ser Arg Gly Tyr Thr His Ile
705                 710                 715                 720
```

```
Asn Ser Ser Asp Ile Glu Asp Pro Val Val Ile Asp Pro Gln Tyr Tyr
            725                 730                 735

Ser His Pro Leu Asp Val Asp Val His Val Ala Ser Thr Gln Leu Ala
            740                 745                 750

Arg Ser Ile Leu Asn Ala Pro Gly Leu Ala Ser Ile Asn Ser Gly Glu
            755                 760                 765

Val Glu Pro Gly Glu Lys Val Gln Ser Asp Glu Asp Val Arg Lys Trp
        770                 775                 780

Leu Ser Asp Asn Val Arg Ser Asp Trp His Pro Val Gly Thr Cys Ala
785                 790                 795                 800

Met Leu Pro Arg Lys Leu Gly Gly Val Val Asp Ser Lys Leu Lys Val
                805                 810                 815

Tyr Gly Thr Ala Asn Leu Arg Ile Val Asp Ala Ser Ile Ile Pro Leu
                820                 825                 830

Glu Ile Ser Ser His Leu Met Gln Pro Val Tyr Ala Val Ser Glu Arg
                835                 840                 845

Ala Ala Asp Ile Ile Lys Ser Ser Ser Lys Lys
        850                 855
```

<210> SEQ ID NO 119
<211> LENGTH: 2580
<212> TYPE: DNA
<213> ORGANISM: Artificial
<220> FEATURE:
<223> OTHER INFORMATION: construct

<400> SEQUENCE: 119

| | | | | | |
|---|---|---|---|---|---|
| atgaagctcc | tgtcgagagt | cggcgcaact | gcgttggccg | ctacactctc | actgaaacaa | 60 |
| tgcgcagcgc | agatgaccga | gggcacgtac | acccatgaag | ctactggaat | cacattcaag | 120 |
| acttggacac | cgtcggatgg | atcaacgttc | acctttggtc | ttgccttgcc | tggagatgct | 180 |
| ctcacgaacg | acgcaaccga | gtacatcggc | cttttgcgat | gccagattac | cgatccgtcc | 240 |
| tctcctgggt | attgtggcat | ctcgcacggc | cagtcaggac | aaatgacaca | ggctctcctg | 300 |
| cttgtcgcct | gggcttctga | ggacgtcgtg | tacacgagct | ccgctacgc | aacgggttat | 360 |
| accctccccg | aactgtatac | tggagatgct | aagttgacac | aaattgcaag | ctcggtttct | 420 |
| ggtgactcct | tcgaggtcct | ctttcgttgc | gaaaactgtt | tttcttggga | tcagaatggg | 480 |
| gctacgggct | cagtcagtac | ctctaatgga | gcattggtgc | tgggatatgc | tgcttctaag | 540 |
| agcggtctga | ctggagcgac | atgcccggat | acagccgagt | tcggctttca | taacaatggc | 600 |
| ttcggtcaat | ggggtgcggt | cctggaagga | gcaacctcgg | actcatatga | ggaatgggca | 660 |
| cagcttgcga | ctatcacccc | tcctaccact | tgcgatggaa | atgggcctgg | cgacaaggtt | 720 |
| tgtgtcccgg | ctcctgagga | tacccaacaa | aacaatactg | atacttatga | ctacgtgatc | 780 |
| gtcggaggag | gagtgggtgg | actggctctc | gcttcgcgcc | tctccgagga | taagaacgtt | 840 |
| accgtggctg | tcctggaatc | gggcccttat | gcggatgaca | aattcgtggt | ctacgcccca | 900 |
| gggatgtatg | tcaggctgt | cggaactgac | ctgtgtcctc | tgctcccaac | ggttcctcaa | 960 |
| ccatctatga | caatcgaac | catcactatt | gctacgggac | gtctgctcgg | aggaggttca | 1020 |
| gctgtgaacg | gactggtctg | gacccgtgga | gctatgaagg | atttcgacgc | ttggcaggag | 1080 |
| ctgggaaacc | caggatggaa | tggaccact | atgttcaagt | acttcaagaa | aatcgaaaac | 1140 |
| ttccatcccc | cgaccgagga | acagattcaa | tacggcgcta | cttataacaa | gtctgtccac | 1200 |
| ggtttcaatg | gcccgatcga | tattgccttt | cccgtgttcg | agtttccgca | gtctgctaac | 1260 |

-continued

```
tggaatgcgt cactggccca tctcaacttc acccgccggc aagatctgct cgacggtagt      1320
ctccacggct acagcacgac ccctaacacc ctgaatccac agactgcccg acgtgcggat      1380
gcctacgctg gatatatcca acctaacgtc aatcgaacga acctggctgt cctcgcgaat      1440
cataccgtta gtcgcatcca gtttgaggcg cggaacggta gccaaccact gaaggccatt      1500
ggcgtggaat ggtatactac gggcggagac aagactagta acagacgat caaggcgcgc      1560 cgggagatca ttctgagtag cggagccatt gggtcgccta gctgctcga agtgtccggg      1620 atcggtaaca aagccattgt taccgccgct ggagtgcagt ctctgatcga tctcccaggc      1680
gttggatcaa acatgcaaga ccatgtgcac gctgttaccg tgtcgaccac taatatcgat      1740
gggtacacga ccaactccgt gttcacgaat gagaccctcg cccaggaaca aaggacctg       1800 tactacaaca caagactgg aatctggact acgaccccta caatctcgg gtatcccagt       1860 ccgagccagc tgttcaccaa cactacgttt aagtctggca aagagtttgc ggccatgatc      1920
cgcaacagta ctgataagta cgcccagtac tatgctgcga caatgctac gaacgtcgag       1980 ctgctcaaga aacaatatag tatcgtggcc cgacgttacg aggaaaacta catcagccct      2040
atcgaaatca acttcacgcc aggatacggg ggtaccggga tggctgatct gcagaacaag      2100
aaatatcaaa ccgtgaatca tgtcctggtt gcccccctca gtcggggcta cactcacatc      2160
aactcgtccg atattgagga ccccgttgtg atcgacccgc agtactatag ccatccgctg      2220
gatgtggacg tccacgttgc gagtacccaa ctggcccgaa gcatcctcaa cgcccccgga      2280
ctggcttcta ttaattcagg cgaggtggaa ccgggcgaga aggtccagag cgatgaagac      2340
gttcgcaaat ggctgtcgga taacgtgcgt tccgactggc atccagtcgg aacctgcgct      2400
atgctgccac gaaagctcgg aggagtcgtt gattcgaagc tcaaagtcta cggcaccgcg      2460
aatctgcgta tcgttgacgc ctccatcatt ccgctcgaga tttcttcaca cctgatgcaa      2520
ccagtctatg cggtctccga acgggctgcc gacatcatca aatcctcctc taaaaaataa     2580
```

<210> SEQ ID NO 120
<211> LENGTH: 27
<212> TYPE: PRT
<213> ORGANISM: Artificial
<220> FEATURE:
<223> OTHER INFORMATION: linker

<400> SEQUENCE: 120

Gln Leu Ala Thr Ile Thr Pro Pro Thr Thr Cys Asp Gly Asn Gly Pro
1               5                   10                  15

Gly Asp Lys Val Cys Val Pro Ala Pro Glu Asp
            20                  25

<210> SEQ ID NO 121
<211> LENGTH: 81
<212> TYPE: DNA
<213> ORGANISM: Artificial
<220> FEATURE:
<223> OTHER INFORMATION: linker

<400> SEQUENCE: 121

```
cagcttgcga ctatcacccc tcctaccact tgcgatggaa atgggcctgg cgacaaggtt      60
tgtgtcccgg ctcctgagga t                                                81
```

<210> SEQ ID NO 122
<211> LENGTH: 29
<212> TYPE: PRT
<213> ORGANISM: Artificial

<220> FEATURE:
<223> OTHER INFORMATION: linker

<400> SEQUENCE: 122

Ala Gln Ala Thr Lys Thr Val Thr Gly Asp Cys Glu Gly Pro Thr Glu
1               5                   10                  15

Thr Ser Val Val Gly Val Pro Val Pro Thr Gly Val Ser
            20                  25

<210> SEQ ID NO 123
<211> LENGTH: 87
<212> TYPE: DNA
<213> ORGANISM: Artificial
<220> FEATURE:
<223> OTHER INFORMATION: linker

<400> SEQUENCE: 123
gcacaagcaa ccaagactgt cacaggcgac tgtgagggtc ctacggaaac ctctgtcgtg    60
ggagtgcctg ttcccacagg ggtctcc                                        87

<210> SEQ ID NO 124
<211> LENGTH: 28
<212> TYPE: PRT
<213> ORGANISM: Artificial
<220> FEATURE:
<223> OTHER INFORMATION: linker

<400> SEQUENCE: 124

Gln Leu Ala Thr Ile Thr Pro Pro Thr Thr Cys Asp Gly Asn Gly Pro
1               5                   10                  15

Gly Asp Lys Val Cys Val Pro Ala Pro Glu Asp Thr
            20                  25

<210> SEQ ID NO 125
<211> LENGTH: 84
<212> TYPE: DNA
<213> ORGANISM: Artificial
<220> FEATURE:
<223> OTHER INFORMATION: linker

<400> SEQUENCE: 125
cagcttgcga ctatcacccc tcctaccact tgcgatggaa atgggcctgg cgacaaggtt    60
tgtgtcccgg ctcctgagga tacc                                           84

<210> SEQ ID NO 126
<211> LENGTH: 30
<212> TYPE: DNA
<213> ORGANISM: Artificial
<220> FEATURE:
<223> OTHER INFORMATION: primer

<400> SEQUENCE: 126
cgcaccacct tcaaaatgaa gttttggggg                                     30

<210> SEQ ID NO 127
<211> LENGTH: 30
<212> TYPE: DNA
<213> ORGANISM: Artificial
<220> FEATURE:
<223> OTHER INFORMATION: primer

<400> SEQUENCE: 127
gatagtcgca agctgagccc actctgaata                                     30

```
<210> SEQ ID NO 128
<211> LENGTH: 25
<212> TYPE: DNA
<213> ORGANISM: Artificial
<220> FEATURE:
<223> OTHER INFORMATION: primer

<400> SEQUENCE: 128
tttgaaggtg gtgcgaactt tgtag                                           25

<210> SEQ ID NO 129
<211> LENGTH: 30
<212> TYPE: DNA
<213> ORGANISM: Artificial
<220> FEATURE:
<223> OTHER INFORMATION: primer

<400> SEQUENCE: 129
cagcttgcga ctatcacccc tcctaccact                                      30

<210> SEQ ID NO 130
<211> LENGTH: 25
<212> TYPE: DNA
<213> ORGANISM: Artificial
<220> FEATURE:
<223> OTHER INFORMATION: primer

<400> SEQUENCE: 130
tttgaaggtg gtgcgaactt tgtag                                           25

<210> SEQ ID NO 131
<211> LENGTH: 37
<212> TYPE: DNA
<213> ORGANISM: Artificial
<220> FEATURE:
<223> OTHER INFORMATION: primer

<400> SEQUENCE: 131
caacaaaaca atactgatac ttatgactac gtgatcg                              37

<210> SEQ ID NO 132
<211> LENGTH: 26
<212> TYPE: DNA
<213> ORGANISM: Artificial
<220> FEATURE:
<223> OTHER INFORMATION: primer

<400> SEQUENCE: 132
cgcaccacct tcaaaatgcg cacctc                                          26

<210> SEQ ID NO 133
<211> LENGTH: 42
<212> TYPE: DNA
<213> ORGANISM: Artificial
<220> FEATURE:
<223> OTHER INFORMATION: primer

<400> SEQUENCE: 133
agtattgttt tgttgggaga ccctgtggg aacaggcact cc                         42

<210> SEQ ID NO 134
<211> LENGTH: 25
<212> TYPE: DNA
<213> ORGANISM: Artificial
<220> FEATURE:
<223> OTHER INFORMATION: primer
```

```
<400> SEQUENCE: 134
tttgaaggtg gtgcgaactt tgtag                                    25

<210> SEQ ID NO 135
<211> LENGTH: 37
<212> TYPE: DNA
<213> ORGANISM: Artificial
<220> FEATURE:
<223> OTHER INFORMATION: primer

<400> SEQUENCE: 135
caacaaaaca atactgatac ttatgactac gtgatcg                       37

<210> SEQ ID NO 136
<211> LENGTH: 28
<212> TYPE: DNA
<213> ORGANISM: Artificial
<220> FEATURE:
<223> OTHER INFORMATION: primer

<400> SEQUENCE: 136
cgcaccacct tcaaaatgaa gctcctgt                                 28

<210> SEQ ID NO 137
<211> LENGTH: 39
<212> TYPE: DNA
<213> ORGANISM: Artificial
<220> FEATURE:
<223> OTHER INFORMATION: primer

<400> SEQUENCE: 137
agtattgttt tgttgggtat cctcaggagc cgggacaca                     39
```